United States Patent
Norville et al.

(10) Patent No.: US 12,421,293 B2
(45) Date of Patent: Sep. 23, 2025

(54) MAJOR HISTOCOMPATIBILITY COMPLEX-BASED CHIMERIC RECEPTORS AND USES THEREOF FOR TREATING AUTOIMMUNE DISEASES

(71) Applicant: Jura Bio, Inc., Boston, MA (US)

(72) Inventors: Julie Norville, Boston, MA (US); Elizabeth Wood, Boston, MA (US)

(73) Assignee: JURA BIO, INC., Somerville, MA (US)

( * ) Notice: Subject to any disclaimer, the term of this patent is extended or adjusted under 35 U.S.C. 154(b) by 0 days.

(21) Appl. No.: 18/490,445

(22) Filed: Oct. 19, 2023

(65) Prior Publication Data

US 2024/0165158 A1 May 23, 2024

Related U.S. Application Data

(62) Division of application No. 16/762,723, filed as application No. PCT/US2018/060227 on Nov. 10, 2018, now Pat. No. 11,826,385.

(60) Provisional application No. 62/584,449, filed on Nov. 10, 2017.

(51) Int. Cl.

| | |
|---|---|
| C07K 14/705 | (2006.01) |
| A61K 40/11 | (2025.01) |
| A61K 40/22 | (2025.01) |
| A61K 40/31 | (2025.01) |
| A61K 40/32 | (2025.01) |
| A61K 40/41 | (2025.01) |
| A61K 40/42 | (2025.01) |
| A61K 40/48 | (2025.01) |
| C07K 14/725 | (2006.01) |
| C07K 14/74 | (2006.01) |
| C12N 15/85 | (2006.01) |

(52) U.S. Cl.
CPC ........ *C07K 14/70521* (2013.01); *A61K 40/11* (2025.01); *A61K 40/22* (2025.01); *A61K 40/31* (2025.01); *A61K 40/32* (2025.01); *A61K 40/416* (2025.01); *A61K 40/42* (2025.01); *A61K 40/48* (2025.01); *C07K 14/7051* (2013.01); *C07K 14/70539* (2013.01); *C07K 14/70596* (2013.01); *C12N 15/85* (2013.01); *A61K 2239/31* (2023.05); *A61K 2239/48* (2023.05)

(58) Field of Classification Search
CPC ........ C07K 14/70539; C07K 14/70521; C07K 14/7051; C07K 14/70596; A61K 40/31; C12N 15/85
See application file for complete search history.

(56) References Cited

U.S. PATENT DOCUMENTS

| | | | |
|---|---|---|---|
| 2004/0086960 A1* | 5/2004 | Reiter | C07K 14/70539 435/325 |
| 2008/0286312 A1 | 11/2008 | Gross et al. | |
| 2012/0148552 A1 | 6/2012 | Jensen | |
| 2015/0139943 A1 | 5/2015 | Campana et al. | |
| 2016/0129133 A1 | 5/2016 | Mccreedy et al. | |

FOREIGN PATENT DOCUMENTS

| | | |
|---|---|---|
| CN | 106535925 A | 3/2017 |
| CN | 106574272 A | 4/2017 |
| CN | 107074969 A | 8/2017 |
| WO | 01/91698 A2 | 12/2001 |
| WO | 2012056407 A1 | 5/2012 |
| WO | 2016033570 A1 | 3/2016 |

OTHER PUBLICATIONS

Mekala et al. Immunotherapy of autoimmune encephalomyelitis with redirected CD4+CD25+ T lymphocytes. Blood, 2005; 105(5): 2090-2092. (Year: 2005).*
Moisini et al. Redirecting Therapeutic T Cells against Myelin-Specific T Lymphocytes Using a Humanized Myelin Basic Protein-HLA-DR2-z Chimeric Receptor. J Immunol, 2008; 180:3601-3611. (Year: 2008).*
Zhang et al. Engineering CAR-T cells. Biomark Res 5, 2017; 22:1-6. (Year: 2017).*
Moisini et al. Redirecting Therapeutic T Cells against Myelin-Specific T Lymphocytes Using a Humanized Myelin Basic Protein-HLA DR2-ζ Chimeric Receptor. J Immunol; 180(5):3601-3611. (Year: 2008).*
Carpenito et al. (Mar. 3, 2009) "Control of Large, Established Tumor Xenografts with Genetically Retargeted Human T Cellscontaining CD28 and CD137 Domains", Proceedings of the National Academy of Sciences of the United States of America, 106(9):3360-3365.
Moisini et al. (Mar. 2008) "Redirecting Therapeutic T Cells against Myelin-Specific T Lymphocytes Using a Humanized Myelin Basic Protein-HLA-DR2-zeta Chimeric Receptor", The Journal of Immunology, 180(5):3601-3611.
Till et al. (2012) "CD20-Specific Adoptive Immunotherapy for Lymphoma Using a Chimeric Antigen Receptor with Both CD28 and 4-1BB Domains: Pilot Clinical Trial Results", Blood, 119(17):3940-3950.
Margalit et al., (Aug. 22, 2003) "Chimeric B2 microglobulin/CD37 polypeptides expressed in T cells convert MHC class I peptide ligands into T cell activation receptors: a potential tool for specific targeting of pathogenic CD8+ T cells", International Immunology, 15(11), 1379-1387.

(Continued)

*Primary Examiner* — Daniel E Kolker
*Assistant Examiner* — Maureen Varina Driscoll
(74) *Attorney, Agent, or Firm* — Mintz, Levin, Cohn, Ferris, Glovsky and Popeo, P.C.

(57) ABSTRACT

Major histocompatibility complex-based chimeric receptors (MHC-CAR) for use in targeting autoreactive immune cells. Also provided herewith are genetically engineered immune cells expressing the MHC-CAR for use in treating autoimmune diseases such as multiple sclerosis.

17 Claims, 10 Drawing Sheets

Specification includes a Sequence Listing.

(56) References Cited

OTHER PUBLICATIONS

Mekala et al., (Mar. 15, 2005) "IL-10-dependent suppression of experimental allergic encephalomyelitis by Th2-differentiated, anti-TCR redirected T lymphocytes", The Journal of Immunology, 174(6), 3789-3797.

Mekala et al., (Nov. 4, 2004) "Immunotherapy of autoimmune encephalomyelitis with redirected CD4+ CD25+ T lymphocytes", Blood, 105(5), 2090-2092.

Moisini Ioana, (Jul. 17, 2024) "Humanized Chimeric Receptors in the Therapy of Multiple Sclerosis", Theses and Dissertations (ETD). Paper 184 [retrieved from internet Jul. 17, 2024] <url: https://dc.uthsc.edu/dissertations/184/ >, doi:10.21007/etd.cghs.2007.0215, 163.

\* cited by examiner

Single chain - Class II

Single chain - Class I

Multi-chain: Class II

Multi-chain: Class I

MAJOR HISTOCOMPATIBILITY COMPLEX-BASED CHIMERIC RECEPTORS AND USES THEREOF FOR TREATING AUTOIMMUNE DISEASES

RELATED APPLICATIONS

This application is a divisional of U.S. application Ser. No. 16/762,723, filed on May 8, 2020, which is a national stage filing under 35 U.S.C. § 371 of International Application No. PCT/US2018/060227, filed on Nov. 10, 2018, which claims the benefit of filing date of U. S. Provisional Application Ser. No. 62/584,449, filed on Nov. 10, 2017. The entire contents of each of the prior applications are incorporated by reference herein.

REFERENCE TO SEQUENCE LISTING

The application contains a Substitute Sequence Listing that has been filed electronically in XML format, created Feb. 5, 2024, and named "063640-501D01US SeqList_ST26.xml" (493,151 bytes), the contents of which are incorporated by reference herein in their entirety.

BACKGROUND OF THE INVENTION

Autoimmune diseases are characterized by abnormal immune responses against self-antigens, leading to damage or disruption of tissues. Multiple sclerosis (MS) is a central nervous system autoimmune disease, in which activated autoreactive T cells invade the blood brain barrier, initiating an inflammatory response that leads to myelin destruction and axonal loss. Although the etiology of MS, the mechanisms associated with its onset and progression, and determination of its outcome remains unelucidated, all available evidence suggests that therapies specifically targeting the pathologic immune cells responsible for MS would have improved therapeutic outcomes over available therapies. Reinhard et al., *Proceedings of the National Academy of Sciences*, 101(suppl 2):14599-14606; 2004. This strategy could be extended to other immune disorders with similar mechanisms, including rheumatoid arthritis. Carol et al., *Nature Reviews Immunology*, 2(2):85-95, 2002.

The major histocompatibility complex (MHC), known as human leukocytes (HLA) in humans, is a set of cell surface proteins essential for the immune system to recognize foreign agents. MHC complexes bind to antigens derived from pathogens and display such to T cells, which are then activated, leading to elimination of cells displaying foreign antigens. MHC complexes may also display intact, and in some cases misfolded, host-derived proteins to B cells thereby inducing the autoantibody responses characteristic of autoimmune disorders. Jiang et al., *International immunology*, 25(4):235-246 (2013), and Busch et al., *The EMBO journal*, 15(2):418, (1996).

SUMMARY OF THE INVENTION

In aspect, the disclosure features a major histocompatibility complex (MHC)-based chimeric receptor (CAR), comprising: (i) an extracellular domain of a MHC molecule conjugated to an antigenic peptide from an antigen involved in an autoimmune disease; and (ii) a cytoplasmic signaling domain, at least one co-stimulatory domain, or a combination thereof. The MHC-based CAR may further comprises a hinge domain located between (i) and (ii). The antigenic peptide is dependent on the autoimmune disorder and may be from myelin basic protein (MBP), proteolipid protein (PLP), insulin, glutamate decarboxylase, or the additional exemplary self-antigens as described in Table 1.

In some examples, the MHC-based chimeric receptor comprises at least one co-stimulatory domain, which may be a co-stimulatory domain from 4-1BB (CD137), a co-stimulatory domain from CD28, or a combination thereof. In other examples, the MHC-based chimeric receptor as described herein may be free of a cytoplasmic signaling domain. Alternatively or in addition, the MHC-CAR comprises a cytoplasmic signaling domain of CD3ζ.

In some embodiments, the MHC molecule in the MHC-CAR is a class I MHC, for example, a human class I MHC. In some instances, the extracellular domain of the chimeric receptor comprises an extracellular domain of the alpha chain of the class I MHC, which is fused to the antigenic peptide. For example, the chimeric receptor may be a fusion polypeptide comprising (i) the extracellular domain of the class I MHC molecule, and (ii) the cytoplasmic domain, the at least one co-stimulatory domain, or the combination thereof. In one example, the chimeric receptor is a fusion polypeptide, which comprises, from N-terminus to C-terminus, a signal peptide, a first peptide linker, the antigenic peptide, a second peptide linker, an extracellular domain of macroglobulin, a third peptide linker, the class I MHC molecule, a transmembrane domain, the at least one co-stimulatory domain, and CD3ζ.

In other embodiments, the MHC-based chimeric receptor as described herein comprises a class II MHC (e.g., a human MHC II) or a portion thereof. Such a chimeric receptor may comprise a first polypeptide, which comprises an extracellular domain of a first MHC class II, and a second polypeptide, which comprises an extracellular domain of a beta chain of a second MHC class II, and wherein the antigenic peptide is fused to either the first polypeptide or the second polypeptide, and wherein either the first polypeptide or the second polypeptide further comprises the cytoplasmic signaling domain, the at least one co-stimulatory domain, or the combination thereof. In some examples, the chimeric receptor can be a fusion polypeptide comprising (i) an extracellular domain of the alpha chain of a first MHC class II molecule, (ii) an extracellular domain of the beta chain of a second MHC class II molecule, (iii) the antigenic peptide, and (iv) the cytoplasmic signaling domain, the at least one co-stimulatory domain, or the combination thereof. In some examples the antigenic protein may not be linked to the MHC class II and may instead be expressed as a separate fusion polypeptide with an alternative signal peptide (such as that from CD150, i.e., MDPKGLLSLTFVLFLSLAFG (SEQ ID NO: 388)). In some examples, the first MHC class II is HLA-DRA*1010. Alternatively or in addition, the second MHC class II is HLA-DRB1*1501.

In another aspect, the present disclosure features a nucleic acid or a nucleic acid set, which collectively encodes any of the MHC-based chimeric receptors described herein. In some instances, the nucleic acid or nucleic acid set can be located in one or more vectors, for example, viral vector(s).

Further, the present disclosure provides a genetically modified immune cell (e.g., a T cell), which expresses any of the MHC-based chimeric receptors described herein. In some instances, the activity of the endogenous T cell receptor (TCR) can be suppressed, which may be achieved by mutating or deleting the alpha chain of the endogenous TCR, the beta chain of the endogenous TCR, or both to disrupt surface expression of the endogenous TCR. Alternatively or in addition, the expression of the endogenous CD52 can be disrupted.

In some embodiments, the genetically modified immune cell as described herein may further express a suicide gene (e.g., RQR8), a marker gene (e.g., GFP), or both. When necessary, the immune cell can be further modified for lymph node or tertiary lymphoid organ delivery and retention. For example, the immune cell can be further engineered to overexpress VAP-1, L-selectin. CCR7, CXCR5, or a combination thereof. In some instances, the expression of endogenous sphingosine-1-phosphate receptor 1 can be disrupted in the genetically modified immune cell.

In some embodiments, the immune cell can be engineered to travel to the site of inflammation, for instance using a chemokine receptor such as CCR6 (e.g., to the site of Th17 cells), CXCR3 or CXCR4 (e.g., to the site of plasma cells), or through a membrane linked, antigen targeted antibody. Alternatively or in addition, the genetically modified immune cell may further comprise a genetic modification that results in blockade of PD-1 signaling. If needed and the disorder is especially severe the MHC-CAR cells can also be designed to remove or inactive bystander B cells (with a CD19 or CD20-CAR) or plasma cells (with a CS 1-CAR and/or CS1 knockout).

In some embodiments, the genetically modified immune cell as described herein may be a regulatory T cell, which can be CD25+, and optionally CD4+. In some instances, the regulatory T cell can be derived from CD25++CD45R+ T cells isolated from peripheral blood mononuclear cells or from cord blood. In other instance, the regulatory T cell may comprise a transgene coding for CD25. Any of the Treg cells disclosed herein may further express a chimeric receptor specific to CD19, a chimeric receptor specific to CS-1, or both. Alternatively or in addition, the regulatory T cell may further express CCR6, CXCR5, PD-1, or a combination thereof. In some examples, the regulatory T cell may display an antibody specific to MOG.

In yet another aspect, the present disclosure provides a method for suppressing autoreactive immune cells in a subject having an autoimmune disease (e.g., multiple sclerosis). The method may comprise administering to the subject an effective amount of genetically modified immune cells as described herein, which can be T cells.

In some embodiments, the genetically modified immune cells are autologous. In other embodiments, the genetically modified immune cells are allogeneic. Any of the genetically modified immune cells may be administered to a lymph node of the subject. In some instances, the subject is undergoing a therapy comprising an antibody specific to CD52.

In some embodiments, the subject is a human patient having or at risk for multiple sclerosis and the genetically modified T cells are Treg cells or cytotoxic lymphocytes (CTLS) as described herein.

In some examples, the human patient is an early-stage MS patient and the Treg cells express the MHC-CAR and have one or more of the following genetic modifications: (i) PD-L1 and/or PD-1 knockout; (ii) surface expression of CCR6 and/or CXCR5; (iii) surface display of an antibody or an antigen-binding fragment thereof that is specific to MOG; and (iv) surface expression of a chimeric receptor targeting CD19. In some examples the patient may first, simultaneously, or alternatively be treated with cytotoxic CTLs with modifications of the same type.

In some examples, the human patient has relapsing-remitting MS or early-stage progressive MS and the Treg cells express the MHC-CAR and have one or more of the following modifications: (i) surface display of an antibody or antigen binding fragment that is specific to MOG; and (ii) surface expression of CCR6. In some examples the patient may first, simultaneously, or alternatively be treated with cytotoxic CTLs with modifications of the same type.

In some examples, the human patient has relapsing-remitting MS or early-stage progressive MS and the Treg cells express the MHC-CAR and have one or more of the following modifications: (i) surface expression of a chimeric receptor targeting CD19; and (ii) surface expression of CXCR5. In some examples the patient may first, simultaneously, or alternatively be treated with CTLs with the same modifications.

In some examples, the human patient has MS in chronic progressive form and the Treg cells express the MHC-CAR and have one or more of the following modifications: (i) surface expression of a chimeric receptor targeting CS-1; and (ii) surface expression of an agent CXCR4, CCR6, and/or CXCR5. In some examples the patient may first, simultaneously, or alternatively be treated with CTLs with the same modifications.

In some embodiments, the subject is a human patient having or at risk for systemic lupus erythematosus, rheumatoid arthritis, juvenile idiopathic arthritis (also known as juvenile idiopathic arthritis), Sjögren's syndrome, systemic sclerosis, ankylosing spondylitis, Type 1 diabetes, autoimmune thyroid diseases (Grave's and Hashimoto's), multiple sclerosis myasthenia gravis, inflammatory bowel disease (Crohn's or ulcerative colitis), Psoriasis, or a diseases mentioned in Table 1 and the genetically modified T cells are Treg cells and/or CTLs as described herein.

In some examples, the human patient is an early-stage patient of any of the autoimmune disorders described herein (e.g., those listed in Table 1) and the Treg cells express the MHC-CAR and have one or more of the following genetic modifications: (i) PD-L1 and/or PD-1 knockout; (ii) surface expression of CCR6 and/or CXCR5; (iii) surface display of an antibody or an antigen-binding fragment thereof that is specific to a relevant protein described as an autoantigen in Table 1 for that autoimmune disorder; and (iv) surface expression of a chimeric receptor targeting CD19. In some examples the patient may first, simultaneously, or alternatively be treated with CTLs with the same modifications.

In some examples, the human patient has moderately severe disease state of any of the autoimmune disorders as described herein (e.g., those listed in Table 1) and the Treg cells express the MHC-CAR and have one or more of the following modifications: (i) surface display of an antibody or antigen binding fragment that is specific to a relevant protein described as an autoantigen in Table 1 for that autoimmune disorder; and (ii) surface expression of CCR6. In some examples the patient may first, simultaneously, or alternatively be treated with CTLs with the same modifications.

In some examples, the human patient has moderately severe disease state of any of the autoimmune disorders as described herein (e.g., those listed in Table 1) and the Treg cells express the MHC-CAR and have one or more of the following modifications: (i) surface expression of a chimeric receptor targeting CD19; and (ii) surface expression of CXCR5. In some examples the patient may first, simultaneously, or alternatively be treated with CTLs with the same modifications.

In some examples, the human patient has severe disease state of any of the autoimmune disorders described herein (e.g., those listed in Table 1) and the Treg cells express the MHC-CAR and have one or more of the following modifications: (i) surface expression of a chimeric receptor targeting CS-1; and (ii) surface expression of an agent targeting CXCR4, CCR6, and/or CXCR5. In some examples the patient may first, simultaneously, or alternatively be treated with CTLs with the same modifications.

Also within the scope of the present disclosure are pharmaceutical compositions for use in treating an autoimmune disease, the composition comprising genetically modified immune cells expression MHC-CAR as described herein such as Treg cells and a pharmaceutically acceptable carrier, and uses of such genetically modified immune cells for manufacturing a medicament for use in treating the target autoimmune disease.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1 is a schematic illustration of an exemplary design of a lentiviral expression vector for expression of an antigen-specific T cell receptor (TCR). mRNA and multicistronic mRNA designs are similar.

FIG. 8A depicts exemplary designs of MHC Class I moieties linked to antigenic peptides. "N" refers to the N-terminus of a polypeptide. Circled black dots refer to the antigenic peptides. FIG. 8B depicts an exemplary expression cassette for a MHC Class I CAR construct.

DETAILED DESCRIPTION OF THE INVENTION

Figure 1:
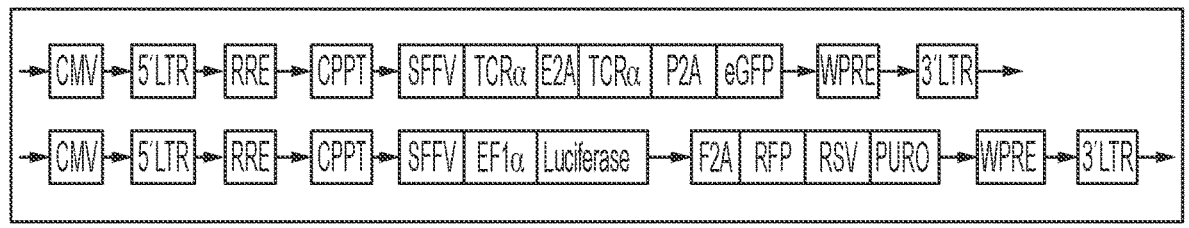

Autoreactive T cells, (e.g., those for myelin components involved in multiple sclerosis) exist in normal individuals. The majority of determinant of disease induction is in the class of immune response that occurs when these autoreactive T cells are triggered in autoimmune patients (e.g., in MS patients). Generation of pathologic autoreactive T cells is favored both by specific major histocompatibility complex (MHC) and non-MHC genes, which determine the protein sequences an individual reacts against and the class of the immune response.

Once an immune attack begins on an initial autoantigen (for example, a myelin antigen in MS), there is a spreading of reactivity to other autoantigens; that is, if a T cell attacks one autoantigen (for example, a brain protein in MS), other structures are damaged and they can sensitize additional T cells to attack other targets in a process called "epitope-spreading", a process that is shared by all autoimmune disorders and common to disease response in general.

B cells are ordinary components of the immune reaction in the early disease lesion caused by initial autoreactive attacks, for example, active MS lesion as well. B cell accumulation occurs as packed aggregates or ectopic B cell follicles. Serafini et al., *Brain Pathol.* 14: 164-144 (2004); Wekerle, Autoimmunity, 50:1, 57-60 (2017); and Pröbstel, et al., International journal of molecular sciences, 16(7), pp. 16576-16592 (2015). In MS, B cells were reported to be found in the brain and spinal cord of RR-, SP-, and β-stage MS patients. Therapeutic treatments that target B cells either directly or indirectly have proven beneficial in treatment of autoimmune diseases such as MS. Wekerle, 2017.

Both CD4+ and CD8+ T cells are present in MS lesions and are believed to play a central role in disease development. Increased frequencies of myelin-reactive (MBP, PLP, and MOG) CD4 and CD8 cells are found in MS patients compared to healthy controls. Cao, et al., Sci. Transl. Med. 7 (287), 287ra74 (2014); Martin, et al., J. Exp. Med. 173 (Jan. 1, 1991), Ota, et al., Nature 346, 183 (Jul. 12, 1990); Pette, et al., Neurology 40, 1770 (1990): and Raddassi, et al., J. Immunol. 187, 1039 (2011).

Th1 cells producing IFN-gamma and Th17 cells are uniquely pathogenic. Factors that favor the development of Th1 cells are elevated in MS patients and are also triggered by viral infections: gamma interferon; IL-12—in almost all treatments that affect the immune system and help MS, almost all decrease Th1 response and increase Th2 and TH3 response. Th17 cells are present at sites of tissue inflammation and are implicated in autoimmune/chronic inflammatory conditions. Th17 producing CD4 and CD8 cells are increased in the lesions, blood, and CSF of patients. [Tzartos 2008; Matusevicius 1999: Bruchlacher-Waldert 2009]. The CCR6 and CD161 on Th17 cells are hypothesized to be homing molecules to inflamed tissues [Cosmi, 2008].

Th17 cells are also implicated in a number of other autoimmune diseases such as systemic lupus erythematosus, rheumatoid arthritis, juvenile idiopathic arthritis (also known as juvenile idiopathic arthritis), Sjögren's syndrome, systemic sclerosis, ankylosing spondylitis, Type 1 diabetes, autoimmune thyroid diseases (Grave's and Hashimoto's), myasthenia gravis, inflammatory bowel disease (Crohn's or ulcerative colitis), and psoriasis. Tabarkiewicz et al., Archivum immunologiae et therapiae experimentalis, 63(6): 435-449 (2015).

The ultimate goal of any treatment for autoimmune disease is a complete suppression of pathology. In the case of multiple sclerosis and other autoimmune disorders, pathologic lymphocytes (both B and T cells, and if necessary plasma cells for very severe cases) are expected to be eliminated or controlled to halt the disease course, and interventions at different stages of disease progression require different cellular targets and therefore therapeutic cells.

Disclosed herein are major histocompatibility complex (MHC)-based chimeric receptors (MHC-CAR) for targeting autoreactive immune cells such as autoreactive T cells. A MHC-CAR as described herein comprises one or more MHC polypeptides or an extracellular domain thereof and one or more cell signaling domains, for example, a cytoplasmic signaling domain (e.g., that from CD3ζ), at least one co-stimulatory domain (e.g., that from 4-1BB or CD28), or both. The MHC-CAR may further comprise an antigenic peptide from an autoantigen or a foreign antigen that mimics an autoantigen in eliciting autoimmune responses. Also herein are nucleic acids encoding the MHC-CAR, vectors carrying such, and genetically engineered immune cells such as T cell and natural killer (NK) cells expressing the MHC-CAR. Such genetically engineered immune cells can be used to target autoreactive immune cells, thereby benefiting treatment of autoimmune diseases involving the autoreactive immune cells.

Also disclosed herein are genetically modified regulatory T (Treg) cells expressing an MHC-based chimeric receptor as disclosed herein. Such Treg cells may be further modified with chimeric receptor(s) targeting T cell and/or B cell surface markers, as well as additional genetic engineering for, e.g., targeting specific tissue sites (e.g., lymph nodes or inflammation sites) or modulating immune responses (e.g., checkpoint modulation). The genetically modified Treg cells may be used to inhibit pathogenicity at an early stage of a target disease, to control disease progression at a middle stage of the disease (e.g., relapsing or remitting MS), or to suppress pathology via, e.g., inducing cytotoxicity of pathologic CD8+ T cells at a late stage of the disease (e.g., chronic progressive MS).

I. Major histocompatibility complex (MHC)-based chimeric receptors (MHC-CARs)

The MHC based chimeric receptor (MHC-CAR) described herein comprises an MHC moiety, which is conjugated to an antigenic peptide (e.g., a misfolded one), and at least one cell signaling moiety, which can be a cytoplasmic signaling domain (e.g., that of CD3), one or more co-stimulatory domains (e.g., that of 4-1BB or CD28), or a combination thereof. In some instances, the antigenic peptide can be part of a fusion polypeptide of the MHC-CAR. In other instances, the antigenic peptide does not form a fusion polypeptide with the MHC-CAR but forms a complex with the MHC-CAR As used herein, the term "conjugated" means that at least two components are physically associated, either via covalent bonds or via non-covalent interactions.

In some examples, the MHC-CAR can be a single fusion polypeptide containing the MHC moiety, the antigenic peptide, and the at least one cell signaling moiety. Such a single fusion polypeptide may form complexes with endogenous cell membrane proteins (e.g., β-microglobulin) when expressed in a suitable immune cells.

In other examples, the MHC-CAR described herein may be a multi-chain protein complex, for example, a heterodimer, comprising one polypeptide that comprises the antigenic peptide. In some instances, the antigenic peptide or polypeptide may be expressed as a separate polypeptide, which may form a complex (e.g., a trimer) with the MHC components. The antigenic polypeptide can be a misfolded antigenic protein that binds to the MHC. Optionally, the MHC-CAR may further comprise a hinge domain, which may be adjacent to the antigenic peptide and/or the MHC moiety, a signal peptide at the N-terminus, and/or one or more tagging sites, for example, a histidine protein tag and/or an RQR domain that additionally acts as a kill-switch site.

(i) Components oJMHC-CARs (a) MHC Moiety

The MHC-CAR constructs disclosed herein comprise an MHC moiety, which may comprise one or more MHC polypeptides or an extracellular domain thereof. The MHC moiety may be derived from a suitable source, for example, human or a non-human mammal (e.g., monkey, mouse, rat, rabbit, pig, etc.) In some instances, the MHC moiety is from a human MHC molecule (also known as HLA). In some instances the domains that interact with molecules from other cells (TCR or BCR) are from a human MHC molecule. There are primarily two classes of MHC molecules, MHC class I molecules and MHC class II molecules, both of which can be used for constructing the MHC-CARs described herein. Sequences of MHC class I and class II molecules of various species (e.g., human, non-human primates, canids, fish, ovids, bovines, equids, suids, murids, and gallus) are available from public gene datasets, for example, the IPD-MHC database and the IMGT/IHLA database provided by EMBL-EBI and the dbMHC database provided by National Center for Biotechnology Information (NCBI).

MHC class I molecules are heterodimers containing an alpha chain and β-microglobulin. The extracellular domain of an alpha chain includes three subdomains, α1, α2, and α3. In some embodiments, the MHC moiety may include the alpha chain of a MHC class I molecule, or an extracellular domain thereof, for example, the α1 domain, the α2 domain, the α3 domain, or a combination thereof. The MHC class I molecule may be a human HLA-A molecule, a human HLA-B molecule, or a human HLA-C molecule. In some instances, the alpha chain of the MHC class I molecule may be fused with β-microglobulin to produce a single chain fusion protein. In some examples, the MHC Class I moiety is from HLA A3, which can be co-used with a PLP peptide. Honma et al., J. Neuroimmunol, 73:7-14 (1997). In other examples, the MHC Class I is from HLA A2, which can be used with the same PLP peptide and display of a viral peptide such as TAX. TAX is from the protein tax or p40 (Genbank accession no. BAB20130.1) that is a molecular mimic of a human neuronal protein and from the HTLV-1 virus, which is implicated in diseases such as rheumatoid arthritis, system lupus erythematosus, and Sjogren's syndrome. Garboczi, et al. The Journal of Immunology. 157 (12):5403-5410, 1996. Quaresma, et al., 2015. *Viruses,* 8(1):5 2015. The class I protein and peptide may additionally contain modifications to enable more robust peptide loading such replacement of the invariant tyrosine at position 84 of the heavy chain with alanine; or alternatively the position 84 tyrosine can be replaced with cysteine as can the second position of the peptide-02m linker to create a disulfide trap. Hansen et al. *Trends in immunology,* 3/(10):363 (2010).

Like MHC class 1 molecules, MHC class II molecules are also heterodimers consisting of two homogenous peptides, an α-chain and a β-chain. The extracellular domain of each of the α-chain and the β-chain contains two subdomains α1/α2, and β1/β2. When a MHC class II molecule is used for constructing a MHC-CAR, the MHC moiety may include two subunits, one including the α-chain or a portion thereof, for example, an extracellular domain thereof (e.g., α1, α2, or both), the other including the b-chain or a portion thereof, for example, an extracellular domain thereof (e.g., β1, β2, or both). In cases where only the region that interacts with other cell types is used (i.e., α1 and β1), specific amino acid modifications may be required to enhance the folding of the mini-MHC, see mini-sequence with shaded regions and Bimbaum et al. The MHC class II molecule may be a human HLA DP molecule, a human HLA DM molecule, a human HLA DOA molecule, a human HLA DOB molecule, a human HLA DQ molecule, or a human HLA DR molecule. In some examples, the MHC class II molecule is a human HLA DR molecule, for example HLA DR*1501.

(b) Antigenic Peptides

The antigenic peptides of the MHC-CAR described herein are an antigenic peptide that is recognizable by pathogenic immune cells (e.g., autoreactive T cells or B cells) involved in an autoimmune disease. When presented by a suitable MHC molecule, such an antigenic peptide would interact with the antigen-specific T cell receptors of pathogenic T cells, leading to downstream immune responses.

In some instances, a specific antigenic peptide can be designed for a specific autoimmune disease patient such as an MS patient, using methods known in the art. Programs like NetMHC enable personalized design of antigenic peptides that are specific to the patients MHC, and have been used to develop personalized cancer vaccines. Hacohen et al., Cancer immunology research, 1(1):11-15 (2013). Also within the scope of the present disclosure are personalized CAR T and Treg therapies for autoimmune disorders. For disorders with very strong MHC associations (such as MS), a personalized therapy can be utilized to treat a large patient class at different stages of the disease. Recent studies have also demonstrated that Class II MHCs and specifically the HLAs implicated in autoimmune disorders can display entire antigenic proteins rather than just processed peptides. Jiang et al., International immunology, 25(4):235-246, (2013). These MHC-protein complexes appear to induce autoantibody production in autoimmune disorders, including antibodies that do not bind to properly folded proteins as well as autoantibodies that are specific to those with specific autoimmune disorders. The inventors impute that display of antigenic proteins in MHC-CAR can provide a specific route to remove or deactivate autoimmune specific B cells, such as those in MS which produce oligoclonal bands whose specificity to proteins has not been unraveled, despite many rigorous attempts. Owens et al., Annals of neurology, 65(60):639-649, 2009; Chastre et al., New England Journal of Medicine, 374(15):1495-1496, 2016; Housley et al., Clinical Immunology, 161(1):51-58, 2015; Larman et al., 2013. Journal of autoimmunity, 43:1-9, 2013. In the event that the antigenic protein does not bind the MHC, then that specific MHC-CAR will not be expressed, but as a Treg or CTL it can still play a bystander role in modifying the immune response depending upon its other characteristics and as part of a patient specific population of MHC-CAR T and Treg cells with different specificities.

The antigenic peptides used herein may be fragments of autoantigens involved in autoimmune diseases, for example, myelin basic protein (MBP), myelin oligodendrocyte glycoprotein (MOG), and proteolipid protein (PLP) involved in multiple sclerosis, insulin and glutamate decarboxylase (GAD) involved in type I diabetes, tryptase involved in rheumatoid arthritis (RA), and the proteins included in Table 1 below. Alternatively, the antigenic peptide can be a fragment of a pathogen protein such as a viral or a bacterial protein that is highly homologous to a self-antigen involved in an autoimmune disease. Such an antigenic peptide also can target pathogenic T cells. If needed, the antigenic peptide can be a (typically misfolded) antigenic protein or protein fragment that can be expressed separately and binds directly to the MHC moiety of a MHC-CAR described herein. In their natural state (attached to an MHC rather than an MHC moiety of a MHC-CAR), such antigenic protein/MHC complexes stimulate pathogenic B cells to produce autoantibodies. For proteins such as IgGH or rheumatoid factor in rheumatoid arthritis (in et al., *Proceedings of the National Academy of Sciences,* 111(10):3787-3792, 2014), 02-glycoprotein I in antiphospholipid syndrome (Tanimura et al., *Blood,* 125(18):2835-2844, 2015) and recurrent miscarriage (Tanimura et al., *Placenta,* 46:108, 2016), GM-CSF in autoimmune pulmonary alveolar proteinosis (Hamano et al., AVEOLAR MACROPHAGE BIOLOGY B32: A3147-A3147, 2016), tyrosinase in vitiligo (Arase et al. *Journal of Dermatological Science,* 84(1):e87, 2016), and myeloperoxidase in microscopic polyangiitis (Hiwa et al., *Arthritis & Rheumatology.* 69(10):2069-2080, 2017), HLA mediated surface display and in some cases autoantibody binding of misfolded variant/HLA complex can occur.

The antigenic peptides for use in the MHC-CAR described herein may contain up to 20 amino acid residues, the extracellular domain of the antigenic protein, or the full length antigenic protein. When co-used with a MHC class I moiety, the antigenic peptide may be 8-10 amino acid-long. Such antigenic peptides would fit well into the peptide binding site of a MHC class I molecule. Antigenic peptides to be co-used with MHC class II moieties can be longer, for example, containing 15-24 amino acid residues or up to the full length of the antigenic protein, since the antigen-binding groove of MHC class II molecules is open at both ends, while the corresponding antigen-binding groove on class I molecules is usually closed at each end. The open antigen-binding groove of MHC class II molecules implicated in autoimmune disorders can also frequently display intact (e.g., yet misfolded) antigenic proteins or splice variants. Jiang et al., *International immunology,* 25(4):235-246, 2013.

In some examples, a fragment of human MBP is used for constructing the MHC-CARs described herein. An exemplary amino acid sequence of a human MBP is provided below:

(SEQ ID NO: 1)
MASQKRPSQRHGSKYLATASTMDHARHGFLPRHRDTGILDSIGRFFGGDR

GAPKRGSGKVPWLKPGRSPLPSHARSQPGLCNMYKDSHHPARTAHYGSLP

QKSHGRTQDENPVVHFFKNIVTPRTPPPSQGKGRGLSLSRFSWGAEGQRP

GFGYGGRASDYKSAHKGFKGVDAQGTLSKIFKLGGRDSRSGSPMARRHHH

HHH

Exemplary MBP antigenic peptides include, but are not limited to:

(SEQ ID NO: 2)
GSKYLATASTMDHARHGFLPRHRDTGILDSIGRFFGGDRG, (SEQ ID NO: 3)
KYLATASTMDHARHGFLPRH, (SEQ ID NO: 4)
ATASTMDHARHGFLPRHRDTGIL, (SEQ ID NO: 5)
RDTGILDSIGRFFGGDRGAP, (SEQ ID NO: 6)
IGRFFGGDRGAPKRGSGKDSHHPARTAHY, (SEQ ID NO: 7)
APKRGSGKDSHHAARTAHY, (SEQ ID NO: 8)
GSGKDSHHPARTAHYGSLPQ, (SEQ ID NO: 9)
HHPARTAHYGSLPQKSHGR, (SEQ ID NO: 10)
HAARTAHYGSLPQKSQGHR, (SEQ ID NO: 11)
SLPQSHGRTQDENPVVHF, (SEQ ID NO: 12)
PQDENPVVHFFKNIVTPRTP, (SEQ ID NO: 13)
TQDENPVVHFFKNIVTPRTP, (SEQ ID NO: 14)
QDENPVVHFFKNIVTPRTP, (SEQ ID NO: 15)
DENPVVHFFKNIVTPRTPP, (SEQ ID NO: 16)
ENPVVHFFKNIVTPR, (SEQ ID NO: 17)
ENPVVHFFKNIVTPRTP, (SEQ ID NO: 18)
ENPVVHFFKNIVTP, (SEQ ID NO: 19)
NPVVHFFKNIVTPRTPPPSQ, (SEQ ID NO: 20)
VVHFFKNIVTPRT, (SEQ ID NO: 21)
VVHFFKNIVTPRTPPPSQGK, (SEQ ID NO: 22)
KNIVTPRTPPPSQGKGRGL, (SEQ ID NO: 23)
PSQGKGRGLSLSRFSWGAE, (SEQ ID NO: 24)
GKGRGLSLSRFSWGAEGQRP, (SEQ ID NO: 25)
LSRFSWGAEGQRPGFGYGG, (SEQ ID NO: 26)
QRPGFGYGGRASDYKSAHK, (SEQ ID NO: 27)
ASDYKSAHKGFKGVDAQGT, (SEQ ID NO: 28)
FKGVDAQGTLSKIFKLGGR, (SEQ ID NO: 29)
VDAQGTLSKIFKLGGRDSRS,
and (SEQ ID NO: 30)
SKIFKLGGRDSRSGSPMARR.

An example nucleic acid sequence encoding the MBP antigenic peptide of SEQ ID NO: 15 is provided below:

(SEQ ID NO: 411)
GATGAGAATCCCGTGGTTCATTTTTTTAAGAACATCGTCACACCGCGCAC

CCCACCTG

Specific examples include MBP13-32, MBP89-101, MBP83-99, MBP111-129, or MBP146-170.

Exemplary amino acid sequences for human myelin oligodendrocyte glycoprotein, proteolipid protein, and myelin associated glycoprotein are provided below:
>CAA52617.1 myelin oligodendrocyte glycoprotein [*Homo sapiens*]

(SEQ ID NO: 31)
MASLSRPSLPSCLCSFLLLLLLQVSSSYAGQFRVIGPRHPIRALVGDEVE

LPCRISPGKNATGMEVGWYPRRFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLVFLCLQYRLRGKLRAEIENLHRTFDPH

FLRVPCWKITLFVIVPVLGPLVALIICYNWLHRRLAGQFLEELRNPF

Exemplary MOG antigenic peptides include MOG1-20 or MOG35-55.
>AAA60117.1 proteolipid protein [*Homo sapiens*]

(SEQ ID NO: 32)
MGLLECCARCLVGAPFASLVATGLCFFGVALFCGCGHEALTGTEKLIETY

FSKNYQDYEYLINVIHAFQYVIYGTASFFFLYGALLLAEGFYTTGAVRQI

FGDYKTTICGKGLSATVTGGQKGRGSRGQHQAHSLERVCTCLGKWLGHPD

KFVGITYALTVVWLLVFACSAVPVYIYFNTWTTCQSIAFPSKTSASIGSL

CADARMYGVLPWNAFPGKVCGSNLLSICKTAEFQMTFHLFIAAFVGAAAT

LVSLLTFMIAATYNFAVLKLMGRGTKF

An exemplary antigenic fragment of PLP is underlined and in boldface. Other examples include PLP139-151(4) or PLP178-191.

>AAH93045.1 Myelin associated glycoprotein Homo sapiens|

(SEQ ID NO: 33)
MIFLTALPLFWIMISASRGGHWGAWMPSSISAFEGTCVSIPCRFDFPDEL

RPAVVHGVWYFNSPYPKNYPPVVFKSRTQVVHESFQGRSRLLGDLGLRNC

TLLLSNVSPELGGKYYFRGDLGGYNQYTFSEHSVLDIVNTPNIVVPPEVV

AGTEVEVSCMVPDNCPELRPELSWLGHEGLGEPAVLGRLREDEGTWVQVS

LLHFVPTREANGHRLGCQASFPNTTLQFEGYASMDVKYPPVIVEMNSSVE

-continued

AIEGSHVSLLCGADSNPPPLLTWMRDGTVLREAVAESLLLELEEVTPAED

GVYACLAENAYGQDNRTVGLSVMYAPWKPTVNGTMVAVEGETVSILCSTQ

SNPDPILTIFKEKQILSTVIYESELQLELPAVSPEDDGEYWCVAENQYGQ

RATAFNLSVEFAPVLLLESHCAAARDTVQCLCVVKSNPEPSVAFELPSRN

VTVNESEREFVYSERSGLVLTSILTLRGQAQAPPRVICTARNLYGAKSLE

LPFQGAHRLMWAKIGPVGAVVAFAILIAIVCYITQTRRKKNVTESPSFSA

GDNPPVLFSSDFRISGAPEKYESKEVSTLESH

Table 1 below provides additional exemplary autoantigens associated with other autoimmune diseases.

TABLE 1

Autoantigens of Various Autoimmune Disorders

| Autoantigen | GenBank Accession No. | Associated Autoimmune Disease |
| --- | --- | --- |
| Dopachrome tautomerase | AAH28311.1 | Alopecia areata |
| Melanoma antigen gp100 | AAC60634.1 | Alopecia areata |
| Melanocyte protein Pmel | NP_001186983.1 | Alopecia areata |
| Melanocyte-stimulating hormone receptor | NP_002377.4 | Alopecia areata |
| Trichohyalin | AAA65582.1 | Alopecia areata |
| Tyrosine 3-monooxygenase | NP_954986.2 | Alopecia areata |
| Amyloid beta A4 protein | NP_000475.1 | Alzheimer's |
| Vasoactive intestinal polypeptide receptor 1 | NP_004615.2 | Ankylosing spondylitis |
| Latent membrane protein 2 | CAA57360.1 | Ankylosing spondylitis |
| Nitrogenase iron protein | ART03999.1 | Ankylosing spondylitis |
| Aggrecan core protein | NP_001126.3 | Ankylosing spondylitis |
| Beta-2-glycoprotein 1 | NP_000033.2 | Antiphospholipid syndrome |
| M protein precursor | AAA26918.1 | Antiphospholipid syndrome |
| Large tegument protein | ACL51127.1 | Antiphospholipid syndrome |
| Steroid 21-hydroxylase | NP_000491.4 | Autoimmune adrenalitis |
| Steroid 17-alpha-hydroxylase/17,20 lyase | NP_000093.1 | Autoimmune adrenalitis |
| Potassium-transporting ATPase alpha chain | AAB50172.1 | Autoimmune gastritis |
| Potassium-transporting ATPase beta chain | AAA35987.1 | Autoimmune gastritis |
| Cytochrome P450 2D6 | ABB77909.1 | Autoimmune hepatitis |
| Genome polyprotein | S35630 | Autoimmune hepatitis |
| O-phosphoseryl-tRNA(Sec) selenium transferase | NP_058651.3 | Autoimmune hepatitis |
| Asialoglycoprotein receptor | AAB58308.1 | Autoimmune hepatitis |
| Glutathione S-transferase | CAA48637.1 | Autoimmune hepatitis |
| Cytokeratin 8 | AAB18966.1 | Autoimmune hepatitis |
| M protein | AAA26918.1 | Autoimmune myocarditis |
| Myosin-7 | NP_000248.2 | Autoimmune myocarditis |
| Cardiac myosin light chain 1 | AAF91089.1 | Autoimmune myocarditis |
| Cardiac myosin light chain 2 | AAA91832.1 | Autoimmune myocarditis |
| Cardiac actin | NP_005150.1 | Autoimmune myocarditis |
| Troponin I | AC14461.1 | Autoimmune myocarditis |
| Thyroid peroxidase | AAA61217.2 | Autoimmune thyroiditis |
| Thyrotropin receptor | AAB23390.2 | Autoimmune thyroiditis |
| Thyroglobulin | NP_003226.4 | Autoimmune thyroiditis |
| S-arrestin | NP_000532.2 | Autoimmune uveitis |
| LAMP2 | AAB67314.1 | Autoimmune vasculitis |
| Myeloperoxidase | AAA59863.1 | Autoimmune vasculitis |
| Myeloblastin | NP_002768.3 | Autoimmune vasculitis |
| Alpha-gliadin | AFX69628.1 | Coeliac disease |
| Protein-glutamine gamma-glutamyltransferase 2 | NP_004604.2 | Coeliac disease |
| 75k gamma secalin | ADP95479.1 | Coeliac disease |
| Gamma 1 hordein | AFM77738.1 | Coeliac disease |
| Avenin-3-like | ADA62372.1 | Coeliac disease |
| Glycosyltransferase | ANR93567.1 | Crohn's disease |
| 60 kDa heat shock protein, mitochondrial | NP_002147.2 | Crohn's disease |
| Transmembrane protein UO-44D | NP_002147.2 | Crohn's disease |
| GM-CSF | AAA52578.1 | Crohn's disease |
| Sucrase-isomaltase, intestinal | NP_001032.2 | Crohn's disease |
| Glutathione peroxidase 2 | NP_002074.2 | Crohn's disease |
| 60 kDa chaperonin 2 | ARX70571.1 | Crohn's disease |

TABLE 1-continued

Autoantigens of Various Autoimmune Disorders

| Autoantigen | GenBank Accession No. | Associated Autoimmune Disease |
| --- | --- | --- |
| Pancreatic secretory glycoprotein 2 | NP_001493.2 | Crohn's disease |
| 60 kDa chaperonin 2 | OMH58317.1 | Crohn's disease |
| Cytoskeleton-associated protein 5 | EAW67976.1 | Crohn's disease |
| AhpC | ETZ42359.1 | Crohn's disease |
| Leukotriene B4 receptor 2 | NP_062813.2 | Crohn's disease |
| Chromodomain-helicase-DNA-binding protein 4 | NP_001264.2 | Dermatomyositis |
| Chromodomain-helicase-DNA-binding protein 3 | NP_001005273.1 | Dermatomyositis |
| Beta-1 adrenergic receptor | NP_000675.1 | Dialated cardiomyopathy |
| Muscarinic acetylcholine receptor M2 | NP_001006633.1 | Dialated cardiomyopathy |
| Collagen alpha-3(IV) chain | CAA56335.1 | Goodpasture's syndrome |
| Thyrotropin receptor | AAB23390.2 | Grave's disease |
| Thyroid peroxidase | AAA61217.2 | Grave's disease |
| Thyroglobulin | CAA29104.1 | Grave's disease |
| Glutamate decarboxylase 2 | NP_000809.1 | Grave's disease |
| TSHR protein | AAI27629.1 | Grave's disease |
| Thyroid peroxidase | AAA61217.2 | Hashimoto's thyroiditis |
| Thyroglobin | CAA29104.1 | Hashimoto's thyroiditis |
| Thyroid stimulating hormone receptor | AAI41971.1 | Hashimoto's thyroiditis |
| Insulin | AAA59172.1 | Hypogycemia |
| Insulin receptor | AAA59452.1 | Hypogycemia |
| Integrin beta-3 | NP_000203.2 | Immune thrombocytopenic purpura |
| Integrin alpha-IIb | NP_000410.2 | Immune thrombocytopenic purpura |
| Platelet glycoprotein Ib alpha chain | NP_000164.5 | Immune thrombocytopenic purpura |
| Platelet glycoprotein IIIa | AAA52600.1 | Immune thrombocytopenic purpura |
| Thrombopoietin | AAB03393.1 | Immune thrombocytopenic purpura |
| Insulin receptor | AAA59452.1 | Insulin resistant diabetes |
| Phospholipase A2 | NP_000919.1 | Membranous nephritis |
| Myelin basic protein | AAC41944.1 | Multiple sclerosis |
| Myelin proteolipid protein | AAA59565.1 | Multiple sclerosis |
| Myelin-oligodendrocyte glycoprotein | CAA52617.1 | Multiple sclerosis |
| Epstein-Barr nuclear antigen 1 | Q1HVF7.1 | Multiple sclerosis |
| DNA polymerase catalytic subunit | AMD82168.1 | Multiple sclerosis |
| 2',3'-cyclic-nucleotide 3'-phosphodiesterase | AAB24298.2 | Multiple sclerosis |
| Oligodendrocyte-myelin glycoprotein | AAA59970.1 | Multiple sclerosis |
| Aquaporin-4 | AAH22286.1 | Multiple sclerosis |
| Actin, cytoplasmic 1 | NP_001092.1 | Multiple sclerosis |
| Transposase, mutator family protein | EUA40098.1 | Multiple sclerosis |
| E4 gene product | YP_002640224.1 | Multiple sclerosis |
| Protein BOLF1 | AIE89051.1 | Multiple sclerosis |
| Myelin-associated glycoprotein | AAH93045.1 | Multiple sclerosis |
| Transaldolase | NP_006746.1 | Multiple sclerosis |
| Possible transposase | CCP46656.1 | Multiple sclerosis |
| Claudin-11 | NP_005593.2 | Multiple sclerosis |
| Interferon beta | AAC41702.1 | Multiple sclerosis |
| Alpha-crystallin B chain | ACA05949.1 | Multiple sclerosis |
| Apolipoprotein E | AAB59518.1 | Multiple sclerosis |
| Epstein-Barr nuclear antigen 6 | AAA45895.1 | Multiple sclerosis |
| Trans-activator protein BZLF1 | BAP94413.1 | Multiple sclerosis |
| Hemagglutinin | ALB07770.1 | Multiple sclerosis |
| Protein S100-B | NP_006263.1 | Multiple sclerosis |
| DNA polymerase catalytic subunit | SCL76875.1 | Multiple sclerosis |
| Tripartite terminase subunit UL15 | SCL76864.1 | Multiple sclerosis |
| Glyceraldehyde-3-phosphate dehydrogenase | CAA25833.1 | Multiple sclerosis |
| Alpha-enolase | CAA34360.1 | Multiple sclerosis |
| Neurofilament light polypeptide | NP_006149.2 | Multiple sclerosis |
| Connexin 43 | AAA52131.1 | Multiple sclerosis |
| Neurofilament medium polypeptide | NP_005373.2 | Multiple sclerosis |
| POTE ankyrin domain family member I | NP_001264335.1 | Multiple sclerosis |
| 60 kDa heat shock protein, mitochondrial | NP_002147.2 | Multiple sclerosis |
| Epstein-Barr nuclear antigen 3 | BAP94411.1 | Multiple sclerosis |

TABLE 1-continued

Autoantigens of Various Autoimmune Disorders

| Autoantigen | GenBank Accession No. | Associated Autoimmune Disease |
|---|---|---|
| Putative HTLV-1-related endogenous sequence | CAA34646.1 | Multiple sclerosis |
| Glial fibrillary acidic protein | AAB22581.1 | Multiple sclerosis |
| Phosphomannomutase/phosphoglucomutase | OPA62825.1 | Multiple sclerosis |
| Minor capsid protein L2 | P36745.1 | Multiple sclerosis |
| N-acetylmuramoyl-L-alanine amidase CwlH | KIX84070.1 | Multiple sclerosis |
| ATP-sensitive inward rectifier potassium channel 10 | NP_002232.2 | Multiple sclerosis |
| mRNA export factor ICP27 homolog | YP_401659.1 | Multiple sclerosis |
| Acetylcholine receptor subunit alpha | NP_001034612.1 | Myasthenia gravis |
| Acetylcholine receptor subunit gamma | NP_005190.4 | Myasthenia gravis |
| Acetylcholine receptor subunit delta | NP_000742.1 | Myasthenia gravis |
| Acetylcholine receptor subunit epsilon | NP_000071.1 | Myasthenia gravis |
| Muscarinic receptor | AAB95158.1 | Myasthenia gravis-MUSC |
| Aquaporin 4 | AAH22286.1 | Neuromyelitis optica |
| Alpha-synuclein | NP_000336.1 | Parkinson's disease |
| DNA polymerase processivity factor | SBO07788.1 | Parkinson's disease |
| Desmoglein-3 | NP_001935.2 | Phemphigus |
| Collagen alpha-1(XVII) chain | NP_000485.3 | Phemphigus |
| Desmoglein-1 | NP_001933.2 | Phemphigus |
| Glutamate decarboxylase 2 | NP_000809.1 | Prediabetes |
| 60 kDa heat shock protein, mitochondrial | NP_002147.2 | Prediabetes |
| Insulin | AAA59172.1 | Prediabetes |
| Insulin, isoform 2 | NP_001035835.1 | Prediabetes |
| Islet cell antigen | NP_002837.1 | Prediabetes |
| Dihydrolipoyllysine-residue acetyltransferase component of pyruvate dehydrogenase complex | NP_001922.2 | Primary biliary cirrhosis |
| Dihydrolipoyllysine-residue acetyltransferase component of pyruvate dehydrogenase complex | OAF98393.1 | Primary biliary cirrhosis |
| Dihydrolipoyllysine-residue succinyltransferase component of 2-oxoglutarate dehydrogenase complex | WP_032229692.1 | Primary biliary cirrhosis |
| Glycogen phosphorylase | AAC18079.1 | Primary biliary cirrhosis |
| Nuclear pore glycoprotein 210 | NP_079199.2 | Primary biliary cirrhosis |
| Sarcosine dehydrogenase | AAD32214.1 | Primary biliary cirrhosis |
| Sulfite oxidase | AAA74886.1 | Primary biliary cirrhosis |
| Transglutaminase | BAA14329.1 | Primary biliary cirrhosis |
| Nuclear autoantigen Sp-100 | NP_001073860.1 | Primary biliary cirrhosis |
| Dihydrolipoyllysine-residue succinyltransferase component of 2-oxoglutarate dehydrogenase complex, mitochondrial | NP_001924.2 | Primary biliary cirrhosis |
| Nuclear pore p62 | AAA59990.1 | Primary biliary cirrhosis |
| M protein precursor | AAA26918.1 | Psoriasis |
| Keratin, type I cytoskeletal 16 | NP_005548.2 | Psoriasis |
| Keratin, type I cytoskeletal 17 | NP_000413.1 | Psoriasis |
| ADAMTS-like protein 5 | NP_998769.2 | Psoriasrs |
| Transcriptional activator | AHF70996.1 | Psoriatic arthritis |
| Fibrinogen alpha chain | AAI01936.1 | Psoriatic arthritis |
| Vimentin | NP_003371.2 | Psoriatic arthritis |
| Nebulin-related-anchoring protein | AI26408.1 | Psoriatic arthritis |
| M protein | CAM31002.1 | Rheumatic fever |
| Myosin-2 | NP_060004.3 | Rheumatic fever |
| Fibrinogen beta chain | AAI06761.1 | Rheumatoid arthritis |
| Vimentin | NP_003371.2 | Rheumatoid arthritis |
| Rheumatoid factor (IgG) | AAH73766.1 | Rheumatoid arthritis |
| Glucose-6-phosphate isomerase | ARJ36701.1 | Rheumatoid arthritis |
| Collagen alpha-1(II) chain | NP_001835.3 | Rheumatoid arthritis |
| Fibrinogen alpha chain | AAI01936.1 | Rheumatoid arthritis |
| Alpha-enolase | CAA34360.1 | Rheumatoid arthritis |
| Tryptase precursor | AAA86934.1 | Rheumatoid arthritis |
| Filaggrin | NP_002007.1 | Rheumatoid arthritis |
| Aggrecan core protein | NP_001126.3 | Rheumatoid arthritis |
| Small nuclear ribonucleoprotein Sm D1 | NP_008869.1 | Rheumatoid arthritis |
| Ribosomal protein L23a | AAB17510.1 | Rheumatoid arthritis |
| 60 kDa chaperonin 2 | OMH58317.1 | Rheumatoid arthritis |
| Trans-activator protein BZLF1 | BAP94413.1 | Rheumatoid arthritis |
| Epstein-Barr nuclear antigen 1 | YP_401677.1 | Rheumatoid arthritis |
| Chaperone protein DnaJ | EDV64758.1 | Rheumatoid arthritis |

TABLE 1-continued

Autoantigens of Various Autoimmune Disorders

| Autoantigen | GenBank Accession No. | Associated Autoimmune Disease |
| --- | --- | --- |
| 60 kDa heat shock protein, mitochondrial | NP_002147.2 | Rheumatoid arthritis |
| Chitinase-3-like protein 1 | NP_001267.2 | Rheumatoid arthritis |
| mRNA export factor ICP27 homolog | YP_401659.1 | Rheumatoid arthritis |
| Arrestin | AAC50992.1 | Rheumatoid arthritis, iritis |
| Protein BOLF1 | AIE89051.1 | Rheumatoid arthritis, juvenile |
| 60 kDa heat shock protein, mitochondrial | NP_002147.2 | Rheumatoid arthritis, juvenile |
| Major DNA-binding protein | BAX36606.1 | Rheumatoid arthritis, juvenile |
| Keratin, type II cytoskeletal 3 | NP_476429.2 | Rheumatoid arthritis, juvenile |
| Fibrillin 1 | BAD16739.1 | Rheumatoid arthritis, juvenile |
| Tenascin precursor | NP_002151.2 | Rheumatoid arthritis, juvenile |
| Stromelysin-1 preproprotein | NP_002413.1 | Rheumatoid arthritis, juvenile |
| Interstitial collagenase | NP_002412.1 | Rheumatoid arthritis, juvenile |
| OspA | CAA32579.1 | Rheumatoid arthritis, Lyme |
| Integrin alpha-L | NP_002200.2 | Rheumatoid arthritis, Lyme |
| DNA topoisomerase 1 | NP_003277.1 | Scleroderma/Systemic sclerosis |
| Histone H3-like centromeric protein A | NP_001800.1 | Scleroderma/Systemic sclerosis |
| Small nuclear ribonucleoprotein Sm D1 | NP_008869.1 | Scleroderma/Systemic sclerosis |
| Major centromere autoantigen B | NP_001801.1 | Scleroderma/Systemic sclerosis |
| E3 ubiquitin-protein ligase TRIM21 | NP_003132.2 | Scleroderma/Systemic sclerosis |
| Epstein-Barr nuclear antigen 1 | YP_401677.1 | Scleroderma/Systemic sclerosis |
| U11/U12 snRNP | Q6IEG0 | Scleroderma/Systemic sclerosis |
| rRNA 2'-O-methyltransferase fibrillarin | NP_001427.2 | Scleroderma/Systemic sclerosis |
| Ribonuclease P protein subunit p25 | NP_060263.2 | Scleroderma/Systemic sclerosis |
| 60 kDa SS-A/Ro ribonucleoprotein | NP_001166995.1 | Sjogren's syndrome |
| Lupus La protein | NP_003133.1 | Sjogren's syndrome |
| E3 ubiquitin-protein ligase TRIM21 | NP_003132.2 | Sjogren's syndrome |
| Muscarinic acetylcholine receptor M3 | NP_000731.1 | Sjogren's syndrome |
| Small nuclear ribonucleoprotein Sm D1 | NP_008869.1 | Sjogren's syndrome |
| U1 small nuclear ribonucleoprotein A | NP_004587.1 | Sjogren's syndrome |
| Putative HTLV-1-related endogenous sequence | CAA34646.1 | Sjogren's syndrome |
| Calreticulin | AAB51176.1 | Sjogren's syndrome |
| Spectrin alpha chain, non-erythrocytic 1 | NP_001123910.1 | Sjogren's syndrome |
| Beta-tubulin | AAB59507.1 | Sydenham's chorea |
| Dopamine receptor 1 | NP_000785.1 | Sydenham's chorea |
| Dopamine receptor 2 | NP_000786.1 | Sydenham's chorea |
| 60 kDa SS-A/Ro ribonucleoprotein | NP_001166995.1 | Systemic lupus erythematosis |
| Small nuclear ribonucleoprotein Sm D1 | NP_008869.1 | Systemic lupus erythematosis |
| U1 small nuclear ribonucleoprotein 70 kDa | NP_003080.2 | Systemic lupus erythematosis |
| Natural killer group protein 2-A | AAC17488.1 | Systemic lupus erythematosis |
| Small nuclear ribonucleoprotein-associated proteins B and B' | NP_937859.1 | Systemic lupus erythematosis |
| Small nuclear ribonucleoprotein-associated protein N | NP_001336393.1 | Systemic lupus erythematosis |
| E3 ubiquitin-protein ligase TRIM21 | NP_003132.2 | Systemic lupus erythematosis |
| Epstein-Barr nuclear antigen 1 | YP_401677.1 | Systemic lupus erythematosis |
| U1 small nuclear ribonucleoprotein C | NP_003084.1 | Systemic lupus erythematosis |
| NHP2-like protein 1 | NP_001003796 | Systemic lupus erythematosis |
| 60S acidic ribosomal protein P2 | XP_805182.1 | Systemic lupus erythematosis |
| Histone H1.4 | NP_005312.1 | Systemic lupus erythematosis |
| Glutamate decarboxylase 2 | NP_000809.1 | Type 1 diabetes |
| Insulin | AAA59172.1 | Type 1 diabetes |
| Islet cell antigen | NP_002837.1 | Type 1 diabetes |
| Glucose-6-phosphatase 2 | NP_066999.1 | Type 1 diabetes |
| 60 kDa heat shock protein, mitochondrial | AAH02676.1 | Type 1 diabetes |
| Zinc transporter 8 | AAP44332.1 | Type 1 diabetes |
| Insulin, isoform 2 | NP_001035835.1 | Type 1 diabetes |
| Genome polyprotein | AAX23962.1 | Type 1 diabetes |

TABLE 1-continued

Autoantigens of Various Autoimmune Disorders

| Autoantigen | GenBank Accession No. | Associated Autoimmune Disease |
|---|---|---|
| Islet amyloid polypeptide | NP_000406.1 | Type 1 diabetes |
| Hemagglutinin | ALB07770.1 | Type 1 diabetes |
| Islet amyloid polypeptide | NP_000406.1 | Type 2 diabetes |
| Zinc transporter 8 | AAP44332.1 | Type 2 diabetes |
| Pancreatic secretory glycoprotein 2 | NP_001493.2 | Ulcerative colitis |
| GM-CSF | AAA52578.1 | Ulcerative colitis |
| Myeloblastin | NP_002768.3 | Ulcerative colitis |
| Type VII collagen | AAA96439.1 | Ulcerative colitis |
| Melanocyte protein PMEL | NP_001186983.1 | Vitiligo |
| Melanin-concentrating hormone receptor 1 | NP_05288.3 | Vitiligo |
| Tyrosine 3-monooxygenase | NP_954986.2 | Vitiligo |
| Tyrosinase | NP_000363.1 | Vitiligo |
| L-dopachrome tautomerase | NP_001913.2 | Vitiligo |
| TrpC1 | NP_001238774.1 | Vitiligo |
| Myeloblastin | NP_02768.3 | Wegener's granulomatosis |
| Collagen alpha-1(II) chain | NP_001835.3 | Wegener's granulomatosis |

Table 2 below provides HLA and classes commonly associated with autoimmune disorders though in the exemplary case the HLA or a portion of the HLA will be patient specific and derived from high resolution sequence of the patient suffering from the disorder or a serological equivalent.

TABLE 2

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| DR4 (e,g,, DRB1*04); and DR5 (e.g., DRB1*11 and DRB1*12) | DRB1*04:01; DRB1*11; and DRB1*11:04 | A2 (e.g., A*02) | A*02; A*02:01 and B*07:02 | Alopecia areata |
|  |  | A2 B27 (e.g., B*2701-2759); B40 (e,g,, B*40); B27-B40; and B7 (e.g., B*07) | B*27:02; B*27:05; B*40:01; B*52; and B*38 | Alzheimer's Ankylosing spondylitis |
| DR7 (e.g., DRB1*0701-0705); DR4; DR5; and DR12 (e.g., DRB1*1201-3 and DRB1*1206) | DRB1*09; DRB1*09:01; DRB1*04; DRB1*04:05; and DRB1*14 |  |  | Antiphospholipid syndrome |
| DR17 (e.g., DRB1*0301 and DRB1*0304); DR4; DR4/DR3; DQ2 (e.g., DQB1*02); and DQ8 (e.g., DQB1*0302) | DRB1*03:01; DRB1*04; and DRB1*04:04 |  |  | Autoimmune adrenalitis |
| DR2 (e.g., DRB1*15 and DRB1 DR4; DR5; DR2/DR4; and DR4/DR5 |  |  |  | Autoimmune gastritis |
|  | DRB1*03:01; DRB3*01:01; DRB1*04:01; DRB1*04:05; DRB1*07; and DRB1*13:01 |  |  | Autoimmune hepatitis |
| DR7; DR4; DR11 (e.g., DRB1*1101 to DRB1*1110); DR3 (e.g., | DRB1*04:09; DRB1*07; and DRB1*04 |  |  | Autoimmune myocarditis |

TABLE 2-continued

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| DRB1*03); and DR11-DQ7.5 | | | | |
| | | B27; A29 (e.g., A*29); and B51 (e.g., B*51) | A*29:02; and B*57:01 | Autoimmune uveitis |
| DQ2; DQ8; DR12-DQ7.5; and DR7-DQ2.2 | DQA1*05:01/ DQB1*02:01; DQA1*03/ DQB1*03:02; and DQA1*0505/ DQBA1*0301 | | | Coeliac disease |
| DR1 (e.g., DRB1*01); and DR3 | DRB1*07; DRB1*01:03; DRB1*0301; DRB1*0302; and DRB3*0301/ DRB1*1302 | B27 | | Crohn's disease |
| | DRB1*0301; and DRB1*0302 | | | Dermatomyositis |
| DR4 | DRB1*0302 | | | Dilated cardiomyopathy |
| DR2 | | B8 (e.g., B*08) | | Goodpasture's syndrome |
| DR17; DR52 (e.g., DRB3*); and DR7 | DRB1*03:01; DRB1*04:01; DRB3*01; and DRB3*0202 | | | Grave's disease |
| DR3; and DR5 | | | | Hashimoto's thyroiditis |
| DR4 | | | | Immune thrombocytopenic purpura |
| DR3; DR4; and DR3/DR4 | | | | Insulin resistant diabetes |
| DR3 | DRB1*01:02 | | | Membranous nephritis |
| DR2; DR15 (e.g., DRB1*1505-5 and DRB1*1507); and DR53 (DRB4*) | DRB1*15:01; DRB1*15:01/ DRB1*15:01; DRB1*15:01/ DRB5*01:01; DRB1*15; DRB5*01:01; DPw2; DRB1*04:01; DRB1*04:04; DPA1*01:03/ DPB1*02:01; DPA1*01:03/ DPB1*04:01; DQA1*01:02/ DQB1*05:02; DQB1*06; and DQB1*06:02 | A3 (A*03); and B7 | | Multiple sclerosis |
| DR17; DR3; and DR7 | DRB1*03:01 | | | Myasthenia gravis |
| DR14-DQ5 | | | | Myasthenia gravis-MUSC |
| DR3 | | | | Neuromyelitis optica |
| DR patient specific | | | | Parkinson's disease |
| DR4; and DR6 | DRB1*01:01; and DRB1*04:02 | | | Phemphigus |
| DR3; DR4; and DR3/DR4 | DRB1*03:01; DRB1*04:01; and DRB1*03: 01/*04:01 | | | Prediabetes |
| DR8 (e.g., DRB1*0801-*0807 and DRB1*0810-*0812) | DRB1*0801; and DRB1*0803 | | | Primary biliary cirrhosis |
| DR7 | DRB1*0102 | B27; and Cw6 (C*06:02 and C*06:05) | | Psoriasis |
| | | B16 (e.g., B38 and B39); B17 (e.g., B57 and B58); B27; B39 (e.g., B*39); and Cw6 | | Psoriatic arthritis |

TABLE 2-continued

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| DR7 | | | | Rheumatic fever |
| DR4; DR4-DQ8; DR1; DR12; and DR18 (e.g., DRB1*0302 and DRB1*0303) | DRB1*01:01; DRB1*01:02; DRB1*04:01; DRB1*04:02; DRB1*04:03; DRB1*04:04; DRB1*04:05; DRB1*04:06; DRB1*04:07; DRB1*04:08; DRB1*04:09; DRB1*04:10; DRB1*04:11; DRB1*04:12; DRB1*04:13; homozygous for the above;; DRB1*01:01/*04:04; and DRB1*01:01/*04:01 | | | Rheumatoid arthritis |
| DR4; DR5; DR14 (e.g., DRB1*1401-*1408 and DRB1*1410-*1408); and DR15 | DRB1*04:01; DRB1*04:04; DRB1*04:05; DRB1*14:02; and DRB1*12:01 | | | Rheumatoid arthritis, juvenile |
| DR5; and DR11 | DRB1*04:01; DRBl*10:01; and DRB1*11:02 | | | Rheumatoid arthritis, Lyme |
| DR11; and DR8 | DRB1*11:04 | | | Rheumatoid arthritis, pauciarticular (juvenile) |
| DR5 | DRB1*12:01 | B35 | | Rheumatoid arthritis, iritis |
| DR5 | DQB1*05:01; DRB1*11; DRB1*11:04; DRB1*15:02; DRB1*13:02; DRB1*04:06; DRB1*03 | | | Scleroderma/Systemic sclerosis |
| | DRB1*15; DRB1*03:01/ DRB1*15:01 | | | Sjogren's syndrome |
| DR1 | | B49 (e.g., B*49) | | Sydenham's chorea |
| DR11; and DR53-DR7 | DRB1*03:01; DRB1*15:01; DRB1*04:02; DRB1*04:03; DRB1*04:06; DRB1*11:01; and DRB3*03:01 | | | Systemic lupus erythematosis |
| DR3 | DRB1*03:02; DRB1*04; DRB1*04:01; DRB1*04:02; DRB1*04:05; DRB1*03:01; and DRB1*03:01/ DRB1*04:01 | | | Type 1 diabetes |
| DR4 | | | | Type 2 diabetes |
| DR1 | DRB1*01:03; and DRB1*15:02 | B27 | | Ulcerative colitis |
| | DRB1*07:01 | | A*02:01 | Vitiligo |
| | DPB1*04 | | | Wegener's granulomatosis |

In some embodiments, the antigenic peptides used herein are associated with HLA-DR*1501, for example, GAD peptide TYEIAPVFVLLFYVTLKKMR (SEQ ID NO: 34) (involved in Type I diabetes), the MBP peptides listed above, the following MPP peptides (involved in MS)

LLECCARCLVGAPFASLVATGLCFFGVALFC, (SEQ ID NO: 35)

LVGAPFASLVATGLCFFGVA, (SEQ ID NO: 36)

FGVALFCGCEVEALTGTEKLIETYFSKNYQD, (SEQ ID NO: 37)

LFCGCGHEALTGTEKLIETY, (SEQ ID NO: 38)

TGTEKLIETYFSKNYQDYEY, (SEQ ID NO: 39)

TGTEKLIETYFSKNYQDYEYL, (SEQ ID NO: 40)

YFSKNYQDYEYLINVIHAFQYVIYGTASFFFL, (SEQ ID NO: 41)

GTASFFFLYGALLLAYGFYTTGAVRQIFGDYK, (SEQ ID NO: 42)

LYGALLLAEGFYTTGAVRQI, (SEQ ID NO: 43)

FYYTTGAVRQIFGDYKTTICG, (SEQ ID NO: 44)

AVRQIFGDYKTTICGKGLSATV, (SEQ ID NO: 45)

RQIFGDYKTTCGKGLSATVTGGQKGRGSRGQ, (SEQ ID NO: 46)

KGLSATVTGGQKGRGYRGQH, (SEQ ID NO: 47)

QKGRGSRGQHQAHSLERVCH, (SEQ ID NO: 48)

KGRGSRGQHQAHSLERVCHCLGCWLGHPDKFV, (SEQ ID NO: 49)

LGHPDKFVGITY ALTVVWLLVFACSAVPVYIY, (SEQ ID NO: 50)

SAVPVYIYFNTWTTCQSIAAPCKTSASIGTLC, (SEQ ID NO: 51)

AVPVYIYFNTWTTCQSIAFP, (SEQ ID NO: 52)

WTTCQSIAFPSKTSASIGSL, (SEQ ID NO: 53)

SASIGTLCADARMYGVLPWNAFFGKVCGSNLL, (SEQ ID NO: 54)

KVCGSNLLSICKTAEFQMTFHLFIAAFVGAAA, (SEQ ID NO: 55)

AAFVGAAATLVSLLTFMIAATYNFAVLKLMGR, (SEQ ID NO: 56)

MIAATYNFAVLKLMGRGTKF, and (SEQ ID NO: 57)

MAATYNFAVLKLMGRFTKF. (SEQ ID NO: 58)

In some embodiments, the antigenic peptides or antigenic polypeptides are patient specific and designed for the patient's MHC. For example, a physician can diagnose the patient with an autoimmune disorder and determine the severity of the disease. The patient's Class I (HLA-A, B, and C) and II (HLA-DR, DQ, DP) regions can be typed, which can now be performed at high resolution using DNA sequencing and with comparison to a reference database (www.ebi.ac.uk/ipd/imgt/hla/). The patient's Class I and II MHC with the strongest evidence of autoimmune involvement can be identified for the disorder. Those known to be associated with a particular autoimmune disorder can be used as references. See, e.g., Tables 1 and 2. The strongest evidence based antigens are identified for the disorder (iedb.org/) and Table 1. A set of personalized peptide (cbs.dtu.dk/services/NetMHC/or cbs.dtu.dk/services, NetMHCII/) and protein targets (for Class II) that are expected to bind the patient autoimmune implicated MHC can be identified.

Personalized MHC-CARs lentivirus or mRNA can be prepared for the patient to enable targeting of pathogenic immune cells. The personalized lentivirus is used to prepare autologous or allogeneic T cells (CTL and/or Tregs) that can be combined with receptor or cellular modifications to allow co-treatment with additional therapeutics, desired interactions with pathogenic cells, routing to a desired location (for interaction with pathogenic inflammatory or inflammation generating cells), or secretion of cytokines (to reduce inflammation).

(c) Co-Stimulatory Signaling Domains

Many immune cells require co-stimulation, in addition to stimulation of an antigen-specific signal, to promote cell proliferation, differentiation and survival, as well as to activate effector functions of the cell. The MHC-CAR described herein may comprise one or more co-stimulatory signaling domain. The term "co-stimulatory signaling domain," as used herein, refers to at least a portion of a protein that mediates signal transduction within a cell to induce an immune response such as an effector function. The co-stimulatory signaling domain of the MHC-CAR described herein can be a cytoplasmic signaling domain from a co-stimulatory protein, which transduces a signal and modulates responses mediated by immune cells, such as T cells, NK cells, macrophages, neutrophils, or eosinophils.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the MHC-CAR described herein. Examples of co-stimulatory signaling domains for use in the chimeric receptors can be the cytoplasmic signaling domain of co-stimulatory proteins, including, without limitation, members of the B7/CD28 family (e.g., B7-1/CD80, B7-2/CD86, B7-H1/PD-L1, B7-H2, CD28, CTLA-4, ICOS/CD278, or PD-1): members of the TNF superfamily (e.g., 4-1BB.TNFSF9/CD137, 4-1BB Ligand/TNFSF9, CD40/TNFRSF5, CD40 Ligand/TNFSF5, DR3/TNFRSF25, OX40/fNFRSF4, OX40 Ligand/TNFSF4, or TNF-alpha): and other molecules, such as FRB, and FKBF, that allow co-stimulation to be induced only in the presence of a specific drug molecule (but here in association with a the unique heterodimeric MHC-CAR). Wu et al., *Science,* 350(6258):aab4077, 2015. In some embodiments, any of the cytoplasmic signaling domains of co-stimulatory proteins may be used in receptors targeting inactive bystander B cells (e.g., with a CD19 or CD20-CAR) or plasma cells (e.g., with a CS1-CAR and/or CSI knock-out).

Figure 9:
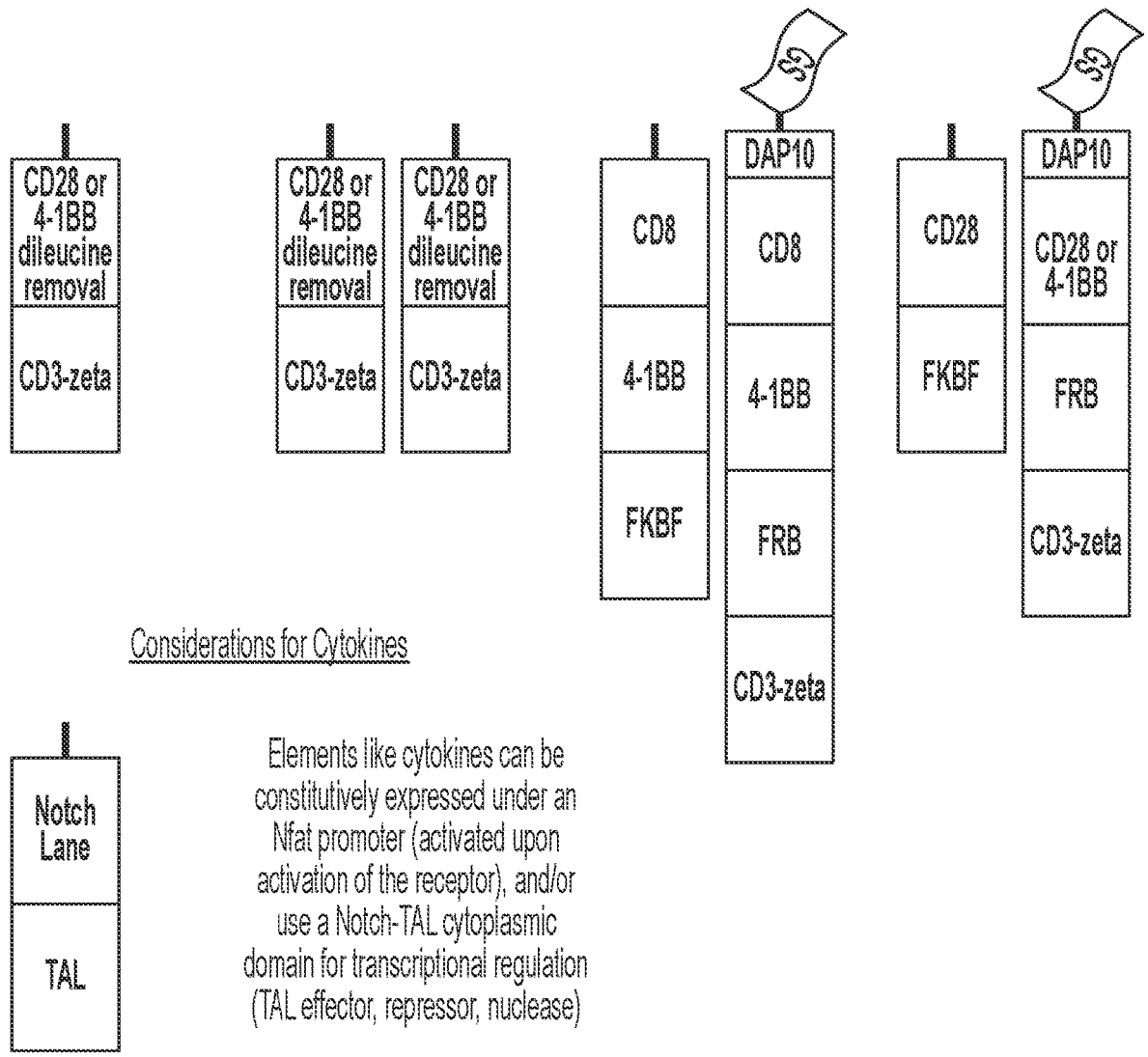
FIG. 9 depicts exemplary co-stimulatory domains and combinations thereof for constructing the MHC-CAR and considerations for co-expression of cytokines.

In some instances, the MHC-CAR may comprise a combination (e.g., 2 or 3) co-stimulatory domains, which may be from the same co-stimulatory receptor or from different co-stimulatory receptors. Examples include: CD28+4-1BB, CD28+FRB, CD28+FKBF, or 4-1BB+FRB. See also FIG. 9. In some examples, the MHC-CAR comprises a co-stimulatory domain from CD28, a co-stimulatory domain from 4-1BB, or both. In some embodiments, the co-stimulatory domain is preceded by a short linker. For example, for a class II MHC-CAR, the short linker may be TS (i.e., a MHC internal Linker): for a class I MHC-CAR, the short linker may be PG.

In some instances, the MHC-CAR constructs described herein may include no co-stimulatory domain. Alternatively, it may contain a non-traditional element such as a TALEN nuclease, activators, or repressors which may now be implemented in a clinically applicable lentiviral form using a recoded or non-repeat containing TAL domain and would be linked to a single chain MHC-CAR through a membrane domain derived from Notch.

Exemplary co-stimulatory domains for use in the MHC-CAR described herein include, but are not limited to:

```
41BB intracellular domain:
                                    (SEQ ID NO: 59)
KRGRKKLLYIFKQPFMRPVQTTQEEDGCSCRFPEEEEGGCEL 41BBe intracellular domain:
                                    (SEQ ID NO: 60)
pgKRGRKKLLYIFKQPFMRPVQTTQEEDGCSCRFPEEEEGGCELaha CD28 intracellular domain:
                                    (SEQ ID NO: 61)
RSKRSRGGHSDYMNMTPRRPGPTRKHYQPYAPPRDFAAYRS CD28e intracellular domain:
                                    (SEQ ID NO: 62)
pgRSKRSRGGHSDYMNMTPRRPGPTRKHYQPYAPPRDFAAYRSaha FRB:
                                    (SEQ ID NO: 63)
EMWHEGLEEASRLYFGERNVKGMFEVLEPLHAMMERGPQTLKETSFNQAY

GRDLMEAQEWDRKYMKSGNVKDLLQAWDLYYHVFRRI

FBP-with linkers
                                    (SEQ ID NO: 64)
(GSSS)4-EMWHEGLEEASRLYFGERNVKGMFEVLEPLHAMMERGPQTLK

ETSFNQAYGRDLMEAQEWCRKYMKSGNVKDLLQAWDLYYHVFRRI- (GSSS)3

FKRB
                                    (SEQ ID NO: 65)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE

FKBP-with linkers
                                    (SEQ ID NO: 66)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE-(GSSS)3
```

(d) Cytoplasmic Signaling Domain

Any cytoplasmic signaling domain comprising an immunoreceptor tyrosine-based activation motif (ITAM) can be used to construct the chimeric receptors described herein. An "ITAM," as used herein, is a conserved protein motif that is generally present in the tail portion of signaling molecules expressed in many immune cells. The motif may comprises two repeats of the amino acid sequence YxxLI separated by 6-8 amino acids, wherein each x is independently any amino acid, producing the conserved motif YxxL/Ix(6-8)YxxL/I. In some examples, the cytoplasmic signaling domain comprising an ITAM is of CD3ζ. In some examples, the MHC-CAR does not comprise a co-stimulatory domain and the cytoplasmic signaling domain is preceded by a short linker. For example, for a class II MHC-CAR, the short linker may be TS (i.e., a MHC internal Linker). For example for a class 1 MHC-CAR, the short linker may be PG. In some cases the linker may be AHA or absent, such as certain instances when a co-stimulatory domain occurs before a signaling domain.

In some embodiments, the MHC-CAR may include no cytoplasmic signaling domain, for example, that of CD3ζ. Such CD3ζ-free MHC-CAR would have suppressive effects against target cells or induce target cell death. Moisini, et al., *The Journal of Immunology*, 180(5), pp. 3601-3611.

Provided below is an exemplary cytoplasmic signaling domain from CD3ζ:

```
                                    (SEQ ID NO: 67)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Provided below are exemplary nucleic acid sequences encoding a cytoplasmic signaling domain from CD3ζ:

```
                                    (SEQ ID NO: 410)
AGAGTAAAGTTTTCCCGAAGTGCGGACGCTCCCGCGTATCAGCAAGGTCA

AAACCAGCTTTACAACGAACTGAACTTGGGACGACGCGAAGAGTACGATG

TTCTTGATAAGCGGAGAGGGCGCGATCCCGAAATGGGGGGAAAGCCTCGG

AGGAAGAACCCACAAGAAGGCCTTTATAATGAACTGCAGAAGGACAAGAT

GGCGGAGGCGTATTCCGAAATAGGCATGAAGGGTGAACGGAGGAGAGGAA

AGGGACATGACGGACTTTATCAAGGATTGTCTACCGCAACTAAAGAaACC

TATGACGCGTTGCACATGCAGGCTCTCCCTCCGAGA (SEQ ID NO: 422)
CGGGTCAAATTTAGCAGATCCGCTGACGCACCGGCCTACCAGCAGGGCCA

GAACCAACTCTACAACGAGCTGAATCTCGGCCGACGGGAAGAGTATGACG

TACTCGACAAGCGGAGAGGTCGAGACCCTGAGATGGGCGGTAAACCGAGA

CGGAAAAATCCCCAAGAGGGTCTTTATAATGAACTCCAGAAGGATAAGAT

GGCTGAAGCCTATTCTGAGATAGGGATGAAAGGCGAGCGGCGGAGGGGTA

AGGGCCATGATGGCCTTTACCAGGGACTCTCCACGGCAACCAAAGATACT

TACGACGCCCTTCACATGCAAGCCCTCCCGCCACGC
```

(e) Additional Components

The MHC-CAR described herein may optionally further include one or more of the following components: a hinge domain, a transmembrane domain, a signal (leader) peptide, and a peptide linker.

In some instances, the antigenic peptide may be linked to a hinge peptide to enhance immune targeting activity of the resultant MHC-CAR and/or to reduce antibody responses by the target cell to the MHC-TCR complex. In some examples, a MHC-CAR containing a hinge peptide may not include a cytoplasmic domain (for example, free of a CD3ζdomain).

A MHC-CAR construct that contains a hinge peptide may also include a MHC class I moiety. The hinge domain may contain about 10-100 amino acids, e.g., 15-75 amino acids, 20-50 amino acids, or 30-60 amino acids. In some embodiments, the hinge domain may be of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some examples, the following peptide linkers can be used in a class I MHC-CAR:

```
MHCILinker 1:
                                            (SEQ ID NO: 68)
GGGGSGGGGSGGGGS MHCILinker 2:
                                            (SEQ ID NO: 69)
GGGGGGSGGGSGGSGG MHCILinker 3:
                                            (SEQ ID NO: 70)
GGGGSGGGGSGGGGSGGGGS MHCILinker 4:
                                            (SEQ ID NO: 68)
GGGGSGGGGSGGGGS
```

Exemplary peptide linkers for a class II MHC-CAR can be GSGSGSGS (MHCII Linker1; SEQ ID NO: 72), GGGGSGGGGSGGGGS (MHC II LinkerII; SEQ ID NO: 68), GGGGSGGGGSGGS (SEQ ID NO: 400), or those described herein as MHCI Linkers (i.e., MHCI Linkers 1-4). An exemplary pre-peptide linker for a class II MHC-CAR can be AS or GS or one or two copies of either AS or GS.

An example nucleic acid sequence encoding the peptide linker provided by SED ID NO: 400 is provided below

```
                                           (SEQ ID NO: 401)
    GGGGGAGGCGGATCTGGCGGAGGCGGGAGTGGAGGCTCA
```

A hinge peptide for use in the MHC-CAR described herein may be derived from a naturally-occurring receptor. Hinge domains of any protein known in the art to comprise a hinge domain are compatible for use in the chimeric receptors described herein. In some embodiments, the hinge domain is a portion of the hinge domain of CD8α, e.g., a fragment containing at least 15 (e.g., 20, 25, 30, 35, or 40) consecutive amino acids of the hinge domain of CD8α. Alternatively, it may be a synthetic peptide.

Exemplary hinge domains include: IYIWAPLAGTCGVLLLSLVIT (SEQ ID NO: 73), and IWAPLAGICVALLLSLIITLI (SEQ ID NO: 74). Additional examples are provided below:
FKBP/FRB-CD8 hinge:

```
FKBP/FRB-CD8 hinge:
                                           (SEQ ID NO: 75)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLEEAAAREAAAREAAAREAAARGRVAILWHEMWHEGLEEASRLYF

GERNVKGMFEVLEPLHAMMERGPQTLKETSFNQAYGRDLMEAQEWCRKYH

KSGNVKDLLQAWDLYYHVFRRITTTPAPRPPTPAPTIASQPLSLRPEACR

PAAGGAVHTRGLDFACD

GS short hinge:
                                           (SEQ ID NO: 68)
GGGGSGGGGSGGGGS GS long hinge:
                                           (SEQ ID NO: 76)
GGGGSGGGGSGGGGSGGGGSGGGGSGGGGSGGGGSGGGGSGGGGS H2-Kb hinge:
                                           (SEQ ID NO: 77)
LRWEPPPSTVSNM HLA-A2 hinge:
                                           (SEQ ID NO: 78)
LRWEPSSQPTIPI HLA-A3 hinge:
                                           (SEQ ID NO: 79)
LRWELSSQPTIPI DAP10 hinge:
                                           (SEQ ID NO: 80)
QTTPGERSSLPAFYPGTSGSCSGCGSLSL DAP10 hinge with linker:
                                           (SEQ ID NO: 81)
(GSSS)4QTTPGERSSLPAFYPGTSGSCSGCGSLSLP DAP12 hinge:
                                           (SEQ ID NO: 82)
LRPVQAQAQSDCSCSTVS DAP12 hinge with linker:
                                           (SEQ ID NO: 83)
(GSSS)4LRPVQAQAQSDCSCSTVSP FcIgGIIIa hinge:
                                           (SEQ ID NO: 84)
GLAVSTISSFFPPGYQ CD8α hinge:
                                           (SEQ ID NO: 85)
TTTPAPRPPTPAPTIASQPLSLRPEACRPAAGGAVHTRGLDFACD IgG1 hinge:
                                           (SEQ ID NO: 86)
EPKSPDKTHTCPPCPAPPVAGPSVFLFPPKPKDTLMIARTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK

DRA*0101 hinge:
                                           (SEQ ID NO: 87)
EFDAPSPLPETTE DRB1*1501 hinge:
                                           (SEQ ID NO: 88)
VEWRARSESAQSK
```

An example nucleic acid sequence encoding a DRA*0101 hinge is provided below.

```
                                           (SEQ ID NO: 417)
     GAGTTCGACGCCCCATCACCGCTTCCAGAAACGACTGAA
```

An example nucleic acid sequence encoding a DRB1*1501 hinge is provided below.

```
                                           (SEQ ID NO: 404)
      GTTGAGTGGAGGGCGCGGTCAGAGAGCGCACAATCTAAA
```

In some embodiments, the MHC-CAR constructs described herein further comprise a transmembrane domain. Any transmembrane domain for use in the MHC-CAR can be in any form known in the art. As used herein, a "transmembrane domain" refers to any protein structure that is thermodynamically stable in a cell membrane, preferably a eukaryotic cell membrane. Transmembrane domains compatible for use in the chimeric receptors used herein may be obtained from a naturally-occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times).

Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the MHC-CAR described herein is derived from a Type I single-pass membrane protein, e.g., CD8α, CD8β, 4-1BB/CD137, or CD28. Transmembrane domains from multi-pass membrane proteins may also be compatible for use in the chimeric receptors described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer. e.g., the N-terminus of the protein is present on the cytoplasmic side of the lipid bilayerand the C-terminus of the protein is present on the extracellular side. Either one or multiple helix passes from a multi-pass membrane protein can be used for constructing the chimeric receptor variant described herein.

Exemplary transmembrane domains for use in constructing the MHC-CAR constructs described herein are provided below:

```
CD8a transmembrane domain:
                                   (SEQ ID NO: 89)
IYIKAFLAGTCGVLLLSLVITLYC HLA-A2 transmembrane domain:
                                   (SEQ ID NO: 90)
VGIIAGLVLFGAVITGAVVAAVMW HLA-A3 transmembrane domain:
                                   (SEQ ID NO: 91)
VGIIAGLVLLGAVITGAVVAAVMW
```

```
Cd3zeta transmembrane domain:
                                   (SEQ ID NO: 92)
LCYLLDGILFIYGVILTALFL DR*1501 transmembrane domain:
                                   (SEQ ID NO: 93)
MLSGVGGFVLGLLFLGAGLFI DR*1501e transmembrane domain:
                                   (SEQ ID NO: 94)
MLSGVGGFVLGLLFLGAGLFIYFRNQ DRA*0101 transmembrane domain:
                                   (SEQ ID NO: 416)
NVVCALGLTVGLVGIIGTIFII DRA*0101e transmembrane domain:
                                   (SEQ ID NO: 418)
NVVCALGLTVGLVGIIGTIFIIKGL
```

An example nucleic acid sequence encoding the DR*1501e transmembrane domain is provided below:

```
                                   (SEQ ID NO: 406)
ATGCTGTCAGGAGTAGGCGGATTTGTACTCGGACTCCTTTTTGGGCGCTG

GGTTGTTTATCTACTTTAGAAACCAA
```

An example nucleic acid sequence encoding the DRA*0101e transmembrane domain is provided below:

```
                                   (SEQ ID NO: 419)
AACGTTGTCTGCGCTCTTGGCCTGACAGTGGGCCTGGTAGGCATTATTAT

CGGGACCATCTTTATCATCAAAGGTTTG
```

Notch transmembrane domain:

```
                                   (SEQ ID NO: 95)
ILDYSFTGGAGRDIPPPQIEEACELPECQVDAGNKVCNLQCNNHACGWDG

GDCSLNFNDPWKNCTQSLQCWKYFSDGHCDSQCNSAGCLFDGFDCQLTEG

QCNPLYDQYCKDHFSDGHCDQGCNSAECEWDGLDCAEHVPERLAAGTLVL

VVLLPPDQLRNNSFHFLRELSHVLHTNVVFKRDAQGQQMIFPYYGHEEEL

RKHPIKRSTVGWATSSLLPGTSGGRQRRELDPMDIRGSIVYLEIDNRQCV

QSSSQCFQSATDVAAFLGALASLGSLNIPYKIEAVKSEPVEPPLPSQLHL

MYVAAAAFVLLBTVGCGVLLSRKRRR
```

Notch 2 transmembrane domain:

```
                                   (SEQ ID NO: 96)
PCVGSNPCYNQGTCEPTSENFFYRCLCPAKFNGLLCMILDYSFTGGAGRD

IPPPQIEEACELPECQVDAGNKVCNLQCNNHACGWDGGDCSLNFNDPWKN

CTQSLQCWKYFSDGHCDSQCNSAGCLFDGFDCQLTEGQCNPLYDQYCKDH

FSDGHCDQGCNSAECEWDGLDCAEHVPESLAAGTLVLVVLLPPDQLRNNS

FHFLRELSHVLHTNVVFKRDAQGQQMIFPYYGHEEELRKHPIKRSTVGWA

TSSLLPGTSGGRQRRELDPMDIRGSIVYLEIDNRQCVQSSSQCFQSATDV

AAFLGALASLGSLNIPYKIEAVKSEPVEPPLPSQLHLMYVAAAAFVLLFF

VGCGVLLSRKRRR
```

In some embodiments, the MHC-CAR may also comprise a signal peptide (also known as a signal sequence or a leader peptide) at the N-terminus of the polypeptide. In general, signal sequences are peptide sequences that target a polypeptide to the desired site in a cell. In some embodiments, the signal sequence targets the MHC-CAR to the secretory pathway of the cell and will allow for integration and anchoring of the MHC-CAR into the lipid bilayer. Signal sequences including signal sequences of naturally occurring proteins or synthetic, non-naturally occurring signal sequences, that are compatible for use in the chimeric receptors described herein will be evident to one of skill in the art. In some embodiments, the signal sequence from CD8α. In some embodiments, the signal sequence is from CD28 (e.g., MLRLLLALNLFPSIQVTG (SEQ ID NO: 97)).

Exemplary signal peptides include, but are not limited to, Beta-2-microglobulin signal peptide (e.g., MSRSVALAVLALLSLSGLEA (SEQ ID NO: 98)), HLA A3 signal peptide (e.g., MAVMAPRTLLLLLSGALALTQTWA (SEQ ID NO: 99) or), DRA*0101 signal peptide (e.g., MAISGVPVLGFFIIAVLMSAQESWA (SEQ ID NO: 100)), DRB1*1501 signal peptide (e.g., MVCLKLPGGSCMTALTVTLMVLSSPLAL (SEQ ID NO: 101)), and DRB5 signal peptide (e.g., MVCLKLPGGSYMAKLTVTLMVLSSPLALA (SEQ ID NO: 102)). Exemplary signal peptides may be followed by flexible pre-peptide linkers such as AS, GS, ASAS, GSGS. In some embodiments, a flexible pre-peptide linker is used when the signal peptide is class II and followed by an introduced peptide. Any of the constructs encoding the MHC-CARs described herein may comprise a nucleic acid sequence encoding any of the pre-peptide linkers above, e.g. AS may be encoded by the nucleic acid sequence GCATCT, TS may be encoded by the nucleic acid sequence ACAAGT. Example nucleic acid sequence encoding beta-2-microglobulin signal peptides are provided below:

(SEQ ID NO: 397)
ATGGTATGCTTGAAGCTCCCGGGCGGGTCCTGCATGACCGCTCTCACTGT

TACTCTTATGGTCCTTAGTTCACCGCTTGCCCTG (SEQ ID NO: 414)
ATGGCAATATCTGGTGTTCCTGTCCTCGGGTTTTTTATCATAGCCGTACT

GATGTCAGCACAGGAATCATGGGCG

In some embodiments, the MHC-CAR described herein may include one or more peptide linkers between the other components as described herein. Examples include a (Gly$_x$Ser)$_n$ linker, wherein x and n, independently can be an integer between 3 and 12, including 3, 4, 5, 6, 7, 8, 9, 10, 11, 12, or more. In some examples, the peptide linker can be (Gly$_4$Ser)$_n$ (SEQ ID NO: 103), wherein n can be an integer between 3 and 20. Specific examples include (Gly$_4$Ser)$_3$ (SEQ ID NO: 68),(Gly$_4$Ser)$_6$ (SEQ ID NO: 69). (Gly$_4$Ser)k (SEQ ID NO: 76),(Gly$_4$Ser)$_{12}$ (SEQ ID NO: 105), and (Gly$_4$Ser)$_{15}$ (SEQ ID NO: 106).

(ii) Configuration of MHC-CARs

The MHC-CAR constructs disclosed herein, comprising one or more components described herein, may be configured in any suitable format. Exemplary MHC class I constructs and MHC class II constructs are provided in FIGS. 7 and 8.

A MHC-CAR construct containing a MHC class I moiety as described herein may be a single fusion polypeptide that comprise the MHC class I moiety, the antigenic peptide, and a signaling domain (e.g., a co-stimulatory domain, a cytoplasmic signaling domain, or a combination thereof), and optionally one or more of the additional components described herein. See, e.g., FIG. 8. In some examples, a MHC Class I CAR construct contains a hinge domain adjacent to the antigenic peptide. A MHC class I CAR may not contain 02-microglobulin (b2m). When expressed on cell surface, such a MHC-CAR may form a heterodimer with endogenous b2m. Alternatively, a MHC class I CAR may also include b2m, which may be fused with the alpha chain to produce a single polypeptide. In some instances, a MHC class I CAR may contain two subunits, one including the alpha chain or a portion thereof (e.g., an extracellular domain), and the other including b2m or a portion thereof (e.g., an extracellular domain). In some examples, the antigenic peptide may be fused to the alpha chain. In other examples, the antigenic peptide may be fused to b2m. Optionally, a MHC class I CAR may contain peptide linkers between two components. One example is provided in FIG. 8B.

In some examples, the MHC-CAR comprises a class 1 molecule or a portion thereof, for example, HLA A3 or HLA A2, and a antigenic peptide suitable for presentation by the class I molecule (e.g., the PLP fragment KLIETYFSK (SEQ ID NO: 107) or the TAX fragment LLFGYPVYV (SEQ ID NO: 108)). Optionally, the MHC-CAR may further comprise b2m. Alternatively, the b2m molecule may be expressed separately from the class I MHC-CAR. Examples of the class I molecules and b2m sequences are provided below:

HLA A2:
(SEQ ID NO: 109)
GSHSMRYFFTSVSRPGRGEPRFIAVGYVDDTQFVRFDSDAASQRMEPRAP

WIEQSGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGSDQTQDTELVETRPAGDGTFQKWAAVVVP

SGQEQRYTCHVQHEGLPKPLT

HLA A3:
(SEQ ID NO: 110)
GSHSMRYFFTSVSRPGRGEPRFIAVGYVDDTQFVRFDSDAASQRMEPRAP

WIEQEGPEYWDQSTRNVKAQSQTDRVDLGTLRGYYNQSSAGSHTIQIMYG

CDVGSDGRFLRGYRQDAYDGKDYIALNEDLRSWTAADMAAQITKRKWEAA

HEAEQLPAYLDGTCVEWLRRYLENGKETLQRTDPPKTHMTHHPISDHEAT

LRCWALGFYPAEITLTWQRDGEDQTQDTELVETRPAGDGTFQKWAAVVVP

SGEEQRYTCHVQHEGLPKPLT

Microextension for above:
(SEQ ID NO: 111)
LRWE

HLA A2 with H-2K$^b$ alpha3 domain
(underlined/italicized)
(SEQ ID NO: 112)
GSHSMRYFFTSVSRPGRGEPRFIAVGYVDDTQFVRFDSDAASQRMSPRAP

WIEQSGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRT*DSPKAHVTHHSRPEDKVT*

*LRCWALGFYPADITLTWQLNGEELIQDMELVETRPAGDGTFQKWASVVVP*

*LGKEQYYTCHVYHQGLPEPLT*

HLA A3 with H-2K$^b$ alpha3 domain
(underlined/italicized)
(SEQ ID NO: 113)
GSHSMRYFFTSVSRPGRGEPRFIAVGYVDDTQFVRFDSDAASQRMEPRAP

WIEQEGPEYWDQETRNVKAQSQTDRVDLGTLRGYYNQSSAGSHTIQIMYG

CDVGSDGRFLRGYRQDAYDGKDYIALNEDLRSWTAADMAAQITKRKWEAA

HEASQLRAYLDGTCVEWLRRYLENGKETLQRT*DSPKAHVTHHSRPEDKVT*

*LRCWALGFYPADITLTWQLNGEELIQDMELVETRPAGDGTFQKWASVVVP*

*LGKEQYYTCHVYHQGLPEPLT*

Microextension for above:
(SEQ ID NO: 111)
LRWE

Beta-2-microglobulin (human):
(SEQ ID NO: 114)
IQRTPKIQVYSRHPAENGKSNFLNCYVSGFHPSDIEVDLLKNGERISKVE

HSDLSFSKDWSFYLLYYTEFTPTEKDEYACRVNHVTLSQPKIVKWDRDM

Beta-2-microglobuiin (mouse):
(SEQ ID NO: 115)
IQKTPQIQVYSRHPPENGKPNILNCYVTQFHPPHIEIQMLKNGKKIPKVE

MSDMSFSKDWSFYILAHTEFTPTETDTYACRVKHASMAEPKTVYWDRDM

Figure 7:
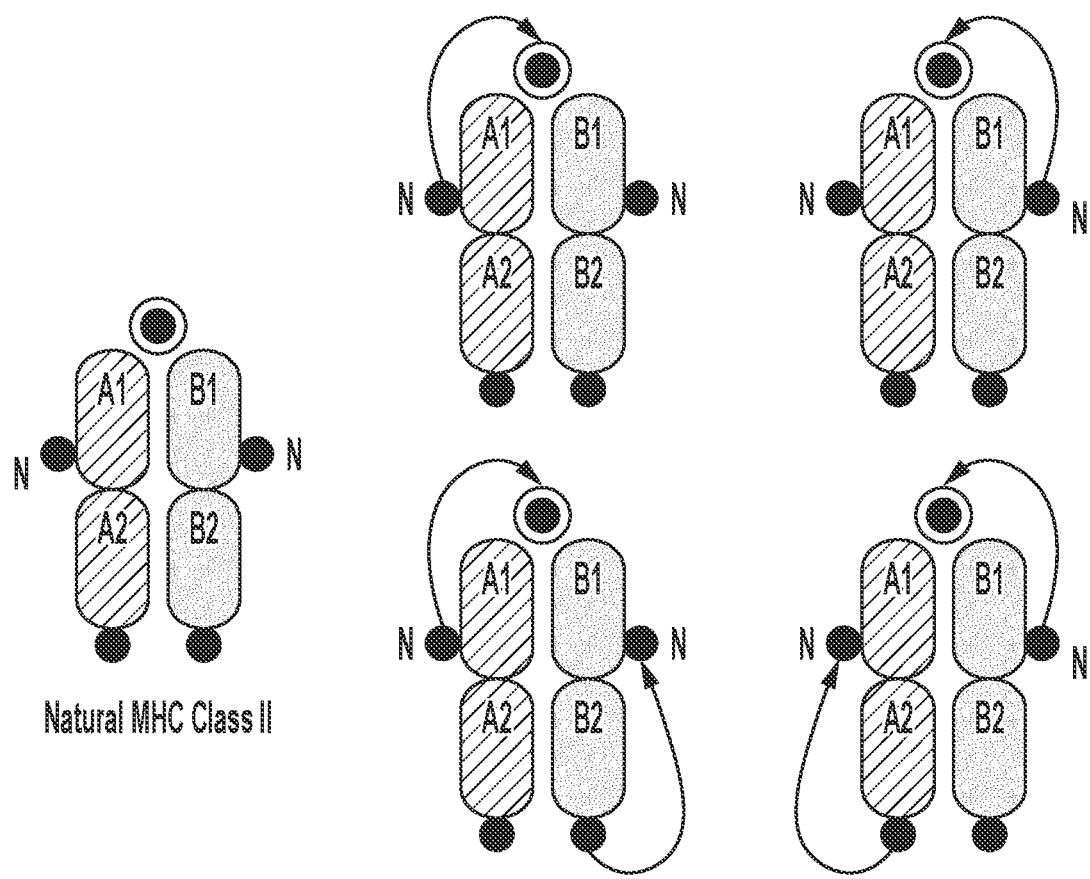
FIG. 7 is a schematic illustration of exemplary designs of MHC Class II moieties linked to antigenic peptides. "N" refers to the N-terminus of a polypeptide. Circled black dots refer to the antigenic peptides.
Figure 8A:
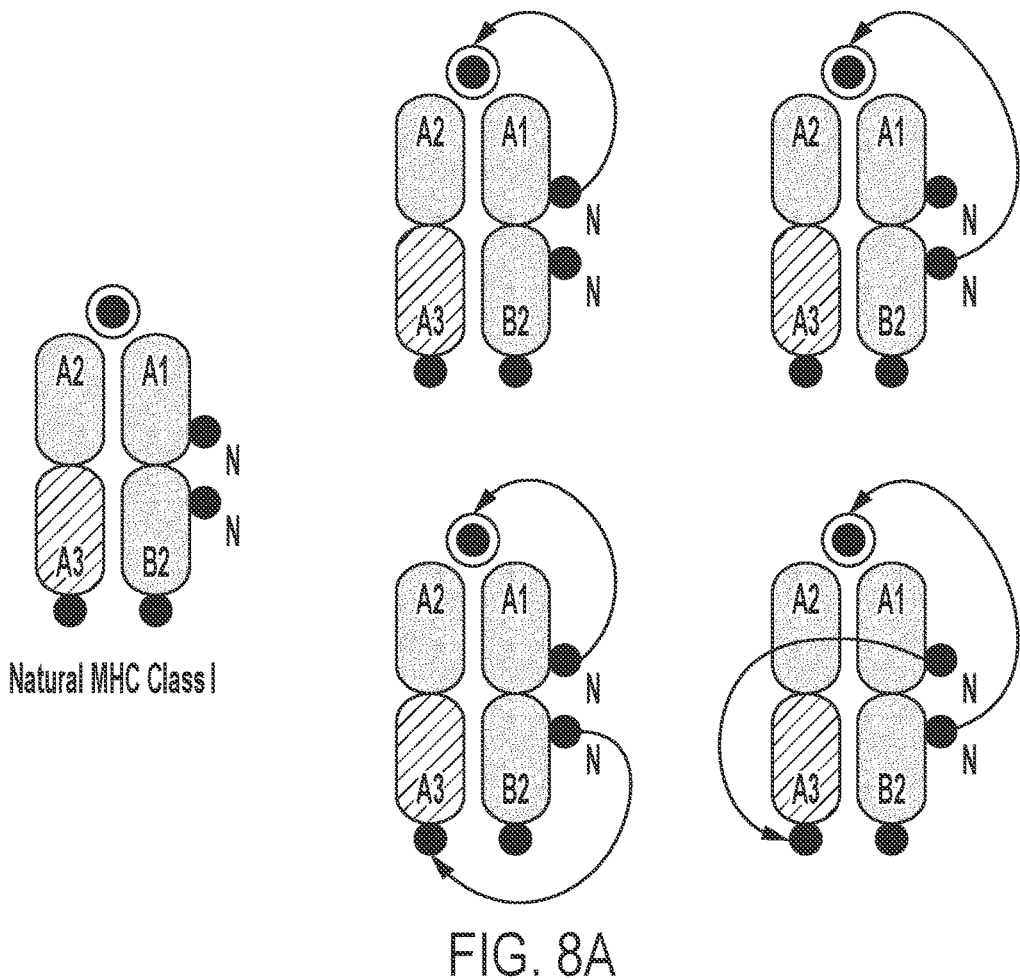
FIG. 8A and FIG. 8B are schematic illustrations of MHC Class I exemplary constructs.
Figure 8B:
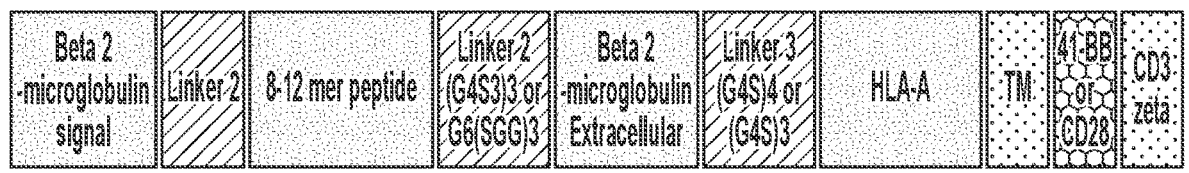

FIG. 7 provides a number of exemplary designs of MHC class II CAR constructs. Typically, a MHC class II CAR construct contains two subunits, one including the alpha chain or a portion thereof (e.g., an extracellular domain) and the other including the beta chain or a portion thereof (e.g., an extracellular domain). The antigenic peptide can be fused to either the alpha chain or the beta chain. In some instances, a MHC class II CAR can also be in a single fusion polypeptide format, in which the alpha and beta chains are fused to form a single polypeptide. The alpha chain and beta chain of a MHC class II CAR may be derived from the same MHC class II molecule. Alternatively, they may be from different MHC class II molecules. For example, a MHC class II CAR may contain an alpha chain from HLA DRA*1010 and a beta chain from HLA DRB1*1501, which may be fused with an antigenic peptide, such as an MBP peptide.

In some examples, the MHC-CAR comprises a class II molecule or a portion thereof, for example, DRB1*1501 or DRA*O101, and a antigenic peptide suitable for presentation by the class II molecule (e.g., the MBP fragment DENPVVHFFKNIVTPRTPP (SEQ ID NO: 15)). Examples of the class II molecule sequences are provided below;

DRB1*1501:
(SEQ ID NO: 117)
GDTRPRFLWQPKRSCHFFNGTERVRFLDRYFYNQEESVRFDSDVGSFRAV

TELGRPDAEYWNSQKDILEQARAAVDTYCRHNYGVVESFTVQRRVQPKVT

VYPSKTQPLQHHNLLVCSVSGFYPGSIEVRWFLNGQEEKAGMVSTGLIQN

GDWTFQTLVMLETVPRSGEVYTCQVEHPSVTSPLT

DRA*0101
(SEQ ID NO: 118)
IKEEHVIIQAEFYLNPDQSGEFMFDFDGDEIFHVDMAKKETVWRLESFGR

FASFEAQGALANIAVDKANLEIMTKRSNYTPITNVPPEVTVLTNSPVELR

EPNVLICFIDKFTPPVVNVTWLRNGKPVTTGVSETVFLPREDHLFRKFHY

LPFLPSTEDVYDCRVEHWGLDSPLLKHW

DRB1*1501 human/IA-Dbeta mouse (mutated
residues in boldface and underlined)
(SEQ ID NO: 119)
IKEEHVIIQAESYLNPDQSGEFKFDFDGDEIFHVDMAKKETVWRLEEFGR

FASFEAQGALANIAVDKANLEIMTKRSNYTPIEETEVPTSLRRLEQPNVA

ISLSRTEALNHHNTLVCSVTDFYPAKIKVRWFRNGQEETVGVSSTQLIRN

GDWTFQVLVMLEMTPHQGEVYTCHVEWPSLKSPIT

DRA*0101 human/IA-Dalpha mouse (mutated
residues in boldface and underlined)
(SEQ ID NO: 120)
IKEEHVIIQAESYLNPDQSGEFKFDFDGDEIFHVDMAKKETVWRLESFGR

FASFEAQGALANIAVDKANLEIMTKRSNYTPIATNEAPQATVFPKSPVLL

GQPHTLICFVDNIFPPVINITWLRNSKSVTDGVYETSFLVNRDHSFHKLS

YLTFIPSDDDIYDCKVEHWGLEEPVLKHWEPEI

DR-2$_{beta}$ mini (mutated residue in boldface
and underlined)
(SEQ ID NO: 121)
RPRFLWQSKRECHFFNGTERVRFLDRYFYNQEESVRFDSDVGEFRAVTEL

GRPDAEYWNSQKDILEQARAAVDTYCRHNYGVVESFTVQR

DR-2$_{alpha}$ mini
(SEQ ID NO: 122)
IKEEHVIIQAESYLNPDQSGEFKFDFDGDEIFHVDMAKKETVWRLEEFGR

FASFEAQGALANIAVDKANLSIMTKRSNYTPI

An example nucleic acid sequence encoding DRB1*1501 is provided below:

(SEQ ID NO: 402)
GGAGACACAAGACCCCGATTCTTGTGGCAGCCCAAAAGGGAGTGCCATTT

TTTCAATGGGACGGAACGAGTTCGCTTCCTTGATCGGTACTTTTACAACC

AAGAAGAGAGTGTACGGTTCGACTCAGATGTCGGCGAGTTCCGAGCGGTT

ACGGAATTGGGGCGACCTGACGCGGAGTACTGGAACTCCCAAAAGGATAT

TTTGGAGCAGGCACGAGCAGCTGTGGACACCTATTGTCGACATAATTATG

GTGTGGTGGAATCCTTTACAGTTCAGCGGCGGGTGCAACCTAAAGTGACC

GTGTATCCATCTAAAACGCAACCCCTCCAACACCATAACCTCCTGGTGTG

TTCCGTAAGCGGCTTCTATCCCGGGTCAATTGAGGTCAGGTGGTTCCTCA

ACGGTCAGGAGGAGAAGGCCGGAATGGTAAGTACTGGTCTTATCCAGAAC

GGAGACTGGACCTTCCAAACTTTGGTAATGTTGGAAACGGTGCCGCGATC

CGGGGAGGTGTATACATGCCAAGTTGAACACCCGAGTGTTACGAGCCCCC

TGACG

An example nucleic acid sequence encoding DRA*0101 is provided below:

(SEQ ID NO: 415)
ATAAAAGAAGAGCACGTGATAATACAGGCGGAGTTTTATTTGAACCCGGA

CCAGAGCGGTGAGTTCATGTTCGATTTTGATGGCGACGAGATATTTCACG

TTGACATGGCAAAAAAGGAAACGGTGTGGAGACTTGAGGAGTTTGGACGA

TTCGCATCATTTGAGGCACAAGGAGCACTCGCCAATATCGCGGTGGACAA

GGCCAACCTGGAGATCATGACAAAACGCTCCAATTATACGCCTATCACTA

-continued

```
ATGTGCCCCCTGAGGTTACTGTGCTCACAAATTCTCCCGTAGAACTTAGG

GAACCTAACGTCCTCATATGTTTCATCGACAAGTTCACTCCTCCGGTGGT

CAATGTAACGTGGCTTCGGAATGGTAAGCCGGTCACCACGGGTGTCTCAG

AGACCGTATTTCTGCCCAGAGAAGACCACCTCTTCCGCAAATTTCATTAC

CTTCCCTTTCTTCCTTCAACGaAAGACGTTTACGACTGCAGGGTCGAACA

TTGGGGGCTTGACGAGCCACTTCTCAAGCATTGG
```

Any of MHC class I and MHC class II constructs described herein can be further fused to one or more signaling domains and optionally one or more of the additional components. In some instances, the MHC-CAR constructs described herein are free of singling domains.

Preferably, a MHC-CAR as described herein contains matched MHC moiety and antigenic peptide, e.g., a MHC molecule that would present the antigenic peptide or homologous analogs in natural state. In some instances, a MHC-CAR described herein may contain an alpha chain or a beta chain from HLA DRB1*1501 and an antigenic peptide associated with this HLA allele, e.g., those MBP peptides described herein and others as well. The association between antigenic peptides involved in an autoimmune disease and a specific HLA allele is well known in the art or can be identified via routine practice, for example, library screening.

One exemplary MHC-CAR may have the following formula (+/− means that the specific component is optional):
Single chain (MHC Class I or II+peptide) (+/−hinge)+ single chain CD28/4-1BB (+/−dileucine motifs) (+/−cd3zeta)). (Additional short peptide linkers can be added between components as described previously.)

Figure 10:
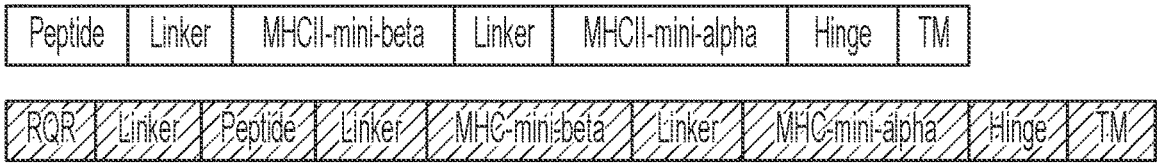
FIG. 10 depicts exemplary single-chain and multi-chain MHC Class I and Class 11 MHC-CAR constructs, including multi-chain MHC-CAR constructs containing both MHC Class I and Class II components.
Figure 10:
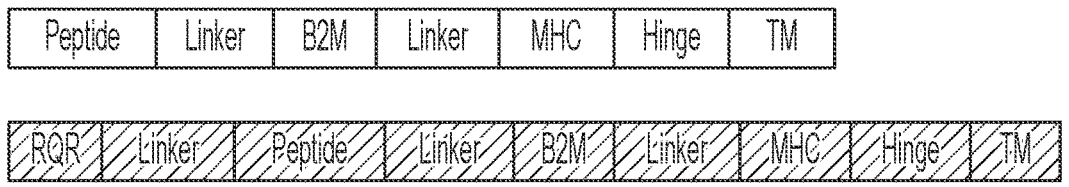
Figure 10:
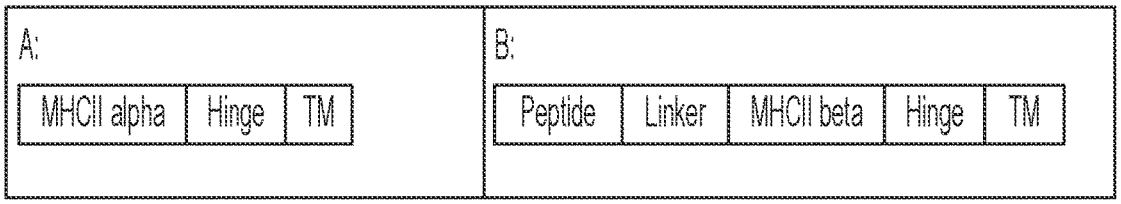
Figure 10:
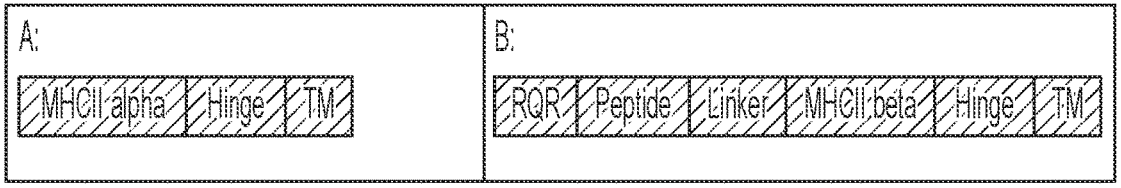
Figure 10:
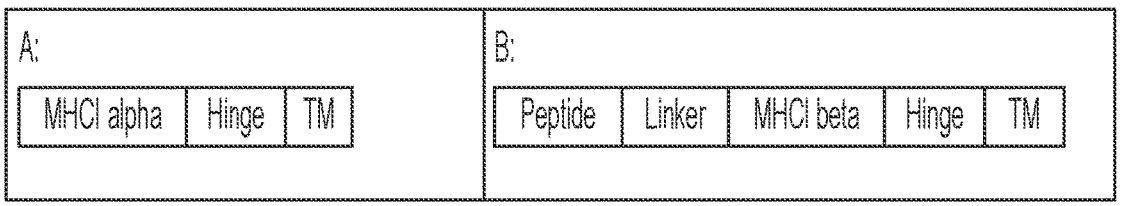
Figure 10:
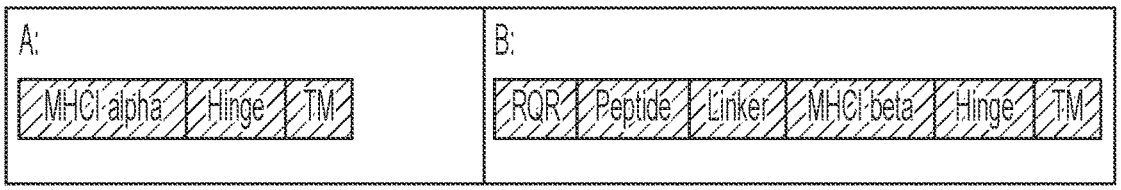
Figure 10:
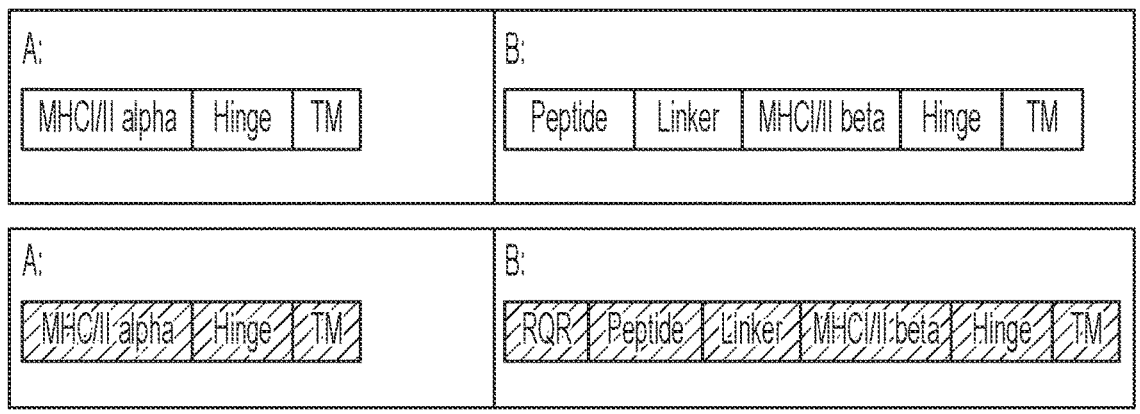

Other exemplary MHC-CAR designs (single chain and multi-chain) are illustrated in FIG. 10. In the case of multi-chain constructs, one or more short hinges may be used to enhance successful expression of the MHC-CAR. Further, it may be desirable to replace a portion of the structure with conserved domains from mice domains to prevent cross-reactivity. Note that in some cases, the internal domain may only be attached to one of the chains.

The amino acid sequence of a MHC-CAR binding (that displays MBP) TCR is provided below:

```
TCR alpha MBP:
                                        (SEQ ID NO: 123)
METLLGVSLVILWLQLARVNSQQGEEDPQALSIQEGENATMNCSYKTSIN

NLQWYRQNSGRGLVHLILIRSNEREKHSGRLRVTLDTSKKSSSLLITASR

AADTASYFCATAAVGGFKTIFGAGTRLFVKANIQNPDPAVYQLRDSKSSD

KSVCLFTDFDSQTNVSQSKDSDVYITDKTVLDMRSMDFKSNSAVAWSNKS

DFACANAFNNSIIPEDTFFPSPESSCDVKLVEKSFETDTNLNFQNLSVIG

FRILLLKVAGFNLLMTLRLWSS

TCR beta MBP
                                        (SEQ ID NO: 124)
MLLLLLLLGLAGSGLGAWSQHPSWVISKSGTSVKIECRSLDSFQATTMFW

YRQFPKQSLMLMATSNEGSKATYEQGVEKDKFLINHASLTLSTLTVTSAH

PEDSSFYICSARDLTSGANNEQFFGPGTRLTVLSDLKNVFPPEVAVFEPS

EAEISHTQKATLVCLATGFYPDHVELSWWVNGKEVHSGVSTDPQPLKEQP

ALNDSRYSLSSRLRVSATFWQNPRNHFRCQVQFYGLSENDEWTQDRAKPV

TQIVSAEAWGRADCGFTSESYQQGVLSATILYEILLGKATLYAVLVSALV

LMAMVKRKDSRG

TCR alpha class I
                                        (SEQ ID NO: 125)
mamllgasvl ilwlqpdwvn sqqkndd

QQVKQNSPSLSVQEGRISILNCDYTNSMFDYFLWYKKYPAEGPTFLISIS

SIKDKNADGRFTVFLNKSAKHLSLHIVPSQPGDSAVYFCAAMEGAQKLVF

GQGTRLTINPNIQNPDPAVYQLRDSKSSDKSVCLFTDFDSQTNVSQSKDS

DVYITDKTVLDMRSMDFKSNSAVAWSNKSDFACANAFNNSIIPSDTFFPS

PESS

Cdvklve ksfetdtnln fqnlsvigfr illlkvagfn llmclrlwss

TCR beta class I:
                                        (SEQ ID NO: 126)
msigllccaa lsllwagpv

NAGVTQTPKFQVLKTGQSMTLQCAQDMNHEYMSWYRQDPGMGLRLIHYSV

GAGITDQGEVPNGYNVSRSTTEDFPLRLLSAAPSQTSVYFCASSYPGGGF

YEQYFGPGTRLTVTEDLKNVFPPEVAVFEPSEASISHTQKATLVCLATGF

YPDHVELSWWVNGKEVHSGVSTDPQPLKEQPALNDSRYALSSRLRVSATF

WQDPRNHFRCQVQFYGLSENDEWTQDRAKPVTQIVSAEAWGRAD cgftse syqqgvlsat ilyeillgka tlyavlvsal vlmamvkrkd srg
```

The amino acid sequences of exemplary CD19 targeting CAR constructs are provided below (note that these designs contain a 4-1BB domain which may be replaced with a cd28 domain):

```
4G7-CAR version 1:
                                        (SEQ ID NO: 127)
MALPVTALLLPLALLLHAARPEVQLQQSGPELIKPGASVKMSCKASGYTF

TSYVMHWVKQKPGQGLEWIGYINPYNDGTKYNEKFKGKATLTSDKSSSTA

YMELSSLTSEDSAVYYCARGTYYYGSRVFDYWGQGTTLTVSSGGGGSGGG

GSGGGGSDIVMTQAAPSIPVTPGESVSISCRSSKSLLNSNGNGSGSGTAF

TLRISRVEAEDVGVYYCMQHLEYPFTAGTKLELKRSDPTTTPAPRPPTPA

PTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR

4G7-CAR version 2:
                                        (SEQ ID NO: 128)
METDTLLLWV LLLWVPGSTG EVQLQQSGPE LIKPGASVKM

SCKASGYTFT SYVMHWVKOK PGOGLEWIGY INPYNDGTKY

NEKFKGKATL TSDKSSSTAY MELSSLTSED SAVYYCARGT

YYYGSRVEDY WGQGTTLTVS SGGGGSGGGG SGGGGSDIVM
```

-continued
TQAAPSIPVT PGESVSISCR SSKSLLNSNG NTYLYWFLQR

PGQSPQLLIY RMSNLABGVP DRFSGSGSGT AFTLRISRVE

AEDVGVYYCM QHLEYPFTFG AGTKLELKRS DPTTTPAPRP

PTPAPTIASQ PLSLRPEACR PAAGGAVHTR GLDEACDIYI

WAPLAGTCGV LLLSLVITLY CKRGRKKLLY IFKQPFMRPV

QTTQEEDGCS CRFPEEEEGG CELRVKFSRS ADAPAYQQGQ

NQLYNELNLG RREEYDVLDK RRGRDPEMGG KPRRKNPQEG

LYNELQKDKM ALAYSEIGMK GEPPRGKGHD GLYQGLSTAT

KDTYDALHMQ ALPPR

The nucleic acid sequences of exemplary CD19 targeting CAR constructs are provided below.

4G7-CAR version 2:
(SEQ ID NO: 390)
atggagacagacactcttctcctttgggtcttgctgctgtgggtt cccggaagcacaggagaagtacagttgcaacagtctgggcagaa ctcatcaaacccggagcttctgtaaaaatgtcatgcaaagctagt ggatatacatttacttcttacgtgatgcactgggtaaaacagaaa cctggtcaggggcttgagtggatcggcacattaacccatataat gacggcaccaaatataacgagaaattcaaggggaaaggctacgctt acascagataagtccagtagcaccgcttatatggaacccagcagc cttacttccgaagattccgcggtgcactactgcgcgagagggact tactactacggggagtcgagtattcgattattggggtcaaggcacg acgctcacggtgagctcaggtggtggagggtctgggggtggcggc agtggtggggggggctcagacatcgtgatgacccaggcagcacct tctatcccggtaaccccaggcgagtctgtatctatcagstgtcgg tccagcaagcctcttctcaacagtaacggcaatacatatctccac tggttcctccaaaggcctgggcaaagtcctcaacttcttatatat cggatgtccaatcttgcgagtggcgtacccgacaggttttcaggg tctgggagcggaacagcttttacgttgagaatatccagggtagaa gctgaggacgtcggtgtatattattgcatgcaacatctcgaatac ccctttaccttcggcgctggtacaaagctcgaattgaaacgcagc gatccaaccacgacgccagcgccacgaccacctacgcccgctcca actattgcctcccagcccctgagtcttcggccagaagcgtgtaga cctgctgccggcggggccgttcacacgcgggccttgactttgca tgtgatatctatatgggctcctttggcgggaacttgcggagtg cttcttttgtcactcgtgataacgttgtattgtaaaagggtcga aagaaactcctctatatatttaagcagccctttatgaggcccgtg caaacaacacaagaaggaggacggatgctcttgtcgattcccggaa gaggaggaggggggggtgtgagctcaggtcaagtttttctcgctct gccgacgcgccagcctatcaacagggccaaaaccagctgtataac gaactcaacctcgggcgccgggaagagtatgacgtccttgacaag -continued
cggcgcggtcgcgaccctgaaatgggtggaaaaccgaggcgaaag aaccccaggagggactttacaacgaattgcaaaaagacaagatg gccgaagcctattccgaaattggaatgaaaggcgagcggagacga ggtaaggggcatgacggcctgtatcaagggctctctacggccacg aaggatacttacgacgcccttcatatgcaagctcttccaccacgg MHC-CAR1 containing MHC-CAR1 part B (MHC-DRB CAR)-HLA DRB1*1501 (signal peptide), MBP peptide, HLA DRB1*1501 (external, hinge, transmembrane) CD3ζ (cytoplasmic signaling domain) is provided below:

(SEQ ID NO 412)
MVCLKLPGGSCMTALTVTLMVLSSPLALASDENPVVH

FFKNIVTPRTPPGGGGSGGGGSGGSGDTRPRFLWQPK

RECHFFNGTERVRFLDRYFYNQSESVRFDSDVGEFRA

VTSLGRPDASYWNSQKDILEQARAAVDTYCRHNYGVV

ESFTVQRRVQPKVTVYPSKTQPLQHHNLLVCSVSGFY

PGSIEVRWFLNGQEEKAGMVSTGLIQNGDWTFQTLVM

LETVPRSGSVYTCQVEHPSVTSPLTVEWRARSSSAQS

KMLSGVGGFVLGLLFLGAGLFIYFRNQTSRVKFSRSA

DAPAYQQGQNQLYNELNLGRREEYDVLDKRRGRDPEM

GGKPRRKNPQEGLYNELQKDKMAEAYSEIGMKGERRR

GKGHDGLYQGLSTATKDTYDALHMQALPPR

An example nucleic acid sequence encoding a MHC_CAR1 containing MHC-CAR1 part B (MHC-DRB CAR)-HLA DRB1*1501 (signal peptide), MBP peptide. HLA DRB1*1501 (external, hinge, transmembrane) CD3ζ (cytoplasmic signaling domain) is provided below:

(SEQ ID NO: 413)
ATGGTATGCTTGAAGCTCCCGGGCGGGTCCTGCATGA

CCGCTCTCACTGTTACTCTTATGGTCCTTAGTTCACC

GCTTGCCCTGGCATCTGATGAGAATCCCGTGGTTCAT

TTTTTTAAGAACATCGTCACACCGCGCACCCCACCTG

GGGGAGGCGGATCTGGCGGAGGCGGGAGTGGAGGCTC

AGGAGACACAAGACCCCGATTCTTGTGGCAGCCCAAA

AGGGAGTGCCATTTTTTCAATGGGACGGAACGAGTTC

GCTTCCTTGATCGGTACTTTTACAACCAAGAAGAGAG

TGTACGGTTCGACTCAGATGTCGGCGAGTTCCGAGCG

GTTACGGAATTGGGGCGACCTGACGCGGAGTACTGGA

ACTCCCAAAGGATATTTTGGAGCAGGCACGAGCAGC

TGTGGACACCTATTGTCGACATAATTATGGTGTGGTG

GAATCCTTTACAGTTCAGCGGCGGGTGCAACCTAAAG

TGACCGTGTATCCATCTAAAACGCAACCCCTCCAACA

CCATAACCTCCTGGTGTGTTCCGTAAGCGGCTTCTAT

CCCGGGTCAATTGAGGTCAGGTGGTTCCTCAACGGTC

```
AGGAGGAGAAGGCCGGAATGGTAAGTACTGGTCTTAT

CCAGAACGGAGACTGGACCTTCCAAACTTTGGTAATG

TTGGAAACGGTGCCGCGATCCGGGGAGGTGTATACAT

GCCAAGTTGAACACCCGAGTGTTACGAGCCCCCTGAC

GGTTGAGTGGAGGGCGCGGTCAGAGAGCGCACAATCT

AAAATGCTGTCAGGAGTAGGCGGATTTGTACTCGGAC

TCCTCTTTTTGGGCGCTGGGTTGTTTATCTACTTTAG

AAACCAAACAAGTAGAGTAAAGTTTTCCCGAAGTGCG

GACGCTCCCGCGTATCAGCAAGGTCAAAACCAGCTTT

ACAACGAACTGAACTTGGGACGACGCGAAGAGTACGA

TGTTCTTGATAAGCGGAGAGGCGCGATCCCGAAATG

GGGGGAAAGCCTCGGAGGAAGAACCCACAAGAAGGCC

TTTATAATGAACTGCAGAAGGACAAGATGGCGGAGGC

GTATTCCGAAATAGGCATGAAGGGTGAACGGAGGAGA

GGAAAGGGACATGACGGACTTTATCAAGGATTGTCTA

CCGCAACTAAAGACACCTATGACGCGTTGCACATGCA

GGCTCTCCCTCCGAGA
```

MHC-CAR containing MHC-CAR1 part A (MHC-DRA CAR) HLA-DRA*1010 (signal peptide, external, hinge, transmembrane), CD3ζ(cytoplasmic signaling domain) is provided below:

```
                                        (SEQ ID NO: 423)
MAISGVPVLGFFIIAVLMSAQESWAIKEEHVIIQAEFYLNPDQS

GSFMFDEDGDEIFHVDMAKKETVWRLEEFGRFASFEAQGALANI

AVDKANLEIMTKRSNYTPITNVPPEVTVLiTNSPVELREPNVLI

CFIDKFTPPWNVTWLRNGKPVTTGVSETVFLPREDHLFRKFHYL

PFLPSTEDVYDCRVEHWGLDEPLLKHVJEFDAPSPLPETTENWC

ALGLTVGLVGIIIGTIFIIKGLTSRVKFSRSADAPAYQQGQKQL

YNELNLGRREEYDVLDKRRGRDPEMGGKPRRKNPQEGLYNELQK

DKMAEAYSEIGMKGERRRGKGHDGLYQGLSTATKDTYDALHMQA

LPPR
```

An example nucleic acid sequence encoding a MHC-CAR1 part A (MHC-DRA CAR) HLA-DRA*1010 (signal peptide, external, hinge, transmembrane), CD3ζ (cytoplasmic signaling domain) is provided below:

```
                                        (SEQ ID NO: 424)
ATGGCAATATCTGGTGTTCCTGTCCTCGGGTTTTTTATCATAGC

CGTACTGATGTCAGCACAGGAATCATGGGCGATAAAAGAAGAGC

ACGTGATAATACAGGCGGAGTTTTATTTGAACCCGGACCAGAGC

GGTGAGTTCATGTTCGATTTTGATGGCGACGAGATATTTCACGT

TGACATGGCAAAAAGGAAACGGTGTGGAGACTTGAGGAGTTTG

GACGATTCGCATCATTTGAGGCACAAGGAGCACTCGCCAATATC
```

```
GCGGTGGACAAGGCCAACCTGGAGATCATGACAAAACGCTCCAA

TTATACGCCTATCACTAATGTGCCCCCTGAGGTTACTGTGCTCA

CAAATTCTCCCGTAGAACTTAGGGAACCTAACGTCCTCATATGT

TTCATCGACAAGTTCACTCCTCCGGTGGTCAATGTAACGTGGCT

TCGGAATGGTAAGCCGGTCACCACGGGTGTCTCAGAGACCGTAT

TTCTGCCCAGAGAAGACCACCTCTTCCGCAAATTTCATTACCTT

CCCTTTCTTCCTTCAACGGAAGACGTTTACGACTGCAGGGTCGA

ACATTGGGGCTTGACGAGCCACTTCTCAAGCATTGGGAGTTCG

ACGCCCCATCACCGCTTCCAGAAACGACTGAAAACGTTGTCTGC

GCTCTTGGCCTGACAGTGGGCCTGGTAGGCATTATTATCGGGAC

CATCTTTATCATCAAAGGTTTGACTTCCCGGGTCAAATTTAGCA

GATCCGCTGACGCACCGGCCTACCAGCAGGGCCAGAACCAACTC

TACAACGAGCTGAATCTCGGCCGACGGGAAGAGTATGACGTACT

CGACAAGCGGAGAGGTCGAGACCCTGAGATGGGCGGTAAACCGA

GACGGAAAAATCCCCAAGAGGGTCTTTATAATGAACTCCAGAAG

GATAAGATGGCTGAAGCCTATTCTGAGATAGGGATGAAAGGCGA

GCGGCGGAGGGGTAAGGGCCATGATGGCCTTTACCAGGGACTCT

CCACGGCAACCAAAGATACTTACGACGCCCTTCACATGCAAGCC

CTCCCGCGACGC
```

Construct 1 (CD 19 CAR and CCR6 region) is provided below:

```
                                        (SEQ ID NO: 425)
METDTLLLWVLLLWVPGSTGEVQLQQSGPELIKPGASVKMSCKA

SGYTFTSYVMHWVKQKPGQGLEWIGYINPYNDGTKYNEKFKGKA

TLTSDKSSSTAYMELSSLTSEDSAVYYCARGTYYYGSRVFDYWG

QGTTLTVSSGGGGSGGGGSGGGGSDIVMTQAAPSIPVTPGESVS

ISCRSSKSLLNSNGNTYLYWFLQRPGQSPQLLIYRMSNLASGVP

DRFSGSGSGTAFTLRISRVEAEDVGVYYCMQHLEYPFTFGAGTK

LELKRSDPTTTPAPRPPTPAPTIASQPLSLRPEACRPAAGGAVH

TRGLDFACDIYIWAPLAGTCGVLLLSLVITLYCKRGRKKLLYIF

KQPFMRPVQTTQEEDGCSCSFPEEEEGGCELRVKFSRSADAPAY

QQGQNQLYNELNLGRREEYDVLDKRRGRDPEMGGKPRRKNPQSG

LYNELQKDKMAEAYSEIGMKGERRRGKGHDGLYQGLSTATKDTY

DALHMQALPPRGSSGSGEGRGSLLTCGDVSENPGPMSGESMNFS

DVFDSSEDYFVSVNTSYYSVDSEMLLCSLQEVRQFSRLFVPIAY

SLICVFGLLGNILVVITFAFYKKARSMTDVYLLNMAIADILFVL

TLPFWAVSHATGAWVFSNATCKLLKGIYAINFNCGMLLLTCISM

DRYIAIVQATKSFRLRSRTLPRSKIICLVVWGLSVIXSSSTFVF

NQKYNTQGSDVCEPKYQTVSEPIRWKLLMLGLELLFGFFIPLMF

MIFCYTFIVKTLVQAQNSKRHKAIRVIIAVVLVFLACQIPHNMV

LLVTAANLGKMNRSCQSEKLIGYTKTVTEVLAFLHCCLNPVLYA
```

-continued

FIGQKFRNYFLKILKDLWCVRRKYKSSGFSCAGRYSENISRQTS

ETADNDNASSFTM

Construct 1 (CD 19 CAR, CCR6. GFP region) is provided below:

(SEQ ID NO: 429)
METDTLLLWVLLLWVPGSTGEVQLQQSGPELIKPGASVKMSCKASGYT

FTSYVMHWVKQKPGQGLEWIGYINPYNDGTKYNEKFKGKATLTSDKSS

STAYMELSSLTSEDSAVYYCARGTYYYGSRVFDYWGQGTTLTVSSGGG

GSGGGGSGGGGSDIVMTQAAPSIPVTPGESVSISCRSSKSLLNSNGNT

YLYWFLQRPGQSPQLLIYRMSNLASGVPDRFSGSGSGTAFTLRISRVE

AEDVGVYYCMQHLEYPFTFGAGTKLELKRSDPTTTPAPRPFTPAPTIA

SQPLSLRPEACRPAAGGAVHTRGLDFACDIYIWAPLAGTCGVLLLSLV

ITLYCKRGRKKLLYIFKQPFMRPVQTTQEEDGCSCRFPEEEEGGCELR

VKFSRSADAPAYQQGQNQLYNSLNLGRRESYDVLDKRRGRDPEMGGKP

RRKNPQEGLYNELQKDKMAEAYSEIGMKGERRRGKGHDGLYQGLSTAT

KDTYDALHMQALPPRGSSGSGEGRGSLLTCGDVEENPGPMSGESMNFS

DVFDSSEDYFVSVNTSYYSVDSEMLLCSLQEVRQFSRLFVPIAYSLIC

VFGLLGNILVVITFAFYKKARSMTDVYLLNMAIADILFVLTLPFWAVS

HATGAWVFSNATCKLLKGIYAINFNCGMLLLTCISMDRYIAIVQATKS

FRLRSRTLPRSKIICLVVWGLSVIISSSTFVFNQKYNTQGSDVCSPKY

QTVSEPIRWKLLMLGLELLFGFFIPLMFMIFCYTFIVKTLVQAQNSKR

HKAIRVIIAVVLVFLACQIPHNMVLLVTAANLGKMNRSCQSEKLIGYT

KTVTEVLAFLHCCLNPVLYAFIGQKFRNYFLKILKDLWCVRRKYKSSG

FSCAGRYSENISRQTSETADNDNASSFTMGSGATNFSLLKQAGDVEEN

PGPVSKGEELFTGVVPILVELDGDVNGHKFSVSGEGEGDATYGKLTLK

FICTTGKLPVPWPTLVTTLTYGVQCFSRYPDHMKQHDFFKSAMPSGYV

QERTIFFKDDGNYKTRAEVKFEGDTLVNRIELKGIDFKEDGNILGHKL

EYNYNSHNVYIMADKQKNGIKANFKIRHNIEDGSVQLADHYQQNTPIG

DGPVLLPDNHYLSTQSALSKDPNEKRDHMVLLEFVTAAGITLGMDELY

K

An example nucleic acid sequence encoding Construct 1 (CD19 CAR, CCR6, GFP region) is provided below:

(SEQ ID NO: 430)
atggagacagacactcttctcctttgggtcttgctgctgtgggttccc ggaagcacaggagaagtacagttgcaacagtctgggccagaacccatc aaacccggagcccctgtaaaaatgtcacgcaaagctagtggatacaca tttacttcttacgtgatgcactgggtaaaacagaaacctggtcagggg cttgagtggatcgggcacattaacccatataatgacggcaccaaatat aacgagaaattcaagggaaaggctacgcttacatcagataagtccagt agcaccgcttatatggaacttagcagccttacttccgaagattccgcg gtgtattactgcgcgagagggacttactactacgggagtcgagtaccc gattattggggtcaaggcacgacgctcacggcgagctcaggtggtgga gggtctgggggtggcggcagtggtggggggggctcagacatcgtgatg acccaggcagcaccttctatcccggtaacccaggcgagtctgtatct atcagttgtcggtccagcaagtctcttctcaacagtaatggcaataca tatctttactggttcctccaaaggcctgggcaaagtcctcaacttctt atatatcggatgtccaatcttgcgagtggcgtacccgacaggttttca gggtctgggagcggaacagcttttacgttgagaatatccagggtagaa gctgaggacgtcggtgtatattattgcatgcaacatctcgaataccc tttaccttcggcgctggtacaaagctcgaattgaaacgcagcgatcca accacgacgccagcgccacgaccacctacgcccgctccaactattgcc tcccagccctgagtcttcggccagaagcgtgtagacctgctgccggc ggggccgttcatacgcggggccttgactttgcatgtgatatctatata tgggctccttggcgggaacttgcggagtgcttcttttgtcactcgtg ataacgttgtattgtaaaaggggtcgaaagaaactcctctatatattt aagcagccctttatgaggcccgtgcaaacaacacaagaagaggacgga tgctcttgtcgattcccggaagaggaggagggggggtgtgagctcagg gtcaagttttctcgctctgccgacgcgccagcctatcaacagggccaa aaccagctgtataacgaactcaacctcgggcgccgggaagagtatgac gtccttgacaaacggcgcggtcgcgaccctgaaatgggtggaaaaccg aggcgaaagaaccccaggagggactttacaacgaattgcaaaaagac aagatggccgaagcctattccgaaattggaatgaaaggcgagcggaga cgaggtaagggcacgacggcctgtatcaagggctctctacggccacg aaggatacttacgacgcccttcatatgcaagctcttccaccacggggt tcgagcggcagtggagagggcagaggaagtctgctaacatgcggtgac gtcgaggagaatcctggcccaatgagtggggaaagtatgaacttcagc gatgtatttgactcctccgaagattactttgtatctgtgaatacgagc tattactccgtcgatagtgaaatgctgctctgtagtctccaagaagtc cgccaattcagtcgcctcttcgttcccatcgcgtactccctttatttgt gttttggccttctgggtaacatcctggttgtaatcacattcgctttc tataaaaagctcggagtatgactgatgtttaccttcttaacatggct atagcggacattcttttttgtgcttactctcccattctgggctgtgagc catgcaacaggggcgtgggttttttcaaatgccacatgtaagctgctt aaagggatctatgcaataaacttcaattgcgggatgctcctgctgaca tgcatcagtatggatcgatacatagctatagtacaggcgactaagtcc ttccgcctgcgatcccgcacactgctaggagcaaaattatttgcctc gtcgtatggggctctcagtgatcatctcctccagtacgtttgtcttt aaccagaaatataacacacagggtctgatgtatgtgaaccaaagcat cagacagtgagtgaaccaatacggtggaagttgcttatgttgggcttg gagctgcttttgggttttcatcccactgatgttcatgattttctgt tatacatttattgttaagaccttggttcaggcgcaaaatagcaagaga

```
cataaggcaattcgagtcatcattgccgtggtgttggtcttcttggcc tgtcagatcccccataatatggttctgctcgtcaccgccgctaacttg ggtaagatgaatcgatcttgtcagtccgagaagttgatcggatacacc aaaactgtgacagaagtgctggccttccttcactgttgtctgaaccca gttttgtatgcttttataggacagaagtttcgaaattacttcttgaaa atcctcaaggacctctggtgtgttcgaaggaagtacaagagctctggc tttagttgcgctgggcgctacagtgagaatatatcccggcagacctcc gagactgctgataatgacaacgcaagttccttcactatgggatccggc gcaacaaacttctctctgctgaaacaagccggagatgtcgaagagaat cctggaccggtgagcaagggcgaggagctgttcaccggggtggtgccc atcctggtcgagctggacggcgacgtaaacggccacaagttcagcgtg tctggcgagggcgagggcgatgccacctacggcaagctgaccctgaag ttcatctgcaccaccggcaagctgcccgtgccctggcccaccctcgtg accaccctgacctacggcgtgcagtgcttcagccgctaccccgaccac atgaagcagcacgacttcttcaagtccgccatgcccgaaggctacgtc caggagcgcaccatcttcttcaaggacgacggcaactacaagacccgc gccgaggtgaagttcgagggcgacaccctggtgaaccgcatcgagctg aagggcatcgacttcaaggaggacggcaacatcctggggcacaagctg gagtacaactacaacagccacaacgtctatatcatggccgacaagcag aagaacggcatcaaggcgaacttcaagatccgccacaacatcgaggac ggcagcgtgcagctcgccgaccactaccagcagaacacccccatcggc gacggccccgtgctgctgcccgacaaccactacctgagcacccagtcc gccctgagcaaagaccccaacgagaagcgcgatcacatggtcctgctg gagttcgtgaccgccgccgggatcactctcggcatggacgagctgtac aagtaa
```

Construct 2 MHC CAR region (MHC-CAR1 part B, MHC-CAR 1 part A region) is provided below:

(SEQ ID NO: 431)
MVCLKLPGGSCMTALTVTLMVLSSPLALASDENPVVHFFKNIVTPRTP

PGGGGSGGGGSGGSGDTRPRFLWQPKRECHFFNGTERVRFLDRYFYNQ

SSSVRFDSDVGEFRAVTELGRPDAEYWNSQKDILSQARAAVDTYCRHN

YGVVESFTVQRRVQPKVTVYPSKTQPLQHHNLLVCSVSGFYPGSIEVR

WFLNGQEEKAGMVSTGLIQNGDWTFQTLVMLETVPRSGEVYTCQVEHP

SVTSPLTVEWRARSESAQSKMLSGVGGFVLGLLFLGAGLFIYFRNQTS

RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPRGSSGSGEGRGSLLTCGDVEENPGPMAISGVPV

LGFFIIAVLMSAQESWAIKEEHVIIQAEFYLNPDQSGEFMFDFDGDEI

FHVDMAKKSTVWRLESFGRFASFEAQGALANIAVDKANLEIMTKRSNY

TPITNVPPEVTVLTNSPVELREPNVLICFIDKFTPPVVNVTWLRNGKP

VTTGVSETVFLPREDHLFRKFHYLPFLPSTEDVYDCRVEHWGLDEPLL

KHWEFDAPSPLPETTENVVCALGLTVGLVGIIIGTIFIIKGLTSRVKF

SRSADAPAYQQGQNQLYNELNLGRRSEYDVLDKRRGRDPEMGGKPRRK

NPQEGLYNELQKDKMAEAYSEIGMKGERRRGKGHDGLYQGLSTATKDT

YDALHMQALPPR

An example nucleic acid sequence encoding the Construct 2 MI-C CAR region (MHC-CAR1 part B, MHC-CAR1 part A) is provided below:

(SEQ ID NO: 71)
```
atggtatgcttgaagctcccgggcgggtcctgcatgaccgctctcact gttactctcatggtccttagttcaccgccttgccctggcatctgatga gaatcccgtggtccattttttaagaacatcgtcacaccgcgcacccc acctgggcggaggcggatctggcggaggcgggagtggaggctcaggag acacaagaccccgattcttgtggcagcccaaaaggcgagtgccatttt ttcaatgggacggaacgagttcgcttccttgatcggtacttttacaac caagaagagagtgtaccggttcgactcagatgccggcgagttccgagc ggttacggaattggggcgacctgacgcggagtactggaactccccaaa aggatattttggagcaggcacgagcagctgtggacacctattgtcgac ataaccatggtgtggtggaatccctttacagttcagcggcgggtgcaa cctaaagtgaccgtgtatccatctaaaacgcaaccctccaacaccat aaccctcctggtgtgttccgtaagcggcttctatcccgggtcaattga ggtcaggtggttcctcaacggtcaggaggagcaaggccggaatggtaa gtactggtcttatccagaacggagactggaccttccaaactttggtaa tgttggaaacgcgtgccgcgatccggggaggtgtatacatgccaagtt gaacacccgagtgttacgagcccctgacggttgagtggcagggcgcg gtcagagagcgcacaatctaaaatgctgtcaggagtaggcggatttgt actcggactcctcttttttgcggcgctgggttgtttatctactttagaa accaaacaagtagagtaaagttttcccgaagtgcggacgctcccgcgc tatcagcaaggtcaaaaccagctttacaacgaactgaacttgggacga cgcgaagagtacgatgttcttgataagccggagagggcgcgatcccga aatgggggggaaagcctcggaggaagaacccacaagaaggcctttataa tgaaccgccagaaggacaagatggcggaggcgtattccgaaataggca tgaagggtgaacggaggagaggaaagggacatgaccggactttatcaa ggattgtctaccgcaactaaagacacctatgacgcgttgcacatgcag gctctccctccgagacggttcgagcggcagtggagagggcagaggaag tctgctaacatgcggtgacgtcgaggagaatcctggcccaatgcgcaa tatctggtgttcctgtcctcgggttttttatcatagccgtactgatgt cagcacaggaatcatgggcgatacaaagaagagcacgtgataatacag gcggagttttatttgaacccgaccagagcggtgagttcatgttcgat tttcgatgcgacgagatatctcacgttgacatggcaaaaaaggaaac ggtgcggagacttgaggagtttggacgattccgcatcatttgaggcac
```

-continued

```
aaggagcactcgccaatatcgcggtggacaaggccaacctggagatca
tgacaaaacgcctccaattatacgcctatcactaatgtgcccctgag
gttactgtgctcacaaattctcccgtagaacttagggaaccctaacgt
cctcatatgtttcatcgacaagttcactcctccggtggtcaatgtaac
gtggcttcggaatggtaagcccggtcaccacgggtgtctcagagaccg
tatttctgcccagagaagaccacctcttccgcaaatttcattaccttc
cccttcttccttcaacggaagacgtttacgactgcagggtcgaacat
tgggggcttgacgaaccacttctcaagccattgggagttcgacgcccc
atcaccgcttccagaaacgactgaaaacgttgtctgcgctcttggcct
gacagtgcggcctggtaggcattattatcgggaccatctttatcatca
aaggtttgacttcccgggtcaaatttagcagatcccgctgacgcaccg
gcccaccagcagggccagaaccaactctacaacgagctgaatctcggc
cgacgggaagagtatcgacgtactcgacaagcggagaggtcgagaccc
tgagatgggcggtaaaccgagacggaaaaatccccaagagggtcctt
ataatgaactccagaaggacaagatggctgaagcctattctgagatag
ggatgaaaggcgagcggcggaggcggtaagggccatgatggcctttac
cagggactctccacggcaaccaaagatacttacgacgcccttcacatg
caacgccctcccgccacgc
```

Construct 2 kill switch and MHC CAR region (RQR8, MHC-CAR1 part B. MHC-CAR 1 part A region) is provided below:

(SEQ ID NO: 211)
MGTSLLCWMALCLLGADHADACPYSNPSLCSGGGGSELPTQGTFSNVS
TNVSPAKPTTTACPYSNPSLCSGGGGSPAPRPPTPAPTIASQPLSLRP
EACRPAAGGAVHTRGLDFACDIYIWAPLAGTCGVLLLSLVITLYCNHR
NRRRVCKCPRPVVRSGSGQCTNYALLKLAGDVESNPGPPTGMVCLKLP
GGSCMTALTVTLMVLSSPLALASDENPVVHFFKNIVTPRTPPGGGGSG
GGGSGGSGDTRPRFLWQPKRECHFFNGTERVRFLDRYFYNQEESVRFD
SDVGEFRAVTELGRPDASYWNSQKDILEQARAAVDTYCRHNYGVVESF
TVQRRVQPKVTVYPSKTQPLQHHNLLVCSVSGFYPGSIEVRWFLNGQE
EKAGMVSTGLIQNGDWTFQTLVMLETVPRSGEVYTCQVEHPSVTSPLT
VEWRARSESAQSKMLSGVGGFVLGLLFLGAGLFIYFRNQTSRVKFSRS
ADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDA
LHMQALPPRGSSGSGEGRGSLLTCGDVEENPGPMAISGVPVLGFFIIA
VLMSAQESWAIKEEHVIIQAEFYLNPDQSGEFMFDFDGDEIFHVDMAK
KETVWRLEEFGRFASFSAQGALANIAVDKANLEIMTKRSNYTPITNVP
PEVTVLTNSPVELREPNVLICFIDKFTPPVVNVTWLRNGKPVTTGVSE
TVFLPREDHLFRKFHYLPFLPSTEDVYDCRVEHWGLDEPLLKHWEFDA
PSPLPETTENVVCALGLTVGLVGIIIGTIFIIKGLTSRVKFSRSADAP
AYQQGQNQLYNELNLGRREEYDVLDKRRGRDPEMGGKPRRKNPQEGLY

NELQKDKMAEAYSEIGMKGERRRGKGHDGLYQGLSTATKDTYDALHWQ
ALPPR
```

An example nucleic acid sequence encoding Construct 2 kill switch and MHC CAR region (RQR8, MHC-CAR1 part B, MHC-CAR1 part A region) is provided below:

(SEQ ID NO: 403)
```
atgggtacttcactgttgtgctggatggcactttgtcttttgggtgcc
gatcatgctgatgcatgtccgtactccaatcctagcctgtgctccggg
ggggagggagtgaactccctacacagggaaccttctctaatgtctcc
accaacgtctccctgcaaaaccgaccacaacagcttgcccctatagt
aaccctccctctgtagtggaggggggggttcacctgctccacgccct
cctaccccgcgccaacgatcgcgccacaacgctcagtcttaggccg
gaagcctgtaggccagcggctggcggtgcggttcatacgcgggattg
gattttgcctgcgacatttacatttgggctccgctggccggtacttgt
ggggtattgctgttgtctcttgttattacgctttattgcaatcacagg
aacaggcgacgagtatgcaaatgcccgcggcccgtcgtgagatctggg
tccggccaatgtactaactacgctttgttgaaactcgctggcgatgtt
gaaagtaaccccggtcctccaacaggtatggtatgcttgaagctcccg
ggcgggtcctgcatgaccgctctcactgttactcttatggtccttagt
tcaccgcttgccctggcatctgatgagaatcccgtggttcatttttt
aagaacatcgtcacccgcgcacccacctgggggaggcggatctggc
ggaggcgggagtggaggctcaggagacacaagacccgattcttgtgg
cagcccaaaagggagtgccatttttcaatgggacggaacgagttcgc
ttccttgatcggtacctctacaaccaagaagagtgtacggttcgac
tcagatgtcggcgagttccgagcggttacggaatcggggcgacctgac
gcggagtactggaactcccaaaaggatatttggagcaggcacgagca
gctgtggacacctattgtcgacataattatggtgtggtggaatccttt
acagttcagcggcgggtgcaacctaaagtgaccgtgtatccatctaaa
acgcaacccctccaacaccataacctcctggtgtgttccgtaagcggc
ttctatcccgggtcaattgaggtcaggtggttcctcaacggtcaggag
gagaaggccggaatggtaagtactggtcttatccagaacggagactgg
accttccaaactttggtaatgttggaaacggtgccgcgatccggggag
gtgtatacatgccaagttgaacacccgagtgttacgagcccctgacg
gttgagtggagggcgcggtcagagagcgcacaatctaaaatgctgtca
ggagtaggcggatttgtactcggactcctcttttgggcgctggggttg
tttatctactttagaaaccaaacaagtagagtaaagttttcccgaagt
gcggacgccccgcgtatcagcaaggccaaaaccagctttacaacgaa
ctgaacttgggacgacgcgaagagtacgatgttcttgataagcggaga
gggcgcgatcccgaaatgggggaaagcctcggaggaagaacccacaa
gaaggcctttataatgaactcagaaggacaagatggcggaggcgtat
tccgaaataggcatgaagggtgaacggaggagaggaaagggacatgac
```

```
ggactttatcaaggattgtctaccgcaactaaagacacctatgacgcg
ttgcacatgcaggctctccctccgagaggttcgagcggcagtggagag
ggcagaggaagtccgctaacatgcggtgacgtcgaggagaatcctggc
ccaatggcaatatctggtgttcctgtcctcggttttttatcatagcc
gtactgatgtcagcacaggaatcatgggcgataaaagaagagcacgtg
ataatacaggcggagttttatttgaacccggaccagagcggtgagttc
atgttcgattttgatggcgacgagatatttcacgttgacatggcaaaa
aaggaaacggtgtggagacttgaggagtttggacgattcgcaccattt
gaggcacaaggagcactcgccaatatcgcggtggacaaggccaacctg
gagatcatgacaaaacgctccaattatacgcctatcactaatgtgccc
cctgaggttactgtgctcacaaattctcccgtagaacttagggaacct
aacgtcctcatatgtttcatcgacaagttcactcctccggtggtcaat
gtaacgtggcttcggaatggtaagccggtcaccacgggtgtctcagag
accgtatttctgcccagagaagaccacctcttccgcaaatttcattac
cttccctttcttccttcaacgaagacgtttacgactgcagggtcgaa
cattgggggcttgacgagccacttctcaagcattgggagttcgacgcc
ccatcaccgcttccagaaacgactgaaaacgttgtctgcgctcttggc
ctgacagtgggcctggtaggcattattatcgggaccatctttatcatc
aaaggtttgacttcccgggtcaaatttagcagatccgctgacgcaccg
gcctaccagcagggccagaaccaactctacaacgagctgaatctcggc
cgacgggaagagtatgacgtactcgacaagcggagaggtcgagaccct
gagatgggcggtaaaccgagacggaaaaatccccaagagggtctttat
aatgaactccagaaggataagatggctgaagcctattctgagataggg
atgaaaggcgagcggcggaggggtaagggccatgatggcctCCaccag
ggactctccacggcaaccaaagatacttacgacgcccttcacatgcaa
gccctcccgccacgc
```

Construct 2 (RQR8, MHC-CAR1 part B, MHC-CAR1 part A, GFP region) is provided below.

(SEQ ID NO: 405)
MGTSLLCWMALCLLGADHADACPYSNPSLCSGGGGSELPTQGTFSNVS
TNVSPAKPTTTACPYSNPSLCSGGGGSPAPRPPTPAPTIASQPLSLRP
EACRPAAGGAVHTRGLDFACDIYIWAPLAGTCGVLLLSLVITLYCNHR
NRRRVCKCPRPVVRSGSGQCTNYALLKLAGDVESNPGPPTGMVCLKLP
GGSCMTALTVTLMVLSSPLALASDENPVVHFFKNIVTPRTPPGGGGSG
GGGSGGSGDTRPRFLWQPKRECHFFNGTERVRFLDRYFYNQEESVRFD
SDVGEFRAVTELGRPDAEYWNSQKDILEQARAAVDTYCRHNYGVVESF
TVQRRVQPKVTVYPSKTQPLQHHNLLVCSVSGFYPGSIEVRWFLNGQE
EKAGMVSTGLIQNGDWTFQTLVMLETVPRSGEVYTCQVEHPSVTSPLT
VEWRARSESAQSKMLSGVGGFVLGLLFLGAGLFIYFRNQTSRVKFSRS
ADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDA

LHMQALPPRGSSGSGEGRGSLLTCGDVEENPGPMAISGVPVLGFFTIA
VLMSAQSSWAIKEEHVIIQAEFYLNPDQSGEFMFDFDGDEIFHVDMAK
KETVWRLEEFGRFASFEAQGALANIAVDKANLSIMTKRSNYTPITNVP
PEVTVLTNSPVELREPNVLICFIDKFTPPVVNVTWLRNGKPVTTGVSE
TVFLPREDHLFRKFHYLPFLPSTEDVYDCRVEHWGLDEPLLKHWEFDA
PSPLPETTENVVCALGLTVGLVGIIIGTIFIIKGLTSRVKFSRSADAP
AYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQ
ALPPRGSGATNFSLLKQAGDVEENPGPVSKGEELFTGVVPILVELDGD
VNGHKFSVSGEGSGDATYGKLTLKFICTTGKLPVPWPTLVTTLTYGVQ
CFSRYPDHMKQHDFFKSAMPEGYVQERTIFFKDDGNYKTRAEVKFEGD
TLVNRIELKGIDFKEDGNILGHKLEYNYNSHNVYIMADKQKNGIKANF
KIRHNIEDGSVQLADHYQQNTPIGDGPVLLPDNHYLSTQSALSKDPNE
KRDHMVLLEFVTAAGITLGMDSLYK*

An example nucleic acid sequence encoding Construct 2 (RQR8, MHC-CAR 1 part B, MHC-CAR1 part A, GFP region) is provided below:

(SEQ ID NO: 409)
```
atgggtacttcactgttgtgctggatggcactttgtcttttgggtg
ccgatcatgctgatgcatgtccgtactccaatcctagcctgtgctc
cggggggggagggagtgaactccctacacagggaacctctctctaat
gtctccaccaacgtctcccctgcaaaaccgaccacaacagcttgcc
cctatagtaacccttccctctgcagtggaggggggggttcacctgc
tccacgccctcctaccccgcgccaacgatcgcgtcacaaccgctc
agtcttaggccggaagcctgtaggccagcggctggcggtgcggttc
atacgcggggattggattttgcctgcgacatttacatttgggctcc
gctggccggtacttgtggggtattgctgttgtctcttgttattacg
cttttattgcaatcacaggaacaggcgacgagtatgcaaatgcccgc
ggcccgtcgtgagatctgggtccggccaatgtactaactacgcttt
gttgaaacccgctggcgatgttgaaagcaacccggtcctccaaca
ggtatggtatgctcgaagctcccggcgggccctgcatgaccgctc
tcactgttactcttatggtccttagttcaccgcttgccctggcatc
tgatgagaatcccgtggttcatttttttaagaacatCgtcacaccg
cgcaccccacctgggggaggcggatctggcggaggcgggagtggag
gctcaggagacacaagaccccgattcttgtggcagcccaaaaggga
gtgccatttttcaatgggacggaacgagttcgcttccttgatcgg
tacttttacaaccaagaagagtgtacggctcgactcagatgtcg
gcgagttccgagcggtcacggaattgggcgacctgacgcggagta
ctggaactcccaaaaggatattttggagcaggcacgagcagctgtg
gacacctattgtcgacataattatggtgtggtggaatcctttacag
ttcagcggcgggtgcaacctaaagtgaccgtgtatccacctaaaac
```

-continued

```
gcaaccccccaacaccataacctcctggtgtgttccgtaagcggc ttctatcccgggtcaattgaggtcaggtggttcctcaacggtcagg aggagaaggccggaatggtaagtactggtcttatccagaacggaga ctggaccttccaaactttggtaatgttggaaacggtgccgcgatcc ggggaggtgtatacatgccaagttgaacacccgagtgttacgagcc ccctgacggttgagtggagggcgcggtcagagagcgcacaatctaa aatgctgtcaggagtaggcggatttgtactcggactcctcttttg ggcgctgggttgtttatctactttagaaaccaaacaagtagagtaa agttttcccgaagtgcggacgctcccgcgtatcagcaaggtcaaaa ccagctttacaacgaactgaacttgggacgacgcgaagagtacgat gttctcgataagcggagagggcgcgatcccgaaatgggggaaagc ctcggaggaagaacccacaagaaggcctttataatgaactgcagaa ggacaagatggcggaggcgtattccgaaataggcatgaagggtgaa cggaggagaggaaaggacatgacggactttatcaaggattgccta ccgcaactaaagacacctatgacgcgttgcacatgcaggctctccc tccgagaggttcgagcggcagtggagagggcagaggaagtctgcta acatgcggtgacgtcgaggagaatcctggcccaatggcaatatctg gtgttcctgtcctcgggttttttatcatagccgtactgatgtcagc acaggaatcatgggcgataaaagaagagcacgtgataatacaggcg gagttttatttgaacccggaccagagcggtgagttcatgttcgatt ttgatggcgacgagatatttcacgttgacatggcaaaaaaggaaac ggtgtggagacttgaggagtttggacgattcgcatcatttgaggca caaggagcactcgccaataccgcggtggacaaggccaacctggaga tcatgacaaaacgctccaattatacgcctatcactaatgtgccccc tgaggttactgtgctcacaaattctcccgtagaacttagggaacct aacgtcctcatatgtttcatcgacaagttcactcctccggtggtca atgtaacgtggcttcggaatggtaagccggtcaccacgggtgtctc agagaccgtatttctgcccagagaagaccacccttccgcaaattt cattaccttcccttcttccttcaacggaagacgtctacaactgca
```

```
gggtcgaacattgggggcttgacgagccacttctcaagcatcggga gttcgacgccccataccgcttccagaaacgactgaaaacgttgtc tgcgctcttggcctgacagtgggcctggtaggcattattatcggga ccatctttatcatcaaaggtttgacttcccgggtcaaatttagcag atccgctgacgcaccggcctaccagcagggccagaaccaactctac aacgagctgaatctcggccgacgggaagagtatgacgtactcgaca agcggagaggtcgagaccctgagatgggcggtaaaccgagacggaa aaatccccaagagggtctttataatgaactccagaaggataagatg gctgaagcctattctgagatagggatgaaaggcgagcggcggaggg gtaagggccatgatggcctttaccagggactctccacggcaaccaa agatacttacgacgcccttcacatgcaagccctcccgccacgcgga tccggcgcaacaaacttctctctgctgaaacaagccggagatgtcg aagagaatcctggaccggtgagcaagggcgaggagctgttcaccgg ggtggtgcccatcctggtcgagctggacggcgacgtaaacggccac aagttcagcgtgtctggcgagggcgagggcgatgccacctacggca agctgaccctgaagttcatctgcaccaccggcaagctgcccgtgcc ctagcccaccctcgtgacccacctgacctacggcgtgcagtgcttc agccgctaccccgaccacatgaagcagcacgacttcttcaagtccg ccatgcccgaaggctacgtccaggagcgcaccatcttcttcaagga cgacggcaactacaagacccgcgccgaggtgaagttcgagggcgac acccctggtgaaccgcatcgagctgaagggcatcgacttcaaggagg acggcaacatcctggggcacaagctggagtacaactacaacagcca caacgtctatatcatggccgacaagcagaagaacggcatcaaggcg aacttcaagatccgccacaacatcgaggacggcagcgtgcagctcg ccgaccactaccagcagaacacccccatcggcgacggccccgtgct gctgcccgacaaccactacctgagcacccagtccgccctgagcaaa gaccccaacgagaagcgcgatcacatggtcctgctggagttcgtga ccgccgcgggatcactctcggcatggacgagctgtacaagtaa
```

The amino acid sequences of exemplary CS-1 targeting CAR constructs are provided below (note that these designs contain a 4-1BB domain which may be replaced with a CD28 domain):

Anti-CS1-CAR-v1 (Luc63-V1 CAR):

(SEQ ID NO: 129)

MALPVTALLLPLALLLHAARPEVKLLESGGGLVQPGGSLKLSCAASGFDFSRYWMSWVRQAPGKGLEWIGEINPD

SSTINYTPSLKDKFIISRDNAKNTLYLQMSKVRSEDTALYYCARPDGNYWYFDVWGAGTTVTVSSGGGGSGGGGS

GGGGSDIVMTQSHKFMSTVGDRVSITCKASQDVGIAVAWYQQKPGQSPKLLIYWASTRHTGVPDRFTGSGSGTD

FTLTISNVQSEDLADYFCQQYSSYPYTFGGGTKLEIKGLAVSTISSFFPPGYQKRGRKKLLYIFKQPFMRPVQTT

QEEDGCSCRFPEEEEGGCELRVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

-continued

Anti-CS1-CAR-v2 (Luc63-V2 CAR):

(SEQ ID NO: 130)
MALPVTALLLPLALLLHAARPEVKLLESGGGLVQPGGSLKLSCAASGFDFSRYWMSWVRQAPGKGLEWIGEINPD
SSTINYTPSLKDKFIISRDNAKNTLYLQMSKVRSEDTALYYCARPDGNYWYFDVWGAGTTVTVSSGGGGSGGGGS
GGGGSDIVMTQSHKFMSTSVGDRVSITCKASQDVGIAVAWYQQKPGQSPKLLIYWASTRHTGVPDRFTGSGSGTD
FTLTISNVQSEDLADYFCQQYSSYPYTFGGGTKLEIKTTTPAPRPPTPAPTIASQPLSLRPEACRPAAGGAVHTR
GLDFACDIYIWAPLAGTCGVLLLSLVITLYCKRGRKKLLYIFKQPFMRPVQTTQEEDGCSCRFPEEEEGGCELRV
KFSRSADAPAYQQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

Anti-CS1-CAR-v3 (Luc63-V3 CAR):

(SEQ ID NO: 131)
MALPVTALLLPLALLLHAARPEVKLLESGGGLVQPGGSLKLSCAASGFDFSRYWMSWVRQAPGKGLEWIGEINPD
SSTINYTPSLKDKFIISRDNAKNTLYLQMSKVRSEDTALYYCARPDGNYWYFDVWGAGTTVTVSSGGGGSGGGGS
GGGGSDIVMTQSHKFMSTSVGDRVSITCKASQDVGIAVAWYQQKPGQSPKLLIYWASTRHTGVPDRFTGSGSGTD
FTLTISNVQSEDLADYFCQQYSSYPYTFGGGTKLEIKEPKSPDKTHTCPPCPAPPVAGPSVFLFPPKPKDTLMIA
RTPEVTCVWDVSHEDPEVKFNVfYVDGVEVHNAKTKPREEQYNSTYRVVSVLTVLHQDWLNGKSYKCKVSNKALP
APIEKTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGKKRGRKKLLYIFKQPFMRPVQTTQEEDGCSCRF
PEEEEGGCELRVKFSRSADAPAYQQGQNQLYNELNLGRREEYDVLDKRRGRDPEMGGKPRRKNPQEGLYNSLQKD
KMAEAYSEIGMKGERRRGKGHDGLYQGLSTATKDTYDALHMQALPPR

Anti-CS1-CAR-v4 (Luc90-V1 CAR):

(SEQ ID NO: 132)
MALPVTALLLPLALLLHAARPQVQLQQPGASLVRPGASVKLSCKASGYSFTTYWMNWVKQRPGQGLEWIGMIHPS
DSETRLNQKFKDKATLTVDKSSSTAYMQLSSPTSEDSAVYYCARSTMIATRAMDYWGQGTSVTVSSGGGGSGGGG
SGGGGSDIVMTQSQKSMSTSVGDRVSITCKASQDVITGVAWYQQKPGQSPKLLIYSASYRYTGVPDRFTGSGSGT
DFTFTISNVQAEDLAVYYCQQHYSTPLTFGAGTKLELKGLAVSTISSFFPPGYQKRGRKKLLYIFKQPFMRPVQT
TQEEDGCSCREPESEEGGCELRVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR

Anti-CS1-CAR-v5 (Luc90-V2 CAR):

(SEQ ID NO: 133)
MALPVTALLLPLALLLHAARPQVQLQQPGAELVRPGASVKLSCKASGYSFTTYWMNWVKQRPGQGLEWIGMIHPS
DSETRLNQKFKDKATLTVDKSSSTAYMQLSSPTSEDSAVYYCARSTMIATRAMDYWGQGTSVTVSSGGGGSGGGG
SGGGGSDIVMTQSQKSMSTSVGDRVSITCKASQDVITGVAWYQQKPGQSPKLLIYSASYRYTGVPDRFTGSGSGT
DFTFTISNVQAEDLAVYYCQQHYSTPLTFGAGTKLELKTTTPAPRPPTPAPTIASQPLSLRPSACRPAAGGAVHT
RGLDFACDIYIWAPLAGTCGVLLLSLVITLYCKRGRKKLLYIFKQPFMRPVQTTQSEDGCSCRFPEEEEGGCELR
VKFSRSADAPAYQQGQNQLYNSLNLGRREEYDVLDKRRGRDPEMGGKPRRKNPQEGLYNELQKDKMAEAYSEIGM
KGERRRGKGHDGLYQGLSTATKDTYDALHMQALPPR

Anti-CS1-CAR-v6 (Luc90-V3 CAR):

(SEQ ID NO: 134)
MALPVTALLLPLALLLHAARPQVQLQQPGAELVRPGASVKLSCKASGYSFTTYWMNWVKQRPGQGLEWIGMIHPS
DSETRLNQKFKDKATLTVDKSSSTAYMQLSSPTSEDSAVYYCARSTMIATRAMDYWGQGTSVTVSSGGGGSGGGG
SGGGGSDIVMTQSQKSMSTSVGDRVSITCKASQDVITGVAWYQQKPGQSPKLLIYSASYRYTGVPDRFTGSGSGT
DFTFTISNVQAEDLAVYYCQQHYSTPLTFGAGTKLELKSPKSPDKTHTCPPGPAPPVAGPSVFLFPPKPKDTLMI
ARTPEVTCVVVDVSHEDPEVKFNWYVDGVSVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNSLQK

DKMAEAYSEIGMKGSRRRGKGHDGLYQGLSTATKDTYDALHMQALPPR

Anti-CA1-CAR-v7 (Luc34-V1 CAR):

(SEQ ID NO: 135)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKGLAVSTISSFFPPGYQKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

Anti-CS1-CAR-v8 (Luc34-V2 CAR):

(SEQ ID NO: 136)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKTTTPAPRPPTPAPTIASQPLSLRPEACRPAAGGAVH

TRGLDFACDIYIWAPLAGTCGVLLLSLVITLYCKRGRKKLLYIFKQPFMRPVQTTQEEDGCSCRFPEEEEGGCEL

RVKFSRSADAPAYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

Anti-CS1-CAR-v9 (Luc34-V3 CAR):

(SEQ ID NO: 137)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKEPKSPDKTHTCPPCPAPPVAGPSVFLFPPKPKDTLM

IARTPEVTCVVVDVSHEDPSVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGKKRGRKKLLYIFKQPFMRPVQTTQEEDGCSC

RFPEEEEGGCELRVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

Anti-CS1-CAR-v10 (LucX1-V1 CAR)

(SEQ ID NO: 138)

MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSETTVTQSPASLSMAIGEKVTIRCITSTDIDDDMNWYQQKPGEPPKLLISEGNTLRPGVPSRFSSSGYGT

DFVFTIENMLSEDVADYYCLQSDNLPLTFGGGTKLEIKGLAVSTISSFFPPGYQKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Anti-CS1-CAR-v11 (LucX1-V2 CAR)

(SEQ ID NO: 139)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISCATSLETGVPSRFSGSGSG

KDYTLSITSLQTEDVATYYCQQYWSTPWTFGGGTKLEIKTTTPAPRPPTPAPTIASQPLSLRPFACRPAAGGAVH

TRGLDFACDIYIWAPLAGTCGVLLLSLVITLYCKRGRKKLLYIFKQPFMRPVQTTQEEDGCSCRFPEEEEGGCEL

Anti-CS1-CAR-v12 (LucX1-V3 CAR):

(SEQ ID NO: 140)
MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSETTVTQSPASLSMAIGEKVTIRCITSTDIDDDMNWYQQKPGEPPKLLISEGNTLRPGVPSRFSSSGYGT

DFVFTIENMLSEDVADYYCLQSDNLPLTFGGGTKLEIKEPKSPDKTHTCPPCPAPPVAGPSVFLFPPKPKDTLMI

ARTPEVTCVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNELQK

DKMAEAYSEIGMKGSRRGKGHDGLYQGLSTATKDTYDALHMQALPPR

Anti-CS1-CAR-v13 (LucX2-V1 CAR):

(SEQ ID NO: 141)
MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGSDIVMTQSHKFMSTSVGDRVSITCKASQDVSTAVAWYQQKPGQSPKLLIYSASYRYTGVPDRFTGSGSGTD

FTFTISSVQAEDLAVYYCQQHYSTPPYTFGGGTKLEIKGLAVSTISSFFPPGYQKRGRKKLLYIFKQPFMRPVQT

TQEEDGCCRFPEEEEGGCELRVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

Anti-CS1-CAR-v14(LucX2-V2 CAR):

(SEQ ID NO: 142)
MALPVTALLLPLALLLHAARPQVQLQQSGPSLVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSDIVMTQSHKFMSTSVGDRVSITCKASQDVSTAVAWYQQKPGQSPKLLIYSASYRYTGVPDRFTGSGSGT

DFTFTISSVQAEDLAVYYCQQHYSTPPYTFGGGTKLEIKTTTPAPRPPTPAPTIASQPLSLRPEACRPAAGGAVH

TRGLDFADIYIWAPLAGTCGVLLLSLVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGLYNELQKDKMAEAYSSIGM

KGERRRGKGHDGLYQGLSTATKDTYDALHMQALPPR

Anti-CS1-CAR-v15 (LucX2-V3 CAR):

(SEQ ID NO: 143)
MALPVTALLLPLALLLHAARPQVQLQQSGPSLVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSDIVMTQSHKFMSTSVGDRVSITCKASQDVSTAVAWYQQKPGQSPKLLIYSASYRYTGVPDRFTGSGSGT

DFTFTISSVQAEDLAVYYCQQHYSTPPYTFGGGTKLEIKEPKSPDKTHTCPPCPAPPVAGPSVFLFPPKPKDTLM

IARTPEVCVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNSLQK

DKMAEAYSEIGMKGERRRGKGHDGLYQGLSTATKDTYDALHMQALPPR (iii) Preparation of MHC-CARs

Any of the MHC-CAR constructs described herein can be prepared by a routine method, such as recombinant technology. Methods for preparing the chimeric receptors herein involve generation of a nucleic acid or a nucleic acid set that encodes or collectively encodes a MHC-CAR construct (including a single polypeptide or two subunits). In some embodiments, the nucleic acid also encodes a self-cleaving peptide (e.g., P2A, T2A, or E2A peptide) between the coding sequences for the two subunits of a MHC-CAR, or between the coding sequence for a MHC-CAR and the coding sequence for other genes to be co-expressed with the MHC-CAR in a host cell (see discussions below).

Sequences of each of the components of the MHC-CARs may be obtained via routine technology, e.g., PCR amplification from any one of a variety of sources known in the art. In some embodiments, sequences of one or more of the components of the MHC-CARs are obtained from a human cell. Alternatively, the sequences of one or more components of the MHC-CARs can be synthesized. Sequences of each of the components (e.g., domains) can be joined directly or indirectly (e.g., using a nucleic acid sequence encoding a peptide linker) to form a nucleic acid sequence encoding the MHC-CAR, using methods such as PCR amplification or ligation. Alternatively, the nucleic acid encoding the MHC-CAR may be synthesized. In some embodiments, the nucleic acid is DNA. In other embodiments, the nucleic acid is RNA.

Any of the MHC-CAR proteins, nucleic acid encoding such, and expression vectors carrying such nucleic acid, all of which are within the scope of the present disclosure, can be mixed with a pharmaceutically acceptable carrier to form a pharmaceutical composition, which is also within the scope of the present disclosure. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids: hydrophobic polymers; monosaccharides; disaccharides; and other carbohydrates; metal complexes; and/or non-ionic surfactants. See, e.g. *Remington: The Science and Practice of Pharmacy* 20th Ed. (2000) Lippincott Williams and Wilkins, Ed. K. E. Hoover.

II. Genetically Engineered Immune Cells Expressing MHC-CARs (i) MHC-CAR-Expressing Immune Cells Immune cells expressing the MHC-CAR described herein provide a specific population of cells that can recognize pathogenic cells (e.g., autoreactive T cells) involved in autoimmune diseases via MHC/peptide-TCR engagement. The interaction between the MHC-peptide portion of the MHC-CAR and the cognate TCR on the pathogenic cells would activate the MHC-CAR expressing immune cells via the signaling domains(s) of the MHC-CAR (optionally by recruiting cell membrane signaling molecules of the immune cells), leading to proliferation and/or effector functions of the MHC-CAR-expressing immune cells, which in turn eliminate the pathogenic cells. The immune cells can be T cells, NK cells, macrophages, neutrophils, eosinophils, or any combination thereof. In some embodiments, the immune cells are T cells. In some embodiments, the immune cells are NK cells. Specific examples are provided in Examples below.

The population of immune cells can be obtained from any source, such as peripheral blood mononuclear cells (PBMCs), bone marrow, tissues such as spleen, lymph node, thymus, tumor tissue, or established cell lines. A source suitable for obtaining the type of immune cells desired would be evident to one of skill in the art. In some embodiments, the population of immune cells is derived from PBMCs. The type of immune cells desired (e.g., T cells, NK cells, macrophages, neutrophils, eosinophils, or any combination thereof) may be expanded within the population of cells obtained by co-incubating the cells with stimulatory molecules, for example, anti-CD3 and anti-CD28 antibodies may be used for expansion of T cells.

To construct the immune cells that express any of the MHC-CAR constructs described herein, expression vectors for stable or transient expression of the chimeric receptor construct may be constructed via conventional methods as described herein and introduced into immune host cells. For example, nucleic acids encoding the MHC-CAR may be cloned into a suitable expression vector, such as a viral vector (e.g., a lentiviral vector) in operable linkage to a suitable promoter. The nucleic acids and the vector may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the chimeric receptors. The synthetic linkers may contain nucleic acid sequences that correspond to a particular restriction site in the vector. The selection of expression vectors/plasmids/viral vectors would depend on the type of host cells for expression of the chimeric receptors, but should be suitable for integration and replication in eukaryotic cells.

A variety of promoters can be used for expression of the MHC-CAR constructs described herein, including, without limitation, cytomegalovirus (CMV) intermediate early promoter, a viral LTR such as the Rous sarcoma virus LTR, HIV-LTR, HTLV-1 LTR, the simian virus 40 (SV40) early promoter, herpes simplex tk virus promoter. Additional promoters for expression of the chimeric receptors include any constitutively active promoter in an immune cell. Alternatively, any regulatable promoter may be used, such that its expression can be modulated within an immune cell.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9), and reporter gene for assessing expression of the MHC-CAR.

In some embodiments, the marker/sorting/suicide molecules for use in the present disclosure can be used for killing with rituximab and/or for sorting with QBEND. Philip et al., Blood 124(8):1277-87; 2014). One example is RQR8, which contains rituximab mimotope and QBEND-10 epitope. Exemplary sequences are provided below:

(SEQ ID NO: 144)
MGTSLLCWMALCLLGADHADACPYSNPSLCSGGGGSELPTQGTFSNVSTN

VSPAKPTTTACPYSNPSLCSGGGGSPAPPPTPAPTIASQPLSLRPEACRP

```
                                                          -continued
AAGGAVHTRGLDFACDIYIWAPLAGTCGVLLLSLVITLYCNHRNRRRVCK

CPRPVV (SEQ ID NO: 394)
MGTSLLCWMALCLLGADHADACPYSNPSLCSGGGGSELPTQGTFSNVSTN

VSPAKPTTTACPYSNPSLCSGGGGSPAPRPPTPATIASQPLSRPEACRP

AAGGAVHTRGLDFACDIYIWAPLAGTCGVLLLSLVITLYCNHRNRRRVCK

CPRPVV
```

An exemplary nucleic acid sequence encoding a RQR8 is provided below.

```
                                                     (SEQ ID NO: 395)
ATGGGTACTTCACTGTTGTGCTGGATGGCACTTTGTCTTTTGGGTGCCGA

TCATGCTGATGCATGTCCGTACTCCAATCCTAGCCTGTGCTCCGGGGGG

GAGGGAGTGAACTCCCTACACAGGGAACCTTCTCTAATGTCTCCACCAAC

GTCTCCCCTGCAAAACCGACCACAACAGCTTGCCCCTATAGTAACCCTTC

CCTCTGTAGTGGAGGGGGGGGTTCACCTGCTCCACGCCCTCCTACCCCCG

CGCCAACGATCGCGTCACAACCGCTCAGTCTTAGGCCGGAAGCCTGTAGG

CCAGCGGCTGGCGGTGCGGTTCATACGCGGGGATTGGATTTTGCCTGCGA

CATTTACATTTGGGCTCCGCTGGCCGGTACTTGTGGGGTATTGCTGTTGT

CTCTTGTTATTACGCTTTATTGCAATCACAGaAACAGGCGACGAGTATGC

AAATGCCCGCGGCCCGTCTG
```

In another example, the following exemplary RQR sequence tag can be affixed to a MHC-CAR construct as disclosed herein:

```
                                                     (SEQ ID NO: 145)
ACPYSNPSLCSGGGGS*ELPTQGTFSNVSTNVSPAKPTTTA*CPYSNPSLCS

GGGGS
```

The boldfaced fragment is the rituximab minotope and the underlined/italicized fragment is the QBEND-10 epitope.

Suitable vectors and methods for producing vectors containing transgenes are well known and available in the art. Any of the vectors comprising a nucleic acid sequence that encodes a MHC-CAR construct described herein is also within the scope of the present disclosure. Such a vector may be delivered into host immune cells by a suitable method. Methods of delivering vectors to immune cells are well known in the art and may include DNA electroporation, RNA electroporation, transfection reagents such as liposomes, or viral transduction. In some embodiments, the vectors for expression of the MHC-CAR are delivered to host cells by viral transduction. Exemplary viral methods for delivery include, but are not limited to, recombinant retroviruses (see, e.g., PCT Publication Nos. WO 90/07936; WO 94/03622; WO 93/25698: WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191: WO 94/28938; WO 95/11984 and WO 95/00655). In some embodiments, the vectors for expression of the chimeric receptors are retroviruses. In some embodiments, the vectors for expression of the chimeric receptors are lentiviruses.

In examples in which the vectors encoding chimeric receptors are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

Following introduction into the host cells a vector encoding any of the MHC-CAR provided herein, the cells are cultured under conditions that allow for expression of the chimeric receptor. In examples in which the nucleic acid encoding the MHC-CAR is regulated by a regulatable promoter, the host cells are cultured in conditions wherein the regulatable promoter is activated. In some embodiments, the promoter is an inducible promoter and the immune cells are cultured in the presence of the inducing molecule or in conditions in which the inducing molecule is produced. Determining whether the MHC-CAR is expressed will be evident to one of skill in the art and may be assessed by any known method, for example, detection of the chimeric receptor-encoding mRNA by quantitative reverse transcriptase PCR (qRT-PCR) or detection of the chimeric receptor protein by methods including Western blotting, fluorescence microscopy, and flow cytometry. See also Examples below. Alternatively, expression of the MHC-CAR may take place in vivo after the immune cells are administered to a subject.

Alternatively, expression of a MHC-CAR construct in any of the immune cells disclosed herein can be achieved by introducing RNA molecules encoding the MHC-CAR constructs. Such RNA molecules can be prepared by in vitro transcription or by chemical synthesis. The RNA molecules can then introduced into suitable host cells such as immune cells (e.g., T cells, NK cells, macrophages, neutrophils, eosinophils, or any combination thereof) by, e.g., electroporation. For example, RNA molecules can be synthesized and introduced into host immune cells following the methods described in Rabinovich et al., Human Gene Therapy, 17:1027-1035 and WO WO2013/040557.

The methods of preparing host immune cells expressing any of the MHC-CARs described herein may comprise expanding the host immune cells ex vivo. Expanding host immune cells may involve any method that results in an increase in the number of cells expressing MHC-CAR, for example, allowing the host cells to proliferate or stimulating the host cells to proliferate. Methods for stimulating expansion of host cells will depend on the type of host cell used for expression of the chimeric receptors and will be evident to one of skill in the art. In some embodiments, the host immune cells expressing any of the MHC-CAR described herein can be expanded ex vivo prior to administration to a subject.

(ii) Additional Genetic Modifications

One or more additional genetic modifications can be introduced into host immune cells before, concurrently with, or after the transfection of the MHC-CAR construction. For example, one or more marker and/or suicide genes may be introduced into the host immune cells. Examples include green fluorescent protein (GFP), enhanced blue fluorescent protein (eBFP), and RQR genes, such as RQR8 (a compact marker/suicide gene for T cells which combines target epitopes from CD34 and CD20. Philip et al., *Blood* 124(8):

1277-87; 2014). Such marker/suicide genes may be constructed in one expression cassette with the MHC-CAR components.

An example of an amino acid sequence of GFP is provided below:

```
                                        (SEQ ID NO: 427)
VSKGEELFTGVVPILVELDGDVNGHKFSVSGEGEGDATYGKLTLKFICTT

GKLPVPWPTLVTTLTYGVQCFSRYPDHMKQHDFFKSAMPEGYVQERTIFF

KDDGNYKTRAEVKFEGDTLVNRIELKGIDFKEDGNILGHKLEYNYNSHNV

YIMADKQKNGIKANFKIRHNIEDGSVQLADHYQQNTPIGDGPVLLPDNHY

LSTQSALSKDPNEKRDHMVLLEFVTAAGITLGMDELYK
```

An example of a nucleic acid sequence encoding GFP is provided below:

```
                                        (SEQ ID NO: 428)
gtgagcaagggcgaggagctgttcaccggggtggtgcccatcctggtgga gctggacggcgacgtaaacggccacaagttcagcgtgtctggcgagggcg agggcgatgccacctacggcaagctgaccctgaagttcatctgcaccacc ggcaagctgcccgtgccctggcccaccctcgtgaccaccctgacctacgg cgtgcagtgcttcagccgctaccccgaccacatgaagcagcacgacttct tcaagtccgccatgcccgaaggctacgtccaggagcgcaccatcttcttc aaggacgacggcaactacaagacccgcgccgaggtgaagttcgagggcga caccctggtgaaccgcatcgagctgaagggcatcgacttcaaggaggacg gcaacatcctggggcacaagctggagtacaactacaacagccacaacgtc tatatcatggccgacaagcagaagaacggcatcaaggcgaacttcaagat ccgccacaacatcgaggacggcagcgtgcagctcgccgaccactaccagc agaacacccccatcggcgacggccccgtgctgctgcccgacaaccactac ctgagcacccagtccgccctgagcaaagaccccaacgagaagcgcgatca catggtcctgctggagttcgtgaccgccgccgggatcactctcggcatgg acgagctgtacaagtaa
```

In some instances, the endogenous TCR (alpha chain, beta chain, or both) can be disrupted such that the host immune cells do not express the endogenous TCR. Deficiency in endogenous TCR could avoid undesired T cell activation. Alternative or in addition, certain cell surface receptors can be knocked out. Such surface receptors may be target receptors for disease treatment, for example, CD52, which is a target for MS treatment. Knock-out such target receptors from the MHC-CAR immune cells allows for the co-use of the MHC-CAR immune cells with therapeutic agents specific to the target receptor (e.g., and anti-CD52 antibodies such as alemtuzumab).

In some embodiments, the host immune cells may be modified with synthetic surface proteins to enhance their retention in a specific organ or tissue, for example, in the lymph nodes, in tertiary lymphoid organs, or at sites of inflammation. Doing so would allow the modified immune cells to access target pathogenic cells, while minimizing fatal off-target effects due to penetration of the blood brain barrier or free travel of the immune cells through peripheral blood. Cells early in the T cell differentiation pathway (e.g., naïve, stem cell memory, and central memory T cells) travel freely to the lymph nodes. As differentiation progresses, most effector T cells leave the lymph node. Pathologic immune cells can also travel to and accumulate at sites of inflammation. Treatment by activated CAR-T cells has a number of undesirable effects when they react with undesired targets. Interaction with heart tissue can be fatal to cardiac protein, and permeation of the brain can lead to fatal cerebral edema. Recent progress has been made in treatment of the brain cancer gliobastoma using lower doses of CAR T therapy than in systemic treatments for cancer using CD19 CAR T therapy. Brown et al., New England Journal of Medicine, 375(26):2561-2569, 2016. Resolution of inflammation has the potential to transform pathologic to protective environments. Gagliani et al., Nature, 523(7559):221-225, 2015.

Introducing one or more of lymph node retention proteins into the immune cells can enhance retention of the immune cells in the lymph node, wherein the immune cells still have access to target pathogenic cells, while undesired effects as noted above can be significantly reduced. Naïve lymphocytes enter the lymph node via high endothelial venules (HEVs). Thus, expressing or overexpressing proteins involved in HEV anchoring and/or entry can facilitate the immune cells entering into lymph node. Exemplary lymph node retention proteins include, but are not limited to, CCR7 (a chemokine receptor), MECA79 (a peripheral lymph node addressin), vascular adhesion protein-1 (VAP-1) and CD62 (selectin, a family of the cell adhesion molecules). Azzi et al., Blood 124(4):476-477, 2016; Streeter et al., J. Cell. Biol. 107:1853-186; 1988: Michie et al., Amer, J. Path. 143:1688-1698; 1993; Berg et al., J. Cell. Biol. 114:343-349: 1991; Berg et al., Nature 366:695-698; 1993; and Hemmerich et al., J. Exp. Med. 180:2219-2226; 1994. Alternatively, genes encoding proteins (e.g., sphingosine-1-phosphate receptor-1 or SIP) involved in lymphocyte egress from the thymus and lymph organs can be knocked out from the immune cells.

Chemokine receptors and adhesion receptors that promote trafficking to sites of inflammation can also bring MHC-CAR immune cells in contact with pathogenic cells that propagate immune disease [Barreiro et al., Cardiovascular research, 86(2):174-182, 2010] see Table 3 and 4. Receptors involved in recruiting immune cells that propagate inflammation include receptors (i.e., CXCR5, CCR7, CCR6) that recruit to tertiary lymphoid organs (where CXCL13, CCL19, CCL2, CCL21 are expressed).

One or more genes encoding proteins involved in targeting other organs/tissues, for example brain/CNS, bone marrow, pancreas, intestine, liver, lungs, spleen, and/or thymus, may also be introduced into or knocked-out from the immune cells.

The genes (in Table 3 and 4), by means of virally induced or temporary RNA mediated expression (possibly combined with knockout of the endogenous gene) in the therapeutic cell, may be used to route either Treg or CTL cells to the desired location or to treat-remove the desired cells. Barreiro, et al. Cardiovascular research, 86(2):174-182, 2010. If mRNA transfection is utilized then it can allow expression of the chemokine or adhesion receptor for a week. Wang and Riviere. Molecular Therapy-Oncolytics, 3:16015 2016.

TABLE 3

Chemokine receptors and natural context

| Receptor | Typically expressed on | GenBank Accession number | Ligands |
|---|---|---|---|
| CXCR1 | Neutrophils | AAY21515.1 | CXCL8, CXCL6 |
| CXCR2 | Neutrophils | NP_001548.1 | CXCL1, 2, 3, 4, 5, 7 |
| CXCR3 | T cells and some B cells | NP_001495.1 | CXCL9, 10, 11 |
| CXCR4 | Most mature and immature hematopoietic cells | CAA12166.1 | CXCL12 |
| CXCR5 | B cells and Tfh cells | NP_001707.1 | CXCL13 |
| CXCR6 | Inflammation response T cells but weak chemotaxis | NP_006555.1 | CXCL16 |
| CXCR7 | Memory B cells, T cells | NP_064707.1 | CXCL12 |
| CCR1 | Peripheral lymphocytes, memory T cells | NP_001286.1 | CCL4, CCL5, CCL6, CCL14, CCL15, CCL16, CCL23 |
| CCR2 | Monocytes, activated memory T cells, B cells, basophils | AAA19119.1 | CCL11, CCL26, CCL7, CCL13, CCL15, CCL24 & CCL5, CCL28 |
| CCR3 | Plays a role in allergic reactions, B and T cells to mucous, eosinophils, basophils | NP_001828.1 | CCL11, CCL26, CCL7, CCL13, CCL15, CCL24, CCL5 |
| CCR4 | Th2 lymphocytes, dendritic cells | NP_005499.1 | CCL3, CCL5, CCL17, CCL22 |
| CCR5 | Peripheral blood dendritic cells, CD34+ hematopoietic progenitors, activated/memory Th1 | NP_000570.1 | CCL2, CCL3, CCL4, CCL5, CCL11, CCL13, CCL14, CCL16 |
| CCR6 | Inactivated memory T cells, dendritic cells, Th17, downregulated on activated T cells | AAC51124.1 | CCL20 |
| CCR7 | Trafficking of B, T, and dendritic cells across HEV and into T cell zone of lymph nodes | AAH35343.1 | CCL19, CCL21 |
| CCR8 | Th2 cells, thymus, lymph nodes, spleen, brain, monocytes | NP_005192.1 | CCL1, CCL16 |
| CCR9 | Thymus, gut | NP_112477.1 | CCL25 |
| CCR10 | Skin, mucous layers, regulatory T cells | NP_057686.2 | CCL27, CCL28 |
| XCR1 | | NP_005274.1 | XCL1, XCL2 |
| CX3CR1 | | NP_001164642.1 | CX3CL1 |

The amino acid sequence of CCR6, provided by AAC51124.1 is shown below:

(SEQ ID NO: 391)
MSGESMNFSDVFDSSEDYEVSVNTSYYSVDSEMLLCSLQEVRQFSRLFVP

IAYSLICVFGLLGNILVVITFAFYKKARSMTDVYLLNMAIADILFVLTLP

FWAVSHATGAWVFSNATCKLLKGIYAINFNCGMLLLTCISMDRYIAIVQA

TKSFRLRSRTLPRSKIICLVVWGLSVIISSSTFVFNQKYNTQGSDVCEPK

YQTVSEPIRWKLLMLGLELLFGFFIPLMFMIFCYTFIVKTLVQAQNSKRH

KAIRVIIAVVLVFLACQIPHNMVLLVTAANLGKMNRSCQSEKLIGYTKTV

TEVLAFLHCCLNPVLYAFIGQKFRNYFLKILKDLWCVRRKYKSSGFSCAG

RYSENISRQTSETADNDNASSFTM

Example nucleic acid sequences of CCR6 are shown below:

(SEQ ID NO: 392)
atgagtggggaaagtatgaacttcagcgatgtatttgactcctccgaaga ttactttgtatctgtgaatacgagctattactccgtcgatagtgaaatgc

```
tgctctgtagtctccaagaagtccgccaattcagtcgcctcttcgttccc atcgcgtactcccttatttgtgttttggccttctgggtaacatcctggt tgtaatcacattcgctttctataaaaaagctcggagtatgactgatgttt accttcttaacatggctatagcggacattcttttttgtgcttactctccca ttctgggctgtgagccatgcaacaggggcgtgggttttttcaaatgccac atgtaagctgcttaaagggatctatgcaataaacttcaattgcgggatgc tcctgctgacatgcatcagtatggatcgatacatagctatagtacaggcg actaagtccttccgcctgcgatcccgcacactgcctaggagcaaaattat ttgcctcgtcgtatgggggctctcagtgatcatctcctccagtacgtttg tctttaaccagaaatataacacacagggttctgatgtatgtgaaccaaag tatcagacagtgagtgaaccaatacggtggaagttgcttatgttgggctt ggagctgcttttttgggttttttcatcccactgatgttcatgattttctgtt atacatttattgttaagaccttggttcaggcgcaaaatagcaagagacat aaggcaattcgagtcatcattgccgtggtgttggtcttcttggcctgtca gatccccataatatggttctgctcgtcaccgccgctaacttgggtaaga tgaatcgatcttgtcagtcgagaagttgatoggatacaccaaaactgtg acagaagtgctggccttccttcactgttgtctgaacccagttttgtatgc ttttataggacagaagtttcgaaattacttcttgaaaatcctcaaggacc tctggtgtgttcgaaggaagtacaagagctctggctttagttgcgctggg cgctacagtgagaatatatcccggcagacctccgagactgctgataatga caacgcaagttccttcactatg
                                    (SEQ ID NO: 393)
ATGAGCGGGGAATCAATGAATTTCAGCGATGTTTTCGACTCCAGTGAAGA

TTATTTTGTGTCAGTCAATACTTCATATTACTCAGTTGATTCTGAGATGT

TACTGTGCTCCTTGCAGGAGGTCAGGCAGTTCTCCAGGCTATTTGTACCG

ATTGCCTACTCCTTGATCTGTGTCTTTGGCCTCCTGGGGAATATTCTGGT

GGTGATCACCTTTGCTTTTTATAAGAAGGCCAGGTCTATGACAGACGTCT

ATCTCTTGAACATGGCCATTGCAGACATCCTCTTTGTTCTTACTCTCCCA

TTCTGGGCAGTGAGTCATGCCACTGGTGCGTGGGTTTTCAGCAATGCCAC

GTGCAAGTTGCTAAAAGGCATCTATGCCATCAACTTTAACTGCGGGATGC

TGCTCCTGACTTGCATTAGCATGGACCGGTACATCGCCATTGTACAGGCG

ACTAAGTCATTCCGGCTCCGATCCAGAACACTACCGCGCACGAAATCAT

CTGCCTTGTTGTGTGGGGCTGTCAGTCATCATCTCCAGCTCAACTTTTG

TCTTCAACCAAAAATACAACACCCAAGGCAGCGATGTCTGTGAACCCAAG

TACCAGACTGTCTCGGAGCCCATCAGGTGGAAGCTGCTGATGTTGGGCT

TGAGCTACTCTTTGGTTTCTTTATCCCTTTGATGTTCATGATATTTTGTT

ACACGTTCATTGTCAAAACCTTGGTGCAAGCTCAGAATTCTAAAAGGCAC

AAAGCCATCCGTGTAATCATAGCTGTGGTGCTTGTGTTTCTGGCTTGTCA

GATTCCTCATAACATGGTCCTGCTTGTGACGGCTGCAAATTTGGGTAAAA

TGAACCGATCCTGCCAGAGCGAAAAGCTAATTGGCTATACGAAAACTGTC

ACAGAAGTCCTGGCTTTCCTGCACTGCTGCCTGAACCCTGTGCTCTACGC

TTTTATTGGGCAGAAGTTCAGAAACTACTTTCTGAAGATCTTGAAGGACC

TGTGGTGTGTGAGAAGGAAGTACAAGTCCTCAGGCTTCTCCTGTGCCGGG

AGGTACTCAGAAAACATTTCTCGGCAGACCAGTGAGACCGCAGATAACGA

CAATGCGTCGTCCTTCACTATG
```

TABLE 4

Adhesion receptors and natural context

| Receptor | Typically expressed on | Accession number | Ligands |
|---|---|---|---|
| VLA-1 or α₁β₁ | Many cell types | NP_852478.1, AAH20057.1 | Collagens, laminins |
| VLA-2 or α₂β₁ | Many cell types | NP_002194.2, AAH20057.1 | Collagens, laminins |
| VLA-3 or α₃β₁ | Many cell types | AAI50191.1, AAH20057.1 | Laminin-5 |
| VLA-4 or α₄β₁ | Hematopoietic cells | NP_000876.3, AAH20057.1 | Fibronectin and proteinases |
| VLA-5 or α₅β₁ | Many cell types | NP_002196.4, AAH20057.1 | Fibronectin, VCAM-1 |
| VLA-6 or α₆β₁ | Many cell types | AAI36456.1, AAH20057.1 | Laminins |
| α₄β₇ | Gut | NP_000876.3, NP_00880.1 | MADCAM1 |
| α₇β₁ | Muscle | AAQ89241.1, AAH20057.1 | Laminins |
| α_Lβ₂ | T lymphocytes | NP_002200.2, NP_000202.3 | I-CAM1, I-CAM2 |
| MAC-1 or α_Mβ₂ | Neutrophils and monocytes | AAB24821.1, NP_000202.3 | I-CAM1 |
| α_IIbβ₃ | Platelets | AAI26443.1, AAI27668.1 | Fibrinogen, fibronectin |
| α_Vβ₁ | Melanocytes | AAA61631.1, AAH20057.1 | Vitronectin, fibrinogen |
| α_Vβ₃ | Activated endothelial cells | AAA61631.1, AAI27668.1 | Vitronectin, fibronectin, fibrinogen, osteopontin, Cyr61, tyroxine, Tetrac |
| α_Vβ₅ | Epithelial cells and fibroblasts | AAA61631.1, NP_002204.2 | Vitronectin |
| α_Vβ₆ | Lung, mammary gland | AAA61631.1, NP_000879.2 | Fibrinonectin and TGF-β 1, 3 |
| α_Vβ₈ | Neural tissues | AAA61631.1, NP_002205.1 | Fibrinonectin and TGF-β 1, 3 |
| α₆β₄ | Epithelial cells | AAA61631.1, CAB61345.1 | Laminin |

Alternatively or in addition, genes that may enhance immune cell functions, e.g. proliferation, cytotoxicity, etc., can also be introduced into or knocked-out from the immune cells. Examples include TNFTNFR2 overexpression (for short-lived but more effective CD8 T cells), gld (FasL mutant; for lymphoproliferation; CTLs do not kill via Fas-FasL pathway); lpr (Fas mutant, for upregulation of FasL—target cells resistant to FasL-mediated apoptosis)c Granzyme B* deficient (delayed nuclear apoptotic changes in target cells); Granzyme A & B* deficient (delayed nuclear apoptotic changes in target cells); Perform deficient (complete absence of granule-mediated apoptosis); Perforin and FasL deficient (defective granule-mediated and Fas-mediated apoptosis); Cathepsin C (dipeptidyl-peptidase) deficient (fails to produce active granzymes and some haematopoietic serine proteases); FAS (CD95) underexpression; and/or FASL overexpression.

Table 5 below lists additional genetic modifications of the MHC-CAR T cells or co-treatment described herein and the accompanying advantages arising therefrom.

TABLE 5

Genetic Modifications or Co-Treatment and Benefits Thereof

| Genetic Modifications | Advantages |
|---|---|
| TCR knockout<br>CIITA deletion (to remove endogenous MHC class II expression)<br>CS-1 (CD319) deletion (which is present on T cells) | Reduce fraternal killing of MHC-CAR T cells by natural CD8+ T cells with an affinity to the peptide-MHC in the MHC-CAR, thereby extending the life-span of the MHC-CAR T cells. (Without the genetic modifications, the MHC-CAR T cells would still be cytotoxic and effective, but would have a short life-span.) |
| Fas deletion, which optionally can be in combination of FasL overexpression<br>PD-1 deletion, which optionally can be in combination with PD-L1 and/or PD-L2 overexpression<br>Co-express of CS-1 CAR (conventional CAR construct having an extracellular domain specific to CS-1)<br>Co-express of CD19 CAR (conventional CAR construct having an extracellular domain specific to CD19) | Enhance activity to eliminate CD8 cytotoxic T cells, antigen-presenting cells (APCs), and/or B cells |
| PD-L1 overexpression, which may optionally be in combination with PD-1 deletion<br>PD-L1 + CTLA4-Ig, which may optionally may be in combination with PD-1 deletion<br>FasL overexpression, which may optionally be in combination with Fas deletion<br>Galectin 9 expression, which may optionally be in combination with Tim-3 deletion<br>CS-1 deletion (when CS-1 CAR is used to reduce fraternal killing)<br>Include a hinge in a MHC-CAR | Reduce the level of MHC-CAR T cell elimination by other immune cells; Inclusion of hinge may decrease/prevent killing with cell TCR by, e.g., decreasing ability for it to engage CD4 or CD8 |
| TCR knockout when allogenic cells are used (cells can be sorted to remove non-edited cells) | Reduce the risk of graft-v-host disease |
| Treg cells expressing MHC-CAR PD-1 and/or PD-L1 knockout CXCR5 expression | Reduce humoral responses to the peptide-MHC of interest (e.g., antibody responses), especially a B cell response |
| IL-35 expression<br>Inhibitors (e.g., antibodies) targeting cytokine producing B cells (e.g., targeting CD10) and/or other activated immune cells (e.g., targeting CS-1) | Reduce inflammation and/or enhance tolerogenic environment |
| Relevent chemokine receptor expression to either direct to relevant organ (Schall et al., Nature Reviews Immunology, 11(5): 355-363, 2011) or to interact with relevant cell type (example, CXCR5 for B cell, CCR6 for Th17)<br>Antigen targeting antibody scFv that contains a CD8 hinge, a transmembrane domain, and optional stimulatory and co-stimulatory domain (for Treg only). (for example an anti-MOG antibody). The relevant antibody sequence (for a subset of antigen targets in Table 1) can be generated from sequencing of commercially available human-targeted monoclonal variants using mass spectrometry. Tran et al. Scientific reports, 6: 31730, 2016. | Routing to inflamed or antigen presenting or antigen targeting environment |
| Genetically encoded kill-switches | Reduce cytokine crisis |

In some embodiments, genetic modification that lead to PD blockade can be introduced into the immune cells that express a MHC-CAR as described herein. Such modifications include one or more of PD-1 knockout, PD-L1 or L2 overexpression, or PD-L1 knockout. PD blockade may be combined with an immune-inhibitor (e.g., knockouts of CTLA-4, TIM-3, LAG3, TIGIT, IDO, or Arginase, or CTLA-41g secretion), an immunostimulator (e.g., anti-OX40, anti-CD137, IL-2, TLR ligands, or STING), and/or a kinase inhibitor (e.g., Braf inhibitor or MEK inhibitor)

Table 6 below provides exemplary genetic modifications for PD blockade, immune inhibitor, death receptor, immunostimulator, toll like receptor, kinase inhibition, master regulator, cytokine signaling, cell interaction reduction, and drug interaction related edits. The tables also provides target sequences for guide RNA using Cas9 in T cells as well as Genbank accession numbers for sequences that can be used for expression/overexpression. Genome editing using gRNAs is performed through transduction of lentivirus (lentiCRISPRv2) containing the desired gRNA and the *Streptococcus pyogenes* Cas9 nuclease. This can be perform as an alternative to delivery of TALEN RNA in the protocols. Sanjana, et al. *Nature Methods* (2014) 11(8):783-784.

TABLE 6

Exemplary Genes for Genetic Modification and Corresponding Cas9-Mediated Edits

| PD blockade related edits | Genbank accession no. | Genomic sequences (gRNA) for Cas9 targeting |
|---|---|---|
| Programmed cell death protein 1 (PDCD1) | NP_005009.2 | TGACGTTACCTCGTGCGGCC (SEQ ID NO: 146), CACGAAGCTCTCCGATGTGT (SEQ ID NO: 147), GCGTGACTTCCACATGAGCG (SEQ ID NO: 148), |

TABLE 6-continued

Exemplary Genes for Genetic Modification and Corresponding Cas9-Mediated Edits

| | | |
|---|---|---|
| | | TTGGAACTGGCCGGCTGGCC (SEQ ID NO: 149), GTGGCATACTCCGTCTGCTC (SEQ ID NO: 150), GATGAGGTGCCCATTCCGCT (SEQ ID NO: 151), |
| Programmed cell death 1 ligand 1 (CD274) | NP_005009.2 | TACCGCTGCATGATCAGCTA (SEQ ID NO: 152), AGCTACTATGCTGAACCTTC (SEQ ID NO: 153), GGATGACCAATTCAGCTGTA (SEQ ID NO: 154), ACCCCAAGGCCGAAGTCATC (SEQ ID NO: 155), TCTTTATATTCATGACCTAC (SEQ ID NO: 156), ACCGTTCAGCAAATGCCAGT (SEQ ID NO: 157) |

| Immune-inhibitor related edits | Genbank accession no. | Genomic sequences for Cas9 targeting |
|---|---|---|
| Cytotoxic T-lymphocyte protein 4 (CTLA4) | NP_005205.2 | GTACCCACCGCCATACTACC (SEQ ID NO: 158), TTGCCTATGCCCAGGTAGTA (SEQ ID NO: 159), CCTTGTGCCGCTGAAATCCA (SEQ ID NO: 160), ACCCCGAACTAACTGCTGCA (SEQ ID NO: 161), ACATAGACCCCTGTTGTAAG (SEQ 1D NO: 162), ATCCTTGCAGCAGTTAGTTC (SEQ ID NO: 163) |
| CTLA4-Ig (Orencia) | APZ76727.1 | |
| Serine/threonine-protein phosphatase 2A catalytic subunit alpha isoform (PPP2CA) | NP_002706.1 | ACATCGAACCTCTTGCACGT (SEQ ID NO: 164), TACAGCTCACCTTCTCGCAG (SEQ ID NO 165):, GGTATATCTCCTCGAGGAGC (SEQ ID NO: 166), TACACTGCTTGTAGCTCTTA (SEQ 1D NO: 167), GAGCTCTAGACACCAACGTG (SEQ ID NO: 168), CAAGCAGCTGTCCGAGTCCC (SEQ ID NO: 169) |
| Serine/threonine-protein phosphatase 2A catalytic subunit beta isoform (PPP2CB) | CAA31183.1 | AATGTGTAGCCAGCACCACG (SEQ ID NO: 170), GAACTTCCTGTAAACGATCC (SEQ 1D NO: 171), TACATACCTCCATTACAAGC (SEQ ID NO: 172), CCATCTACTAAAGCTGTAAG (SEQ ID NO: 173), CTCAATATTGTAATGCGTTC (SEQ ID NO: 174), CTCTCCATCCATAGACACAC (SEQ ID NO: 175) |
| Protein tyrosine phosphatase, non-receptor type 6 (PTPN6) | AAA35963.1 | TAAGACCTACATCGCCAGCC (SEQ ID NO: 176), GAAGAACTTGCACCAGCGTC (SEQ ID NO: 177), GTCAGCCGCATTCACCCTCG (SEQ ID NO: 178), CTGCCAGAAGTCATTGACCG (SEQ ID NO: 179), CCCAGCCGTACTATGCCACG (SEQ ID NO: 180), GCCGCTGCCCTTCCAGACGC (SEQ ID NO: 181) |

TABLE 6-continued

Exemplary Genes for Genetic Modification and Corresponding Cas9-Mediated Edits

| Gene | Accession | Sequences |
|---|---|---|
| Tyrosine-protein phosphatase non-receptor type 22 (PTPN22) | AAD00904.1 | GTAGCGGAATCCTCATCAG (SEQ ID NO: 182), CAAAACCTATCCTACAACTG (SEQ ID NO: 183), TTAGGGAGTTTATGGACCCA (SEQ ID NO: 184), CTCAGCCACAGTTGTAGGAT (SEQ ID NO: 185), TCACTGTACCTTAATGAAGT (SEQ ID NO: 186), TCCTTTATCTACAACCCTCC (SEQ ID NO: 187) |
| Lymphocyte activation gene 3 protein (LAG3) | CAA36243.3 | TCCATAGGTCCCCAACGCTC (SEQ ID NO: 188), GTTCCGGAACCAATGCACAG (SEQ ID NO: 189), GCGAGAAGTCCCCGCGCTGC (SEQ ID NO: 190), TGACCCCTGCTCTTCGCAGA (SEQ ID NO: 191), CGCCGGCGAGTACCGCGCCG (SEQ ID NO: 192), TGGGCGGTCAGGGCGGCTGA (SEQ ID NO: 193) |
| Hepatitis A virus cellular receptor 2 (Tim3, HAVCR2) | AAM19100.1 | CTAAATGGGGATTTCCGCAA (SEQ ID NO: 194), ATCCCCATTTAGCCAGTATC (SEQ ID NO: 195), GTGAAGTCTCTCTGCCGAGT (SEQ ID NO: 196), AGGTCACCCCTGCACCGACT (SEQ ID NO: 197), CTTACTGTTAGATTTATATC (SEQ ID NO: 198), TATAGCAGAGACACAGACAC (SEQ ID NO: 199) |
| B- and T-lymphocyte attenuator (BTLA) | AAP44003.1 | GTGACTTGGTGCAAGCTCAA (SEQ ID NO: 200), TCTGCTTGCCATTTCGTCCT (SEQ ID NO: 201), CTGTTAGCACAGTATTTCAC (SEQ ID NO: 202), CCAAAGGAAGTAAACGATAC (SEQ ID NO: 203), ATGTTCCAGATGTCCAGATA (SEQ ID NO: 204), CTTCTTCTTAATCCCATATC (SEQ ID NO: 205) |
| CD160 antigen (CD160) | AAC72302.1 | AGTTTAGTCGCGTTCCTTCC (SEQ ID NO: 206), CACTGTGCAACGGTGTGACT (SEQ ID NO: 207), GGATGTCCACAATTGCCAGC (SEQ ID NO: 208), AACTGAGAGTGCCTTCATTA (SEQ ID NO: 209), GACAGGGAACTACACAGTGA (SEQ ID NO: 210), GACAGGGAACTACACAGTGA (SEQ ID NO: 210), ATTGTGGACATCCAGTCTGG (SEQ ID NO: 212) |
| T-cell immunoreceptor with Ig and ITIM domains (TIGIT) | BAC04973.1 | TCGCTGACCGTGAACGATAC (SEQ ID NO: 213), TGGGGCCACTCGATCCTTGA (SEQ ID NO: 214), GCAGATGACCACCAGCGTCG (SEQ ID NO: 215), TCAGGCCTTACCTGAGGCGA (SEQ ID NO: 216), CATCTGCACAGCAGTCATCG (SEQ ID NO: 217), |

TABLE 6-continued

Exemplary Genes for Genetic Modification and Corresponding Cas9-Mediated Edits

| | | |
|---|---|---|
| | | ATTGAAGTAGTCATGCAGCT (SEQ ID NO: 218) |
| T-cell surface protein tactile (CD96) | AAA36662.1 | AGGCACAGTAGAAGCCGTAT (SEQ ID NO: 219), GCTGTCTATCATCCCCAATA (SEQ ID NO: 220), ACTTACCACCGACCATGCAT (SEQ ID NO: 221) |
| Cytotoxic and regulatory T-cell molecule (CRTAM) | AAC80267.1 | CACACTTTAGAGTGAGCGTC (SEQ ID NO: 222), CTCCAGTGGCTGACCCCCTC (SEQ ID NO: 223), CCACAGCAGCCCACCAGTAC (SEQ ID NO: 224) |
| Leukocyte-associated immunoglobulin-like receptor 1 (LAIR1) | AF013249.1 | TTATAATAGATGCAGCGATA (SEQ ID NO: 225), TCATTGIGACTGTTGTCCGA (SEQ ID NO: 226), GCCAGGCACCGTGATCCCCC (SEQ ID NO: 227) |
| Sialic acid-binding Ig-like lectin 7 (SIGLEC7) | AF170485.1 | CATCCTTATCCCCGGTACCC (SEQ ID NO: 228), CAGAGAGCTTCTGAGCTCGAC (SEQ ID NO: 229), AGTGTTGCTGGGGGCGGTCG (SEQ ID NO: 230 |
| Sialic acid-binding Ig-like lectin 9 (SIGLEC9) | AF135027.1 | GACGATGCAGAGTTCCGTGA (SEQ ID NO: 231), ACTCACAGGACACGTTGAGA (SEQ ID NO: 232), TACCCTGGCCCAGTAGTTCA (SEQ ID NO: 233) |
| Natural killer cell receptor 2B4 (CD244) | AF105261.1 | ACCTTCGTCTGTATGCTGTT (SEQ ID NO: 234), ACCAAACAGCATACAGACGA (SEQ ID NO: 235), CTACTCTATGATCCAGTCCC (SEQ ID NO: 236) |
| Death receptors and pathway edits | | |
| Tumor necrosis factor ligand superfamily member 10 (TRAIL) | AAC50332.1 | ACTCCGTCAGCTCGTTAGAA (SEQ ID NO: 237), GTTCATACTCTCTTCGTCAT (SEQ ID NO: 238), AGAGTAGCAGCTCACATAAC (SEQ ID NO: 239) |
| Tumor necrosis factor receptor superfamily member 10B (TNFRSF10B) | AF018657.1 | TTCCAGAGCTCACAACGACC (SEQ ID NO: 240), ATAGTCCTGTCCATATTTGC (SEQ ID NO: 241), AGATACTCACGATCTCATTG (SEQ ID NO: 242) |
| Tumor necrosis factor receptor superfamily member 10A (TNFRSF10A) | AAC51226.1 | AGGTCAAGGATTGTACGCCC (SEQ ID NO: 243), GAAGTCCCTGCACCACGACC (SEQ ID NO: 244), TTTGGTTGTTCCGTTGCTGT (SEQ ID NO: 245) |
| Caspase-8 (CASP8) | CAA66853.1 | TGATCGACCCTCCGCCAGAA (SEQ ID NO: 246), GGGTCGATCATCTATTAATA (SEQ ID NO: 247), TCCTTTGCGGAATGTAGTCC (SEQ ID NO: 248) |
| Caspase-10 (CASP10) | AAC50644.1 | CTATGTATCCTTTCGGCATG (SEQ ID NO: 249), |

TABLE 6-continued

Exemplary Genes for Genetic Modification and Corresponding Cas9-Mediated Edits

| | | |
|---|---|---|
| | | TCTTCTGCCGTATGATATAG (SEQ ID NO: 250), GTGAGACATGATCTCCCGAA (SEQ ID NO: 251) |
| Caspase-3 (CASP3) | AAA65015.1 | ATGTCGATGCAGCAAACCTC (SEQ ID NO: 252), ATTATACATAAACCCATCTC (SEQ ID NO: 253), AATGGACTCTGGAATATCCC (SEQ ID NO: 254) |
| Caspase-6 (CASP6) | AAC50168.1 | ATAGAGACAATCTTACCCGC (SEQ ID NO: 255), AAGATTGTCTCTATCTGCGC (SEQ ID NO: 256), AAATGTGATTGCCTTCGCCA (SEQ ID NO: 257) |
| Caspase-7 (CASP7) | AAC50303.1 | CGTTTGTACCGTCCCTCTTC (SEQ ID NO: 258), TGCGATCCATCAAGACCACC (SEQ ID NO: 259), TTGATATTTAGGCTTGCCGA (SEQ ID NO: 260) |
| FAS-associated death domain protein (FADD) | AAA86517.1 | AGTCGTCGACGCGCCGCAGC (SEQ ID NO: 261), AGCGGCCCATCAGGACGCTT (SEQ ID NO: 262), GCGGCGCGTCGACGACTTCG (SEQ ID NO: 263) |
| Tumor necrosis factor receptor superfamily member 6 (FAS) | AAA63174.1 | GTGTAACATACCTGGAGGAC (SEQ ID NO: 264), TACATCTGCACTTGGTATTC (SEQ ID NO: 265), CTAAAACTTACTTGGTGCAA (SEQ ID NO: 266) |
| IDO | AAA36081.1 | TCTCAACTCTTTCTCGAAGC (SEQ ID NO: 267), CTGCCTGATCTCATAGAGTC (SEQ ID NO: 268), CAGATACTTACTCATAAGTC (SEQ ID NO: 269) |
| Arginase EIF2AK4 | AAH09350.2 | CGCTGAGAAATGACTGCACG (SEQ ID NO: 270), CATATACTTCTTCACCAGTT (SEQ ID NO: 271), ATGTACTCACACATCTGGAT (SEQ ID NO: 272) |
| Immunostimulator edits | | |
| OX40 (TRAF2) | BAA14259.1 | ACCGAATGTCCCGCGTGCAA (SEQ ID NO: 273), GCCTTTGCACGCGGGACATT (SEQ ID NO: 274), GGGGACCCTGAAAGAATACG (SEQ ID NO: 275) |
| CD137 (TNFRSF9) | TNFRSF9 | CCTGCGCTGGAGAAACTATT (SEQ ID NO: 276), CCTTGTAGTAACTGCCCAGC (SEQ ID NO: 277), CATAGTAGCCACTCTGTTGC (SEQ ID NO: 278) |
| IL2 | CAA25292.1 | CAATATCAACGTAATAGTTC (SEQ ID NO: 279), GACTTAGTGCAATGCAAGAC (SEQ ID NO: 280), GATATTGCTGATTAAGTCCC (SEQ ID NO: 281) |

TABLE 6-continued

Exemplary Genes for Genetic Modification and Corresponding Cas9-Mediated Edits

| | | |
|---|---|---|
| Stimulator of interferon genes protein (STING or TMEM173) | AC146648.1 | GCGGGCCGACCGCATTTGGG (SEQ ID NO: 282), CATATTACATCGGATATCTG (SEQ ID NO: 283), ACTCTTCTGCCGGACACTTG (SEQ ID NO: 284) |
| Toll like receptor edits | | |
| TLR1 | AAC34137.1 | TTATAGAGGAACCCTACTAA (SEQ ID NO: 285), TTGTGGGCACCTTACTGAGT (SEQ ID NO: 286), CGAACACATCGCTGACAACT (SEQ ID NO: 287) |
| TLR2 | AAC34377.1 | GTTAACGTTTCCACTTTACC (SEQ ID NO: 288), TTCCCGCTGAGCCTCGTCCA (SEQ ID NO: 289), TATCTAATTTATCGTCTTCC (SEQ ID NO: 290) |
| TLR3 | AAC34134.1 | TTCGGAGCATCAGTCGTTGA (SEQ ID NO: 291), TTCAACGACTGATGCTCCGA (SEQ ID NO: 292), CATGCACTCTGTTTGCGAAG (SEQ ID NO: 293) |
| TLR4 | AAC80227.1 | TTCTCCCAGAACCAAACGA (SEQ ID NO: 294), GATGATGTCTGCCTCGCGCC (SEQ ID NO: 295), ATGCCCCATCTTCAATTGTC (SEQ ID NO: 296) |
| TLR5 | AAC34376.1 | TATTCGGCCATCAAAGGAGC (SEQ ID NO: 297), GACTAAGCCTCAACTCCAAC (SEQ ID NO: 298), TATACAACICTATTAGCTGCG (SEQ ID NO: 299) |
| TLR6 | BAA78631.1 | GAACTACATCGCTGAGCTIC (SEQ ID NO: 300), GCCATCCTATTGTGAGTTTC (SEQ ID NO: 301), TGTCTCCAATTTAACTAACG (SEQ ID NO: 302) |
| TLR7 | AAF60188.1 | AAGGAATAGTCACCTCCGTA (SEQ ID NO: 303), AATGGGGCATTATAACAACG (SEQ ID NO: 304), GGTGAGGTTCGTGGTGTTCG (SEQ ID NO: 305) |
| TLR8 | AAF64061.1 | GTGCAGCAATCGTCGACTAC (SEQ ID NO: 306), AATCCCGGTATACAATCAAA (SEQ ID NO: 307), CTCGAGTTGCTTGACTTACG (SEQ ID NO: 308) |
| TLR9 | AAF72189.1 | GGCTCACGGCTATTCGGCCG (SEQ ID NO: 309), GCGTCTCCGTGACAATTACC (SEQ ID NO: 310), CCGACAGGTCCACGTAGCGC (SEQ ID NO: 311) |
| TLR10 | AAK26744.1 | CCCACATTTACGCCTATCCT (SEQ ID NO: 312), TAACATTAATAGCAGCTCGA (SEQ ID NO: 313), |

TABLE 6-continued

Exemplary Genes for Genetic Modification and Corresponding Cas9-Mediated Edits

| | | |
|---|---|---|
| | | GACCCCAGCCACAACGACAC (SEQ ID NO: 314) |
| Kinase inhibition edits | | |
| Serine/threonine-protein kinase B-raf (BRAF) | AAA35609.2 | CCCCACCAAATTTGTCCAAT (SEQ ID NO: 315), GAGGCCCTATTGGACAAATT (SEQ ID NO: 316), GTTGCTCCGTGCCACATCTG (SEQ ID NO: 317) |
| Dual specificity mitogen-activated protein kinase kinase 1 (MAP2K or MEK) | AAA36318.1 | CCATACTTACTCCGCAGAGC (SEQ ID NO: 318), TATGGTGCGTTCTACAGCGA (SEQ ID NO: 319), CCCGACGGCTCTGCAGTTAA (SEQ ID NO: 320) |
| Master regulator edits | | |
| FoxP3 | AAG53607.1 | |
| Cytokine signaling edits (The goal of one or both of these edits is to prevent or minimize conversion of therapeutic Tregs into Th17 cells due to endogeonous IL-6. Gagliani et al. *Nature*, 523(7559): 221-225 2015, Korn et al. *Proceedings of the National Academy of Sciences*, 105(47): 18460-18465, 2008. | | |
| Interleukin-6 receptor subunit alpha (IL6R) | CAA31312.1 | TCGGTGCAGCTCCACGACTC (SEQ ID NO: 321), AACTATTCATGCTACCGGGC (SEQ ID NO: 322), CGTGGTGCAGCTTCGTGCCC (SEQ ID NO: 323) |
| Interleukin-6 receptor subunit beta (IL6ST or GP130) | AAA59155.1 | AGATGCCTCAACTTGGAGCC (SEQ ID NO: 324), TTTGAGTTGCATTGTGAACG (SEQ ID NO: 325), ATTCGCTGTATGAAGGAAGA (SEQ ID NO: 326) |
| Cell interaction reducing edits TCR alpha see preferred talen edit) TCR beta (see preferred talen edit) | | |
| CIITA | CAA52354.1 | TTCCTACACAATGCGTTGCC (SEQ ID NO: 327), GATATTGGCATAAGCCTCCC (SEQ ID NO: 328), TCAACTGCGACCAGTTCAGC (SEQ ID NO: 329) |
| B7-1(CD80) | AAA36045.1 | TCGTATGTGCCCTCGTCAGA (SEQ ID NO: 330), GAGTGAATCAGACCTTCAAC (SEQ ID NO: 331), TATGGCCCGAGTACAAGAAC (SEQ ID NO: 332) |
| B7-2(CD86) | AAB03814.1 | GTAACCGTGTATAGATGAGC (SEQ ID NO: 333), ATACTCGATAGTTGAATTCT (SEQ ID NO: 334), CATCAGATCTTTCAGGTATA (SEQ ID NO: 335) |
| b2m | AAA51811.1 | ACTCACGCTGGATAGCCTCC (SEQ ID NO: 336), GAGTAGCGCGAGCACAGCTA (SEQ ID NO: 337), |

TABLE 6-continued

Exemplary Genes for Genetic Modification and Corresponding Cas9-Mediated Edits

| | | |
|---|---|---|
| | | CAGTAAGTCAACTTCAATGT (SEQ ID NO: 338) |
| UL18 | CAA68399.1 | |
| PDL2 | AAK31105.1 | |
| FasL | AAC50071.1 | GGTTGTTGCAAGATTGACCC (SEQ ID NO: 339), GAGGAACTCTAAGTATCCCC (SEQ ID NO: 340), TCTGGTTGCCTTGGTAGGAT (SEQ ID NO: 341) |
| Perforin (PRF1) | CAA31612.1 | CGCAGCCACAAGTTCGTGCC (SEQ ID NO: 342), GGAGCTGGGTGGCCGCATAT (SEQ ID NO: 343), CCCGAACAGCAGGTCGTTAA (SEQ ID NO: 344) |
| Galectin 9 (LGALS9) | AA88922.1 | |
| PVT/CD155 | AAA36461.1 | |
| Drug interaction related edits | | |
| CD52 | CAA44323.1 | CTCTTACCTGTACCATAACC (SEQ ID NO: 345), AATGCCTCCGCTTATGTTGC (SEQ ID NO: 346), TGGCATTGGCCACGAAGAAA (SEQ ID NO: 347) |
| tocilizumab-like heavy chain (for scfv) | BAJ21229.1 | |
| tocilizumab-like light chain (for scfv) | BAJ21230.1 | |
| Integrin alpha-4 (ITGA4) | CAA34852.1 | CGACTACTTCGGTAGTATGC (SEQ 1D NO: 348), CAGCATACTACCGAAGTAGT (SEQ ID NO: 349), GTGTTTGTGTACATCAACTC (SEQ ID NO: 350) |

The table below provides target sequences for TALEN edits as well as protein sequences.

TABLE 7

Primarily TALEN mediated edits

| | Sequence or Genbank Accession no. |
|---|---|
| CS1 edit related | |
| CS1 | NP_067004.3 |
| CS1v1 TALEN target | tgacttccagagag caatatggct ggttccccaa catgcctca (SEQ ID NO: 351) |
| CS1v1 left TALEN target | tgacttccagagagcaa (SEQ ID NO: 352) |
| CS1v1 left TALEN protein | MDYKDHDGDYKDHDIDYKDDDDKMAPKKKRKVGIHGVPAAVDTATLGYSQQQQEKIKPK VRSTVAQHHEALVGHGFTHAHIVALSQHPAALGTVAVKYQDMIAALPEATHEAIVGVGKQ WSGARALEALLTVAGE-LRGPPLQLDTGQLLKIAKRGGVTAVEAVHAWRNALTGAPLNLTP EQVNAIASNNGGKQALETVQRLLPVLCQAHGLTPEQVVAIASNIGGKQALETVQLLPVLC QAHGLTPEQVVAIASHDGGKQALETVQRLLPVLCQAHGLTPEQVVAIASNGGKQALETVQ RLLPVLCQAHGLTPEQVVAIASNGGGKQALETVQRLLPVLCQAHGLTPEQVVAIASHDGGK QALETQRLLPVLCQAHGLTPEQVVAIASHDGGKQALETVQRLLPVLCQAHGLTPEQVVAI ASNIGGKQALETVQRLLPVLCQAHGLTEQVVAIASNNGGKQALETVQRLLPVLCQAHGLT PEQVVAIASNIGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASNNGGKQALETVQ RLLPVLCQAHGLTPEQVVAIASHDGGKQALETVQRELLPVLCQAHGLTPEQVVAIASNIGGKQ ALETVQRLLPVLCQAHGLTPEQVVAIASNIGGRPALESIVQLSRPDPALAALTNDHLVALA |

TABLE 7-continued

Primarily TALEN mediated edits

Sequence or Genbank Accession no.

| | |
|---|---|
| | CLGGRPALDAVKKGLPHAPALIKRTNRRIPERTSHRVAGSQLVKSELEEKKSELRHKLKYVP HEYIELIEIARNSQDRILEMKVMEFFMKVYGYRGKHLGGSRKPDGAIYTVGSPIDYGVIVDT KAYSGGYNLPIGQADEMQRYVEENQTRNKHINPNEWWKVYPSSVTEFKFLFVSGHFKGNY KAQLTRLNHITNCNGAVLSVEELLIGGEMIKAGTLTLEEVRRKFNNGEINFRS (SEQ ID NO: 353) |
| CS1v1 right TALEN target | aacatgcctc accctca (SEQ ID NO: 354) |
| CS1v1 right TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVVNAIASNNGGKQALETVQRLLPVLCQAHGLTPEQVVAIASNIGGKQALETVQRLLPVLC QNHGLTPEQVVAIASNNGGKQALETVQRLLPVLCQAHGLTPEQVVAIASNNGGKQALETVQ RLLPVLCQAHGLTPEQVVAIASNNGGKQALETVQRLLPVLCQAHGLTPEQVVAIASNGGGK QALETVQALLPVLCQAHGLTPEQVVAIASNNGGKQALETVQRLLPVLCQAHGLTPEQVVAI ASNIGGKQALETNQRLLPVLCQAHGLTPEQVVAIASNNGGKQALETVQRLLPVLCQAHGLT PEQVVAIASNNGGIKQALETVQRLLPVLCQAHGLTPEQVVAIASHDGGKQALETVQRLLPVL CQAHGLTPEQVVIVASNIGGKQALETVQRLLPVLCQAHGLTPEQVVAIASNGGGKQALETV QRLLPVLCQAHGLTPEQVVAIASNNGGKQALETVQRLLPVLCQAHGLTPEQVVAIASNGGG KQALETVQRLLPVLCQAHGLTPEQVVAIASNGGGRPALESIVAQLSRPDRALAALTNDHLVA LACLGGRPALDAVKKGLPHAPALIKRTNRRIPERTSHRVAGSQLVKSELEEKKSELRHKLKY VPHEYIELIEIARNSTQDRILEIMVMEFFMKVYGYRGKHLGGSRKPDGAIYTVGSPIDYGVIV DTKAYSGGYNLPIGQADEMQRYVEENQTRNKHINPNEWWKVYPSSVTEFKFLFVSGHFKG NYKAQLTRLNHITNCNGAVLSVEELLIGGEMIKAGTLTLEEVRRKFTNNGEINFRS (SEQ ID NO: 355) |
| CS1v2 TALEN target | ttccagagag caatatggct ggttccccaa catgcctcac cctcatcta (SEQ ID NO: 356) |
| CS1v2 left TALEN target | ttccagagag caatatg (SEQ ID NO: 357) |
| CS1v2 left TALEN protein | MDYKLMIDGDYKTYRDIDYKDDDDKMARKKKRKVGIEGVPAAVDERTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVVAIASNGGGKQALETNQRLLPVLCQAHGLTPEQVVAIASHDGGKQALETVQRLLPVLC QAHGLTPEQVVAIASHDGGKQALETVQRLLPVLCQAHGLTPEQVVAIASNIGGKQALETVQ RLLPVCQAHGLTPEQVVAIASNNGGKQALETVQRLLPVLCQAHGLTPEQVVAIATASNIGGKQ ALETVQRLLPVLCQAHGLTPEQVVAIASNNGGKQALETVQRLLPVLCQAHGLTPEQVVAIA SNIGGKQALETVQRLLPVLCQAHGLTPEQVVAIASNNGGKQALETVQRLLPVLCQAHGLTP EQVVAIASHDGGKQALETVQRLLPVLCQAHGLTPEQVVAIASNIGGKQALETVQRLLPVLC QAHGLTPEQVVAIASNIGGKQALETVQRLLPVLCQAHGLTPEQVVAIASNGGGKQALETVQ RLLPVLCQAHGLTPEQVVAIASNIGGKQALETVQRLLPVLCQAHGLTPEQVVAIASNGGGKQ ALETVQRLLPVLCQAHGLTPEQVVAIASNNGGKQALETVQRLLPVLCQAHGLTPEQVVALA CLGGRPALDAVKKGLPHAPALIKRTNRRIPERTSHRVAGSQLVKSELEEKKSELRHKLKYVP HEYIELIEIARNSTQDRTIEMKVMEFFMKVYGYRGKHLGGSRKPDGAIYTVGSPIDYGVIVDT KAYSGGYNLPIGQADEMQRYVEENQTRNKHINPNEWWKVYPSSVTEFKFLFVSGHFKGY KAQLTRLNHTITNCNGAVLSVEELLIGGEMIKAGTLTLEEVRRKFNNGEINFRS (SEQ ID NO: 358) |
| CS1v2 right TALEN target | tgcctcaccc tcatcta (SEQ ID NO: 359) |
| CS1v2 right TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAYKYQDMIAALPEATHEAIVGVGKQ WSGARALEALLTVAGELRGPPLQLDTGQLLKIAKGGVTAVTAVEAVHAWRNALTGAPLNLTP EQVVAIASNIGGKQALETVQRLLPVLCQAHGLTPEQVVAIASNNGGKQALETVQRLLPVLC QAHGLTPEQVVAIASNIGGKQALETVQRLLPVCQAHGLTPEQVVAIASNGGGKQALETVQ RLLPVLCQAHGLTPEQVVAIASNNGGKQALETVQRLLPVLCQAHGLTPEQVVAIASNIGGKQ ALETVQRLLPVLCQAHGLTPEQVVAIASNNGGKQALETVQALLPVLCQAHGLTPEQVVAIA SNNGGKQALETVQRLLPVLCQAHGLTPEQVVAIASNNGGKQALETVQRLLPVLCQAHGLTP EQVVAIASNGGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASNNG GKQALETVQRLLPVLCQAHGLTPEQVVAIASNNGGKQALETVQRLLPVLCQAHGLTPEQVV AIASHDGGKQALETVQRLLPVLCQAHGLFPEQVVAIASNIGGRPALESIVAQLSRPDPALAAL TNDHLVALACLGGRPALDAVKKGLPHAPALIKRTNRRIPERTSHRVAGSQLVKSELEEKKSE LRHKLKYVPHEYIELIEIARNSTQDRILEMKVMEFFMKVYGYRGKHLGGSRKPDGAIYTVGS PIDYGVIVDTKAYSGCNLPIGQADEMQRYVEENQTRNKHINPNEWWKYPSSVTEFKFLF VSGHFKGNYKAQLTRLNHITNCNGAVLSVEELLIGGEMIKAGTLTLEEVRRKFNNGEINFRS (SEQ ID NO: 360) |
| CS1v3 target | ttgactctat tgtctgacc ttcaacacaa ccctcttgt caccataca (SEQ ID NO: 361) |
| CS1v3 left TALEN target | ttgactctat tgtagg (SEQ ID NO: 362) |

татьTABLE 7-continued

Primarily TALEN mediated edits

Sequence or Genbank Accession no.

| | |
|---|---|
| CS1v3 left TALEN protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNNGGKQALETVQRLLPVLC<br>QAHGLTPEQVVAIASNIGGKQALETVQRLLPVLCQAHGLTPEQVVAIASHDGGKQALETVQ<br>RLLPVLCQAHGLTPEQVVAIASNGGGKQALETVQRLLPVLCQAHGLTPEQVVAIASHDGGK<br>QALETVQRLLPVLCQAHGLTPEQVVAIASNGGGKQALETVQRLLPVLCQAHGLTPEQVVAI<br>ASNIGGKQALETVQRLLPVLCQAHGLTPEQVVAIASNGGGKQALETVQRLLPVLCQAHGLT<br>PEQVVAIASNGGGKQALETVQRLLPVLCQAHGLTPEQVVAIASNNGGKQALETVQRLLPVL<br>CQAHGLTPEQVVIVASNGGGKQALETVQRLLPVLCQAHGLTPEQVVAIASHDGGKQALETV<br>QRLLPVLCQAHGLTPEQVVAIASNGGGKQALETVQRLLPVLCQAHGLTPEQVVAIASNNGG<br>KQALETVQRLLPVLCQAHGLTPEQVVIASNNGGRPALESIVAQLSRPDPALAALTNDHLVA<br>LACLGGRPALDAVKKGLPHAPALIKRTNRRIPERTSHRVAGSQLVKSELEEKKSELRHKLKY<br>VPHEYIELIEIARNSTQDRILEMKVMEFFMKVYGYRGKHLGGSRKPDGAIYTVGSPIDYGVIV<br>DTKAYSGGYNLPIGQADEMQRYVEENQTRNKHINPNEWWKVYPSSVTEFKFLFVSGHFKG<br>NYKAQLTRLNHITNCNGAVLSVEELLIGGEMIKAGTLTLEEVRRKFNNGEINFRS (SEQ ID<br>NO: 363) |
| CS1v3 right TALEN target | cacttgtca ccataca (SEQ ID NO: 364) |
| Cs1v3 right TALEN protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNGGGKQALETVQRLLPVLC<br>QAHGLTPEQVVAIASNIGGKQALETVQRLLPVLCQAHGLTPEQVVAIASNGGGKQALETVQ<br>RLLPVLCQAHGLTPEQVVAIASNNGGKQALETVQRLLPVLCQAHGLTPEQVVAIASNNGGK<br>QALETVQRLLPVLCQAHGLTPEQVVAIASNGGGKQALETVQRLLPVLCQAHGLTPEQVVAI<br>ASNNGGKQALETVQRLLPVLCQAHGLTPEQVVAIASNIGGKQALETVQRLLPVLCQAHGLT<br>PEQVVAIASHDGGKQALETVQRLLPVLCQAHGLTPEQVVAIASNIGGKQALETVQRLLPVLC<br>QAHGLTPEQVVAIASNIGGKQALETVQRLLPVLCQAHGLTPEQVVAIASNNGGKQALETVQ<br>RLLPVLCQAHGLTPEQVVAIASNIGGKQALETVQRLLPVLCQAHGLTPEQVVAIASNNGGKQ<br>ALETVQRLLPVLCQAHGLTPEQVVAIASNNGGRPALESIVAQLSRPDPALAALTNDHLVALA<br>CLGGRPALDAVKKGLPHAPALIKRTNRRIPERTSHRVAGSQLVKSELEEKKSELRHKLKYVP<br>HEYIELIEIARNSTQDRILEMKVMEFFMKVYGYRGKHLGGSRKPDGAIYTVGSPIDYGVIVDT<br>KAYSGGYNLPIGQADEMQRYVEENQTRNKHINPNEWWKVYRSSVTEFKFLFVSGHFKGNY<br>KAQLTRLNHITNCNGAVLSVEELLIGGEMIKAGTLTLEEVRRKFNNGEINFRS (SEQ ID<br>NO: 365) |
| CIITA edit related | |
| CIITA | NP_001273331.1 |
| CIITA TALEN target | TTCCCTCCCAGGCAGCTCacagtgtgccaccaTGGAGTTGGGGCCCCT<br>A (SEQ ID NO: 366) |
| CIITA left TALEN target | TTCCCTCCCAGGCAGCTC (SEQ ID NO: 367) |
| CITTA left TALEN protein | MDYKDHDGDYKDHDIDYKDDDDKMAPKKKRKVGIHGVPAAVDERTLGYSQQQQEKIKPK<br>VRSTVAQHHEALVGHGFTHAHIVALSQHPAALGTVAVKYQDMIAALPEATHEAWGVGKQ<br>WSGSRALEALLTVGELRGPPLQLDTGQLLKIAKRGGVTAVEAVHAWRNALTGAPLNLTP<br>EQVVAIASNGGGKQALETVQRLLPVLCQAHGLTPEQVVAIASHDGGKQALTEVQRLLPVLC<br>QAHGLTPEQVVAIASHDGGKQALETVQRLLPVLCQAHGLTPEQVVAIASHDGGKQALETVQ<br>RLLPVLCQAHGLTPEQVVAIANGGGKQALETVQRLLPVLCQAHGLTPEQVVAIASHDGGK<br>QALETVQRLLPVLCQAHGLTPEQVVAIASHDGGKQALETVQRLLPVLCQAHGLTPEQVVAI<br>ASHDGGKQALETVQRLLPVLCQAHGLTPEQVVAIASNIGGKQALETVQRLLPVLCQAHGLT<br>PEQVVAIASNNGGKQALETVQRLLPVLCQAHGLTPEQVVAIASNNGGKQALETVQRLLPVL<br>CQAHGLTPEQVVAIASHDGGKQALETVQRLLPVLCQAHGLTPEQVVAIASNIGGKQALETV<br>QRLLPVLCQAHGLTPEQVVAIASSNNGGKQALETVQRLLPVLCQAHGLTPEQVVAIASHDGG<br>KQALETVQRLLPVLCQAHGLTPEQVVAIASNGGGKQALETVQRLLPVLCQAHGLTPEQVVA<br>IASHDGGRPALESIVAQLSRPDPALAALTNDHLVALACLGGRPALDAYKKGLPHAPLIKRT<br>NRRIPERTSHRVAGSQLVKSELEEKKSELRHKLKYVPHEYIELIEIARNSTQDRILEMKVMEFF<br>MKVYGYRGKHLGGSRKPDGAIYTVGSPIDYGVIVDTKAYSGGYNLPIGQADEMQRYNEEN<br>QTRNKHINPNEWWKVYPSSVTEFKFLFVSGHFKGNYKAQLTRLNHITNCNGAVLSVEELLIG<br>GEMIKAGTLTLEEVRRKFNGEINFRS (SEQ ID NO: 368) |
| CIITA right target | TGGAGTTGGGGCCCCTA (SEQ ID NO: 369) |
| CIITA right protein | MDYKDHDGDYKDHDIDYKDDDDKMAPKKKRKVGIHGVPAAVDLRTLGYSQQQQEKIKPK<br>VRSTVAQHEEALVGHGFTHIAHIVALSQHPAALGTVAVKYQDMIAALPEATHEAIVGVGKQ<br>WSGARALEALLTVAGELRGPRLQLDTGQLLKIAKRGGVTAVEAVHAWRNALTGAPLNLTP<br>EQVVAIASNIGGKQALETVQRLLPVLCQAHGLTPEQVVAIASNNGGKQALETVQRLLPVLC<br>QAHGLTPEQVVAIASNNGGKQALETVQRLLPVLCQAHGLTPEQVVAIASNNGGKQALETVQ<br>RLLPVLCQAHGLTPEQVVAIASNNGGKQALETVQRLLPVLCQAHGLTPEQVVAIASHDGGK<br>QALETVQRLLPVLCQAHGLTPEQVVAIASHDGGKQALETVQRLLPVLCQAHGLTPEQVVAI<br>ASHDGGKQALETVQRLLPVLCQAHGLTPEQVVAILASHDGGKQALETVQRLLPVLCQAHGLT |

TABLE 7-continued

Primarily TALEN mediated edits

Sequence or Genbank Accession no.

|  |  |
|---|---|
|  | PEQVVAIASNIGGKQALETVQRLLPVLCQAHGLTPEQVVAIASNIGGKQALETVQRLLPVLC<br>QAHGLTPEQVVAIASHDGGKQALETVQRLLPVLCQAHGLTPEQVVAIASNGGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNIGGRPALESIVAQLSRPDPALAALTNDHLVAL<br>ACLGGRPALDAVKKGLPHAPALIKRINRKPERTSHRVAGSQLVKSELEEKKSELRHKLKYV<br>PHEYIELIEIARNSTQDRILEMIKVMEFFMKVYGYRGKHLGGSRKPDGAIYTVGSPIDYGVIVD<br>TKAYSGGYNLPIGQADEMQRYVEENQTRNKHKNPNEWWKVYPSSVTEFKFLSGHFKGN<br>YKAQLTRLNHITNCNGAVLSVEELLIGGEMIKAGTLTLEEVRRKFNNGEINFRS (SEQ ID<br>NO: 370) |
| CD52 edit related |  |
| CD52 | NP_001794.2 |
| CD52 target | TTCCTCCTACTCACCATcagcctcctggttatGGTACAGGTAAGAGCAA<br>(SEQ ID NO: 371) |
| CD52 left target | TTCCTCCTACTCACCAT (SEQ ID NO: 372) |
| CD52 left protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASHDGGKQALETVQRLLPVLC<br>QAHGLTPEQVVAIAHDGGKQALETVQRLLPVLCQAHGLTPEQVVAIASNGGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNGGGKQALETVQRLLPVLCQAHGLTPEQVVAI<br>ASNIGGKQALETVQRLLPVLCQAHGLTPEQVVAIASHDGGKQALETVQRLLPVLCQAHGLT<br>PEQVVAIASNGGGKQALETVQRLLPVLCQAHGLTPEQVVAIASHDGGKQALETVQRLLPVL<br>CQAHGLTPEQVVAIASNIGGKQALETVQRLLPVLCQAHGLTPEQVVAIASHDGGKQALETV<br>QRLLPVLCQAHGLTPEQVVAIASNGGGKQALETVQRLLPVLCQAHGLTPEQVVAIASNIGGK<br>QALETVQRLLPVLCQAHGLTPEQVVAIASNGGGRPALESIVAQLSRPDPALAALTNDHLVAL<br>ACLGGRPALDAVKKGLPHAPALIKRTNRRIPERTSHRVAGSQLVKSELEEKKSELRHKLKYV<br>PHEYIELEIARNSTQDRILEMKVMEFEMKVYGYRGKHLGGSRKPDGAIYINGSPIDYGVIND<br>TKAYSGGYNLPIGQADEMQRYVLENQTRNKHINPNEWWKVYPSSVTEFKFLEVSGHFKGN<br>YKAQLTRLNHITNCNGAVLSVEELLIGGEMIKAGTLTLEEVRRKFNNGEINFRS (SEQ ID<br>NO: 373) |
| CD52 right target | GGTACAGGTAAGAGCAA (SEQ ID NO: 374) |
| CD52 right protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNNGGKQALETVQRLLPVLC<br>QAHGLTPEQVVAIASHDGGKQALETVQRLLPVLCQAHGLTPEQVVAIASNGGGKQALETVQ<br>RLLPVLCQAHGLTPEQVVAIASHDGGKQALETVQRLLPVLCQAHGLFPEQVVAIASNGGGK<br>QALETVQRLLPVLCQAHGLTPEQVVAIASNGGGKQALETVQRLLPVLCQAHGLTPEQVVAI<br>ASNIGGKQALETVQRLLPVLCQAHGLTPEQVVAIASHDGGKQALETVQRLLPVLCQAHGLT<br>PEQVVAIASHDGGKQALETVQRLLPVLCQAHGLTPEQVVAIASNGGGKQALETVQRLLPVL<br>CQAHGLTPEQVVAIASNNGGKQALETVQRLLPVLCQAHGLTPEQVVAIASNGGGKQALETV<br>QRLLPVLCQAHGLTPEQVVAIASNIGGKQALETVQRILLPVLCQAHGLTPEQVVAIASHDGGK<br>QALETVQRLLPVLCQAHGLTPEQVVAIASHDGGRPALESIVAQLSRPDPALAALTNDHLVAL<br>ACLGGRPALDAVKKGLPHAPALIKRTNRRIPERTSHRVAGSQLVKSLLEEKKSELRHKLKYV<br>PHEYIELEIARNSTQDRILEMKVMEFFMKVYGYRGKHLGGSRKPDGAIYTVGSPIDYGVIVD<br>TKAYSGGYNLPIGQADEMQRYVEENQTRNKHINPNEWWKVYPSSVTEFKFLFVSGHFKGN<br>YKAQLTRLNHITNCNGAVLSVEELLIGGEMIKAGTLTLEEVRRKFNNGEINFRS (SEQ ID<br>NO: 375) |
| TRAC edit related |  |
| TRAC | CAA26435.1 |
| TRAC TALEN target | TTGTCCCACAGATATCCagaaccctgaccctgCCGTGTACCAGCTGAGA<br>(SEQ ID NO: 376) |
| TRAC left TALEN target | TTCTTCCCACAGATATCC (SEQ ID NO: 377) |
| TRAC left protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNNGGKQALETVQRLLPVLC<br>QAHGLTPEQVVAIASNGGGKQALETVQRLLPVLCQAHGLTPEQVVAIASHDGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNIGGKQALETVQRLLPVLCQAHGLTPEQVVAIA<br>SHDGGKQALETVQRLLPVLCQAHGLTPEQVVAIASNIGGKQALETVQRLLPVLCQAHGLTP<br>EQVVAIASNGGGKQALETVQRLLPVLCQAHGLTPEQVVAIASNIGGKQALETVQRLLPVLC<br>QAHGLTPEQVVAIASNGGGKQALETVQRLLPVLCQAHGLTPEQVVAIASNIGGKQALETVQ |

TABLE 7-continued

Primarily TALEN mediated edits

Sequence or Genbank Accession no.

| | |
|---|---|
| | RLLPVLCQAHGLTPEQVVAIASNGGGKQALETVQRELPVLCQAHGLTPEQVVAIASHDGGK<br>QALETVQRLLPVLCQAHGLTPEQVVAIASHDGGRPALESIVAQLSRPDPALAALTNDHLVAL<br>ACLGGRPALDAVKKGLHNPALIKRTNRRIPERTSHRVAGSQLVKSELEEKKSELRHKLKYV<br>PHEYIELIEIARNSTQDRILEMKVMEFFMKVYGYRGKHLGGSRKPDGAIYTVGSPIDYGVIVD<br>TKAYSGGYNLPIGQADEMQRYVEENQTRNKHINPNEWWKVYPSSVTEFKFLFVSGHFKGN<br>YKAQLTRLNTNUGAVLSVEELLIGGEMIKAGTLTLEEVRRKFNNGEINFRS (SEQ ID<br>NO: 378) |
| TRAC right TALEN target | CCGTGTACCAGCTGAGA (SEQ ID NO: 379) |
| TRAC TALEN right | MDYKDHDGDYKDRDIDYKDDDDKMAPKKKRKVGIHGVPAAVDLRELGYSQQQQEKIKPK<br>VRSTVAQHEEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNTP<br>EQVVAIASHDGGKQALETVQRLLVVLCQAHGLITEQVVATASNGGGKQALETVQRLLPVLC<br>QAHGLTPEQVVAIASHDGGKQALETVQRLLPVLCQAHGLTPEQVVAIASNIGGKQALETVQ<br>RLLPVLCQAHGLTPEQVVAIASNGGGKQALETVQRLLPVLCQAHGLTPEQVVAIASHDGGK<br>QALETVQRLLPVLCQAHGLTPEQVVAIASNGGGKQALETVQRLLPVLCQAHGLTPEQVAAI<br>ASNNGGKQALETVQRLLPVLCQAHGLTPEQVVAIASNNGGKQALETVQRLLPVLCQAHGLT<br>PEQVVAIASNGGGKQALETVQRLLPVLCQAHGLTPEQVVAIASNIGGKQALETVQRLLPVLC<br>QAHGLTPEQVVAIASHDGGKQALETVQRLLPVLCQAHGLTPEQVVAIASNIGGKQALETVQ<br>RLLPVLCQAHGLTPEQVVAIASHDGGKQALETVQRELLPVLCQAHGLTPEQVVAIASNNGGK<br>QALETVQRLLPVLQAHGLTPEQVVAIASNNGGRPALESIVAQLSRPDPALAALTNDHLVAL<br>ACLGGRPALDAVKKGLPHAPALIKRTNRRIPERTSHRVAGSQLVKSELEEKKSELRHKLKYV<br>PHEYIELIEIARNSTQDRILEMKVMEFFMKVYGYRGKHLGGSRKPDGAINTVGSPIDYGVIVD<br>TKAYSGGYNLPIGQADEMQRYVEENQTRNKHINPNEWWKVYPSSVTEFKFLFVSGHFKGN<br>YKAQLTRLNHITNCNGAVLSVEELLIGGEMIKAGTLTLEEVRRKFNNGEINFRS (SEQ ID<br>NO: 380) |
| PDCD1 edit related | |
| PDCD1 | NG_012110:1 |
| PDCD1 talen target | ttctccccag ccctgctcgt ggtgaccgaa ggggacaacg ccaccttca (SEQ ID NO: 381) |
| PDCD1 talen left | MGDPKKKRKVIDYPYDVPDYAIDIADLRTLGYSQQQQEKIKPKVRSTVAQHHEALVGHGFT<br>HAHIVALSQHPAALGTVAVKYQDMIAALPEATHEAIVGVGKQWSGARALEALLTVAGELR<br>GPPLQLDTGQLLKIAKRGGVTAVEAVHAWRNALTGARLNLTPQQVVAIASNGGGKQALET<br>VQRLLPVLCQAHGLTPEQVVAIASHDGGKQALETVQRLLPVLCQAGLTPQQVVAIASNGG<br>GKQALETVQRLLPVLCQAHGLTEQVVAIASHDGGKQALETVQRLLPVLCQAHGLTPEQVV<br>AIASHDGGKQALETVQRLLPVLCQAHGLTPEQVVAIASHDGGKQALETVQRLLPVLCQAHG<br>LTPEQVVAIASHDGGKQALETVQRLLPVLCQAHGLTPEQVVAIASNIGGKQALETVQALLTV<br>LCQAHGLTPQQVVAIASNNGGKQALETVQRLLPVLCQAHGLTPEQVVAIASHDGGKQALET<br>VQRLLPVLCQAHGLTPEQVVAIASHDGGKQALETVQRLLPVLCQAHGLTPEQVVAIASHDG<br>GKQALETVQRLLPVLCQAHGLTPQQVVAIASNGGGKQALETVQRLLPVLCQAHGLTPQQV<br>VAIASNNGGKQALETVQRLLPVLCQAHGLTPEQVVAIASHDGGKQALETVQRLLPVLCQAH<br>GLTPQQVVAIASNGGGRPALESIVAQLRPDPALAALTNDHLVALACLGGRPALDAVKKGL<br>GDPISRSQLVKSELEEKKSELRHKLKYVPHEYIELIEIARNSTQDRILEMKVMEFFMKVYGR<br>GKHLGGSRKPDGAIYTVGSPIDYGVIVDTKAYSGGYNLPIGQADEMQRYVEENQTRNKHIN<br>PNEWWKVYPSSVTEFKFLFVSGHFKGNYKAQLTRLNHITNCNGAVLSVEELLIGGEMIKAG<br>TLTLEEVRRKFNNGEINFAAD (SEQ ID NO: 382) |
| PDCD1 talen right | MGDPKKKRKVIDKETAAAKFERQHMDSIDIADLRTLGYSQQQQEKIKPKVRSTVAQHHEAL<br>VGHGFTHAHIVALSQHPAALGTVAVKYQDMIAALPEATHEAIVGVGKQWSGARALEALLT<br>VAGELRGPPLQLDTGQLLKIAKRGGVTAVEAVHAWRNALTGAPLNLTPEQVVAIASHDGG<br>KQALETVQRLLPVLCQAHGLTPQQVVAIASNGGGKQALETVQRLLPVLCQAHGLTPEQVVA<br>IASHDGGKQALETVQRLLPVLCQAHGLTPQQVVALASNGGGKQALETVQRLLPVLCQAHGL<br>TPQQVVAIASNGGGKQALETVQRLLPVLCQAHGLTPQQAVVAIASNGGGKQALETVQRLLPV<br>LCQAHGLTPQQVVAIASNNGGKQALETVQRLLPVLCQAHGLTPEQVVAIASNIGGKQALET<br>VQALLPVLCQAHGLTPQQVVVAIASNGGGKQALETVQRLLPVLCQAHGLTPEQVVAIASHDG<br>GKQALETVQRLLPVLCQAHGLTPQQVVAIASNGGGKQALETVQRLLPVLCQAHGLTPQQV<br>VAIASNNGGKQALETVQRLLPVLCQAHGLTPEQVVAIASNGGKQALETVQRLLPVLCQAHG<br>LTPQQVVAIASNNGGKQALETVQRLLPVLCQAHGLTPEQVVAIASHDGGKQALETVQRLLP<br>VLCQAHGLTPQQVVAIASNGGGRPALESIVAQLSRPDPALAALTNDHLVALACLGGRPALD<br>AVKKGLGDPISRSQLVKSELEEKKSELRHKLKYVPHEYIELIEIARNSTQDRILEMKVMEFFM<br>KVYTYRGKHLGGSRKPDGAIYTVGSPIDYGVIVDTKAYSGGYNLPIGQADEMQRYVEENQT<br>RNKHINPNEWWKVYPSSVTEFKFLFVSGHFKGNYKAQLTRLNHITNCNGAVLVEELLIGGE<br>MIKAGTLTLEEVRRKFNNGEINFAAD (SEQ ID NO: 383) |

(iii) Exemplary Genetic Modification Approaches

Any conventional genetic modification approaches can be used to genetically modify the immune cells in a manner as described herein. In some embodiments, the genetic modification is performed using genome editing. "Genome editing" refers to a method of modifying the genome, including any protein-coding or non-coding nucleotide sequence, of an organism to knock out the expression of a target gene. In general, genome editing methods involve use of an endonuclease that is capable of cleaving the nucleic acid of the genome, for example at a targeted nucleotide sequence. Repair of the double-stranded breaks in the genome may be repaired introducing mutations and/or exogenous nucleic acid may be inserted into the targeted site.

Genome editing methods are generally classified based on the type of endonuclease that is involved in generating double stranded breaks in the target nucleic acid. These methods include use of zinc finger nucleases (ZFN), transcription activator-like effector-based nuclease (TALEN), meganucleases, and CRISPR/Cas systems.

In some instances, genetic modification of the immune cells as described herein is performed using the TALEN technology known in the art. TALENs are engineered restriction enzymes that can specifically bind and cleave a desired target DNA molecule. A TALEN typically contains a Transcriptional Activator-Like Effector (TALE) DNA-binding domain fused to a DNA cleavage domain. The DNA binding domain may contain a highly conserved 33-34 amino acid sequence with a divergent 2 amino acid RVD (repeat variable dipeptide motif) at positions 12 and 13. The RVD motif determines binding specificity to a nucleic acid sequence and can be engineered according to methods known to those of skill in the art to specifically bind a desired DNA sequence (see, e.g., Juillerat, et al. (January 2015). Scientific reports, 5; Miller et. al. (February 2011). Nature Biotechnology 29 (2): 143-8; Zhang et. al. (February 2011). Nature Biotechnology 29 (2): 149-53; Geipler, et al., Boch, (2011). PLoS ONE 6 (5): e19509; Boch (February 2011). Nature Biotechnology 29 (2): 135-6; Boch, et. al. (December 2009). Science 326 (5959): 1509-12; and Moscou et al, (December 2009). Science 326 (5959): 1501. The DNA cleavage domain may be derived from the FokI endonuclease, which is active in many different cell types. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

TALENs specific to sequences in a target gene of interest (e.g., TCR, CD52, MHC, and others described herein) can be constructed using any method known in the art, including various schemes using modular components. Zhang et al. (2011) *Nature Biotech.* 29: 149-53: Geibler et al. (2011) PLoS ONE 6: e19509.

A TALEN specific to a target gene of interest can be used inside a cell to produce a double-stranded break (DSB). A mutation can be introduced at the break site if the repair mechanisms improperly repair the break via non-homologous end joining. For example, improper repair may introduce a frame shift mutation. Alternatively, a foreign DNA molecule having a desired sequence can be introduced into the cell along with the TALEN. Depending on the sequence of the foreign DNA and chromosomal sequence, this process can be used to correct a defect or introduce a DNA fragment into a target gene of interest, or introduce such a defect into the endogenous gene, thus decreasing expression of the target gene.

In some instances, genetic modification of the immune cells as described herein is performed using CRISPR technology as known in the art (CRISPR/Cas systems). Such modification may include the deletion or mutation of a sequence in a target gene of interest can be constructed using a CRISPR-Cas system, where the Clustered Regularly Interspaced Short Palindromic Repeats (CRISPR)-Cas system is an engineered, non-naturally occurring CRISPR-Cas system. The present disclosure utilizes the CRISPR/Cas system that hybridizes with a target sequence in a target gene of interest, where the CRISPR/Cas system comprises a Cas endonuclease and an engineered crRNA/tracrRNA (or single guide RNA ("sgRNA"). In some embodiments, the CRISPR-Cas system includes a crRNA and does not include a tracrRNA sequence. CRISPR/Cas complex can bind to the lineage specific protein polynucleotide and allow the cleavage of the protein polynucleotide, thereby modifying the polynucleotide.

The CRISPR/Cas system of the present disclosure may bind to and/or cleave the region of interest within a target gene of interest, within or adjacent to the gene, such as, for example, a leader sequence, trailer sequence or intron, or within a non-transcribed region, either upstream or downstream of the coding region. The guide RNAs (gRNAs) used in the present disclosure may be designed such that the gRNA directs binding of the Cas enzyme-gRNA complexes to a pre-determined cleavage sites (target site) in a genome. The cleavage sites may be chosen so as to release a fragment that contains a region of unknown sequence, or a region containing a SNP, nucleotide insertion, nucleotide deletion, rearrangement, etc. Cleavage of a gene region may comprise cleaving one or two strands at the location of the target sequence by the Cas enzyme. In one embodiment, such, cleavage can result in decreased transcription of a target gene. In another embodiment, the cleavage can further comprise repairing the cleaved target polynucleotide by homologous recombination with an exogenous template polynucleotide, wherein the repair results in an insertion, deletion, or substitution of one or more nucleotides of the target polynucleotide.

The terms "gRNA," "guide RNA" and "CRISPR guide sequence" may be used interchangeably throughout and refer to a nucleic acid comprising a sequence that determines the specificity of a Cas DNA binding protein of a CRISPR/Cas system. A gRNA hybridizes to (complementary to, partially or completely) a target nucleic acid sequence in the genome of a host cell. The gRNA or portion thereof that hybridizes to the target nucleic acid may be between 15-25 nucleotides, 18-22 nucleotides, or 19-21 nucleotides in length. In some embodiments, the gRNA sequence that hybridizes to the target nucleic acid is 15, 16, 17, 18, 19, 20, 21, 22, 23, 24, or 25 nucleotides in length. In some embodiments, the gRNA sequence that hybridizes to the target nucleic acid is between 10-30, or between 15-25, nucleotides in length.

In addition to a sequence that binds to a target nucleic acid, in some embodiments, the gRNA also comprises a scaffold sequence. Expression of a gRNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gRNA may be referred to as a single guide RNA (sgRNA).

As used herein, a "scaffold sequence," also referred to as a tracrRNA, refers to a nucleic acid sequence that recruits a Cas endonuclease to a target nucleic acid bound (hybridized) to a complementary gRNA sequence. Any scaffold sequence that comprises at least one stem loop structure and recruits an endonuclease may be used in the genetic elements and vectors described herein. Exemplary scaffold sequences will be evident to one of skill in the art and can be found, for example, in Jinek, et al. *Science* (2012) 337(6096):816-821, Ran, et al. *Nature Protocols* (2013) 8:2281-2308, PCT Application No. WO2014/093694, and PCT Application No. WO2013/176772. In some embodiments, the CRISPR-Cas system does not include a tracrRNA sequence.

In some embodiments, the gRNA sequence does not comprise a scaffold sequence and a scaffold sequence is expressed as a separate transcript. In such embodiments, the gRNA sequence further comprises an additional sequence that is complementary to a portion of the scaffold sequence and functions to bind (hybridize) the scaffold sequence and recruit the endonuclease to the target nucleic acid.

In some embodiments, the gRNA sequence is at least 50%, 55%, 60%, 65%. 70%, 75%, 80%, 85%, 900%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (Upadhyay, et al. Genes Genome Genetics (2013) 3(12):2233-2238). In some embodiments, the gRNA sequence is at least 50%, 55%, 60%, 65%, 70%, 75%, 80%, 85%. 90%, 95%, 96%, 97%, 98%, 990%, or at least 1000% complementary to the 3' end of the target nucleic acid (e.g., the last 5, 6, 7, 8, 9, or 10 nucleotides of the 3' end of the target nucleic acid).

Example sgRNA sequences, including both modified and unmodified sgRNAs, targeting the T cell receptor alpha constant (TRAC) gene are provided herein. As will be evident to one of ordinary skill in the art, selection of sgRNA sequences may depend on factors such as the number of predicted on-target and/or off-target binding sites. In some embodiments, the sgRNA sequence is selected to maximize potential on-target and minimize potential off-target sites.

In some embodiments, the Cas endonuclease is a Cas9 nuclease (or variant thereof) or a Cpf1 nuclease (or variant thereof). Cas9 endonucleases cleave double stranded DNA of a target nucleic acid resulting in blunt ends, whereas cleavage with Cpf1 nucleases results in staggered ends of the nucleic acid.

In general, the target nucleic acid is flanked on the 3' side or 5' side by a protospacer adjacent motif (PAM) that may interact with the endonuclease and be further involved in targeting the endonuclease activity to the target nucleic acid. It is generally thought that the PAM sequence flanking the target nucleic acid depends on the endonuclease and the source from which the endonuclease is derived. For example, for Cas9 endonucleases that are derived from *Streptococcus pyogenes*, the PAM sequence is NGG, although the PAM sequences NAG and NGA may be recognized with lower efficiency. For Cas9 endonucleases derived from *Staphylococcus aureus*, the PAM sequence is NNGRRT. For Cas9 endonucleases that are derived from *Neisseria meningitidis*, the PAM sequence is NNNNGATT. Cas9 endonucleases derived from *Streptococcus thermophilus*, StlCas9 an dSt3Cas9, the PAM sequences are NNAGAAW and NGGNG, respectively. For Cas9 endonuclease derived from *Treponema denticola*, the PAM sequence is NAAAAC. In some embodiments, the Cas endonuclease is a Cpf1 nuclease. In contrast to Cas9 endonucleases, Cpf1 endonuclease generally do not require a tracrRNA sequence and recognize a PAM sequence located at the 5' end of the target nucleic acid. For a Cpf1 nuclease, the PAM sequence is TYTN. In some embodiments, the Cas endonuclease is MAD7 (also referred to as Cpf1 nuclease from *Eubacterium rectale*) and the PAM sequence is YTiTN.

In some embodiments, genetically engineering a cell also comprises introducing a Cas endonuclease, or nucleic acid sequence encoding such (e.g., mRNA encoding a Cas endonuclease), into the cell. In some embodiments, the Cas endonuclease and the nucleic acid encoding the gRNA are provided on the same nucleic acid (e.g., a vector). In some embodiments, the Cas endonuclease and the nucleic acid encoding the gRNA are provided on different nucleic acids (e.g., different vectors). In some embodiments, the Cas endonuclease is provided as an mRNA encoding the Cas endonuclease and the gRNA is provided as a modified gRNA molecule. Alternatively or in addition, the Cas endonuclease may be provided or introduced into the cell in protein form.

In some embodiments, the Cas endonuclease is a Cas9 enzyme or variant thereof. In some embodiments, the Cas9 endonuclease is derived from *Streptococcus pyogenes, Staphylococcus aureus, Neisseria meningitidis, Streptococcus thermophilus*, or *Treponema denticola*. In some embodiments, the nucleotide sequence encoding the Cas endonuclease may be codon optimized for expression in a host cell. In some embodiments, the endonuclease is a Cas9 homolog or ortholog.

In some embodiments, the nucleotide sequence encoding the Cas9 endonuclease is further modified to alter the activity of the protein. In some embodiments, the Cas9 endonuclease has been modified to inactivate one or more catalytic resides of the endonuclease. In some embodiments, the Cas9 endonuclease has been modified to inactivate one of the catalytic residues of the endonuclease, referred to as a "nickase" or "Cas9n". Cas9 nickase endonucleases cleave one DNA strand of the target nucleic acid. In some embodiments, the methods described herein involve two distinct cleavage reactions, in which one Cas9 nickase is directed to cleave one DNA strand of the target nucleic acid and a Cas9 nickase is directed to cleave the second DNA strand of the target nucleic acid.

(iv) MHC-CAR Regulatory T cells (Treg)

Any of the MHC-CAR-expressing T cells disclosed herein can be regulatory T cells (Treg), which may mimic the immune modulation activity of follicular regulatory cells. As used herein, regulatory T cells or Treg cells, which are also known as suppressor T cells, refer to a subpopulation of T cells that modulate the immune system, maintain tolerance to self-antigens, and/or prevent autoimmune disease. Treg cells function as immunesuppressors to suppress or downregulate induction and/or proliferation of effector T cells, such as pathologic CD4+ and/or CD8+cells involved in autoimmune diseases.

The genetically modified Treg cells disclosed herein express one or more of the biomarkers associated with Treg cells in nature, for example, CD4, FOXP3, CD25, CD45R (e.g., CD45RA or CD45RO), or a combination thereof. The Treg cells may be prepared using (derived from) peripheral blood mononuclear cells (PBMCs) isolated from a suitable donor (e.g., the human patient subject to the treatment). Methods for isolating the subpopulation of Treg cells from PBMCs are well known in the art, for example, cell sorting. Expression vectors for a suitable MHC-CAR construct, as well as other genetic modification (e.g., those described herein) can be introduced into the Treg subpopulation via methods as described herein, or other methods known in the art. Alternatively, the genetically modified Treg cells may be prepared by introducing a transgene coding for CD25 and/or other Treg cell markers into suitable T cells, which can be further modified to introduce the expression cassette for the MHC-CAR and optionally other genetic modification as described herein.

In some embodiments, the genetically modified Treg cells may be further modified to display (e.g., surface express or surface attach) molecules targeting a specific type of pathologic cells (e.g., CD4+cells or CD8+cells) and/or display molecules targeting a specific tissue site (e.g., lymph node or an inflammation site).

In some examples, the genetically modified Treg cells further express a chimeric receptor (CAR) comprising an extracellular domain such as a single-chain antibody (scFv) specific to a B cell surface marker, for example, CD19. Alternatively or in addition, the Treg cells may further express a chimeric receptor comprising an extracellular domain (e.g., scFv) specific to a T cell surface marker, for example, CS-1. Such a chimeric receptor can be a cell-surface receptor comprising an extracellular domain, a transmembrane domain, and a cytoplasmic domain (e.g., comprising a co-stimulatory domain, a cytoplasmic signaling domain such as CD3ζ, or a combination thereof) in a combination that is not naturally found together on a single protein.

The Treg cell may further display a molecule targeting lymph nodes and/or germinal center, for example, CXCR5, and/or display a molecule targeting an inflammation site, for example, CCR6. Targeting germinal center B cells (GC B cells) may be mediated, at least in part, by a specialized helper T cell subset, the CXCR5highPD-lhigh T follicular helper (TFH) cells. Foxp3+Treg can be diverted to become TFH repressors via expression of Bcl6 and SAP-mediated interaction with B cells. The resulting follicular regulatory T cells (TFR) are expected to share features of both TFH and Treg cells, localize to germinal centers, and regulate the size of the TFH cell population and germinal centers in vivo.

Further, the Treg cells disclosed herein may include one or more of the additional genetic modification as described herein, for example, checkpoint molecule knock out.

The Treg cells expressing B-cell or T-cell specific CAR may target pathologic B cells and/or T cells involved in an autoimmune disease. For example, the genetically modified Treg cells as described herein would be expected to exhibit functions similar to follicular regulatory cells, e.g., targeting B cells, T cells, and/or dendritic cells, thereby. e.g., down-regulating B cell stimulation, secreting suppressive cytokines that can inhibit activation of germinal center (GCB cells (such as Il-10 and TGF-Beta), inducing cytolysis of Tfh (through MHC CAR) and GC) B (e.g., through the CD19 CAR), and/or mechanical disrupting signaling transduction to GC B cells or to T follicular helper (Tfh) cells (e.g., through binding to GC B and MHC-peptide Tfh). Alternatively or in addition, the Treg cells may potentially engage both helper T cells, B cells, and/or antigen presenting cells, or in some instances, physically blocking the engagement.

III. Application of Immune Cells Expressing MHC-CAR in Immunotherapy

Host immune cells expressing MHC-CAR (the encoding nucleic acids or vectors comprising such) described herein are useful for targeting and eliminating pathogenic cells involved in autoimmune diseases, such as MS, type I diabetes, lupus, rheumatoid arthritis, etc. In some embodiments, the subject is a mammal, such as a human, monkey, mouse, rabbit, or domestic mammal. In some embodiments, the subject is a human, for example, a human patient having, suspected of having, or at risk for an autoimmune disease (e.g., MS).

The MHC-CAR-expressing immune cells can be mixed with a pharmaceutically acceptable carrier to form a pharmaceutical composition, which is also within the scope of the present disclosure. To perform the methods described herein, an effective amount of the immune cells expressing any of the MHC-CAR constructs described herein can be administered into a subject in need of the treatment. The immune cells may be autologous to the subject, i.e., the immune cells are obtained from the subject in need of the treatment, genetically engineered for expression of the MHC-CAR constructs and optionally contains one or more of the additional genetic modifications as described herein, and then administered to the same subject. Administration of autologous cells to a subject may result in reduced rejection of the immune cells as compared to administration of non-autologous cells. Alternatively, the immune cells are allogeneic cells, i.e., the cells are obtained from a first subject, genetically engineered for expression of the MHC-CAR construct, and administered to a second subject that is different from the first subject but of the same species. For example, allogeneic immune cells may be derived from a human donor and administered to a human recipient who is different from the donor.

In some embodiments, the immune cells are co-used with a therapeutic agent for the target immune disease, for example, Alemtuzumab for treating MS. Such immunotherapy is used to treat, alleviate, or reduce the symptoms of the target immune disease for which the immunotherapy is considered useful in a subject.

The efficacy of the MHC-CAR immunotherapy may be assessed by any method known in the art and would be evident to a skilled medical professional. For example, the efficacy of the immunotherapy may be assessed by survival of the subject and/or reduction of disease symptoms in the subject.

In some embodiments, the immune cells expressing any of the MHC-CAR disclosed herein are administered to a subject who has been treated or is being treated with a therapeutic agent for an autoimmune disease. The immune cells expressing any one of the MHC-CAR disclosed herein may be co-administered with the therapeutic agent. For example, the immune cells may be administered to a human subject simultaneously with the therapeutic agent. Alternatively, the immune cells may be administered to a human subject during the course of a treatment involving the therapeutic agent. In some examples, the immune cells and the therapeutic agent can be administered to a human subject at least 4 hours apart, e.g., at least 12 hours apart, at least 1 day apart, at least 3 days apart, at least one week apart, at least two weeks apart, or at least one month apart.

To practice the method disclosed herein, an effective amount of the immune cells expressing MHC-CAR or compositions thereof can be administered to a subject (e.g., a human MS patient) in need of the treatment via a suitable route, such as intravenous administration. Any of the immune cells expressing MHC-CAR or compositions thereof may be administered to a subject in an effective amount. As used herein, an effective amount refers to the amount of the respective agent (e.g., the immune cells expressing MHC-CAR or compositions thereof) that upon administration confers a therapeutic effect on the subject. Determination of whether an amount of the cells or compositions described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject is a human cancer patient.

In some embodiments, the subject is a human patient suffering from an autoimmune disease, which is characterized by abnormal immune responses attacking a normal body part. Examples of autoimmune diseases include multiple sclerosis, systemic lupus erythematosus, rheumatoid arthritis, juvenile idiopathic arthritis (also known as juvenile idiopathic arthritis), Sjögren's syndrome, systemic sclerosis, ankylosing spondylitis, Type 1 diabetes, autoimmune thyroid diseases (Grave's and Hashimoto's), multiple sclerosis myasthenia gravis, inflammatory bowel disease (Crohn's or ulcerative colitis), Psoriasis, or a diseases mentioned in Table 1.

There are numerous stages in the immune cascade where, in general, an autoimmune disease can be impacted. There is a continuum of interventions made possible by the combination of edits that the methods disclosed herein comprises. For example, Treg cells displaying a distinct set of surface molecules, in addition to the MHC-CAR, can be used for treating the autoimmune disease at different stages.

In the early stage of many immune disorders, including MS, there exist unexplained deficits in regulatory mechanisms and/or tolerance induction exists in MS and there begin repeated attacks on the nervous system by T cells. Treg cells expressing a suitable MHC-CAR and anti-CD19 CAR (optionally with other genetic modifications as described herein) may be used for intervention.

An advantage of autoreactive Treg cells is their ability to act as "bystander" suppressors, to dampen inflammation at a site-specific manner in response to cognate antigen expressed locally by affected tissues. The induction of regulatory T cells (by autoantigens) can suppress disease progression even when there are a variety of autoantigens (or when the initiating/primary) autoantigen is unknown. Tregs can travel relatively freely, and inhibit T cells and B cells and prevent return to an inflammatory environment. These autoreactive Tregs are advantageous in their ability to act as bystander suppressors and dampen inflammation in a site-specific manner in response to cognate antigen expressed locally by affected tissues.

Thus, the genetically modified Treg cells may be designed to mimic the suppressor function of the autoreactive Treg cells. Such Treg cells may be modified, for example, to have PD-L1/PD-1 knocked out, to display CCR6 and/or scFv targeting MOG to route to the site of inflammation, to express a suitable MHC-CAR and/or anti-CD19-CAR. Alternatively, the Treg cells may be modified, for example, to have PD-L1/PD-1 knocked out, to display CXCR5 to route to germinal centers and/or ectopic lymph nodes, to express a suitable MHC-CAR and/or anti-CD19-CAR. These types of Treg cells may interact with pathogenic cells at the site of inflammation, block pathogenic interactions, and/or calm inflammatory environment. They can be used at an early disease stage (to inhibit pathogenicity) or after cytotoxic therapy (to prevent return to an inflammatory environment).

Relapsing-remitting MS (mid-stage) naturally regulates itself, and treatments which augment these natural regulatory mechanisms will help control the disease process. In successful disease treatment, there is a shift from Th1 cells to Th2 and Th3 cells, and the appearance of other regulatory cells. At this stage, therapeutic targets will include both pathogenic B and pathogenic T cells. Treg cells for treating such mid-stage disease may express a suitable MHC-CAR as described herein, and an additional CAR targeting B cells (e.g., an anti-CD19 CAR) or targeting T cells such as CD8+cells. The Treg cells may further display CXCR5 or free of CXCR5 targeting. Treg cells expressing anti-CD19 CAR may be used to eliminate B cells in the germinal center.

When MS changes from relapsing remitting to the chronic progressive form (late-stage), T cells enter a state of chronic activation and degenerative processes occur. Aggressive treatment against cytotoxic CD8+ T cells requires a CAR augmentation that is sufficiently cytotoxic. At this point, a treatment may shift from one primarily driven by Treg cells to one driven by MHC-CAR CD8+ T cells and even MHC-CAR CS-1 cells. The ultimate goal remains the same: to suppress pathology through cytotoxicity enhanced by bystander effect. Genetically engineered T cells for use at this disease stage may express a suitable MHC-CAR, and an additional CAR targeting pathologic T cells involved in the late stage of the disease, for example, CD8+ T cells. In some examples, the additional CAR may target CS-1 (also known as SLAMF7), which is a glycoprotein expressed on CD8+ T cells. CS1 is a promising antigen that can be used to target and kill CD8+ T cells and plasma cells. CS1-CAR T cells secrete more IFN-gamma as well as IL-2, expressing higher levels of activation marker CD69, higher capacity for degranulation, and display enhanced cytotoxicity. Anti-CS1 CAR will target CD8+ T-cells. The genetically modified T cells may further display a molecule for bone-marrow targeting of plasma cells, such as CXCR4, and their targeting to inflamed tissues, with CXCR3.

Hiepe et al., Nature Reviews Rheumatology, 7(3):170-178, 2011. Examples include targeting of plasma cells in lupus.

IV. Kits for Therapeutic Uses

The present disclosure also provides kits for use of the MHC-CAR-expressing immune cells for use in suppressing pathogenic immune cells such as autoreactive T cells in autoimmunity. Such kits may include one or more containers comprising compositions comprising immune cells expressing MAR-CAR such as those described herein), and a pharmaceutically acceptable carrier.

In some embodiments, the kit can comprise instructions for use in any of the methods described herein. The included instructions can comprise a description of administration of the MHC-CAR-expressing immune cells to a subject who needs the treatment, e.g., an MS patient. The kit may further comprise a description of selecting a subject suitable for treatment based on identifying whether the subject is in need of the treatment. In some embodiments, the instructions comprise a description of administering the immune cells to a subject who is in need of the treatment.

The instructions relating to the use of the immune cells expressing the MHC-CAR described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device. A kit may have a sterile access port (for example, the container may be an intravenous solution bag or a vial having a stopper pierceable by a hypodermic injection needle). The container may also have a sterile access port. At least one active agent in the pharmaceutical composition is immune cells expressing MHC-CAR as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The instant examples focuses on the development of a cellular immunotherapy utilizing chimeric receptors to selectively redirect therapeutic T cells against myelin basic protein (MBP)-specific T lymphocytes implicated in MS [16]. The results of this program can support the further development of redirected therapeutic T cells able to counteract pathologic, self-specific T lymphocytes, and specifically validate humanized MBP-DR2-chimeric receptors as a therapeutic target in MS [29].

Example 1: Construction of Modified T-Cells Specific to Myelin Basic Protein

A construct for an antigen-specific T-cell receptor (TCR) that targets a MBP-loaded major histocompatibility complex-chimeric antigen receptor (MHC-CAR) is designed for reintroduction into cells with TCR knockouts for assays. Design of the TCR constructs is based on an antigen-specific TCR with a published structure and TCR expression constructs validated in human cell lines [17, 46, 51, 52]. Green fluorescent protein (eGFP) or luciferase is genetically encoded for labeling [28]. Exemplary lentiviral expression vectors comprising the TCR construct and reporting gene are provided in FIG. 1.

Several cell lines are selected for testing TCR expression and activity, including Jurkat E6-4 (a control strain that expresses TCR), Jurkat J.RT3-T3.5 (a strain that lacks TCRb), SupT1 (a strain with damaged TCRa), and primary human T cells (which contain a diverse population of TCR clonotypes).

Jurkat E6-1 cells are an established human T lymphocyte cell line from peripheral blood. It is used as a control cell line expressing TCR [15, 18].

Jurkat RT3-T3.5 lacks TCRβ due to a mutation that precludes expression of the TCR β-chain. It also fails to express surface CD3 or produce the T-cell receptor α,β heterodimer. It is therefore used for validating T-cell receptor gene transfer [1, 6, 21, 49].

SupT1 is a human lymphoblast line expressing multiple T lineage markers and is used because it encodes a non-functional receptor and fails to express TCRα 1491.

PMBC-derived primary human T cells contain a diverse repertoire of TCR clonotypes.

Lentiviral vectors containing the antigen-specific TCR as illustrated in FIG. 1 are used to transduce cancer cell lines lacking at least one TCR chain, and are subsequently assessed for expression using fluorescence-activated cell sorting (FACs). In cancer cell lines containing the antigen-specific TCR, luciferase is added to the cell line following successful stable expression to enable its use in mouse studies.

TCR constructs for mRNA, multicistronic mRNA, and lentiviral transduction proceed straightforwardly, via a screen based on the genetically encoded eGFP and labeling with anti-TCR or anti-CD3 antibody [3, 19].

Figure 2:
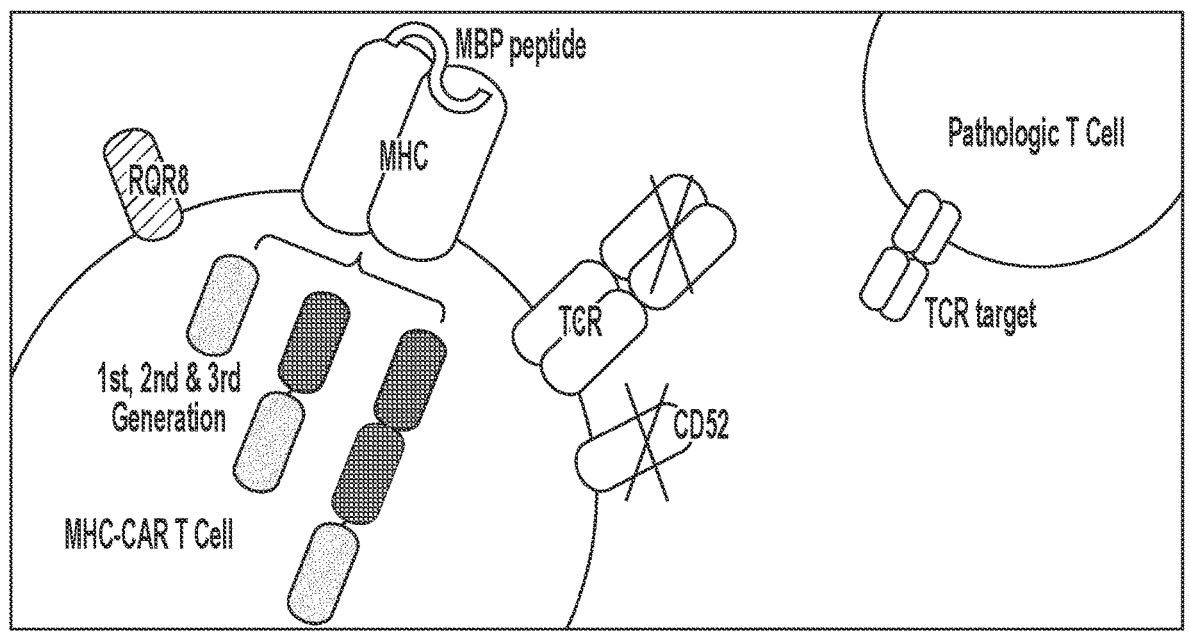
FIG. 2 is a schematic illustration of an MHC-CAR T cell, which expresses various designs of MHC-CAR as indicated in conjugation with a myelin basic protein (MBP) peptide for targeting pathologic T cells involved in multiple sclerosis (MS). Optionally, the MHC-CAR T cell may have the endogenous TCR and/or CD52 knocked out. The MHC-CAR T cell may further express RQR8 on the cell surface.

Example 2: Construction of MHC-Based Chimeric Receptors (MHC-CAR) and T-cells Expressing Such (i) Design of MHC-CAR Constructs Receptors for adoptive cell therapy that genetically link the MBP 84-102 epitope to human leukocyte antigen HLADR2 are generated and, either incorporate or lack chimeric intracellular signaling domains [29]. The antigen-major histocompatibility complex (Ag-MHC) domain serves as receptor, binding the TCR of MBP-specific target cells. The Ag-MHC-CAR has been validated in preclinical mouse models with CD3-((i.e. a first-generation signaling domain), which may optionally be in combination with additional co-stimulatory signaling domains (i.e. second- or third-generation signaling domains) for efficacy in humans, following the methodology provided in [9, 25]. A schematic illustration of the various designs of MHC-CAR is provided in FIG. 2.

Figure 3:
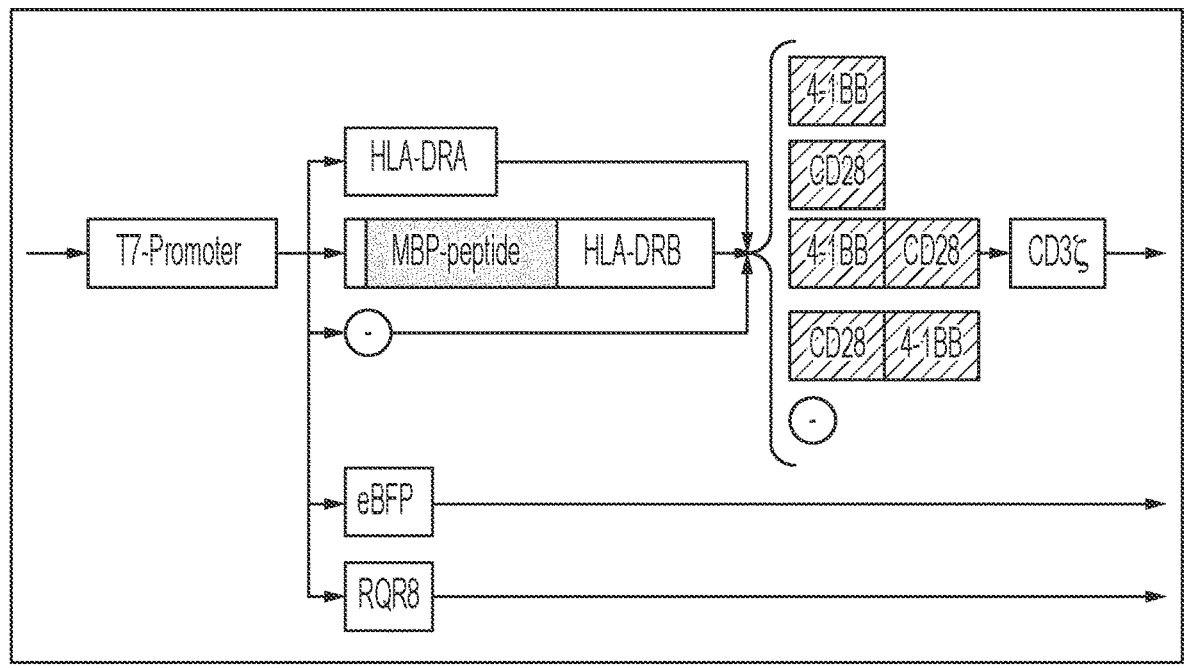
FIG. 3 is a schematic illustration of exemplary designs for various MHC-CAR constructs. The exemplary MHC-CAR constructs may have two subunits: an α-chain containing a leader sequence, a DRA*1010 domain, and a cytoplasmic domain, and a 0-chain that includes a leader sequence from HLA-DRB1*1501, a peptide from MBP, and a domain from HLA-DRB1*1501. The DNA used to create mRNA contains either single chains or are multicistronic and separated by orthogonal 2A sequences. RQR8 and eBFP (or GFP) are used for both cell control and labeling.
Figure 4:
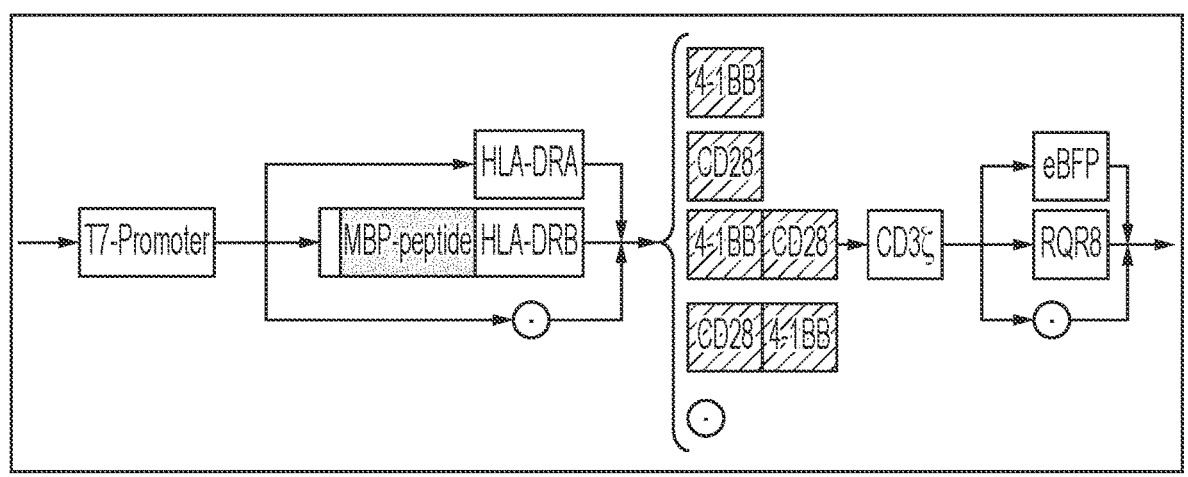
FIG. 4 is a schematic illustration of exemplary designs of expression cassettes for various MHC-CAR constructs containing a MBP peptides, which may further include eBFP (or GFP) or RQR8.
Figure 5:
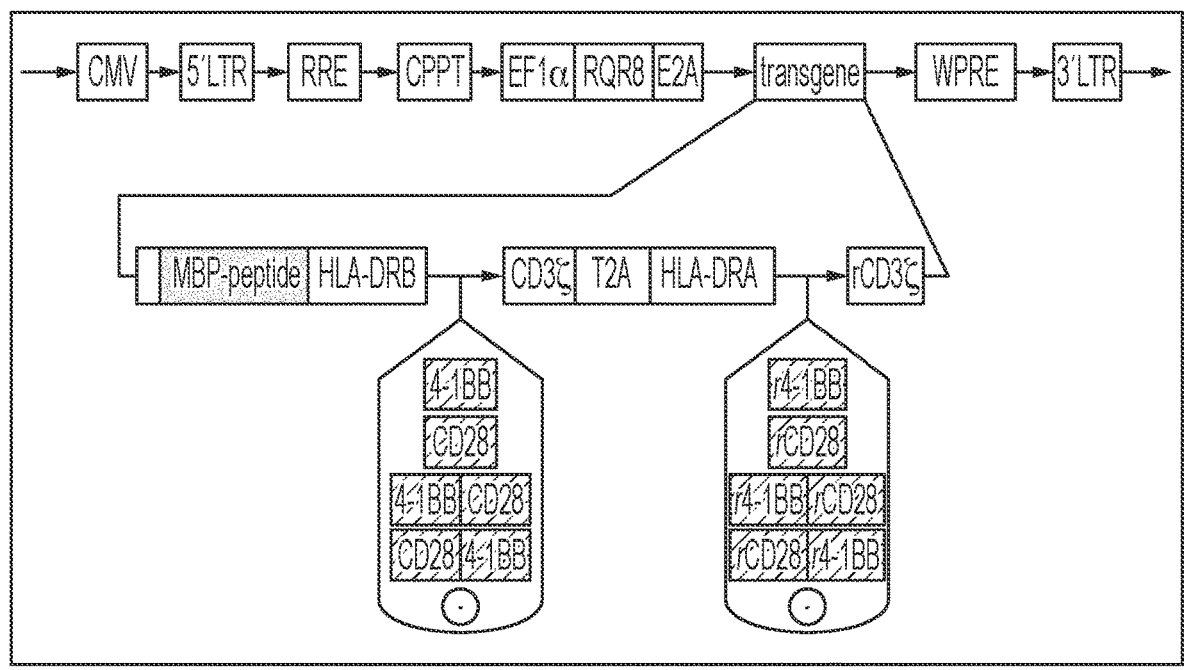
FIG. 5 is a schematic illustration of an exemplary design of a lentiviral expression construct for MHC-CARs and optionally label proteins such as eBFP and/or RQR8. Such an expression cassette would be sufficiently small to be included in one lentiviral package.

MHC-CARs are designed based on the structure of HLA-DR, and combined with a variety of internal cytoplasmic costimulatory domains. The MHC-CAR has two subunits: (i) an α-chain that contains the leader sequence, DRA*1010 domain, and a cytoplasmic domain; and (ii) a β-chain that contains a leader sequence (from HLA-DRB1*1501), a peptide (DENPVVHFFKNIVTPRTPP (SEQ ID NO: 15) from myelin basic protein), a domain (from HLA-DRB1*1501), and a cytoplasmic signal domain, for example, CD3z [291. FIG. 3. The DNA used to create mRNA contains either single chains (shown as one embodiment in FIG. 4) or are multicistronic and separated by orthogonal 2A sequences as illustrated in FIG. 5. Genetically encoded eBFP or RQR8 are introduced into the cells for cell-labeling or to provide a mechanism for depletion [4, 5, 37, 40]. FIGS. 3 and 5.

Figure 6:
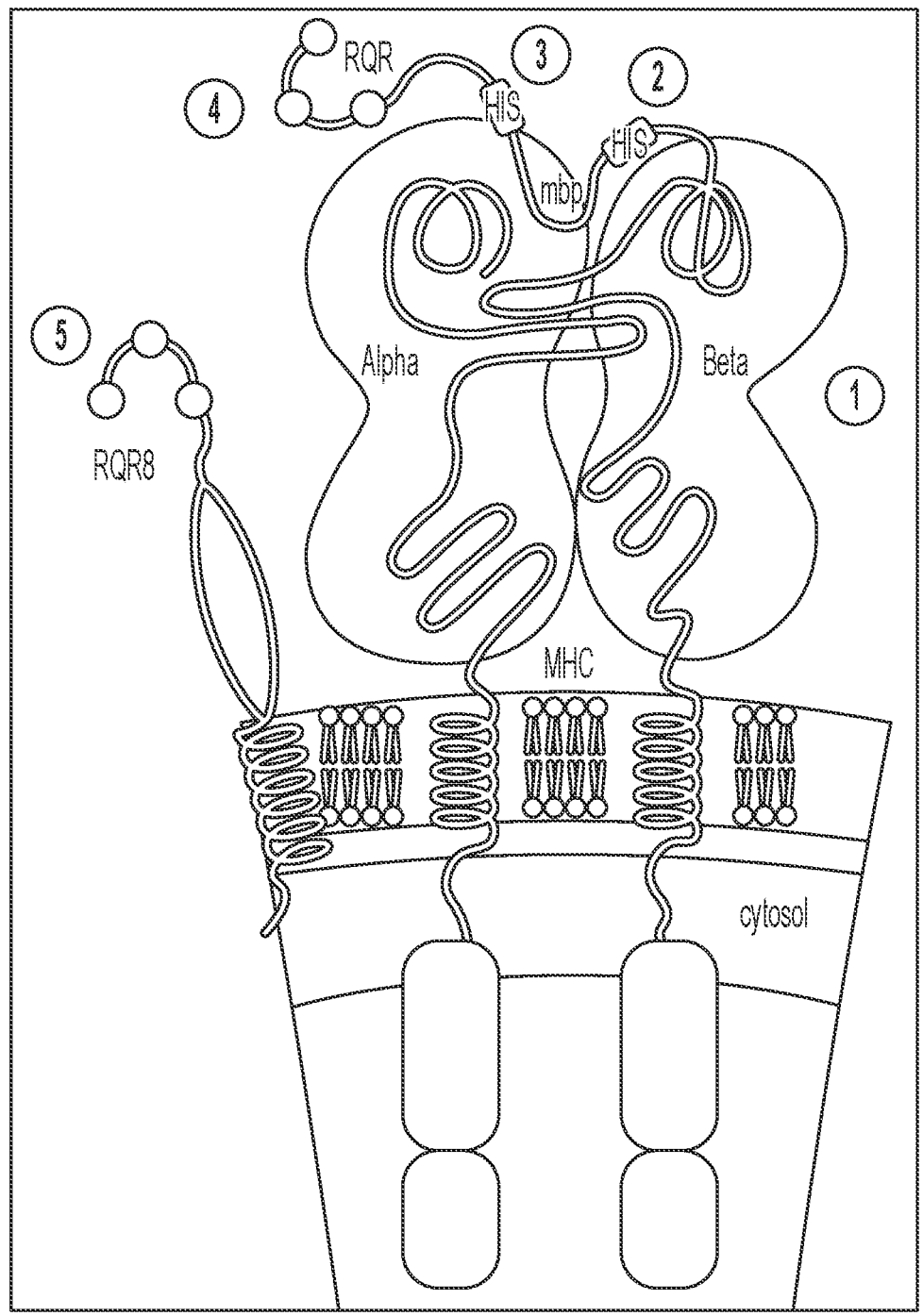
FIG. 6 is a schematic illustration of an exemplary design of MHC-CAR, which may include a number of sites for tagging. Site 1 is an HLA-DR antibody binding site for cases where naïve HLA-DR is either not expressed or due to CIITA editing. Sites 2 and 3 are potential insertion sites for polyhistidine-tag motifs. Sites 4 and 5 represent RQR and RQR8, respectively.

As illustrated in FIG. 6, the designed MHC-CAR has a number of sites for tagging. Site 1 is an HLA-DR antibody binding site for cases where native HLA-DR is either not expressed due to CIITA editing 126, 38]. Sites 2 and 3 are potential insertion sites for polyhistidine-tag motifs 1241. Sites 4 and 5 represent RQR and RQR8, respectively [37]. Multiple sclerosis is shown to affect blood brain barrier permeability, so in order to enhance the safety of therapeutic MHC-CAR, genetically encoded RQR would allow for rapid depletion of MHC-CAR T cells upon administration of rituximab, a chimeric monoclonal antibody treatment used off label in the treatment of severe MS [42].

(ii) Construction of T Cell Lines Expressing MHC-CAR

A number of cell lines discussed below are selected for testing the MHC-CAR construct. Assays are then continued in human T cells in order to establish clinically translatable protocols.

K56 cells lack Class I and Class II MHC, allowing for tagless verification of HLA-DR expression using antibodies (HLA-DR is a component of the MHC-CAR) [45]. Expression assays will allow assessment of the MHC-CAR expression relative to RQR8 expression using flow cytometry, and the same lentiviral construct is then used in PMBC-derived T cells [23].

KM-H2 is a human Hodgkin's lymphoma line that can be used as an HLA-DR positive control line [34, 44]. Jurkat E6-1, as noted above, conditionally express HLA-DR upon delivery of CIITA and can be used to evaluate CIITA TALEN if CIITA knockout is used [33].

In addition, primary human T cells can be used. PMBC-derived primary human T cells are purified and enriched from whole blood, and then activated. Transduction follows enrichment. The cells are incubated with recombinant human interleukin-2 (and/or IL-7 and/or IL-15) [7, 12, 43]. Based on preclinical studies and the anticipated therapeutic course, the desired cell type is CD8+ T cells with the molecular and functional features of stem cell memory TSCM, central memory TCM, and naïve cells TN [11, 22, 32, 35]. Antibody staining allows for cell immunotyping [27].

Initial constructs, including a permutation of signaling domains (CD3z, 41BB, CD28) are expressed using mRNA, multicistronic mRNA, and lentiviral strategies in K562 cells. The cell line's lack of MHC Class I and II allow the tagless verification of MHC-CAR expression using the HLA-DR antibodies, following a successfully employed strategy [29]. Quantification of the expression efficiency in more clinically relevant cell lines, including therapeutic T cells, depends on construct, and will be measured using genetically encoded fluorescent reporters (BFP) or antibody staining of the RQR site, a polyhistidine-(HIS)-tag, or the MHCCAR (with an HLA-DR antibody if CIITA is inactivated using TALEN). Labeling sites are indicated in FIG. 6. To test rates of MHC-CAR delivery as a potential therapeutic vector, BFP is removed from constructs while RQR is retained to provide for depletion control. Expression rates of the clinically relevant construct are measured using antibody staining post-editing.

The transcription activator-like effector technology (TALEN) can also be used for preparing T cells expressing MHC-CAR. Human T cell lines are activated, transfected with TALEN, and either transfected or transduced with MHC-CAR They are then stained and analyzed by flow cytometry to assess TALEN gene inactivation and MHC-CAR expression. Upon verification of construct expression in desired cell lines, TALEN transduction (TCRα and CD52 or CIITA as discussed below) into human T cell lines is performed. TALEN is introduced into activated human T cell lines, and the MHC-CAR is subsequently introduced into the same T cell lines for evaluation. The modification of the human T cells can be performed in this order to prevent incidental fratricidal killing of MHC modified cells due to the native TCR [10]. The activity of TALEN-edited MHC-CAR T-cells is to be confirmed.

(iii) Modification of MHC-CAR-Expressing T Cells via Transcription activator-like effectors (TALENs)

Human T cells are selected to confirm inactivation of TCRa, and CD52 or CIITA genes by TALEN, followed by evaluation in combination with MHC-CAR, using TALENs. Transcription activator-like effectors (TALENs) bind DNA in a sequence-specific manner. The DNA binding domain contains a highly conserved 33-34 amino acid sequence with a divergent 2 amino acid RVD (repeat variable dipeptide motif) conferring specific nucleotide recognition [23, 31].

Mutation of either a or P chain of the TCR is sufficient for disruption of surface TCR expression [15, 36]. TALEN is used to inhibit expression of two genes in the therapeutic cell without introducing a proliferative advantage through undesired translocations [39][47]. TCR expression is inhibited through a TRAC-targeted TALEN to prevent graft versus host disease (GvHD) and allow for the creation of an allogeneic therapy [15, 39, 47].

CD52 deletion can be made for alemtuzumab compatibility. Alemtuzumab is a humanized anti-CD52 IgG1 monoclonal antibody that targets and depletes circulating T and B lymphocytes [41]. Alemtuzumab can be used as rescue therapy or as first line drug in severe-onset MS 1501, and will be co-administered in the human patient population. TALEN knockout will make MHC-CAR compatible with concurrent treatment in patients [14, 39]. Further, CIITA deletion can be made for characterization of HLA-DR in MHC-CAR CIITA is a protein coding gene essential for the transcriptional activity of HLA Class 11 promoter [26]. Knockout would allow for the direct measurement of HLA-DR using antibodies for characterization of MHC-CAR expression [38, 53]. The inhibition of CD52 expression allows for concurrent treatment with Lemtrada R (alemtuzumab), an FDA-approved treatment for multiple sclerosis 1421. Alemtuzumab is also used as a lympho-depleting/lympho-suppressive agent that aids in the engraftment of CAR T therapies [39]. A CAR T-cell therapy modified with TRAC- and CD52-targeted TALENs is currently being tested in clinical trials 138, 40, 431.

TALEN to inactivate MHC Class II transactivator (CIITA) in place of CD52, as inactivation of CIITA is expected to inhibit HLA-DR expression [26][38], thus allowing for the direct identification of MHC-CAR-containing cells by HLA-DR antibody staining.

```
Validated TALENs (TRAC:
TTGTCCCACAGATATCCagaaccctgaccctgCCGTGTACCAGCTGAGA
(SEQ ID NO: 376), CD52:
TTCCTCCTACTCACCATcagcctcctggttatGGTACAGGTAAGAGCAA
(SEQ ID NO: 371), CIITA:
TTCCCTCCCAGGCAGCTCacagtgtgccaccaTGGAGTTGGGGCCCCTA
(SEQ ID NO: 366))
``` are obtained from Cellectis or designed to target previously validated sites [38, 43].

Human T cells are activated and electroporated with mRNA encoding variants of 3 different TALEN: TCR-alpha constant chain, CD52, and CIITA. Cells are surface stained with anti-CD3 or anti-TCR (TCR-alpha constant chain), anti-CD52 (CD52), or anti-HLA-DR (CIITA), and then analyzed by flow cytometry.

In the TALEN expression assays, the ability of previously validated TALENs to inactive target genes are re-validated [39]. Translocation studies and off-target studies are reperformed, and several whole-genome sequences confirm results. GUIDE-seq can be used as an alternative to whole genome sequencing to confirm on- and off-target editing [8].

One of more of the following endogenous genes are to be edited to reduce interaction with other cells: TCR (through TCR alpha or beta chain: to reduce targeting to undesired cells), CIITA (regulates expression of MHC Class II genes; target cells for taster deletion), B7-1(CD80) and/or B7-2 (CD86) knockout, and b2m (regulates expression of MHC Class I genes) with NKG2D ligands or UL18.

Further, one or more of the following genes can be edited to modify the function of an interacting cell: PD-L1+1—CTLA4-Ig overexpression; PD-L1/2 overexpression +/−PD-1 knockout; FasL overexpression +/−Fas knockout; Galectin 9 overexpression +/−TIM3 knockout; and/or PVT/CD155 overexpression +/−TIGIT knockout. Defects in PD-1, Fas, TIm3, TIGIT predispose patients to autoimmunity. Some drugs can restore function (for example: Tim3, glatiramer acetate and IFN-beta). If autologous cells from a patient suffering autoimmune disease are utilized they may require patient specific correction of defective genes that influence CTL and Treg function. Their personal mutation set may also determine whether CTL or Treg cells will be the most therapeutically relevant, and whether some cellular modification will be effective, if either autologous or allogeneic cells are used.

Further, the following edits may modify the location and/or function of the cells (for example, to make it more like a follicular regulatory cell):

MHC-CAR-(FOX3P)-(CSI or CD19 CAR)/(CS-1 knockout required for CS-1 CAR)

MHC-CAR-(FOX3P)-(CCR7 or CXCR5)

Moreover, the following edits can enable combination therapies for autoimmune diseases (e.g., MS specific therapeutics)

RQR tag: engineered T cells can be removed with rituximab (kill switch). A tag for the newly approved anti-CD20 antibody Ocrevus could be generated.

Rapamycin switch: CARs only in/active when patient is treated with rapamycin (tacrolimus)

CD52 knockout: allows pretreatment with Lemtrada (alemtuzumab) to decrease number of immune cells present VLA-4 knockout: can treat with tysabri to move pathogenic immune cells to periphery but engineered cells are forced to stay there (may not be ideal for patients with established MS as cells that are stuck in the brain spinal cord; however, simultaneous mRNA expression of VLA-4 can provide temporary access to those locations)

IL-6 antibody (Toclizumab) secretion from engineered T cell: helpful when the engineered T cell must access the brain and spinal cord, but this drug cannot access the locations due to the BBB Example 3: Investigation of MHC-CAR Activities (i) Preparation of Primary T Cells Expressing MHC-CAR Primary T cells can be prepared as follows. T cells are isolated from peripheral blood mononuclear cells (EasySep Human T Cell Enrichment Kit, Stemcell Technologies) and activated (Dynabeads Human T-Activator CD3/CD28, Life Technologies) with (X-Vivo 15 medium. Lonza: 20 mg/ml 11-2, Miltenyi; 5% human AB serum, Seralab). A suitable MHC-CAR construct containing a MBP antigenic peptide is introduced into the primary T cells using a conventional method. Surface expression of the MHC-CAR construct is verified by FACS and antibody staining.

(ii) MHC-CAR Activity Tests In Vitro

Upon verification of construct trafficking and expression (with mRNA, multicistronic mRNA, lentivirus), activity tests are conducted in vitro. All tests are conducted at different effector:target (E:F) cell concentrations. The in vitro tests provide an initial evaluation of MHC-CAR signaling domains and T cell subsets.

(iii) Signaling Domain Assessment by IL-2 Production 24 hours post electroporation, human T cells transiently engineered with MHC-CAR are stimulated with plate-bound HLA-DR antibody, to determine whether MHC-CAR (containing various signaling domains) is functional. 11-2 production is measured 24 hours later using a StemCell IL-2 ELISA kit. This test provides a quick assay as to whether variants should be reengineered or abandoned [29].

(iv) Interaction of MHC-CAR Cells and Pathogenic TCR Cells Through Proliferation Assay Target cell lines transiently expressing TCR are magnetically sorted for TCR expression 24 hours after electroporation and irradiated, in order to test whether engagement of the MHC-CAR with antigen-specific TCR stimulates proliferation of MHC-CAR containing T cells. Alternatively, target cell lines that stably express TCR are irradiated. The irradiated cells displaying (+/−antigen-specific) TCR are incubated with CFSE-labeled MHCCAR cells and proliferation is measured after culture at different T:E ratios [30].

(v) Degranulation Assay

CAR T-cells are labeled through epitopes on RQR (which are not being expressed on the target cells used) or eBFP instead of T cell markers. The assay is performed for cell lines with transient or stable expression (the example of transient expression is described). 24 hours post-electroporation, MHC-CAR human T-cells with either RQR8 or BFP are co-cultured with target (antigen-specific TCR SupT1 or Jurkat) or control (+1—TCR Jurkat or TCR-SupT1) cells for 6 hours. Transiently expressed (and later stably expressing) target cells are electroporated with antigen-specific TCR and sorted with CD3 magnetic beads post-electroporation. The RQR+ or BFP+ MHC-CAR T-cells (as identified with anti-rituximab antibody. QBEnd10 antibody) are analyzed by flow cytometry to detect the expression of the degranulation marker CD107a on their surface [2].

(vi) Cytokine Secretion Assay

The assay is performed for cell lines with transient or stable expression (transient expression is described). The human T cells transiently expressing the MHC-CARs are assessed for cytokine secretion following co-culture with target cells 24 hours post electroporation. Human T cells transiently expressing the MHC-CARs are co-cultured with target (antigen-specific TCR containing Jurkat or SupT1 cells) or control (+/−non-antigen-specific Jurkat or SupT1) cells for 24 hours. The antigen-specific TCR is then killed by irradiation before the assay. The supernatants are harvested and analyzed using the TH1/TH2 cytokine cytometric bead array kit to quantify the cytokines produced by T cells [13]. MHC-CAR T-cells produce IFN and other cytokines in co-culture with antigen-specific TCR expressing target cells but not in co-culture with control cells.

(vii) IFNγ Release Assay

Various levels of MHC-CAR expressing cells are incubated with irradiated TCR T-cells 24 hours after transfection. Co-cultures are maintained for 24 hours. After incubation and centrifugation, supernatants are tested with IFNγ detection by ELISA.

(viii) Cytotoxicity Assay

TCR T-cells are incubated with therapeutic MHC-CAR as well as control cells. Target and control cells are labeled with fluorescent intracellular dyes (CFSE or Cell Trace Violet) before co-culturing with MHC-CAR T-cells. The co-cultures are incubated for 4 hours. After this incubation period, cells are labeled with a fixable viability dye and analyzed by flow cytometry. Viability of each cell population (target or negative control) is determined and the percentage of specific cell lysis is calculated. Cytotoxicity assays are carried out 48 hours after transduction.

(ix) Inhibition Assay

PBMCs are co-cultured with irradiated or mitomycin-treated engineered T cells expressing the MHC-CAR construct. As control, PBMCs are co-cultured with irradiated or mitomycin-treated engineered T cells that do not express the MHC-CAR construct. 7 days later, cell proliferation from a human patient donor A is measured by XTT colorimetric assay or by CFSE dilution (FACS analysis). Although cell proliferation would be observed in control, no or limited cell proliferation is expected when engineered T cells express secreted FP. The results from this experiment aim to show that alloreactive T cells proliferation is inhibited when the MHC-CAR expressing T cells express FP.

(x) Proliferation

To test whether engagement of the MHC-CAR with antigen-specific TCR stimulates proliferation of MHC-CAR containing T cells, target cell lines transiently expressing TCR are magnetically sorted for TCR expression 24 hours after electroporation and irradiated. Alternatively, target cell lines that stably express TCR are irradiated. The irradiated cells displaying (+/−antigen-specific) TCR are incubated with CFSE-labeled MHC-CAR cells and proliferation is measured after culture at different T:E ratios.

(xi) In Vivo Tests

MHC-CAR (with mouse and human MHC) in mouse T cells has previously shown therapeutic efficacy in experimental allergic encephalomyelitis, the mouse model for multiple sclerosis [25, 29]. Here we test whether MHC-CAR in human cells can target human TCR in human T cell lines, using an in vivo mouse model analogous to that in prior CAR T preclinical studies 1391. The in vivo tests allow further evaluation of MHC-CAR signaling domains and T cell subsets.

The In vivo activity of MHC-CAR T-cells can be verified in a mouse xenograft model as illustrated in FIG. 7.

Immunodefficient NOG mice are intravenously injected with antigen-specific TCR-luciferase expressing T-cells as an MS xenograft mouse model. Mice then receive intravenous doses of MHC-CAR T-cells tested at different doses, either 2 or 7 days post-injection with tumor cell line. Intravenous injection with T-cells that are not transduced with the CAR lentiviral vector serve as control. Bioluminescent signals are determined at the day of T-cell injection (D0), at D7, 14, 21, 28 and 40 after T-cell injection in order to follow the expansion of TCR-luciferase expressing cells in different animals [39].

CAR T-cells with similar background modifications (TALEN to inactivate native TCR and minimize graft vs host, TALEN to inactivate CD52 and allow simultaneous treatment with alemtuzumab, and RQR8 to allow depletion) to the ones shown here have been previously validated in mouse models and are now used in a UCART19 clinical trial 1391.

(xii) Kill-Switch Verification

Transduced T cells are exposed to 25% baby-rabbit complement (AbD Serotec) for 4 hours with or without inclusion of pharmaceutical complements (rituximab, tysabri, or alemtuzumab) to examine complement-dependent cytotoxicity (CDC)-mediated sensitivity. Miltenyi CD34 magnetic bead-selected-transduced RQR8 T-cells are compared against a similarly treated population of Q8-transduced T cells to demonstrate specificity of CDC-mediated deletion. Further examination of CDC assay parameters was achieved through time-course/dose-titration assays using RQR8-transduced T cells incubated with pharmaceutical complement at 12.5, 25, 50, and 100 mg/mL and time-point assessments ranging between 1 to 120 minutes.

Example 4: Regulatory T Cells (Treg) Expressing MHC-CAR

Therapies that antigen specifically target pathologic T lymphocytes responsible for multiple sclerosis and other autoimmune diseases are expected to have improved therapeutic indices compared with antigen-nonspecific therapies. This example provides an exemplary cellular immunotherapy that uses chimeric antigen receptors to selectively redirect therapeutic T cells against myelin basic protein-specific T lymphocytes implicated in MS Treg Cell Sorting. Transduction, and Expansion CD4+ T cells are isolated from PMBC via RosetteSep (STEMCELL Technologies) and enriched for CD25+cells (Miltenyi Biotec) prior to sorting into live CD4+CD45RO-CD45RA+CD25+Tregs and CD4+CD45RO-CD45RA+CD25—control T cells by FACS. Sorted T cells are stimulated with artificial APCs (aAPCs) loaded with aCD3 mAbs in 1,000 U/ml or 100 U/ml of IL-2, for Tregs or non-reg control T, respectively. One day later, cells are transduced with lentivirus. At day 7, ΔNGFR+cells were purified with magnetic selection (Miltenyi Biotec), then re-stimulated with aAPCs as above and expanded for 6 to 7 days.

Flow Cytometry:

For phenotypic analysis, cells were stained with fixable viability dye (FVD) (65-0865-14 and 65-0866-14, eBioscience) and for surface markers before fix/perm with FOXP3'Transcription Factor Staining Buffer Set (eBioscience), followed by staining for intracellular proteins. For analysis of cytokine production, cells were stimulated with 10 ng/ml PMA and 500 ng/ml ionomycin, in the presence of brefeldin A (10 µg/ml) (all Sigma-Aldrich) for 4 hours. Samples were analyzed by flow cytometry.

Microscopy:

PBMCs are labeled with PKH26 or PKH67 (Sigma-Aldrich, PKH26GL-1KT and PKH67GL-1KT), and Tregs are labeled with cell proliferation dye (CPD) eFluor450 (eBiosciences, 65-0842-85) and then suspended in a 3D gel of 1.5% rat tail collagen type I (Ibidi) composed of 1×DMEM and 100% FCS per the manufacturer's general 3D gel protocol. The cell suspension is pipetted into a β-Slide Chemotaxis3D and allowed to polymerize for 30 minutes in a humidified incubator at 35° C. and 5% CO2 (Tokai Hit) on a Leica TCS SP8 confocal microscope. The outer chambers are filled with 1×DMEM and images recorded using a ×10/0.30 objective every 2 minutes for 3 hours, eFluor450, PKH67, and PKH26 were excited at 405 nm, 488 nm, and 561 nm, and the fluorescence emission is collected at 415-470 nm, 495-525 nm, and 570-650 nm, respectively. The number of interactions between CAR-Tregs and either target or control cells is quantified every 20 minutes. Cells that do not move were excluded from the analysis. The total numbers of each labeled cell type per field of view can be counted using the analyze particles function in ImageJ (imagej.nih.gov/ij/).

Treg-Specific Demethylated Region (TSDR) Analysis

Treg stable expression of stable Foxp3 is associated with selective demethylation of TSDR within the Foxp3 locus. In order to test for stable expression, DNA from frozen T cell pellets is was isolated with the DNeasy Blood and Tissue Kit (QIAGEN) and bisulfite converted with the EZ Direct Kit (Zymo Research). PCR of BisDNA was performed with the Human FOXP3 Kit (Epigen DX) and prepared for pyrosequencing using PyroMark buffers (QIAGEN), then assayed on a Biotage PyroMark Q96 MD pyrosequencer (QIAGEN). Results were calculated with Pyro Q-CpG software (Biotage).

Cytokine Production

To measure cytokine production, T cell lines are stimulated with K562 cells (1 K562:2 T cells) for 48 hours. Supernatants are collected and cytokine concentration was determined by the Human Th1Ih2/Th17 Cytokine Kit (BD Biosciences) and analyzed.

Suppression of MHC CAR-Specific Proliferation

To test whether Treg specific for target were also capable of suppressing CD4+ T cell proliferation, MHC CAR-specific CD4+T clones are isolated. An Epstein Barr Virus-tranformed B lymphablastoid cell line was transduced with MHC-CAR using lentivirus. EBV cell lines were grown overnight, irradiated at 150 Gy, and cocultured with CPD-labeled MHC CAR-specific CD4+T clones in the absence or presence of CAR-expressing Tregs or conventional T cells. Proliferation is determined after 4 days, and percentage of suppression of MHC CAR-specific clones calculated using percentage of proliferation as follows: (100−[(% proliferated MHC CAR+test)/(% proliferated MHC CAR alone)]—100).

Upon verification of construct trafficking and expression (with mRNA, multicistronic mRNA, and/or lentivirus), activity tests will begin in vitro. All tests are conducted at different effector:target (E:F) cell concentrations. The in vitro tests are expected to provide an initial evaluation of MHC-CAR signaling domains and T cell subsets.

Transient or Lentiviral Expression of Chemokine and Adhesion Receptors in T Cells Receptors are expressed in human T cells after electroporation of mono/polycistronic mRNA or lentiviral transduction. Expression of the receptor is analyzed using flow cytometry. In summary: $5 \times 10^6$ T cells preactivated several days (3-5) with anti CD3/CD28 coated beads and IL2 were re-suspended in cytoporation buffer T, and electroporated with 45 μg of mRNA. Twenty-four hours after electroporation, human T cells engineered using polycistronic mRNAs encoding the multi-chain CARs were labeled with a fixable viability dye eFluor-780 and a PE-conjugated goat anti mouse IgG F(ab')2 fragment specific, and analyzed by flow cytometry. Alternately the receptors were vectorized in lentivirus, expressed, and analyzed similarly.

In Vitro Chemotaxis Assay

Transduced T cells were used in chemotaxis assays as previously described [Bürkle et al., Blood, 110(9):3316-3325, 2007: Wu and Hwang, Journal of immunology, 168(10):5096, 2002.: Singh et al., Journal of immunology. 180(J):214-221, 2008.; Ryu et al., Molecules and Cells. 39.12:898-908, 2016.1. Cells (~20.000 cells in medium, one million cells, $5 \times 10^6$/mL) were placed on top of the 5-μm pore size filters in duplicate, whereas medium with and without chemokines were placed into the lower chamber. After 30 min, 1 h, 3 h, 5 hr, 24 hr at 37° C., migrated cells that had fallen to the bottom of the plate were:

A, photographed using a 4×objective. Three random views from each of two wells were counted using Image Pro Plus (Media Cybernetics, Silver Spring, MD). Three independent experiments were performed with similar results.

B. 400 μL of the cell suspension was added to 100 μL of a solution containing $4 \times 10-7$ M FITC-labeled phalloidin, 0.5 mg/mL 1-alpha-lysophosphatidylcholine (both from Sigma. St Louis, MO), and 7% formaldehyde in phosphate-buffered saline (PBS). The fixed cells were analyzed by flow cytometry on a FACSCalibur. and all time points are plotted relative to the mean relative fluorescence of the sample before addition of the chemokine.

C. the cells in the lower chamber were counted using Countess II FL (Thermo Fisher Scientific, USA) or the O.D, value at 450 nm was measured using a Versamax microplate reader (Molecular Devices).

Example 5: Expression of MHC-Based Chimeric Receptors (MHC-CAR) in HEK293 Cells

Constructs encoding MHC-CARs were constructed as discussed in Example 2 and assessed for expression in HEK293 cells. Briefly. Construct 1 includes an EF1alpha short promoter, CD19 CAR (4G7-CAR), CCR6, and GFP (provided by SEQ ID NO: 426); and Construct 2 includes a EF1alpha short promoter, RQR8, MHC-CAR1 part B MHC-CAR1 part A, and GFP (provided by SEQ ID NO: 409).

Constructs 1, 2, or media control (non-transfected) was transfected into HEK293 cells and cultured. The cells were assessed for expression by microscopy based on GFP expression. Populations of GF-positive cells were observed in the groups that were transfected with Construct 1 or Construct 2. The cells were also assessed for expression of the components encoded by the constructs by flow cytometry. Tables 8 and 9.

Construct 1 Expression

For detection of CCR6, cells were incubated with an anti-CCR6 monoclonal antibody conjugated to APC (17-1969-42, eBioscience); and for detection of CD19, cells were incubated with a biotinylated CD19 (Acro CD9—H8259, Acro Biosystems) followed by a streptavidin-PE (405203, BioLegend@).

TABLE 8

Expression of Construct 1

|  | FITC (GFP) | APC (CCR6) | PE (CD19) |
|---|---|---|---|
| CCR6 Expression | | | |
| Unstained | 71.9 | 0.1 | 17.4 |
| CCR6 | 71.3 | 81.9 | 16.9 |
| CD19 Expression | | | |
| Unstained | 71.9 | 0.1 | 17.4 |
| CD19 | 71.3 | 0.1 | 33.3 |
| streptavidin-PE only | 71.5 | 0.1 | 18.5 |

Construct 2 Expression

For detection of CD34 expression from the epitope included in RQR8, cells were incubated with an anti-CD34 APC-conjugated monoclonal antibody; and for detection of MHC-CAR expression, the cells were incubated an anti-HLA-DR antibody.

TABLE 9

Construct 2 Expression

| GFP Expression | FITC (GFP) | APC (CD34) | PE |
|---|---|---|---|
| Unstained | 62.3 | 0.1 | 2.4 |
| RQR Expression | FITC (GFP) | APC (CD34) | PE |
| Unstained | 62.3 | 0.0 | 2.4 |
| CD34 | 61.8 | 58.0 | 2.5 |
| MHC CAR Expression | FITC (GFP) | APC (HLA-DR) | PE |
| Unstained | 62.3 | 0.0 | 2.4 |
| HLA-DR | 63.9 | 98.1 | 2.1 |

Nucleic acid sequence of Construct 1

(SEQ ID NO: 426)

atggagacagacactcttctcctttgggtcttgctgctgtgggttcccggaagcacaggagaagcacagttgcaa
cagtctgggccagaactcatcaaacccggagcttctgtaaaaatgtcatgcaaagctagtggatatacatttact
tcttacgtgatgcactgggtaaaacagaaacctggtcaggggcttgagtggatcgggtacattaacccatataat
gacggcaccaaatataacgagaaattcaagggaaaggctacgcttacatcagataagtccagtagcaccgcttat
atggaacttagcagccttacttccgaagattccgcggtgtattactgcgcgagagggacttactactacgggagt
cgagtattcgattattggggtcaaggcacgacgctcacggtgagctcaggtggtggagggtctgggggtggcggc
agtggtgggggggctcagacatcgtgatgacccaggcagcaccttctatcccggtaaccccaggcgagtctgta
tctatcagttgtcggtccagcaagtctcttctcaacagtaatggcaatacatatctttactggttcctccaaagg
cctgggcaaagtcctcaacttcttatatatcggatgtccaatcttgcgagtggcgtaccagacaggttttcaggg
tctgggagcggaacagcttttacgttgagaatatccagggtagaagctgaggacgtcggtgtatattattgcatg
caacatctcgaataccccttttaccttcggcgctggtacaaagctcgaattgaaacgcagcgatccaaccacgacg
ccagcgccacgaccacctacgcccgctccaactattgctcccagccctgagtcttcggccagaagcgtgtaga
cctgctgccggcggggccgttcatacgcggggccttgactttgcatgtgatatctatatatgggctcctttggcg
ggaacttgcggagtgcttcttttgtcactcgtgataacgttgtattgtaaaagggtcgaaagaaatcctctat
atatttaagcagccctttatgaggcccgtgcaaacaacacaagaagaggacggatgctcttgtcgattcccggaa
gaggaggaagggggggtgtgagcttagggtcaagttttctcgctctgccgacgcgccagccctcaacagggccaa
aaccagctgtataacgaactcaacctcgggcgccgggaagagtatgacgtccttgacaaacggcgcggtcgcgac
cctgaaatgggtggaaaaccgaggcgaaagaaccccaggagggactttacaacgaattgcaaaaagacaagatg
gccgaagcctattccgaaattggaatgaaaggcgagcggagacgaggtaaggggcatgacggcctgtatcaaggg
ctctctacgccacgaaggatacttacgacgcccttcatatgcaagctcttccaccacggggttcgagcggcagt
ggagagggcagaggaagtctgctaacatgcggtgacgtcgaggagaatcctggcccaatgagtggggaaagtatg
aacttcagcgatgtatttgactcctccgaagattactttgtatctgtgaatacgagccattactccgtcgatagt
gaaatgctgctctgtagtctccaagaagtccgccaattcagtcgcctcctcgttcccatcgcgtactcccttatt
tgtgttttggccttctgggtaacatcctggttgtaatcacattcgctttctataaaaaagctcggagtatgact
gatgtttaccttcttaacatggctatagggacattcttttgtgcttactctcccattctgggctgtgagccat
gcaacagggcgtgggttttttcaaatgccacatgtaagctgcttaaagggatctatgcaataaacttcaattgc
gggatgctcctgctgacatgcatcagtatggatcgatacatagctatagtacacaggactaagtccttccgcctg
cgatcccgcacactgcctaggagcaaaattatttgcctcgtcgtatgggggctctcagtgatcatctcctccagt
acgtttgtctttaaccagaaatataacacacagggttctgatgtatgtgaaccaaagtatcagacagtgagtgaa
ccaatacggtggaagttgcttatgttgggcttggagctgcttttgggttttcatcccactgatgttcatgatt
ttctgttatacatttattgttaagaccttggttcaggcgcaaaatagcaagagacataaggcaattcgagtcacc
attgccgtggtgttggtcttcttggcctgtcagatcccccataatatggttctgctcgtcaccgccgctaacttg
ggtaagatgaatcgatcttgtcagtccgagaagttgatcggatacaccaaaactgtgatagaagtgctggccttc
cttcactgttgtctgaacccagttttgtatgcttttataggacagaagtttcgaaattacttcttgaaaatcctc
aaggacctctggtgtgttcgaaggaagtacaagagctctggctttagttgcgctgggcgctacagtgagaatata
tcccggcagacctccgagactgctgataatgacaacgcaagttccttcactatg Nucleic acid sequence of Construct 2

(SEQ ID NO: 409)

atgggtacttcactgttgtgctggatggcactttgtctttgggtgccgatcatgctgatgcatgtccgtactcc
aatcctagcctgtgctccggggggggagggagtgaactccctacacagggaaccttctctaatgtctccaccaac
gtctcccctgcaaaaccgatcacaatagcttgcccctatagtaacccttccctctgtagtggaggggggggttca -continued

```
cctgctccacgccctcctaccccgcgccaacgatcgcgtcacaaccgctcagtcttaggccggaagcctgtagg
ccagcggctggcggtgcggttcatacgcggggattggattttgcctgcgacatttacatttgggctccgctggcc
ggtacttgtggggtattgctgttgtctcttgttattacgctttattgcaatcacaggaacaggcgacgagtatgc
aaatgcccgcggcccgtcgtgagatctgggtccggccaatgtactaactacgctttgttgaaactcgctggcgat
gttgaaagtaaccccggtcctccaacaggtatggtatgcttgaagctcccgggcgggtcctgcatgaccgctctc
actgttactcttatggtccttagttcaccgcttgccctggcatctgatgagaatcccgtggttcatttttttaag
aacatcgtcacaccgcgcaccccacctgggggaggcggatctggcggaggcgggagtggaggctcaggagacaca
agacccgattcttgtggcagcccaaaagggagtgccatttttttcaatgggacgaacgagttcgcttccttgat
gggcgacctgacgcggagtactggaactcccaaaaggatattttggagcaggcacgagcagctgtggacacctat
tgtcgacataattatggtgtggtggaatcctttacagttcagcggcgggtgcaacctaaagtgaccgtgtatcca
tctaaaacgcaaccccctccaacaccataacctcctggtgtgttccgtaagcggcttctatcccgggtcaattgag
gtcaggtggttcctcaacggtcaggaggagaaggccggaatggtaagtactggtcttatccagaacggagactgg
accttccaaactttggtaatgttggaaacggtgccgcgatccggggaggtgtatacatgccaagttgaacacccg
agtgttacgagcccctgacggttgagtggagggcgcggtcagagagcgcacaatctaaaatgctgtcaggagta
ggcggatttgtactcggactcctcttttgggcgctgggttgtttatctactttagaaaccaaacaagtagagta
aagtttcccgaagtgcggacgccccgcgtatcagcaaggtcaaaaccagctttataacgaactgaacttggga
cgacgcgaagagtacgatgttcttgataagcggagagggcgcgatcccgaaatgggggaaagcctcggaggaag
aacccacaagaaggcctttataatgaactgcagaaggacaagatggcggaggcgtattccgaaataggcatgaag
ggtgaacggaggagaggaaagggacatgacggactttatcaaggattgtctaccgcaactaaagacacctatgac
gcgttgcacatgcaggctctccctccgagaggttcgagcggcagtggagagggcagaggaagtctgctaacatgc
ggtgacgtcgaggagaatcctggcccaatggcaatatctggtgttcctgtcctcgggttttttatcatagccgta
ctgatgtcagcacaggaatcatgggcgataaaagaagagcacgtgataatacaggcggagttttatttgaacccg
gaccagagcggtgagttcatgttcgattttgatggcgacgagatatttcacgttgacatggcaaaaaaggaaacg
gtgtggagacttgaggagtttggacgattcgcatcatttgaggcacaaggagcactcgccaatatcgcggtggac
aaggccaacctggagatcatgacataacgctccaattatacgcctatcactaatgtgcccctgaggttactgtg
ctcacaaattctcccgtagaacttagggaacctaacgtcctcatatgtttcatcgacaagttcactcctccggtg
gtcaatgtaacgtggcttcggaatggtaagccggtcaccacgggtgtctcagagaccgtatttctgcccagagaa
gaccacctcttccgcaaatttcattaccttccctttcttccttcaacggaagacgtttacgactgcagggtcgaa
cattgggggcttgacgagccacttctcaagcattgggagttcgacgcccatcaccgcttccagaaacgactgaa
aacgttgtctgcgctcttggcctgacagtgggcctggtaggcattattatcgggaccatctttatcatcaaggt
ttgacttcccgggtcaaatttagcagatccgctgacgcaccggcctaccagcagggccagaaccaactctacaac
gagctgaatctcggccgacgggaagagtatgacgtactcgacaagcggagaggtcgagaccctgagatgggcggt
aaaccgagacggaaaaatccccaagagggtctttataatgaactccagaaggataagatggctgaagcctattct
gagatagggatgaaaggcgagcggcggagggggtaagggccatgatggcctttaccagggactctccacggcaacc
aaagatacttacgacgcccttcacatgcaagccctcccgccacgcggatccggcgcaacaaacttctctctgctg
aaacaagccggagatgtcgaagagaatcctggaccggtgagcaagggcgaggagctgttcaccggggtggtgccc
atcctggtcgagctggacggcgacgtaaacggccacaagttcagcgtgtctggcgagggcgagggcgatgccacc
tacggcaagctgaccctgaagttcatctgcaccaccggcaagctgcccgtgccctggcccaccctcgtgaccacc
ctgacctacggcgtgcagtgcttcagccgctaccccgaccacatgaagcagcacgacttcttcaagtccgccatg
cccgaaggctacgtccaggagcgcaccatcttcttcaaggacgacggcaactacaagacccgcgccgaggtgaag
```

-continued

```
ttcgagggcgacaccctggtgaaccgcatcgagctgaagggcatcgacttcaaggaggacggcaacatcctgggg cacaagctggagtacaactacaacagccacaacgtctatatcatggccgacaagcagaagaacggcatcaaggcg aacttcaagatccgccacaacatcgaggacggcagcgtgcagctcgccgaccactaccagcagaacacccccatc ggcgacggccccgtgctgctgcccgacaaccactacctgagcacccagtccgccctgagcaaagaccccaacgag aagcgcgatcacatggtcctgctggagttcgtgaccgccgcgggatcactctcggcatggacgagctgtacaag taa'
```

Example 6: Expression of CD3

Expression of CD3 was assessed to determine the efficacy of CRISPR methods targeting the T cell receptor alpha constant (TRAC) gene. Briefly, sgRNAs targeting the TRAC gene were generated by amplifying the target site using forward primer (5'-AGCGCTCTCGTACAGAGTTGG-3' (SEQ ID NO: 385)) and reverse primer (5'-AAAAAAAGCACCGACTCGGTGCC-3' (SEQ ID NO: 386).
The unmodified sgRNA is provided by the nucleic acid sequence:

```
                                        (SEQ ID NO: 384)
5'- GAG AAU CAA AAU CGG UGA AUG UUU UAG AGC UAG AAA

UAG CAA GUU AAA AUA AGG CUA GUC CGU UAU CAA CUU GAA

AAA GUG GCA CCG AGU CGG UGC UUU U -3.
```

The modified sgRNA is provided by the nucleic acid sequence:

```
                                        (SEQ ID NO: 337)
5'- 2'OMe(G(ps)A(ps)G(ps)) AAU CAA AAU CGG UGA AUG

UUU UAG AGC UAG AAA UAG CAA GUU AAA AUA AGG CUA

GUC CGU UAU CAA CUU GAA AAA GUG GCA CCG AGU CGG

UGC 2'OMe(U(ps)U(ps)U(ps) U -3'.
2'OMe = 2'O) -methyl RNA and ps = phosphorothioate.
```

Figure 11:
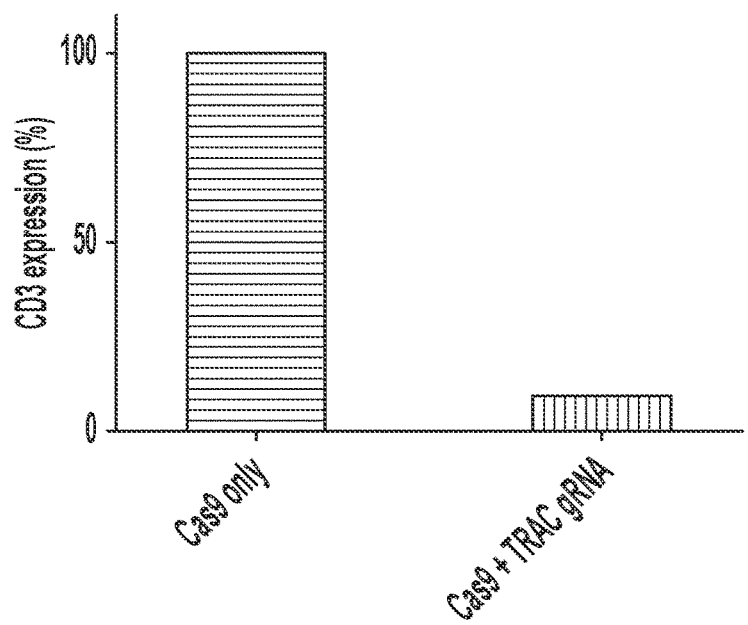
FIG. 11 is a plot showing CD3 expression on primary human stimulated CD3+ T cells (TCELL-0028) transfected with an mRNA encoding Cas9 ("Cas9 only") or an mRNA encoding Cas9 ("Cas9 only") and sgRNAs targeting the gene encoding T cell receptor alpha domain (TRAC) ("Cas9+TRAC gRNA").

Primary human stimulated CD3+ T-cells were transfected with an mRNA encoding Cas9 (Cas9 only) or both an mRNA encoding Cas9 and sgRNAs targeting the TRAC gene. After 7 days post-transfection, expression of CD3 was assessed by flow cytometry. The cells were incubated with a 1:100 dilution of an anti-CD3-APC antibody (clone OKT3; BioLegend®, cat. no. 317318). As shown in FIG. 11, transfection of an mRNA encoding Cas9 and sgRNAs targeting the TRAC gene resulted in a substantial reduction in CD3 expression.

Example 7: Kill Switch Verification

Efficacy of the RQR8 kill switch encoded in example Construct 2 was assessed using a cell viability assay. Briefly, HEK cells were transfected with media only, Construct 1 (SEQ ID NO: X), Construct 2 (which encodes the rituximab-mediated RQR8 kill switch, SEQ ID NO: X), or both Construct 1 and Construct 2. The transfected HEK293 cells were harvested, counted, and resuspended at 1×10^6 cells/mL. 300 uL of the cellular suspension was transferred into each of 4 wells of α48-well tissue culture plate. 100 uL of complete medium and 4 uL of Rituximab were added to the second well, and 100 uL of freshly prepared baby rabbit complement and 4 uL of Rituximab were added to the fourth well. The plates were incubated for 2, 4, or 24 hours. The assay was terminated by the adding 1 uL of chilled Annexin V buffer (150 mMNaCl. 10 mM HEPES, 10 mM CaCl), and then the sample was transferred into a pre-prepared flow cytometry tube containing 3 mL of Annexin V buffer.

Samples were harvested by centrifugation and any residual buffer was blotted with paper towels. The samples were then stained with 1 uL of Annexin V APC, vortexed, and placed in subdued lighting for 15 minutes. The samples were then washed with Annexin V buffer and supplemented with 5 uL of propridium iodide/mL buffer and placed on ice pending flow cytometry performed immediately following final suspension.

Figure 12:
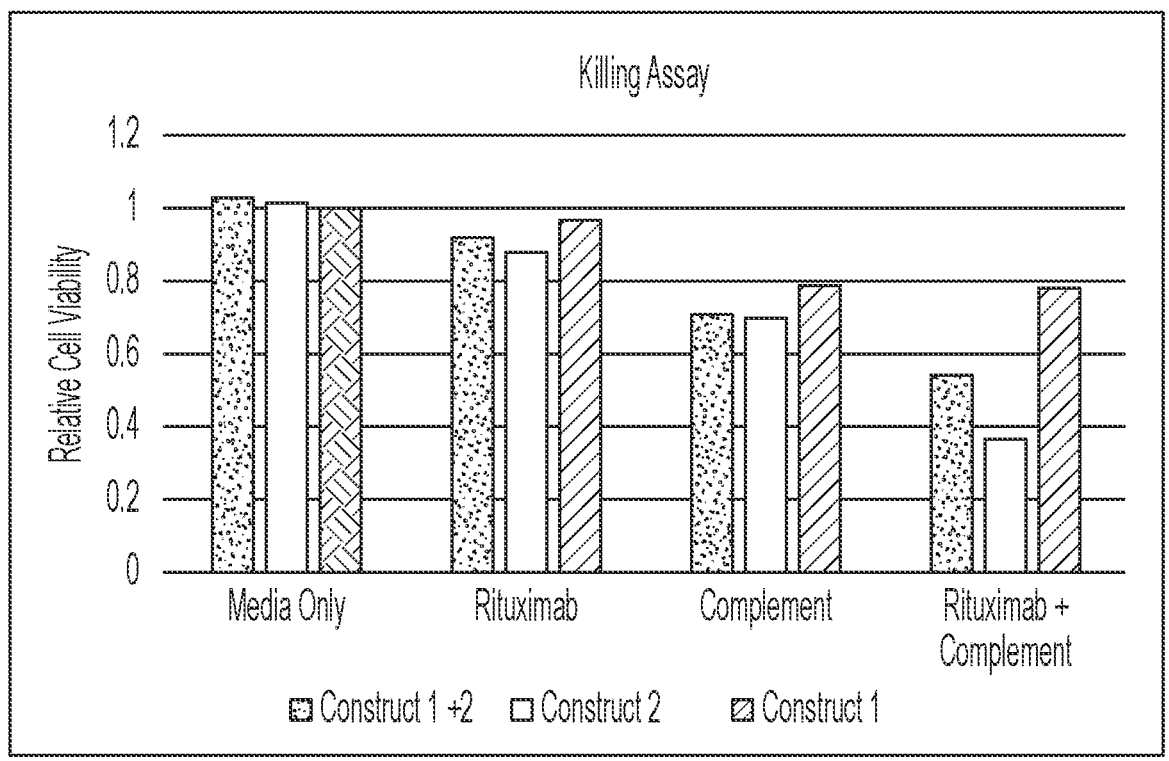
FIG. 12 is a plot showing relative cell viability in a killing assay. HEK-293 cells transfected with Construct 1, Construct 2, or both Constructs 1 and 2 were incubated with media only, rituximab, complement, or both rituximab and complement.

The percentage of GFP-positive cells was quantified to quantify the killing induced by the RQR8 kill switch. As shown in FIG. 12, incubation with complement alone resulted in some cell death, however this reduction in viability was observed in all of the groups of cells. Cell death was observed in cells that expressed Construct 2 or both Constructs 1 and 2 the presence of the combination of rituximab and complement, indicating specific RQR8-mediated cell death.

REFERENCES

[1] Corlien et al., International journal of cancer, 99(1):7-13, 2002.
[2] Betts et Ia., Methods in cell biology, 75:497-512, 2004.
[3] Bimbaum et al. Proceedings of the National Academy of Sciences of the United States of America, 1 11(49):17576, 2014.
[4] Boissel et al., Nucleic acids research, 42(4):2591-2601, 2014.
[5] Cai et al., Blood, 128(22):4039, 2016.
[6] Chung et al., Proceedings of the National Academy of Sciences, 92(9):3712-3716, 1995.
[7] Cieri et al., Blood, 121(4):573-584, 2013.
[8] Corrigan-Curay et al., Molecular Therapy, 23(5):796-806, 2015.
[9] Dotti et al., Immunological reviews. 257(1):107-126, 2014.
[10] WO2015121454
[11] Farber et al., Nature Reviews Immunology, 14(1):24-35, 2014.
[12] US20170183413
[13] Galetto. Publication No. EP3137498 A1, 2017.
[14] US20140120905
[15] Galetto et al., Molecular Therapy-Methods & Clinical Development, 1:14021, 2014.
[16] Goebels et al., Brain, 123(3):508-518, 2000.
[17] Hahn et al., Nature immunology. 6(5):490-496, 2005.
[18] Hall et al., International Immunology, 3(4):359-368, 1991.
[19] Hart et al., Gene Therapy, 15:625-631, 2008.

[20] Hohlfeld et al., Proceedings of the National Academy of Sciences, 101(suppl 2):14599-14606, 2004.
[21] Holst et al., Nature Protocols Electronic Edition, 1(1): 406, 2006.
[22] Jensen et al., Immunological reviews, 257(1):127-144, 2014.
[23] Juillerat et al., Scientific reports. 5:8150, 2015.
[24] Justesen et al., Immunome research, 5(1):2, 2009.
[25] Jyothi et al., Nature biotechnology, 20(12):1215-1220, 2002.
[26] Mach et al., Immunological reviews, 138(1):207-221, 1994.
[27] Maecker et al., Nature Reviews Immunology, 12(3): 191-200, 2012.
[28] Mamonkin et al., Blood, 126(8):983-992, 2015.
[29] Moisini et al., The Journal of Immunology, 180(5): 3601-3611, 2008.
[30] Morris et al., Science translational medicine, 7(272): 272ra10-272ra10, 2015.
[31] Moscou et al., Science, 326(5959):1501-1501, 2009.
[32] Mueller et al., Nature reviews Immunology, 16(2):79-89, 2016.
[33] Nagarajan et al., The Journal of Immunology, 168(4): 1780-1786, 2002.
[34] Nagy et al., Nature medicine, 8(8):801-807, 2002.
[35] Ophir et al., Blood, 121(7):1220-1228, 2013.
[36] Osborn et al., Molecular therapy, 24(3):570-581, 2016.
[37] Philip et al., Blood, 124(8):1277-1287, 2014.
[38] US20170016025
[39] Poirot et al., Cancer research, 75(18):3853-3864, 2015.
[40] Qasim et al., Science translational medicine, 9(374): eaaj2013, 2017.
[41] Ruck et al., International journal of molecular sciences, 16(7):16414-16439, 2015.
[42] Salzer et al., Neurology, 87(20):2074-2081, 2016.
[43] Smith et al., U.S. patent application Ser. No. 14/018,021, 2013.
[44] Steidl et al., Nature, 471(7338):377-381, 2011.
[45] Suhoski et al., Molecular Therapy, 15(5):981-988, 2007.
[46] Taylor et al., Cell, 169(1):108-119, 2017.
[47] Valton et al., Molecular Therapy, 23(9):1507-1518, 2015.
[48] Vanderlugt et al., Nature Reviews Immunology, 2(2): 85-95, 2002.
[49] Walchli et al., PloS one, 6(11):e27930, 2011.
[50] Wingerchuk et al., Mayo Clinic Proceedings, 89:225-240, 2014.
[51] Yang et al., Gene Therapy, 15(21):1411-1423, 2008.
[52] Yang, Journal of Immunotherapy, 31(9):830, 2008.
[53] Zhou et al., Immunology, 122(4):476-485, 2007.
Jiang et al., International immunology, 25(4):235-246, 2013.
Busch et al., The EMBO journal, 15(2):418, 1996.
Akalin et al., Molecular Therapy, 17:S25, 2009.
Jin et al., Proceedings of the National Academy of Sciences, 111(10):3787-3792, 2014.
Tanimura et al., Blood, 125(18):2835-2844, 2015.
Hamano et al., Alveolar Macrophage Biology B32:A3147-A3147, 2016.
Arase et al., Journal of Dermatological Science, 84(1):e87, 2016.
Tanimura et al., Placenta, 46:108, 2016.
Hiwa et al., Arthritis & Rheumatology, 69(10):2069-2080, 2017.
Hansen et al. Trends in immunology, 31(10):363, 2010.
Hacohen et al., Cancer immunology research, 1(1):11-15, 2013.
Owens et al., Annals of neurology, 65(60):639-649, 2009.
Chastre et al., New England Journal of Medicine, 374(15): 1495-1496, 2016.
Housley et al., Clinical Immunology, 161(1):51-58, 2015.
Larman et al., 2013. Journal of autoimmunity, 43:1-9, 2013.
Wu et al., *Science*, 350(6258):aab4077, 2015
Tran et al. Scientific reports, 6:31730, 2016
Schall et al., Nature Reviews Immunology, 11(5):355-363, 2011.
Tabarkiewicz et al., Archivum immunologiae et therapiae experimentalis, 63(6):435-449, 2015.
Brown et al., New England Journal of Medicine, 375(26): 2561-2569, 2016.
Gagliani et al., Nature. 523(7559):221-225, 2015.
Barreiro, et al. Cardiovascular research, 86(2):174-182, 2010
Wang and Rivière. Molecular Therapy-Oncolytics, 3:16015 2016.
Birkle et al., Blood, 110(9):3316-3325, 2007.
Wu and Hwang, Journal of immunology. 168(10):5096, 2002.
Singh et al., Journal of immunology, 180(1):214-221, 2008.
Ryu et al., Molecules and Cells, 39.12:898-908, 2016.
Hiepe et al., Nature Reviews Rheumatology, 7(3):170-178, 2011
Garboczi, et al. *The Journal of Immunology,* 157(12):5403-5410, 1996.
Quaresma, et al., 2015. Viruses, 8(1):5 2015.
Sanjana, et al. Nature methods, 11(8):783-784, 2014.
Korn et al. *Proceedings of the National Academy of Sciences,* 105(47):18460-18465, 2008.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

SEQUENCE LISTING

```
Sequence total quantity: 431
SEQ ID NO: 1            moltype = AA  length = 203
FEATURE                 Location/Qualifiers
source                  1..203
                        mol_type = protein
                        organism = Homo sapiens
```

```
SEQUENCE: 1
MASQKRPSQR HGSKYLATAS TMDHARHGFL PRHRDTGILD SIGRFFGGDR GAPKRGSGKV    60
PWLKPGRSPL PSHARSQPGL CNMYKDSHHP ARTAHYGSLP QKSHGRTQDE NPVVHFFKNI   120
VTPRTPPPSQ GKGRGLSLSR FSWGAEGQRP GFGYGGRASD YKSAHKGFKG VDAQGTLSKI   180
FKLGGRDSRS GSPMARRHHH HHH                                          203

SEQ ID NO: 2            moltype = AA  length = 40
FEATURE                 Location/Qualifiers
source                  1..40
                        mol_type = protein
                        organism = Homo sapiens
SEQUENCE: 2
GSKYLATAST MDHARHGFLP RHRDTGILDS IGRFFGGDRG                          40

SEQ ID NO: 3            moltype = AA  length = 20
FEATURE                 Location/Qualifiers
source                  1..20
                        mol_type = protein
                        organism = Homo sapiens
SEQUENCE: 3
KYLATASTMD HARHGFLPRH                                               20

SEQ ID NO: 4            moltype = AA  length = 23
FEATURE                 Location/Qualifiers
source                  1..23
                        mol_type = protein
                        organism = Homo sapiens
SEQUENCE: 4
ATASTMDHAR HGFLPRHRDT GIL                                           23

SEQ ID NO: 5            moltype = AA  length = 20
FEATURE                 Location/Qualifiers
source                  1..20
                        mol_type = protein
                        organism = Homo sapiens
SEQUENCE: 5
RDTGILDSIG RFFGGDRGAP                                               20

SEQ ID NO: 6            moltype = AA  length = 29
FEATURE                 Location/Qualifiers
source                  1..29
                        mol_type = protein
                        organism = Homo sapiens
SEQUENCE: 6
IGRFFGGDRG APKRGSGKDS HHPARTAHY                                     29

SEQ ID NO: 7            moltype = AA  length = 19
FEATURE                 Location/Qualifiers
source                  1..19
                        mol_type = protein
                        organism = Homo sapiens
SEQUENCE: 7
APKRGSGKDS HHAARTAHY                                                19

SEQ ID NO: 8            moltype = AA  length = 20
FEATURE                 Location/Qualifiers
source                  1..20
                        mol_type = protein
                        organism = Homo sapiens
SEQUENCE: 8
GSGKDSHHPA RTAHYGSLPQ                                               20

SEQ ID NO: 9            moltype = AA  length = 19
FEATURE                 Location/Qualifiers
source                  1..19
                        mol_type = protein
                        organism = Homo sapiens
SEQUENCE: 9
HHPARTAHYG SLPQKSHGR                                                19

SEQ ID NO: 10           moltype = AA  length = 19
FEATURE                 Location/Qualifiers
source                  1..19
                        mol_type = protein
                        organism = Homo sapiens
SEQUENCE: 10
HAARTAHYGS LPQKSQGHR                                                19

SEQ ID NO: 11           moltype = AA  length = 19
```

```
FEATURE                Location/Qualifiers
source                 1..19
                       mol_type = protein
                       organism = Homo sapiens
SEQUENCE: 11
SLPQKSHGRT QDENPVVHF                                                     19

SEQ ID NO: 12          moltype = AA  length = 20
FEATURE                Location/Qualifiers
source                 1..20
                       mol_type = protein
                       organism = Homo sapiens
SEQUENCE: 12
PQDENPVVHF FKNIVTPRTP                                                    20

SEQ ID NO: 13          moltype = AA  length = 20
FEATURE                Location/Qualifiers
source                 1..20
                       mol_type = protein
                       organism = Homo sapiens
SEQUENCE: 13
TQDENPVVHF FKNIVTPRTP                                                    20

SEQ ID NO: 14          moltype = AA  length = 19
FEATURE                Location/Qualifiers
source                 1..19
                       mol_type = protein
                       organism = Homo sapiens
SEQUENCE: 14
QDENPVVHFF KNIVTPRTP                                                     19

SEQ ID NO: 15          moltype = AA  length = 19
FEATURE                Location/Qualifiers
source                 1..19
                       mol_type = protein
                       organism = Homo sapiens
SEQUENCE: 15
DENPVVHFFK NIVTPRTPP                                                     19

SEQ ID NO: 16          moltype = AA  length = 15
FEATURE                Location/Qualifiers
source                 1..15
                       mol_type = protein
                       organism = Homo sapiens
SEQUENCE: 16
ENPVVHFFKN IVTPR                                                         15

SEQ ID NO: 17          moltype = AA  length = 17
FEATURE                Location/Qualifiers
source                 1..17
                       mol_type = protein
                       organism = Homo sapiens
SEQUENCE: 17
ENPVVHFFKN IVTPRTP                                                       17

SEQ ID NO: 18          moltype = AA  length = 14
FEATURE                Location/Qualifiers
source                 1..14
                       mol_type = protein
                       organism = Homo sapiens
SEQUENCE: 18
ENPVVHFFKN IVTP                                                          14

SEQ ID NO: 19          moltype = AA  length = 20
FEATURE                Location/Qualifiers
source                 1..20
                       mol_type = protein
                       organism = Homo sapiens
SEQUENCE: 19
NPVVHFFKNI VTPRTPPPSQ                                                    20

SEQ ID NO: 20          moltype = AA  length = 13
FEATURE                Location/Qualifiers
source                 1..13
                       mol_type = protein
                       organism = Homo sapiens
SEQUENCE: 20
VVHFFKNIVT PRT                                                           13
```

```
SEQ ID NO: 21            moltype = AA   length = 20
FEATURE                  Location/Qualifiers
source                   1..20
                         mol_type = protein
                         organism = Homo sapiens
SEQUENCE: 21
VVHFFKNIVT PRTPPPSQGK                                                         20

SEQ ID NO: 22            moltype = AA   length = 19
FEATURE                  Location/Qualifiers
source                   1..19
                         mol_type = protein
                         organism = Homo sapiens
SEQUENCE: 22
KNIVTPRTPP PSQGKGRGL                                                          19

SEQ ID NO: 23            moltype = AA   length = 19
FEATURE                  Location/Qualifiers
source                   1..19
                         mol_type = protein
                         organism = Homo sapiens
SEQUENCE: 23
PSQGKGRGLS LSRFSWGAE                                                          19

SEQ ID NO: 24            moltype = AA   length = 20
FEATURE                  Location/Qualifiers
source                   1..20
                         mol_type = protein
                         organism = Homo sapiens
SEQUENCE: 24
GKGRGLSLSR FSWGAEGQRP                                                         20

SEQ ID NO: 25            moltype = AA   length = 19
FEATURE                  Location/Qualifiers
source                   1..19
                         mol_type = protein
                         organism = Homo sapiens
SEQUENCE: 25
LSRFSWGAEG QRPGFGYGG                                                          19

SEQ ID NO: 26            moltype = AA   length = 19
FEATURE                  Location/Qualifiers
source                   1..19
                         mol_type = protein
                         organism = Homo sapiens
SEQUENCE: 26
QRPGFGYGGR ASDYKSAHK                                                          19

SEQ ID NO: 27            moltype = AA   length = 19
FEATURE                  Location/Qualifiers
source                   1..19
                         mol_type = protein
                         organism = Homo sapiens
SEQUENCE: 27
ASDYKSAHKG FKGVDAQGT                                                          19

SEQ ID NO: 28            moltype = AA   length = 19
FEATURE                  Location/Qualifiers
source                   1..19
                         mol_type = protein
                         organism = Homo sapiens
SEQUENCE: 28
FKGVDAQGTL SKIFKLGGR                                                          19

SEQ ID NO: 29            moltype = AA   length = 20
FEATURE                  Location/Qualifiers
source                   1..20
                         mol_type = protein
                         organism = Homo sapiens
SEQUENCE: 29
VDAQGTLSKI FKLGGRDSRS                                                         20

SEQ ID NO: 30            moltype = AA   length = 20
FEATURE                  Location/Qualifiers
source                   1..20
                         mol_type = protein
                         organism = Homo sapiens
SEQUENCE: 30
SKIFKLGGRD SRSGSPMARR                                                         20
```

```
SEQ ID NO: 31            moltype = AA   length = 247
FEATURE                  Location/Qualifiers
source                   1..247
                         mol_type = protein
                         organism = Homo sapiens
SEQUENCE: 31
MASLSRPSLP SCLCSFLLLL LLQVSSSYAG QFRVIGPRHP IRALVGDEVE LPCRISPGKN    60
ATGMEVGWYR PPFSRVVHLY RNGKDQDGDQ APEYRGRTEL LKDAIGEGKV TLRIRNVRFS   120
DEGGFTCFFR DHSYQEEAAM ELKVEDPFYW VSPGVLVLLA VLPVLLLQIT VGLVFLCLQY   180
RLRGKLRAEI ENLHRTFDPH FLRVPCWKIT LFVIVPVLGP LVALIICYNW LHRRLAGQFL   240
EELRNPF                                                             247

SEQ ID NO: 32            moltype = AA   length = 277
FEATURE                  Location/Qualifiers
source                   1..277
                         mol_type = protein
                         organism = Homo sapiens
SEQUENCE: 32
MGLLECCARC LVGAPFASLV ATGLCFFGVA LFCGCGHEAL TGTEKLIETY FSKNYQDYEY    60
LINVIHAFQY VIYGTASFFF LYGALLLAEG FYTTGAVRQI FGDYKTTICG KGLSATVTGG   120
QKGRGSRGQH QAHSLERVCT CLGKWLGHPD KFVGITYALT VVWLLVFACS AVPVYIYFNT   180
WTTCQSIAFP SKTSASIGSL CADARMYGVL PWNAFPGKVC GSNLLSICKT AEFQMTFHLF   240
IAAFVGAAAT LVSLLTFMIA ATYNFAVLKL MGRGTKF                            277

SEQ ID NO: 33            moltype = AA   length = 582
FEATURE                  Location/Qualifiers
source                   1..582
                         mol_type = protein
                         organism = Homo sapiens
SEQUENCE: 33
MIFLTALPLF WIMISASRGG HWGAWMPSSI SAFEGTCVSI PCRFDFPDEL RPAVVHGVWY    60
FNSPYPKNYP PVVFKSRTQV VHESFQGRSR LLGDLGLRNC TLLLSNVSPE LGGKYYFRGD   120
LGGYNQYTFS EHSVLDIVNT PNIVVPPEVV AGTEVEVSCM VPDNCPELRP ELSWLGHEGL   180
GEPAVLGRLR EDEGTWVQVS LLHFVPTREA NGHRLGCQAS FPNTTLQFEG YASMDVKYPP   240
VIVEMNSSVE AIEGSHVSLL CGADSNPPPL LTWMRDGTVL REAVAESLLL ELEEVTPAED   300
GVYACLAENA YGQDNRTVGL SVMYAPWKPT VNGTMVAVEG ETVSILCSTQ SNPDPILTIF   360
KEKQILSTVI YESELQLELP AVSPEDDGEY WCVAENQYGQ RATAFNLSVE FAPVLLLESH   420
CAAARDTVQC LCVVKSNPEP SVAFELPSRN VTVNESEREF VYSERSGLVL TSILTLRGQA   480
QAPPRVICTA RNLYGAKSLE LPFQGAHRLM WAKIGPVGAV VAFAILIAIV CYITQTRRKK   540
NVTESPSFSA GDNPPVLFSS DFRISGAPEK YESKEVSTLE SH                      582

SEQ ID NO: 34            moltype = AA   length = 20
FEATURE                  Location/Qualifiers
REGION                   1..20
                         note = Synthetic
source                   1..20
                         mol_type = protein
                         organism = synthetic construct
SEQUENCE: 34
TYEIAPVFVL LFYVTLKKMR                                                20

SEQ ID NO: 35            moltype = AA   length = 31
FEATURE                  Location/Qualifiers
REGION                   1..31
                         note = Synthetic
source                   1..31
                         mol_type = protein
                         organism = synthetic construct
SEQUENCE: 35
LLECCARCLV GAPFASLVAT GLCFFGVALF C                                   31

SEQ ID NO: 36            moltype = AA   length = 20
FEATURE                  Location/Qualifiers
REGION                   1..20
                         note = Synthetic
source                   1..20
                         mol_type = protein
                         organism = synthetic construct
SEQUENCE: 36
LVGAPFASLV ATGLCFFGVA                                                20

SEQ ID NO: 37            moltype = AA   length = 31
FEATURE                  Location/Qualifiers
REGION                   1..31
                         note = Synthetic
source                   1..31
                         mol_type = protein
                         organism = synthetic construct
```

```
SEQUENCE: 37
FGVALFCGCE VEALTGTEKL IETYFSKNYQ D                                       31

SEQ ID NO: 38           moltype = AA  length = 20
FEATURE                 Location/Qualifiers
REGION                  1..20
                        note = Synthetic
source                  1..20
                        mol_type = protein
                        organism = synthetic construct
SEQUENCE: 38
LFCGCGHEAL TGTEKLIETY                                                    20

SEQ ID NO: 39           moltype = AA  length = 20
FEATURE                 Location/Qualifiers
REGION                  1..20
                        note = Synthetic
source                  1..20
                        mol_type = protein
                        organism = synthetic construct
SEQUENCE: 39
TGTEKLIETY FSKNYQDYEY                                                    20

SEQ ID NO: 40           moltype = AA  length = 21
FEATURE                 Location/Qualifiers
REGION                  1..21
                        note = Synthetic
source                  1..21
                        mol_type = protein
                        organism = synthetic construct
SEQUENCE: 40
TGTEKLIETY FSKNYQDYEY L                                                  21

SEQ ID NO: 41           moltype = AA  length = 32
FEATURE                 Location/Qualifiers
REGION                  1..32
                        note = Synthetic
source                  1..32
                        mol_type = protein
                        organism = synthetic construct
SEQUENCE: 41
YFSKNYQDYE YLINVIHAFQ YVIYGTASFF FL                                      32

SEQ ID NO: 42           moltype = AA  length = 32
FEATURE                 Location/Qualifiers
REGION                  1..32
                        note = Synthetic
source                  1..32
                        mol_type = protein
                        organism = synthetic construct
SEQUENCE: 42
GTASFFFLYG ALLLAYGFYT TGAVRQIFGD YK                                      32

SEQ ID NO: 43           moltype = AA  length = 20
FEATURE                 Location/Qualifiers
REGION                  1..20
                        note = Synthetic
source                  1..20
                        mol_type = protein
                        organism = synthetic construct
SEQUENCE: 43
LYGALLLAEG FYTTGAVRQI                                                    20

SEQ ID NO: 44           moltype = AA  length = 21
FEATURE                 Location/Qualifiers
REGION                  1..21
                        note = Synthetic
source                  1..21
                        mol_type = protein
                        organism = synthetic construct
SEQUENCE: 44
FYYTTGAVRQ IFGDYKTTIC G                                                  21

SEQ ID NO: 45           moltype = AA  length = 22
FEATURE                 Location/Qualifiers
REGION                  1..22
                        note = Synthetic
source                  1..22
                        mol_type = protein
```

```
                        organism = synthetic construct
SEQUENCE: 45
AVRQIFGDYK TTICGKGLSA TV                                           22

SEQ ID NO: 46           moltype = AA  length = 31
FEATURE                 Location/Qualifiers
REGION                  1..31
                        note = Synthetic
source                  1..31
                        mol_type = protein
                        organism = synthetic construct
SEQUENCE: 46
RQIFGDYKTT CGKGLSATVT GGQKGRGSRG Q                                 31

SEQ ID NO: 47           moltype = AA  length = 20
FEATURE                 Location/Qualifiers
REGION                  1..20
                        note = Synthetic
source                  1..20
                        mol_type = protein
                        organism = synthetic construct
SEQUENCE: 47
KGLSATVTGG QKGRGYRGQH                                              20

SEQ ID NO: 48           moltype = AA  length = 20
FEATURE                 Location/Qualifiers
REGION                  1..20
                        note = Synthetic
source                  1..20
                        mol_type = protein
                        organism = synthetic construct
SEQUENCE: 48
QKGRGSRGQH QAHSLERVCH                                              20

SEQ ID NO: 49           moltype = AA  length = 32
FEATURE                 Location/Qualifiers
REGION                  1..32
                        note = Synthetic
source                  1..32
                        mol_type = protein
                        organism = synthetic construct
SEQUENCE: 49
KGRGSRGQHQ AHSLERVCHC LGCWLGHPDK FV                                32

SEQ ID NO: 50           moltype = AA  length = 32
FEATURE                 Location/Qualifiers
REGION                  1..32
                        note = Synthetic
source                  1..32
                        mol_type = protein
                        organism = synthetic construct
SEQUENCE: 50
LGHPDKFVGI TYALTVVWLL VFACSAVPVY IY                                32

SEQ ID NO: 51           moltype = AA  length = 32
FEATURE                 Location/Qualifiers
REGION                  1..32
                        note = Synthetic
source                  1..32
                        mol_type = protein
                        organism = synthetic construct
SEQUENCE: 51
SAVPVYIYFN TWTTCQSIAA PCKTSASIGT LC                                32

SEQ ID NO: 52           moltype = AA  length = 20
FEATURE                 Location/Qualifiers
REGION                  1..20
                        note = Synthetic
source                  1..20
                        mol_type = protein
                        organism = synthetic construct
SEQUENCE: 52
AVPVYIYFNT WTTCQSIAFP                                              20

SEQ ID NO: 53           moltype = AA  length = 20
FEATURE                 Location/Qualifiers
REGION                  1..20
                        note = Synthetic
source                  1..20
```

```
                        mol_type = protein
                        organism = synthetic construct
SEQUENCE: 53
WTTCQSIAFP SKTSASIGSL                                                    20

SEQ ID NO: 54           moltype = AA   length = 32
FEATURE                 Location/Qualifiers
REGION                  1..32
                        note = Synthetic
source                  1..32
                        mol_type = protein
                        organism = synthetic construct
SEQUENCE: 54
SASIGTLCAD ARMYGVLPWN AFFGKVCGSN LL                                      32

SEQ ID NO: 55           moltype = AA   length = 32
FEATURE                 Location/Qualifiers
REGION                  1..32
                        note = Synthetic
source                  1..32
                        mol_type = protein
                        organism = synthetic construct
SEQUENCE: 55
KVCGSNLLSI CKTAEFQMTF HLFIAAFVGA AA                                      32

SEQ ID NO: 56           moltype = AA   length = 32
FEATURE                 Location/Qualifiers
REGION                  1..32
                        note = Synthetic
source                  1..32
                        mol_type = protein
                        organism = synthetic construct
SEQUENCE: 56
AAFVGAAATL VSLLTFMIAA TYNFAVLKLM GR                                      32

SEQ ID NO: 57           moltype = AA   length = 20
FEATURE                 Location/Qualifiers
REGION                  1..20
                        note = Synthetic
source                  1..20
                        mol_type = protein
                        organism = synthetic construct
SEQUENCE: 57
MIAATYNFAV LKLMGRGTKF                                                    20

SEQ ID NO: 58           moltype = AA   length = 19
FEATURE                 Location/Qualifiers
REGION                  1..19
                        note = Synthetic
source                  1..19
                        mol_type = protein
                        organism = synthetic construct
SEQUENCE: 58
MAATYNFAVL KLMGRFTKF                                                     19

SEQ ID NO: 59           moltype = AA   length = 42
FEATURE                 Location/Qualifiers
REGION                  1..42
                        note = Synthetic
source                  1..42
                        mol_type = protein
                        organism = synthetic construct
SEQUENCE: 59
KRGRKKLLYI FKQPFMRPVQ TTQEEDGCSC RFPEEEEGGC EL                           42

SEQ ID NO: 60           moltype = AA   length = 47
FEATURE                 Location/Qualifiers
REGION                  1..47
                        note = Synthetic
source                  1..47
                        mol_type = protein
                        organism = synthetic construct
SEQUENCE: 60
PGKRGRKKLL YIFKQPFMRP VQTTQEEDGC SCRFPEEEEG GCELAHA                      47

SEQ ID NO: 61           moltype = AA   length = 41
FEATURE                 Location/Qualifiers
REGION                  1..41
                        note = Synthetic
```

```
                        source            1..41
                                          mol_type = protein
                                          organism = synthetic construct
SEQUENCE: 61
RSKRSRGGHS DYMNMTPRRP GPTRKHYQPY APPRDFAAYR S                          41

SEQ ID NO: 62           moltype = AA  length = 46
FEATURE                 Location/Qualifiers
REGION                  1..46
                        note = Synthetic
source                  1..46
                        mol_type = protein
                        organism = synthetic construct
SEQUENCE: 62
PGRSKRSRGG HSDYMNMTPR RPGPTRKHYQ PYAPPRDFAA YRSAHA                     46

SEQ ID NO: 63           moltype = AA  length = 87
FEATURE                 Location/Qualifiers
REGION                  1..87
                        note = Synthetic
source                  1..87
                        mol_type = protein
                        organism = synthetic construct
SEQUENCE: 63
EMWHEGLEEA SRLYFGERNV KGMFEVLEPL HAMMERGPQT LKETSFNQAY GRDLMEAQEW      60
CRKYMKSGNV KDLLQAWDLY YHVFRRI                                         87

SEQ ID NO: 64           moltype = AA  length = 115
FEATURE                 Location/Qualifiers
REGION                  1..115
                        note = Synthetic
source                  1..115
                        mol_type = protein
                        organism = synthetic construct
SEQUENCE: 64
GSSSGSSSGS SSGSSSEMWH EGLEEASRLY FGERNVKGMF EVLEPLHAMM ERGPQTLKET      60
SFNQAYGRDL MEAQEWCRKY MKSGNVKDLL QAWDLYYHVF RRIGSSSGSS SGSSS          115

SEQ ID NO: 65           moltype = AA  length = 107
FEATURE                 Location/Qualifiers
REGION                  1..107
                        note = Synthetic
source                  1..107
                        mol_type = protein
                        organism = synthetic construct
SEQUENCE: 65
GVQVETISPG DGRTFPKRGQ TCVVHYTGML EDGKKFDSSR DRNKPFKFML GKQEVIRGWE      60
EGVAQMSVGQ RAKLTISPDY AYGATGHPGI IPPHATLVFD VELLKLE                  107

SEQ ID NO: 66           moltype = AA  length = 135
FEATURE                 Location/Qualifiers
REGION                  1..135
                        note = Synthetic
source                  1..135
                        mol_type = protein
                        organism = synthetic construct
SEQUENCE: 66
GSSSGSSSGS SSGSSSGVQV ETISPGDGRT FPKRGQTCVV HYTGMLEDGK KFDSSRDRNK      60
PPKFMLGKQE VIRGWEEGVA QMSVGQRAKL TISPDYAYGA TGHPGIIPPH ATLVFDVELL     120
KLEGSSSGSS SGSSS                                                     135

SEQ ID NO: 67           moltype = AA  length = 112
FEATURE                 Location/Qualifiers
REGION                  1..112
                        note = Synthetic
source                  1..112
                        mol_type = protein
                        organism = synthetic construct
SEQUENCE: 67
RVKFSRSADA PAYQQGQNQL YNELNLGRRE EYDVLDKRRG RDPEMGGKPR RKNPQEGLYN      60
ELQKDKMAEA YSEIGMKGER RRGKGHDGLY QGLSTATKDT YDALHMQALP PR             112

SEQ ID NO: 68           moltype = AA  length = 15
FEATURE                 Location/Qualifiers
REGION                  1..15
                        note = Synthetic
source                  1..15
                        mol_type = protein
                        organism = synthetic construct
```

```
SEQUENCE: 68
GGGGSGGGGS GGGGS                                                        15

SEQ ID NO: 69           moltype = AA  length = 15
FEATURE                 Location/Qualifiers
REGION                  1..15
                        note = Synthetic
source                  1..15
                        mol_type = protein
                        organism = synthetic construct
SEQUENCE: 69
GGGGGGSGGS GGSGG                                                        15

SEQ ID NO: 70           moltype = AA  length = 20
FEATURE                 Location/Qualifiers
REGION                  1..20
                        note = Synthetic
source                  1..20
                        mol_type = protein
                        organism = synthetic construct
SEQUENCE: 70
GGGGSGGGGS GGGGSGGGGS                                                   20

SEQ ID NO: 71           moltype = DNA  length = 2340
FEATURE                 Location/Qualifiers
misc_feature            1..2340
                        note = Synthetic
source                  1..2340
                        mol_type = other DNA
                        organism = synthetic construct
SEQUENCE: 71
atggtatgct tgaagctccc gggcgggtcc tgcatgaccg ctctcactgt tactcttatg      60
gtccttagtt caccgcttgc cctggcatct gatgagaatc ccgtggttca ttttttttaag   120
aacatcgtca caccgcgcac cccacctggg ggaggcggat ctggcggagg cgggagtgga   180
ggctcaggag acacaagacc ccgattcttg tggcagccca aaagggagtg ccatttttc    240
aatgggacgg aacgagttcg cttccttgat cggtactttt acaaccaaga agagagtgta   300
cggttcgact cagatgtcgg cgagttccga gcggttacgg aattgggcg acctgacgcg    360
gagtactgga actcccaaaa ggatattttg gagcaggcac gagcagctgt ggacacctat   420
tgtcgacata attatgtgt ggtggaatcc tttacagttc agcggcgggt gcaacctaaa    480
gtgaccgtgt atccatctaa aacgcaaccc ctccaacacc ataacctcct ggtgtgttcc   540
gtaagcggct tctatcccgg gtcaattgag gtcaggtggt tcctcaacgg tcaggaggag   600
aaggccgaa tggtaagtac tggtcttatc cagaacggag actggacctt ccaaactttg    660
gtaatgttgg aaacggtgcc gcgatccggg gaggtgtata catgccaagt tgaacaccg    720
agtgttacga gcccctgac ggttgagtgg agggcgcggt cagagagcgc acaatctaaa    780
atgctgtcag gagtaggcgg atttgtactc ggactcctct ttttgggcgc tgggttgttt   840
atctacttta gaaaccaaac aagtagagta aagtttttcc gaagtgcgga cgctcccgcg   900
tatcgcaaag gtcaaaacca gctttacaac gaactgaact tgggacgacg cgaagagtac   960
gatgttcttg ataagcggag agggcgcgat cccgaaatgg ggggaaagcc tcggaggaag  1020
aacccacaag aaggccttta taatgaactg cagaaggaca agatggcgga ggcgtattcc  1080
gaaataggca tgaagggtga acggaggaga ggaaagggac atgacggact ttatcaagga  1140
ttgtctaccg caactaaaga cacctatgac gcgttgcaca gcaggcgggt gcaacccatc  1200
ggttcgagcg gcagtggaga gggcagagga agtctgctaa catgcggtga cgtcgaggag  1260
aatcctggcc aatggcaat atcggtgtt cctgtcctcg ggttttttat catagccgta    1320
ctgatgtcag cacaggaatc atgggcgata aagaagagc acgtgataat acaggcggag   1380
tttttatttga acccgacca gagcggtgag ttcatgttcg atttgatgg cgacgagata    1440
tttcacgttg acatggcaaa aaaggaaacg gtgtgagac ttgaggagtt tggacgattc    1500
gcatcatttg aggcacaagg agcactcgcc aatatcgcgg tggacaaggc caacctggag  1560
atcatgacaa aacgctccaa ttatacgcct atcactaatg tgcccctga ggttactgtg    1620
ctcacaaatt ctccgtaga acttagggaa cctaacgtcc tcatatgttt catcgacaag   1680
ttcactcctc cggttggtca tgtaacgtgg cttcggaatg gtaagccggt caccacgggt  1740
gtctcagaga ccgtatttct gcccagagaa gaccacctct tccgcaaatt tcattacctt  1800
ccctttcttc cttcaacgga agacgtttac gactgcaggg tcgaacattg ggggcttgac  1860
gagccacttc tcaagcattg ggagttcgac gccccatcac cgcattccaga aacgactgaa  1920
aacgttgtct gcgctcttgg cctgacagtg ggctggtga gcattattat cgggacaccg  1980
tttatcatca aaggttttgac ttcccgggtc aaatttagca gatccgctga cgcaccggcc  2040
taccagcagg gccagaacca actctacaac gagctgaatc tcggccgacg ggaagagtat  2100
gacgtactcg acaagcggag aggtcgagac cctgagatgg gcgtaaacc gagacggaaa  2160
aatcccaag agggtcttta taatgaactc cagaaggata agatgctga agcctattct    2220
gagataggga tgaaggcga gcggcggagg ggtaagggcc atgatggcct ttaccaggga  2280
ctctccacgg caaccaaaga tacttacgac gcccttcaca tgcaagccct cccgccacgc  2340

SEQ ID NO: 72           moltype = AA  length = 8
FEATURE                 Location/Qualifiers
REGION                  1..8
                        note = Synthetic
source                  1..8
                        mol_type = protein
                        organism = synthetic construct
SEQUENCE: 72
```

```
GSGSGSGS                                                                  8

SEQ ID NO: 73           moltype = AA   length = 21
FEATURE                 Location/Qualifiers
REGION                  1..21
                        note = Synthetic
source                  1..21
                        mol_type = protein
                        organism = synthetic construct
SEQUENCE: 73
IYIWAPLAGT CGVLLLSLVI T                                                  21

SEQ ID NO: 74           moltype = AA   length = 21
FEATURE                 Location/Qualifiers
REGION                  1..21
                        note = Synthetic
source                  1..21
                        mol_type = protein
                        organism = synthetic construct
SEQUENCE: 74
IWAPLAGICV ALLLSLIITL I                                                  21

SEQ ID NO: 75           moltype = AA   length = 267
FEATURE                 Location/Qualifiers
REGION                  1..267
                        note = Synthetic
source                  1..267
                        mol_type = protein
                        organism = synthetic construct
SEQUENCE: 75
GVQVETISPG DGRTFPKRGQ TCVVHYTGML EDGKKFDSSR DRNKPFKFML GKQEVIRGWE         60
EGVAQMSVGQ RAKLTISPDY AYGATGHPGI IPPHATLVFD VELLKLEEAA AREAAAREAA        120
AREAAARGRV AILWHEMWHE GLEEASRLYF GERNVKGMFE VLEPLHAMME RGPQTLKETS        180
FNQAYGRDLM EAQEWCRKYM KSGNVKDLLQ AWDLYYHVFR RITTTPAPRP PTPAPTIASQ        240
PLSLRPEACR PAAGGAVHTR GLDFACD                                           267

SEQ ID NO: 76           moltype = AA   length = 45
FEATURE                 Location/Qualifiers
REGION                  1..45
                        note = Synthetic
source                  1..45
                        mol_type = protein
                        organism = synthetic construct
SEQUENCE: 76
GGGGSGGGGS GGGGSGGGGS GGGGSGGGGS GGGGSGGGGS GGGGS                        45

SEQ ID NO: 77           moltype = AA   length = 13
FEATURE                 Location/Qualifiers
REGION                  1..13
                        note = Synthetic
source                  1..13
                        mol_type = protein
                        organism = synthetic construct
SEQUENCE: 77
LRWEPPPSTV SNM                                                           13

SEQ ID NO: 78           moltype = AA   length = 13
FEATURE                 Location/Qualifiers
REGION                  1..13
                        note = Synthetic
source                  1..13
                        mol_type = protein
                        organism = synthetic construct
SEQUENCE: 78
LRWEPSSQPT IPI                                                           13

SEQ ID NO: 79           moltype = AA   length = 13
FEATURE                 Location/Qualifiers
REGION                  1..13
                        note = Synthetic
source                  1..13
                        mol_type = protein
                        organism = synthetic construct
SEQUENCE: 79
LRWELSSQPT IPI                                                           13

SEQ ID NO: 80           moltype = AA   length = 30
FEATURE                 Location/Qualifiers
REGION                  1..30
```

```
                        note = Synthetic
source                  1..30
                        mol_type = protein
                        organism = synthetic construct
SEQUENCE: 80
QTTPGERSSL PAFYPGTSGS CSGCGSLSLP                                       30

SEQ ID NO: 81           moltype = AA   length = 46
FEATURE                 Location/Qualifiers
REGION                  1..46
                        note = Synthetic
source                  1..46
                        mol_type = protein
                        organism = synthetic construct
SEQUENCE: 81
GSSSGSSSGS SSGSSSQTTP GERSSLPAFY PGTSGSCSGC GSLSLP                     46

SEQ ID NO: 82           moltype = AA   length = 19
FEATURE                 Location/Qualifiers
REGION                  1..19
                        note = Synthetic
source                  1..19
                        mol_type = protein
                        organism = synthetic construct
SEQUENCE: 82
LRPVQAQAQS DCSCSTVSP                                                   19

SEQ ID NO: 83           moltype = AA   length = 35
FEATURE                 Location/Qualifiers
REGION                  1..35
                        note = Synthetic
source                  1..35
                        mol_type = protein
                        organism = synthetic construct
SEQUENCE: 83
GSSSGSSSGS SSGSSSLRPV QAQAQSDCSC STVSP                                 35

SEQ ID NO: 84           moltype = AA   length = 16
FEATURE                 Location/Qualifiers
REGION                  1..16
                        note = Synthetic
source                  1..16
                        mol_type = protein
                        organism = synthetic construct
SEQUENCE: 84
GLAVSTISSF FPPGYQ                                                      16

SEQ ID NO: 85           moltype = AA   length = 45
FEATURE                 Location/Qualifiers
REGION                  1..45
                        note = Synthetic
source                  1..45
                        mol_type = protein
                        organism = synthetic construct
SEQUENCE: 85
TTTPAPRPPT PAPTIASQPL SLRPEACRPA AGGAVHTRGL DFACD                      45

SEQ ID NO: 86           moltype = AA   length = 231
FEATURE                 Location/Qualifiers
REGION                  1..231
                        note = Synthetic
source                  1..231
                        mol_type = protein
                        organism = synthetic construct
SEQUENCE: 86
EPKSPDKTHT CPPCPAPPVA GPSVFLFPPK PKDTLMIART PEVTCVVVDV SHEDPEVKFN      60
WYVDGVEVHN AKTKPREEQY NSTYRVVSVL TVLHQDWLNG KEYKCKVSNK ALPAPIEKTI     120
SKAKGQPREP QVYTLPPSRD ELTKNQVSLT CLVKGFYPSD IAVEWESNGQ PENNYKTTPP     180
VLDSDGSFFL YSKLTVDKSR WQQGNVFSCS VMHEALHNHY TQKSLSLSPG K              231

SEQ ID NO: 87           moltype = AA   length = 13
FEATURE                 Location/Qualifiers
REGION                  1..13
                        note = Synthetic
source                  1..13
                        mol_type = protein
                        organism = synthetic construct
SEQUENCE: 87
EFDAPSPLPE TTE                                                         13
```

```
SEQ ID NO: 88           moltype = AA  length = 13
FEATURE                 Location/Qualifiers
REGION                  1..13
                        note = Synthetic
source                  1..13
                        mol_type = protein
                        organism = synthetic construct
SEQUENCE: 88
VEWRARSESA QSK                                                          13

SEQ ID NO: 89           moltype = AA  length = 24
FEATURE                 Location/Qualifiers
REGION                  1..24
                        note = Synthetic
source                  1..24
                        mol_type = protein
                        organism = synthetic construct
SEQUENCE: 89
IYIWAPLAGT CGVLLLSLVI TLYC                                              24

SEQ ID NO: 90           moltype = AA  length = 24
FEATURE                 Location/Qualifiers
REGION                  1..24
                        note = Synthetic
source                  1..24
                        mol_type = protein
                        organism = synthetic construct
SEQUENCE: 90
VGIIAGLVLF GAVITGAVVA AVMW                                              24

SEQ ID NO: 91           moltype = AA  length = 24
FEATURE                 Location/Qualifiers
REGION                  1..24
                        note = Synthetic
source                  1..24
                        mol_type = protein
                        organism = synthetic construct
SEQUENCE: 91
VGIIAGLVLL GAVITGAVVA AVMW                                              24

SEQ ID NO: 92           moltype = AA  length = 21
FEATURE                 Location/Qualifiers
REGION                  1..21
                        note = Synthetic
source                  1..21
                        mol_type = protein
                        organism = synthetic construct
SEQUENCE: 92
LCYLLDGILF IYGVILTALF L                                                 21

SEQ ID NO: 93           moltype = AA  length = 21
FEATURE                 Location/Qualifiers
REGION                  1..21
                        note = Synthetic
source                  1..21
                        mol_type = protein
                        organism = synthetic construct
SEQUENCE: 93
MLSGVGGFVL GLLFLGAGLF I                                                 21

SEQ ID NO: 94           moltype = AA  length = 26
FEATURE                 Location/Qualifiers
REGION                  1..26
                        note = Synthetic
source                  1..26
                        mol_type = protein
                        organism = synthetic construct
SEQUENCE: 94
MLSGVGGFVL GLLFLGAGLF IYFRNQ                                            26

SEQ ID NO: 95           moltype = AA  length = 326
FEATURE                 Location/Qualifiers
REGION                  1..326
                        note = Synthetic
source                  1..326
                        mol_type = protein
                        organism = synthetic construct
SEQUENCE: 95
```

```
ILDYSFTGGA GRDIPPPQIE EACELPECQV DAGNKVCNLQ CNNHACGWDG GDCSLNFNDP   60
WKNCTQSLQC WKYFSDGHCD SQCNSAGCLF DGFDCQLTEG QCNPLYDQYC KDHFSDGHCD  120
QGCNSAECEW DGLDCAEHVP ERLAAGTLVL VVLLPPDQLR NNSFHFLREL SHVLHTNVVF  180
KRDAQGQQMI FPYYGHEEEL RKHPIKRSTV GWATSSLLPG TSGGRQRREL DPMDIRGSIV  240
YLEIDNRQCV QSSSQCFQSA TDVAAFLGAL ASLGSLNIPY KIEAVKSEPV EPPLPSQLHL  300
MYVAAAAFVL LFFVGCGVLL SRKRRR                                     326

SEQ ID NO: 96           moltype = AA   length = 363
FEATURE                 Location/Qualifiers
REGION                  1..363
                        note = Synthetic
source                  1..363
                        mol_type = protein
                        organism = synthetic construct
SEQUENCE: 96
PCVGSNPCYN QGTCEPTSEN PFYRCLCPAK FNGLLCHILD YSFTGGAGRD IPPPQIEEAC   60
ELPECQVDAG NKVCNLQCNN HACGWDGGDC SLNFNDPWKN CTQSLQCWKY FSDGHCDSQC  120
NSAGCLFDGF DCQLTEGQCN PLYDQYCKDH FSDGHCDQGC NSAECEWDGL DCAEHVPERL  180
AAGTLVLVVL LPPDQLRNNS FHFLRELSHV LHTNVVFKRD AQGQQMIFPY YGHEEELRKH  240
PIKRSTVGWA TSSLLPGTSG GRQRRELDPM DIRGSIVYLE IDNRQCVQSS SQCFQSATDV  300
AAFLGALASL GSLNIPYKIE AVKSEPVEPP LPSQLHLMYV AAAAFVLLFF VGCGVLLSRK  360
RRR                                                                363

SEQ ID NO: 97           moltype = AA   length = 18
FEATURE                 Location/Qualifiers
REGION                  1..18
                        note = Synthetic
source                  1..18
                        mol_type = protein
                        organism = synthetic construct
SEQUENCE: 97
MLRLLLALNL FPSIQVTG                                                18

SEQ ID NO: 98           moltype = AA   length = 20
FEATURE                 Location/Qualifiers
REGION                  1..20
                        note = Synthetic
source                  1..20
                        mol_type = protein
                        organism = synthetic construct
SEQUENCE: 98
MSRSVALAVL ALLSLSGLEA                                              20

SEQ ID NO: 99           moltype = AA   length = 24
FEATURE                 Location/Qualifiers
REGION                  1..24
                        note = Synthetic
source                  1..24
                        mol_type = protein
                        organism = synthetic construct
SEQUENCE: 99
MAVMAPRTLL LLLSGALALT QTWA                                         24

SEQ ID NO: 100          moltype = AA   length = 25
FEATURE                 Location/Qualifiers
REGION                  1..25
                        note = Synthetic
source                  1..25
                        mol_type = protein
                        organism = synthetic construct
SEQUENCE: 100
MAISGVPVLG FFIIAVLMSA QESWA                                        25

SEQ ID NO: 101          moltype = AA   length = 28
FEATURE                 Location/Qualifiers
REGION                  1..28
                        note = Synthetic
source                  1..28
                        mol_type = protein
                        organism = synthetic construct
SEQUENCE: 101
MVCLKLPGGS CMTALTVTLM VLSSPLAL                                     28

SEQ ID NO: 102          moltype = AA   length = 29
FEATURE                 Location/Qualifiers
REGION                  1..29
                        note = Synthetic
source                  1..29
                        mol_type = protein
```

```
                                    organism = synthetic construct
SEQUENCE: 102
MVCLKLPGGS YMAKLTVTLM VLSSPLALA                                           29

SEQ ID NO: 103              moltype = AA   length = 100
FEATURE                     Location/Qualifiers
REGION                      1..100
                            note = Synthetic
REGION                      16..100
                            note = MISC_FEATURE - may be absent
source                      1..100
                            mol_type = protein
                            organism = synthetic construct
SEQUENCE: 103
GGGGSGGGGS GGGGSGGGGS GGGGSGGGGS GGGGSGGGGS GGGGSGGGGS GGGGSGGGGS         60
GGGGSGGGGS GGGGSGGGGS GGGGSGGGGS GGGGSGGGGS                              100

SEQ ID NO: 104              moltype = AA   length = 30
FEATURE                     Location/Qualifiers
REGION                      1..30
                            note = Synthetic
source                      1..30
                            mol_type = protein
                            organism = synthetic construct
SEQUENCE: 104
GGGGSGGGGS GGGGSGGGGS GGGGSGGGGS                                         30

SEQ ID NO: 105              moltype = AA   length = 60
FEATURE                     Location/Qualifiers
REGION                      1..60
                            note = Synthetic
source                      1..60
                            mol_type = protein
                            organism = synthetic construct
SEQUENCE: 105
GGGGSGGGGS GGGGSGGGGS GGGGSGGGGS GGGGSGGGGS GGGGSGGGGS GGGGSGGGGS         60

SEQ ID NO: 106              moltype = AA   length = 75
FEATURE                     Location/Qualifiers
REGION                      1..75
                            note = Synthetic
source                      1..75
                            mol_type = protein
                            organism = synthetic construct
SEQUENCE: 106
GGGGSGGGGS GGGGSGGGGS GGGGSGGGGS GGGGSGGGGS GGGGSGGGGS GGGGSGGGGS         60
GGGGSGGGGS GGGGS                                                         75

SEQ ID NO: 107              moltype = AA   length = 9
FEATURE                     Location/Qualifiers
REGION                      1..9
                            note = Synthetic
source                      1..9
                            mol_type = protein
                            organism = synthetic construct
SEQUENCE: 107
KLIETYFSK                                                                 9

SEQ ID NO: 108              moltype = AA   length = 9
FEATURE                     Location/Qualifiers
REGION                      1..9
                            note = Synthetic
source                      1..9
                            mol_type = protein
                            organism = synthetic construct
SEQUENCE: 108
LLFGYPVYV                                                                 9

SEQ ID NO: 109              moltype = AA   length = 271
FEATURE                     Location/Qualifiers
REGION                      1..271
                            note = Synthetic
source                      1..271
                            mol_type = protein
                            organism = synthetic construct
SEQUENCE: 109
GSHSMRYFFT SVSRPGRGEP RFIAVGYVDD TQFVRFDSDA ASQRMEPRAP WIEQEGPEYW         60
DGETRKVKAH SQTHRVDLGT LRGYYNQSEA GSHTVQRMYG CDVGSDWRFL RGYHQYAYDG        120
KDYIALKEDL RSWTAADMAA QTTKHKWEAA HVAEQLRAYL EGTCVEWLRR YLENGKETLQ        180
```

```
RTDAPKTHMT HHAVSDHEAT LRCWALSFYP AEITLTWQRD GEDQTQDTEL VETRPAGDGT   240
FQKWAAVVVP SGQEQRYTCH VQHEGLPKPL T                                 271

SEQ ID NO: 110           moltype = AA  length = 271
FEATURE                  Location/Qualifiers
REGION                   1..271
                         note = Synthetic
source                   1..271
                         mol_type = protein
                         organism = synthetic construct
SEQUENCE: 110
GSHSMRYFFT SVSRPGRGEP RFIAVGYVDD TQFVRFDSDA ASQRMEPRAP WIEQEGPEYW   60
DQETRNVKAQ SQTDRVDLGT LRGYYNQSEA GSHTIQIMYG CDVGSDGRFL RGYRQDAYDG   120
KDYIALNEDL RSWTAADMAA QITKRKWEAA HEAEQLRAYL DGTCVEWLRR YLENGKETLQ   180
RTDPPKTHMT HHPISDHEAT LRCWALGFYP AEITLTWQRD GEDQTQDTEL VETRPAGDGT   240
FQKWAAVVVP SGEEQRYTCH VQHEGLPKPL T                                 271

SEQ ID NO: 111           moltype = AA  length = 4
FEATURE                  Location/Qualifiers
REGION                   1..4
                         note = Synthetic
source                   1..4
                         mol_type = protein
                         organism = synthetic construct
SEQUENCE: 111
LRWE                                                               4

SEQ ID NO: 112           moltype = AA  length = 271
FEATURE                  Location/Qualifiers
REGION                   1..271
                         note = Synthetic
source                   1..271
                         mol_type = protein
                         organism = synthetic construct
SEQUENCE: 112
GSHSMRYFFT SVSRPGRGEP RFIAVGYVDD TQFVRFDSDA ASQRMEPRAP WIEQEGPEYW   60
DGETRKVKAH SQTHRVDLGT LRGYYNQSEA GSHTVQRMYG CDVGSDWRFL RGYHQYAYDG   120
KDYIALKEDL RSWTAADMAA QTTKHKWEAA HVAEQLRAYL EGTCVEWLRR YLENGKETLQ   180
RTDSPKAHVT HHSRPEDKVT LRCWALGFYP ADITLTWQLN GEELIQDMEL VETRPAGDGT   240
FQKWASVVVP LGKEQYYTCH VYHQGLPEPL T                                 271

SEQ ID NO: 113           moltype = AA  length = 271
FEATURE                  Location/Qualifiers
REGION                   1..271
                         note = Synthetic
source                   1..271
                         mol_type = protein
                         organism = synthetic construct
SEQUENCE: 113
GSHSMRYFFT SVSRPGRGEP RFIAVGYVDD TQFVRFDSDA ASQRMEPRAP WIEQEGPEYW   60
DQETRNVKAQ SQTDRVDLGT LRGYYNQSEA GSHTIQIMYG CDVGSDGRFL RGYRQDAYDG   120
KDYIALNEDL RSWTAADMAA QITKRKWEAA HEAEQLRAYL DGTCVEWLRR YLENGKETLQ   180
RTDSPKAHVT HHSRPEDKVT LRCWALGFYP ADITLTWQLN GEELIQDMEL VETRPAGDGT   240
FQKWASVVVP LGKEQYYTCH VYHQGLPEPL T                                 271

SEQ ID NO: 114           moltype = AA  length = 99
FEATURE                  Location/Qualifiers
source                   1..99
                         mol_type = protein
                         organism = Homo sapiens
SEQUENCE: 114
IQRTPKIQVY SRHPAENGKS NFLNCYVSGF HPSDIEVDLL KNGERIEKVE HSDLSFSKDW   60
SFYLLYYTEF TPTEKDEYAC RVNHVTLSQP KIVKWDRDM                         99

SEQ ID NO: 115           moltype = AA  length = 99
FEATURE                  Location/Qualifiers
source                   1..99
                         mol_type = protein
                         organism = Mus musculus
SEQUENCE: 115
IQKTPQIQVY SRHPPENGKP NILNCYVTQF HPPHIEIQML KNGKKIPKVE MSDMSFSKDW   60
SFYILAHTEF TPTETDTYAC RVKHASMAEP KTVYWDRDM                         99

SEQ ID NO: 116           moltype = DNA  length = 149
FEATURE                  Location/Qualifiers
misc_feature             1..149
                         note = Synthetic
source                   1..149
                         mol_type = other DNA
```

```
                            organism = synthetic construct
SEQUENCE: 116
agcgctctcg tacagagttg gcattataat acgactcact ataggggaga atcaaaatcg    60
gtgaatgttt tagagctaga aatagcaagt taaaataagg ctagtccgtt atcaacttga   120
aaaagtggca ccgagtcggt gcttttttt                                     149

SEQ ID NO: 117          moltype = AA   length = 185
FEATURE                 Location/Qualifiers
REGION                  1..185
                        note = Synthetic
source                  1..185
                        mol_type = protein
                        organism = synthetic construct
SEQUENCE: 117
GDTRPRFLWQ PKRECHFFNG TERVRFLDRY FYNQEESVRF DSDVGEFRAV TELGRPDAEY    60
WNSQKDILEQ ARAAVDTYCR HNYGVVESFT VQRRVQPKVT VYPSKTQPLQ HHNLLVCSVS   120
GFYPGSIEVR WFLNGQEEKA GMVSTGLIQN GDWTFQTLVM LETVPRSGEV YTCQVEHPSV   180
TSPLT                                                               185

SEQ ID NO: 118          moltype = AA   length = 178
FEATURE                 Location/Qualifiers
REGION                  1..178
                        note = Synthetic
source                  1..178
                        mol_type = protein
                        organism = synthetic construct
SEQUENCE: 118
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHW     178

SEQ ID NO: 119          moltype = AA   length = 185
FEATURE                 Location/Qualifiers
REGION                  1..185
                        note = Synthetic
source                  1..185
                        mol_type = protein
                        organism = synthetic construct
SEQUENCE: 119
IKEEHVIIQA ESYLNPDQSG EFKFDFDGDE IFHVDMAKKE TVWRLEEFGR FASFEAQGAL    60
ANIAVDKANL EIMTKRSNYT PIEETEVPTS LRRLEQPNVA ISLSRTEALN HHNTLVCSVT   120
DFYPAKIKVR WFRNGQEETV GVSSTQLIRN GDWTFQVLVM LEMTPHQGEV YTCHVEHPSL   180
KSPIT                                                               185

SEQ ID NO: 120          moltype = AA   length = 183
FEATURE                 Location/Qualifiers
REGION                  1..183
                        note = Synthetic
source                  1..183
                        mol_type = protein
                        organism = synthetic construct
SEQUENCE: 120
IKEEHVIIQA ESYLNPDQSG EFKFDFDGDE IFHVDMAKKE TVWRLEEFGR FASFEAQGAL    60
ANIAVDKANL EIMTKRSNYT PIATNEAPQA TVFPKSPVLL GQPHTLICFV DNIFPPVINI   120
TWLRNSKSVT DGVYETSFLV NRDHSFHKLS YLTFIPSDDD IYDCKVEHWG LEEPVLKHWE   180
PEI                                                                 183

SEQ ID NO: 121          moltype = AA   length = 90
FEATURE                 Location/Qualifiers
REGION                  1..90
                        note = Synthetic
source                  1..90
                        mol_type = protein
                        organism = synthetic construct
SEQUENCE: 121
RPRFLWQSKR ECHFFNGTER VRFLDRYFYN QEESVRFDSD VGEFRAVTEL GRPDAEYWNS    60
QKDILEQARA AVDTYCRHNY GVVESFTVQR                                     90

SEQ ID NO: 122          moltype = AA   length = 82
FEATURE                 Location/Qualifiers
REGION                  1..82
                        note = Synthetic
source                  1..82
                        mol_type = protein
                        organism = synthetic construct
SEQUENCE: 122
IKEEHVIIQA ESYLNPDQSG EFKFDFDGDE IFHVDMAKKE TVWRLEEFGR FASFEAQGAL    60
ANIAVDKANL EIMTKRSNYT PI                                             82
```

```
SEQ ID NO: 123          moltype = AA   length = 272
FEATURE                 Location/Qualifiers
REGION                  1..272
                        note = Synthetic
source                  1..272
                        mol_type = protein
                        organism = synthetic construct
SEQUENCE: 123
METLLGVSLV ILWLQLARVN SQQGEEDPQA LSIQEGENAT MNCSYKTSIN NLQWYRQNSG    60
RGLVHLILIR SNEREKHSGR LRVTLDTSKK SSSLLITASR AADTASYFCA TAAVGGFKTI   120
FGAGTRLFVK ANIQNPDPAV YQLRDSKSSD KSVCLFTDFD SQTNVSQSKD SDVYITDKTV   180
LDMRSMDFKS NSAVAWSNKS DFACANAFNN SIIPEDTFFP SPESSCDVKL VEKSFETDTN   240
LNFQNLSVIG FRILLLKVAG FNLLMTLRLW SS                                 272

SEQ ID NO: 124          moltype = AA   length = 312
FEATURE                 Location/Qualifiers
REGION                  1..312
                        note = Synthetic
source                  1..312
                        mol_type = protein
                        organism = synthetic construct
SEQUENCE: 124
MLLLLLLLGL AGSGLGAVVS QHPSWVISKS GTSVKIECRS LDFQATTMFW YRQFPKQSLM    60
LMATSNEGSK ATYEQGVEKD KFLINHASLT LSTLTVTSAH PEDSSFYICS ARDLTSGANN   120
EQFFGPGTRL TVLEDLKNVF PPEVAVFEPS EAEISHTQKA TLVCLATGFY PDHVELSWWV   180
NGKEVHSGVS TDPQPLKEQP ALNDSRYSLS SRLRVSATFW QNPRNHFRCQ VQFYGLSEND   240
EWTQDRAKPV TQIVSAEAWG RADCGFTSES YQQGVLSATI LYEILLGKAT LYAVLVSALV   300
LMAMVKRKDS RG                                                       312

SEQ ID NO: 125          moltype = AA   length = 278
FEATURE                 Location/Qualifiers
REGION                  1..278
                        note = Synthetic
source                  1..278
                        mol_type = protein
                        organism = synthetic construct
SEQUENCE: 125
MAMLLGASVL ILWLQPDWVN SQQKNDDQQV KQNSPSLSVQ EGRISILNCD YTNSMFDYFL    60
WYKKYPAEGP TFLISISSIK DKNADGRFTV FLNKSAKHLS LHIVPSQPGD SAVYFCAAME   120
GAQKLVFGQG TRLTINPNIQ NPDPAVYQLR DSKSSDKSVC LFTDFDSQTN VSQSKDSDVY   180
ITDKTVLDMR SMDFKSNSAV AWSNKSDFAC ANAFNNSIIP EDTFFPSPES SCDVKLVEKS   240
FETDTNLNFQ NLSVIGFRIL LLKVAGFNLL MTLRLWSS                           278

SEQ ID NO: 126          moltype = AA   length = 312
FEATURE                 Location/Qualifiers
REGION                  1..312
                        note = Synthetic
source                  1..312
                        mol_type = protein
                        organism = synthetic construct
SEQUENCE: 126
MSIGLLCCAA LSLLWAGPVN AGVTQTPKFQ VLKTGQSMTL QCAQDMNHEY MSWYRQDPGM    60
GLRLIHYSVG AGITDQGEVP NGYNVSRSTT EDFPLRLLSA APSQTSVYFC ASSYPGGGFY   120
EQYFGPGTRL TVTEDLKNVF PPEVAVFEPS EAEISHTQKA TLVCLATGFY PDHVELSWWV   180
NGKEVHSGVS TDPQPLKEQP ALNDSRYALS SRLRVSATFW QDPRNHFRCQ VQFYGLSEND   240
EWTQDRAKPV TQIVSAEAWG RADCGFTSES YQQGVLSATI LYEILLGKAT LYAVLVSALV   300
LMAMVKRKDS RG                                                       312

SEQ ID NO: 127          moltype = AA   length = 461
FEATURE                 Location/Qualifiers
REGION                  1..461
                        note = Synthetic
source                  1..461
                        mol_type = protein
                        organism = synthetic construct
SEQUENCE: 127
MALPVTALLL PLALLLHAAR PEVQLQQSGP ELIKPGASVK MSCKASGYTF TSYVMHWVKQ    60
KPGQGLEWIG YINPYNDGTK YNEKFKGKAT LTSDKSSSTA YMELSSLTSE DSAVYYCARG   120
TYYYGSRVFD YWGQGTTLTV SSGGGGSGGG GSGGGGSDIV MTQAAPSIPV TPGESVSISC   180
RSSKSLLNSN GNGSGSGTAF TLRISRVEAE DVGVYYCMQH LEYPFTAGTK LELKRSDPTT   240
TPAPRPPTPA PTIASQPLSL RPEACRPAAG GAVHTRGLDF ACDIYIWAPL AGTCGVLLLS   300
LVITLYCKRG RKKLLYIFKQ PFMRPVQTTQ EEDGCSCRFP EEEEGGCELR VKFSRSADAP   360
AYQQGQNQLY NELNLGRREE YDVLDKRRGR DPEMGGKPRR KNPQEGLYNE LQKDKMAEAY   420
SEIGMKGERR RGKGHDGLYQ GLSTATKDTY DALHMQALPP R                       461

SEQ ID NO: 128          moltype = AA   length = 495
FEATURE                 Location/Qualifiers
REGION                  1..495
                        note = Synthetic
```

```
                         source               1..495
                                              mol_type = protein
                                              organism = synthetic construct
SEQUENCE: 128
METDTLLLWV LLLWVPGSTG EVQLQQSGPE LIKPGASVKM SCKASGYTFT SYVMHWVKQK   60
PGQGLEWIGY INPYNDGTKY NEKFKGKATL TSDKSSSTAY MELSSLTSED SAVYYCARGT  120
YYYGSRVFDY WGQGTTLTVS SGGGGSGGGG SGGGGSDIVM TQAAPSIPVT PGESVSISCR  180
SSKSLLNSNG NTYLYWFLQR PGQSPQLLIY RMSNLASGVP DRFSGSGSGT AFTLRISRVE  240
AEDVGVYYCM QHLEYPFTFG AGTKLELKRS DPTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 129           moltype = AA   length = 432
FEATURE                  Location/Qualifiers
REGION                   1..432
                         note = Synthetic
source                   1..432
                         mol_type = protein
                         organism = synthetic construct
SEQUENCE: 129
MALPVTALLL PLALLLHAAR PEVKLLESGG GLVQPGGSLK LSCAASGFDF SRYWMSWVRQ   60
APGKGLEWIG EINPDSSTIN YTPSLKDKFI ISRDNAKNTL YLQMSKVRSE DTALYYCARP  120
DGNYWYFDVW GAGTTVTVSS GGGGSGGGGS GGGGSDIVMT QSHKFMSTSV GDRVSITCKA  180
SQDVGIAVAW YQQKPGQSPK LLIYWASTRH TGVPDRFTGS GSGTDFTLTI SNVQSEDLAD  240
YFCQQYSSYP YTFGGGTKLE IKGLAVSTIS SFFPPGYQKR GRKKLLYIFK QPFMRPVQTT  300
QEEDGCSCRF PEEEEGGCEL RVKFSRSADA PAYQQGQNQL YNELNLGRRE EYDVLDKRRG  360
RDPEMGGKPR RKNPQEGLYN ELQKDKMAEA YSEIGMKGER RRGKGHDGLY QGLSTATKDT  420
YDALHMQALP PR                                                     432

SEQ ID NO: 130           moltype = AA   length = 485
FEATURE                  Location/Qualifiers
REGION                   1..485
                         note = Synthetic
source                   1..485
                         mol_type = protein
                         organism = synthetic construct
SEQUENCE: 130
MALPVTALLL PLALLLHAAR PEVKLLESGG GLVQPGGSLK LSCAASGFDF SRYWMSWVRQ   60
APGKGLEWIG EINPDSSTIN YTPSLKDKFI ISRDNAKNTL YLQMSKVRSE DTALYYCARP  120
DGNYWYFDVW GAGTTVTVSS GGGGSGGGGS GGGGSDIVMT QSHKFMSTSV GDRVSITCKA  180
SQDVGIAVAW YQQKPGQSPK LLIYWASTRH TGVPDRFTGS GSGTDFTLTI SNVQSEDLAD  240
YFCQQYSSYP YTFGGGTKLE IKTTTPAPRP PTPAPTIASQ PLSLRPEACR PAAGGAVHTR  300
GLDFACDIYI WAPLAGTCGV LLLSLVITLY CKRGRKKLLY IFKQPFMRPV QTTQEEDGCS  360
CRFPEEEEGG CELRVKFSRS ADAPAYQQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                              485

SEQ ID NO: 131           moltype = AA   length = 647
FEATURE                  Location/Qualifiers
REGION                   1..647
                         note = Synthetic
source                   1..647
                         mol_type = protein
                         organism = synthetic construct
SEQUENCE: 131
MALPVTALLL PLALLLHAAR PEVKLLESGG GLVQPGGSLK LSCAASGFDF SRYWMSWVRQ   60
APGKGLEWIG EINPDSSTIN YTPSLKDKFI ISRDNAKNTL YLQMSKVRSE DTALYYCARP  120
DGNYWYFDVW GAGTTVTVSS GGGGSGGGGS GGGGSDIVMT QSHKFMSTSV GDRVSITCKA  180
SQDVGIAVAW YQQKPGQSPK LLIYWASTRH TGVPDRFTGS GSGTDFTLTI SNVQSEDLAD  240
YFCQQYSSYP YTFGGGTKLE IKEPKSPDKT HTCPPCPAPP VAGPSVFLFP PKPKDTLMIA  300
RTPEVTCVVV DVSHEDPEVK FNWYVDGVEV HNAKTKPREE QYNSTYRVVS VLTVLHQDWL  360
NGKEYKCKVS NKALPAPIEK TISKAKGQPR EPQVYTLPPS RDELTKNQVS LTCLVKGFYP  420
SDIAVEWESN GQPENNYKTT PPVLDSDGSF FLYSKLTVDK SRWQQGNVFS CSVMHEALHN  480
HYTQKSLSLS PGKKRGRKKL LYIFKQPFMR PVQTTQEEDG CSCRFPEEEE GGCELRVKFS  540
RSADAPAYQQ GQNQLYNELN LGRREEYDVL DKRRGRDPEM GGKPRRKNPQ EGLYNELQKD  600
KMAEAYSEIG MKGERRRGKG HDGLYQGLST ATKDTYDALH MQALPPR                647

SEQ ID NO: 132           moltype = AA   length = 433
FEATURE                  Location/Qualifiers
REGION                   1..433
                         note = Synthetic
source                   1..433
                         mol_type = protein
                         organism = synthetic construct
SEQUENCE: 132
MALPVTALLL PLALLLHAAR PQVQLQQPGA ELVRPGASVK LSCKASGYSF TTYWMNWVKQ   60
RPGQGLEWIG MIHPSDSETR LNQKFKDKAT LTVDKSSSTA YMQLSSPTSE DSAVYYCARS  120
```

```
TMIATRAMDY WGQGTSVTVS SGGGGSGGGG SGGGGSDIVM TQSQKSMSTS VGDRVSITCK    180
ASQDVITGVA WYQQKPGQSP KLLIYSASYR YTGVPDRFTG SGSGTDFTFT ISNVQAEDLA    240
VYYCQQHYST PLTFGAGTKL ELKGLAVSTI SSFFPPGYQK RGRKKLLYIF KQPFMRPVQT    300
TQEEDGCSCR FPEEEGGCE  LRVKFSRSAD APAYQQGQNQ LYNELNLGRR EEYDVLDKRR    360
GRDPEMGGKP RRKNPQEGLY NELQKDKMAE AYSEIGMKGE RRRGKGHDGL YQGLSTATKD    420
TYDALHMQAL PPR                                                       433

SEQ ID NO: 133           moltype = AA  length = 486
FEATURE                  Location/Qualifiers
REGION                   1..486
                         note = Synthetic
source                   1..486
                         mol_type = protein
                         organism = synthetic construct
SEQUENCE: 133
MALPVTALLL PLALLLHAAR PQVQLQQPGA ELVRPGASVK LSCKASGYSF TTYWMNWVKQ     60
RPGQGLEWIG MIHPSDSETR LNQKFKDKAT LTVDKSSSTA YMQLSSPTSE DSAVYYCARS    120
TMIATRAMDY WGQGTSVTVS SGGGGSGGGG SGGGGSDIVM TQSQKSMSTS VGDRVSITCK    180
ASQDVITGVA WYQQKPGQSP KLLIYSASYR YTGVPDRFTG SGSGTDFTFT ISNVQAEDLA    240
VYYCQQHYST PLTFGAGTKL ELKTTTPAPR PPTPAPTIAS QPLSLRPEAC RPAAGGAVHT    300
RGLDFACDIY IWAPLAGTCG VLLLSLVITL YCKRGRKKLL YIFKQPFMRP VQTTQEEDGC    360
SCRFPEEEG  GCELRVKFSR SADAPAYQQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM    480
QALPPR                                                               486

SEQ ID NO: 134           moltype = AA  length = 648
FEATURE                  Location/Qualifiers
REGION                   1..648
                         note = Synthetic
source                   1..648
                         mol_type = protein
                         organism = synthetic construct
SEQUENCE: 134
MALPVTALLL PLALLLHAAR PQVQLQQPGA ELVRPGASVK LSCKASGYSF TTYWMNWVKQ     60
RPGQGLEWIG MIHPSDSETR LNQKFKDKAT LTVDKSSSTA YMQLSSPTSE DSAVYYCARS    120
TMIATRAMDY WGQGTSVTVS SGGGGSGGGG SGGGGSDIVM TQSQKSMSTS VGDRVSITCK    180
ASQDVITGVA WYQQKPGQSP KLLIYSASYR YTGVPDRFTG SGSGTDFTFT ISNVQAEDLA    240
VYYCQQHYST PLTFGAGTKL ELKEPKSPDK THTCPPCPAP PVAGPSVFLF PPKPKDTLMI    300
ARTPEVTCVV VDVSHEDPEV KFNWYVDGVE VHNAKTKPRE EQYNSTYRVV SVLTVLHQDW    360
LNGKEYKCKV SNKALPAPIE KTISKAKGQP REPQVYTLPP SRDELTKNQV SLTCLVKGFY    420
PSDIAVEWES NGQPENNYKT TPPVLDSDGS FFLYSKLTVD KSRWQQGNVF SCSVMHEALH    480
NHYTQKSLSL SPGKKRGRKK LLYIFKQPFM RPVQTTQEED GCSCRFPEEE EGGCELRVKF    540
SRSADAPAYQ QGQNQLYNEL NLGRREEYDV LDKRRGRDPE MGGKPRRKNP QEGLYNELQK    600
DKMAEAYSEI GMKGERRRGK GHDGLYQGLS TATKDTYDAL HMQALPPR                 648

SEQ ID NO: 135           moltype = AA  length = 434
FEATURE                  Location/Qualifiers
REGION                   1..434
                         note = Synthetic
source                   1..434
                         mol_type = protein
                         organism = synthetic construct
SEQUENCE: 135
MALPVTALLL PLALLLHAAR PQVQLQQSGA ELARPGASVK LSCKASGYTF TSYWMQWVKQ     60
RPGQGLEWIG AIYPGDGDTR YTQKFKGKAT LTADKSSSTA YMQLSSLASE DSAVYYCARG    120
KVYYGSNPFA YWGQGTLVTV SAGGGGSGGG GSGGGGSDIQ MTQSSSYLSV SLGGRVTITC    180
KASDHINNWL AWYQQKPGNA PRLLISGATS LETGVPSRFS GSGSGKDYTL SITSLQTEDV    240
ATYYCQQYWS TPWTFGGGTK LEIKGLAVST ISSFFPPGYQ KRGRKKLLYI FKQPFMRPVQ    300
TTQEEDGCSC RFPEEEEGGC ELRVKFSRSA DAPAYQQGQN QLYNELNLGR REEYDVLDKR    360
RGRDPEMGGK PRRKNPQEGL YNELQKDKMA EAYSEIGMKG ERRRGKGHDG LYQGLSTATK    420
DTYDALHMQA LPPR                                                      434

SEQ ID NO: 136           moltype = AA  length = 487
FEATURE                  Location/Qualifiers
REGION                   1..487
                         note = Synthetic
source                   1..487
                         mol_type = protein
                         organism = synthetic construct
SEQUENCE: 136
MALPVTALLL PLALLLHAAR PQVQLQQSGA ELARPGASVK LSCKASGYTF TSYWMQWVKQ     60
RPGQGLEWIG AIYPGDGDTR YTQKFKGKAT LTADKSSSTA YMQLSSLASE DSAVYYCARG    120
KVYYGSNPFA YWGQGTLVTV SAGGGGSGGG GSGGGGSDIQ MTQSSSYLSV SLGGRVTITC    180
KASDHINNWL AWYQQKPGNA PRLLISGATS LETGVPSRFS GSGSGKDYTL SITSLQTEDV    240
ATYYCQQYWS TPWTFGGGTK LEIKTTTPAP RPPTPAPTIA SQPLSLRPEA CRPAAGGAVH    300
TRGLDFACDI YIWAPLAGTC GVLLLSLVIT LYCKRGRKKL LYIFKQPFMR PVQTTQEEDG    360
CSCRFPEEEE GGCELRVKFS RSADAPAYQQ GQNQLYNELN LGRREEYDVL DKRRGRDPEM    420
GGKPRRKNPQ EGLYNELQKD KMAEAYSEIG MKGERRRGKG HDGLYQGLST ATKDTYDALH    480
MQALPPR                                                              487
```

```
SEQ ID NO: 137           moltype = AA   length = 649
FEATURE                  Location/Qualifiers
REGION                   1..649
                         note = Synthetic
source                   1..649
                         mol_type = protein
                         organism = synthetic construct
SEQUENCE: 137
MALPVTALLL PLALLLHAAR PQVQLQQSGA ELARPGASVK LSCKASGYTF TSYWMQWVKQ    60
RPGQGLEWIG AIYPGDGDTR YTQKFKGKAT LTADKSSSTA YMQLSSLASE DSAVYYCARG   120
KVYYGSNPFA YWGQGTLVTV SAGGGGSGGG GSGGGGSDIQ MTQSSSYLSV SLGGRVTITC   180
KASDHINNWL AWYQQKPGNA PRLLISGATS LETGVPSRFS GSGSGKDYTL SITSLQTEDV   240
ATYYCQQYWS TPWTFGGGTK LEIKEPKSPD KTHTCPPCPA PPVAGPSVFL FPPKPKDTLM   300
IARTPEVTCV VVDVSHEDPE VKFNWYVDGV EVHNAKTKPR EEQYNSTYRV VSVLTVLHQD   360
WLNGKEYKCK VSNKALPAPI EKTISKAKGQ PREPQVYTLP PSRDELTKNQ VSLTCLVKGF   420
YPSDIAVEWE SNGQPENNYK TTPPVLDSDG SFFLYSKLTV DKSRWQQGNV FSCSVMHEAL   480
HNHYTQKSLS LSPGKKRGRK KLLYIFKQPF MRPVQTTQEE DGCSCRFPEE EEGGCELRVK   540
FSRSADAPAY QQGQNQLYNE LNLGRREEYD VLDKRRGRDP EMGGKPRRKN PQEGLYNELQ   600
KDKMAEAYSE IGMKGERRRG KGHDGLYQGL STATKDTYDA LHMQALPPR              649

SEQ ID NO: 138           moltype = AA   length = 433
FEATURE                  Location/Qualifiers
REGION                   1..433
                         note = Synthetic
source                   1..433
                         mol_type = protein
                         organism = synthetic construct
SEQUENCE: 138
MALPVTALLL PLALLLHAAR PQVQLQQSGP ELVKPGASVK ISCKASGYAF SSSWMNWVKQ    60
RPGQGLEWIG RIYPGDGDTK YNGKFKGKAT LTADKSSSTA YMQLSSLTSV DSAVYFCARS   120
TMIATGAMDY WGQGTSVTVS SGGGGSGGGG SGGGGSETTV TQSPASLSMA IGEKVTIRCI   180
TSTDIDDDMN WYQQKPGEPP KLLISEGNTL RPGVPSRFSS SGYGTDFVFT IENMLSEDVA   240
DYYCLQSDNL PLTFGGGTKL EIKGLAVSTI SSFFPPGYQK RGRKKLLYIF KQPFMRPVQT   300
TQEEDGCSCR FPEEEEGGCE LRVKFSRSAD APAYQQGQNQ LYNELNLGRR EEYDVLDKRR   360
GRDPEMGGKP RRKNPQEGLY NELQKDKMAE AYSEIGMKGE RRRGKGHDGL YQGLSTATKD   420
TYDALHMQAL PPR                                                     433

SEQ ID NO: 139           moltype = AA   length = 486
FEATURE                  Location/Qualifiers
REGION                   1..486
                         note = Synthetic
source                   1..486
                         mol_type = protein
                         organism = synthetic construct
SEQUENCE: 139
MALPVTALLL PLALLLHAAR PQVQLQQSGA ELARPGASVK LSCKASGYTF TSYWMQWVKQ    60
RPGQGLEWIG AIYPGDGDTR YTQKFKGKAT LTADKSSSTA YMQLSSLASE DSAVYYCARG   120
KVYYGSNPFA YWGQGTLVTV SAGGGGSGGG GSGGGGSDIQ MTQSSSYLSV SLGGRVTITC   180
KASDHINNWL AWYQQKPGNA PRLLISGATS LETGVPSRFS GSGSGKDYTL SITSLQTEDV   240
ATYYCQQYWS TPWTFGGGTK LEIKTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYQQ QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                             486

SEQ ID NO: 140           moltype = AA   length = 647
FEATURE                  Location/Qualifiers
REGION                   1..647
                         note = Synthetic
source                   1..647
                         mol_type = protein
                         organism = synthetic construct
SEQUENCE: 140
MALPVTALLL PLALLLHAAR PQVQLQQSGP ELVKPGASVK ISCKASGYAF SSSWMNWVKQ    60
RPGQGLEWIG RIYPGDGDTK YNGKFKGKAT LTADKSSSTA YMQLSSLTSV DSAVYFCARS   120
TMIATGAMDY WGQGTSVTVS SGGGGSGGGG SGGGGSETTV TQSPASLSMA IGEKVTIRCI   180
TSTDIDDDMN WYQQKPGEPP KLLISEGNTL RPGVPSRFSS SGYGTDFVFT IENMLSEDVA   240
DYYCLQSDNL PLTFGGGTKL EIKEPKSPDK THTCPPCPAP PVAGPSVFLF PPKPKDTLMI   300
ARTPEVTCVV VDVSHEDPEV KFNWYVDGVE VHNAKTKPRE EQYNSTYRVV SVLTVLHQDW   360
LNGKEYKCKV SNKALPAPIE KTISKAKGQP REPQVYTLPP SRDELTKNQV SLTCLVKGFY   420
PSDIAVEWES NGQPENNYKT TPPVLDSDGS FFLYSKLTVD KSRWQQGNVF SCSVMHEALH   480
NHYTQKSLSL SPGKKRGRKK LLYIFKQPFM RPVQTTQEED GCSCRFPEEE EGGCELRVKF   540
SRSADAPAYQ QGQNQLYNEL NLGRREEYDV LDKRRGRDPE MGGKPRRKNP QEGLYNELQK   600
DKMAEAYSEI GMKGERRGKG HDGLYQGLST ATKDTYDALH MQALPPR                 647

SEQ ID NO: 141           moltype = AA   length = 432
FEATURE                  Location/Qualifiers
REGION                   1..432
```

```
                         note = Synthetic
source                   1..432
                         mol_type = protein
                         organism = synthetic construct
SEQUENCE: 141
MALPVTALLL PLALLLHAAR PQVQLQQSGP ELVKPGASVK ISCKASGYAF SSSWMNWVKQ    60
RPGQGLEWIG RIYPGDGDTK YNGKFKGKAT LTADKSSSTA YMQLSSLTSV DSAVYFCARS   120
TMIATGAMDY WGQGTSVTVS SGGGGSGGGG SGGGGSDIVMT QSHKFMSTSV GDRVSITCKA  180
SQDVSTAVAW YQQKPGQSPK LLIYSASYRY TGVPDRFTGS GSGTDFTFTI SSVQAEDLAV   240
YYCQQHYSTP PYTFGGGTKL EIKGLAVSTI SSFFPPGYQK RGRKKLLYIF KQPFMRPVQT   300
TQEEDGCCRF PEEEEGGCEL RVKFSRSADA PAYQQGQNQL YNELNLGRRE EYDVLDKRRG   360
RDPEMGGKPR RKNPQEGLYN ELQKDKMAEA YSEIGMKGER RRGKGHDGLY QGLSTATKDT   420
YDALHMQALP PR                                                      432

SEQ ID NO: 142           moltype = AA   length = 486
FEATURE                  Location/Qualifiers
REGION                   1..486
                         note = Synthetic
source                   1..486
                         mol_type = protein
                         organism = synthetic construct
SEQUENCE: 142
MALPVTALLL PLALLLHAAR PQVQLQQSGP ELVKPGASVK ISCKASGYAF SSSWMNWVKQ    60
RPGQGLEWIG RIYPGDGDTK YNGKFKGKAT LTADKSSSTA YMQLSSLTSV DSAVYFCARS   120
TMIATGAMDY WGQGTSVTVS SGGGGSGGGG SGGGGSDIVM TQSHKFMSTS VGDRVSITCK   180
ASQDVSTAVA WYQQKPGQSP KLLIYSASYR YTGVPDRFTG SGSGTDFTFT ISSVQAEDLA   240
VYYCQQHYST PPYTFGGGTK LEIKTTTPAP RPPTPAPTIA SQPLSLRPEA CRPAAGGAVH   300
TRGLDFADIY IWAPLAGTCG VLLLSLVITL YCKRGRKKLL YIFKQPFMRP VQTTQEEDGC   360
SCRFPEEEEG GCELRVKFSR SADAPAYQQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                             486

SEQ ID NO: 143           moltype = AA   length = 648
FEATURE                  Location/Qualifiers
REGION                   1..648
                         note = Synthetic
source                   1..648
                         mol_type = protein
                         organism = synthetic construct
SEQUENCE: 143
MALPVTALLL PLALLLHAAR PQVQLQQSGP ELVKPGASVK ISCKASGYAF SSSWMNWVKQ    60
RPGQGLEWIG RIYPGDGDTK YNGKFKGKAT LTADKSSSTA YMQLSSLTSV DSAVYFCARS   120
TMIATGAMDY WGQGTSVTVS SGGGGSGGGG SGGGGSDIVM TQSHKFMSTS VGDRVSITCK   180
ASQDVSTAVA WYQQKPGQSP KLLIYSASYR YTGVPDRFTG SGSGTDFTFT ISSVQAEDLA   240
VYYCQQHYST PPYTFGGGTK LEIKEPKSPD KTHTCPPCPA PPVAGPSVFL FPPKPKDTLM   300
IARTPEVCVV VDVSHEDPEV KFNWYVDGVE VHNAKTKPRE EQYNSTYRVV SVLTVLHQDW   360
LNGKEYKCKV SNKALPAPIE KTISKAKGQP REPQVYTLPP SRDELTKNQV SLTCLVKGFY   420
PSDIAVEWES NGQPENNYKT TPPVLDSDGS FFLYSKLTVD KSRWQQGNVF SCSVMHEALH   480
NHYTQKSLSL SPGKKRGRKK LLYIFKQPFM RPVQTTQEED GCSCRFPEEE EGGCELRVKF   540
SRSADAPAYQ QGQNQLYNEL NLGRREEYDV LDKRRGRDPE MGGKPRRKNP QEGLYNELQK   600
DKMAEAYSEI GMKGERRRGK GHDGLYQGLS TATKDTYDAL HMQALPPR                648

SEQ ID NO: 144           moltype = AA   length = 156
FEATURE                  Location/Qualifiers
REGION                   1..156
                         note = Synthetic
source                   1..156
                         mol_type = protein
                         organism = synthetic construct
SEQUENCE: 144
MGTSLLCWMA LCLLGADHAD ACPYSNPSLC SGGGGSELPT QGTFSNVSTN VSPAKPTTTA    60
CPYSNPSLCS GGGGSPAPPP TPAPTIASQP LSLRPEACRP AAGGAVHTRG LDFACDIYIW   120
APLAGTCGVL LLSLVITLYC NHRNRRRVCK CPRPVV                             156

SEQ ID NO: 145           moltype = AA   length = 55
FEATURE                  Location/Qualifiers
REGION                   1..55
                         note = Synthetic
source                   1..55
                         mol_type = protein
                         organism = synthetic construct
SEQUENCE: 145
ACPYSNPSLC SGGGGSELPT QGTFSNVSTN VSPAKPTTTA CPYSNPSLCS GGGGS         55

SEQ ID NO: 146           moltype = DNA   length = 20
FEATURE                  Location/Qualifiers
source                   1..20
                         mol_type = other DNA
                         organism = Homo sapiens
```

| | | |
|---|---|---|
| SEQUENCE: 146 | | |
| tgacgttacc tcgtgcggcc | | 20 |
| SEQ ID NO: 147 | moltype = DNA  length = 20 | |
| FEATURE | Location/Qualifiers | |
| source | 1..20<br>mol_type = other DNA<br>organism = Homo sapiens | |
| SEQUENCE: 147 | | |
| cacgaagctc tccgatgtgt | | 20 |
| SEQ ID NO: 148 | moltype = DNA  length = 20 | |
| FEATURE | Location/Qualifiers | |
| source | 1..20<br>mol_type = other DNA<br>organism = Homo sapiens | |
| SEQUENCE: 148 | | |
| gcgtgacttc cacatgagcg | | 20 |
| SEQ ID NO: 149 | moltype = DNA  length = 20 | |
| FEATURE | Location/Qualifiers | |
| source | 1..20<br>mol_type = other DNA<br>organism = Homo sapiens | |
| SEQUENCE: 149 | | |
| ttggaactgg ccggctggcc | | 20 |
| SEQ ID NO: 150 | moltype = DNA  length = 20 | |
| FEATURE | Location/Qualifiers | |
| source | 1..20<br>mol_type = other DNA<br>organism = Homo sapiens | |
| SEQUENCE: 150 | | |
| gtggcatact ccgtctgctc | | 20 |
| SEQ ID NO: 151 | moltype = DNA  length = 20 | |
| FEATURE | Location/Qualifiers | |
| source | 1..20<br>mol_type = other DNA<br>organism = Homo sapiens | |
| SEQUENCE: 151 | | |
| gatgaggtgc ccattccgct | | 20 |
| SEQ ID NO: 152 | moltype = DNA  length = 20 | |
| FEATURE | Location/Qualifiers | |
| source | 1..20<br>mol_type = other DNA<br>organism = Homo sapiens | |
| SEQUENCE: 152 | | |
| taccgctgca tgatcagcta | | 20 |
| SEQ ID NO: 153 | moltype = DNA  length = 20 | |
| FEATURE | Location/Qualifiers | |
| source | 1..20<br>mol_type = other DNA<br>organism = Homo sapiens | |
| SEQUENCE: 153 | | |
| agctactatg ctgaaccttc | | 20 |
| SEQ ID NO: 154 | moltype = DNA  length = 20 | |
| FEATURE | Location/Qualifiers | |
| source | 1..20<br>mol_type = other DNA<br>organism = Homo sapiens | |
| SEQUENCE: 154 | | |
| ggatgaccaa ttcagctgta | | 20 |
| SEQ ID NO: 155 | moltype = DNA  length = 20 | |
| FEATURE | Location/Qualifiers | |
| source | 1..20<br>mol_type = other DNA<br>organism = Homo sapiens | |
| SEQUENCE: 155 | | |
| accccaaggc cgaagtcatc | | 20 |
| SEQ ID NO: 156 | moltype = DNA  length = 20 | |
| FEATURE | Location/Qualifiers | |
| source | 1..20<br>mol_type = other DNA | |

-continued

```
                         organism = Homo sapiens
SEQUENCE: 156
tctttatatt catgacctac                                               20

SEQ ID NO: 157           moltype = DNA  length = 20
FEATURE                  Location/Qualifiers
source                   1..20
                         mol_type = other DNA
                         organism = Homo sapiens
SEQUENCE: 157
accgttcagc aaatgccagt                                               20

SEQ ID NO: 158           moltype = DNA  length = 20
FEATURE                  Location/Qualifiers
source                   1..20
                         mol_type = other DNA
                         organism = Homo sapiens
SEQUENCE: 158
gtacccaccg ccatactacc                                               20

SEQ ID NO: 159           moltype = DNA  length = 20
FEATURE                  Location/Qualifiers
source                   1..20
                         mol_type = other DNA
                         organism = Homo sapiens
SEQUENCE: 159
ttgcctatgc ccaggtagta                                               20

SEQ ID NO: 160           moltype = DNA  length = 20
FEATURE                  Location/Qualifiers
source                   1..20
                         mol_type = other DNA
                         organism = Homo sapiens
SEQUENCE: 160
ccttgtgccg ctgaaatcca                                               20

SEQ ID NO: 161           moltype = DNA  length = 20
FEATURE                  Location/Qualifiers
source                   1..20
                         mol_type = other DNA
                         organism = Homo sapiens
SEQUENCE: 161
accccgaact aactgctgca                                               20

SEQ ID NO: 162           moltype = DNA  length = 20
FEATURE                  Location/Qualifiers
source                   1..20
                         mol_type = other DNA
                         organism = Homo sapiens
SEQUENCE: 162
acatagaccc ctgttgtaag                                               20

SEQ ID NO: 163           moltype = DNA  length = 20
FEATURE                  Location/Qualifiers
source                   1..20
                         mol_type = other DNA
                         organism = Homo sapiens
SEQUENCE: 163
atccttgcag cagttagttc                                               20

SEQ ID NO: 164           moltype = DNA  length = 20
FEATURE                  Location/Qualifiers
source                   1..20
                         mol_type = other DNA
                         organism = Homo sapiens
SEQUENCE: 164
acatcgaacc tcttgcacgt                                               20

SEQ ID NO: 165           moltype = DNA  length = 20
FEATURE                  Location/Qualifiers
source                   1..20
                         mol_type = other DNA
                         organism = Homo sapiens
SEQUENCE: 165
tacagctcac cttctcgcag                                               20

SEQ ID NO: 166           moltype = DNA  length = 20
FEATURE                  Location/Qualifiers
source                   1..20
```

```
                              mol_type = other DNA
                              organism = Homo sapiens
SEQUENCE: 166
ggtatatctc ctcgaggagc                                                      20

SEQ ID NO: 167                moltype = DNA   length = 20
FEATURE                       Location/Qualifiers
source                        1..20
                              mol_type = other DNA
                              organism = Homo sapiens
SEQUENCE: 167
tacactgctt gtagctctta                                                      20

SEQ ID NO: 168                moltype = DNA   length = 20
FEATURE                       Location/Qualifiers
source                        1..20
                              mol_type = other DNA
                              organism = Homo sapiens
SEQUENCE: 168
gagctctaga caccaacgtg                                                      20

SEQ ID NO: 169                moltype = DNA   length = 20
FEATURE                       Location/Qualifiers
source                        1..20
                              mol_type = other DNA
                              organism = Homo sapiens
SEQUENCE: 169
caagcagctg tccgagtccc                                                      20

SEQ ID NO: 170                moltype = DNA   length = 20
FEATURE                       Location/Qualifiers
source                        1..20
                              mol_type = other DNA
                              organism = Homo sapiens
SEQUENCE: 170
aatgtgtagc cagcaccacg                                                      20

SEQ ID NO: 171                moltype = DNA   length = 20
FEATURE                       Location/Qualifiers
source                        1..20
                              mol_type = other DNA
                              organism = Homo sapiens
SEQUENCE: 171
gaacttcctg taaacgatcc                                                      20

SEQ ID NO: 172                moltype = DNA   length = 20
FEATURE                       Location/Qualifiers
source                        1..20
                              mol_type = other DNA
                              organism = Homo sapiens
SEQUENCE: 172
tacatacctc cattacaagc                                                      20

SEQ ID NO: 173                moltype = DNA   length = 20
FEATURE                       Location/Qualifiers
source                        1..20
                              mol_type = other DNA
                              organism = Homo sapiens
SEQUENCE: 173
ccatctacta aagctgtaag                                                      20

SEQ ID NO: 174                moltype = DNA   length = 20
FEATURE                       Location/Qualifiers
source                        1..20
                              mol_type = other DNA
                              organism = Homo sapiens
SEQUENCE: 174
ctcaatattg taatgcgttc                                                      20

SEQ ID NO: 175                moltype = DNA   length = 20
FEATURE                       Location/Qualifiers
source                        1..20
                              mol_type = other DNA
                              organism = Homo sapiens
SEQUENCE: 175
ctctccatcc atagacacac                                                      20

SEQ ID NO: 176                moltype = DNA   length = 20
FEATURE                       Location/Qualifiers
```

-continued

```
source                       1..20
                             mol_type = other DNA
                             organism = Homo sapiens
SEQUENCE: 176
taagacctac atcgccagcc                                                   20

SEQ ID NO: 177               moltype = DNA   length = 20
FEATURE                      Location/Qualifiers
source                       1..20
                             mol_type = other DNA
                             organism = Homo sapiens
SEQUENCE: 177
gaagaacttg caccagcgtc                                                   20

SEQ ID NO: 178               moltype = DNA   length = 20
FEATURE                      Location/Qualifiers
source                       1..20
                             mol_type = other DNA
                             organism = Homo sapiens
SEQUENCE: 178
gtcagccgca ttcaccctcg                                                   20

SEQ ID NO: 179               moltype = DNA   length = 20
FEATURE                      Location/Qualifiers
source                       1..20
                             mol_type = other DNA
                             organism = Homo sapiens
SEQUENCE: 179
ctgccagaag tcattgaccg                                                   20

SEQ ID NO: 180               moltype = DNA   length = 20
FEATURE                      Location/Qualifiers
source                       1..20
                             mol_type = other DNA
                             organism = Homo sapiens
SEQUENCE: 180
cccagccgta ctatgccacg                                                   20

SEQ ID NO: 181               moltype = DNA   length = 20
FEATURE                      Location/Qualifiers
source                       1..20
                             mol_type = other DNA
                             organism = Homo sapiens
SEQUENCE: 181
gccgctgccc ttccagacgc                                                   20

SEQ ID NO: 182               moltype = DNA   length = 20
FEATURE                      Location/Qualifiers
source                       1..20
                             mol_type = other DNA
                             organism = Homo sapiens
SEQUENCE: 182
gtagctggaa tcctcatcag                                                   20

SEQ ID NO: 183               moltype = DNA   length = 20
FEATURE                      Location/Qualifiers
source                       1..20
                             mol_type = other DNA
                             organism = Homo sapiens
SEQUENCE: 183
caaaacctat cctacaactg                                                   20

SEQ ID NO: 184               moltype = DNA   length = 20
FEATURE                      Location/Qualifiers
source                       1..20
                             mol_type = other DNA
                             organism = Homo sapiens
SEQUENCE: 184
ttagggagtt tatggaccca                                                   20

SEQ ID NO: 185               moltype = DNA   length = 20
FEATURE                      Location/Qualifiers
source                       1..20
                             mol_type = other DNA
                             organism = Homo sapiens
SEQUENCE: 185
ctcagccaca gttgtaggat                                                   20

SEQ ID NO: 186               moltype = DNA   length = 20
```

-continued

```
FEATURE                 Location/Qualifiers
source                  1..20
                        mol_type = other DNA
                        organism = Homo sapiens
SEQUENCE: 186
tcactgtacc ttaatgaagt                                                     20

SEQ ID NO: 187          moltype = DNA   length = 20
FEATURE                 Location/Qualifiers
source                  1..20
                        mol_type = other DNA
                        organism = Homo sapiens
SEQUENCE: 187
tcctttatct acaaccctcc                                                     20

SEQ ID NO: 188          moltype = DNA   length = 20
FEATURE                 Location/Qualifiers
source                  1..20
                        mol_type = other DNA
                        organism = Homo sapiens
SEQUENCE: 188
tccataggtg cccaacgctc                                                     20

SEQ ID NO: 189          moltype = DNA   length = 20
FEATURE                 Location/Qualifiers
source                  1..20
                        mol_type = other DNA
                        organism = Homo sapiens
SEQUENCE: 189
gttccggaac caatgcacag                                                     20

SEQ ID NO: 190          moltype = DNA   length = 20
FEATURE                 Location/Qualifiers
source                  1..20
                        mol_type = other DNA
                        organism = Homo sapiens
SEQUENCE: 190
gcgagaagtc cccgcgctgc                                                     20

SEQ ID NO: 191          moltype = DNA   length = 20
FEATURE                 Location/Qualifiers
source                  1..20
                        mol_type = other DNA
                        organism = Homo sapiens
SEQUENCE: 191
tgaccctgc tcttcgcaga                                                      20

SEQ ID NO: 192          moltype = DNA   length = 20
FEATURE                 Location/Qualifiers
source                  1..20
                        mol_type = other DNA
                        organism = Homo sapiens
SEQUENCE: 192
cgccggcgag taccgcgccg                                                     20

SEQ ID NO: 193          moltype = DNA   length = 20
FEATURE                 Location/Qualifiers
source                  1..20
                        mol_type = other DNA
                        organism = Homo sapiens
SEQUENCE: 193
tgggcggtca gggcggctga                                                     20

SEQ ID NO: 194          moltype = DNA   length = 20
FEATURE                 Location/Qualifiers
source                  1..20
                        mol_type = other DNA
                        organism = Homo sapiens
SEQUENCE: 194
ctaaatgggg atttccgcaa                                                     20

SEQ ID NO: 195          moltype = DNA   length = 20
FEATURE                 Location/Qualifiers
source                  1..20
                        mol_type = other DNA
                        organism = Homo sapiens
SEQUENCE: 195
atccccattt agccagtatc                                                     20
```

```
SEQ ID NO: 196          moltype = DNA   length = 20
FEATURE                 Location/Qualifiers
source                  1..20
                        mol_type = other DNA
                        organism = Homo sapiens
SEQUENCE: 196
gtgaagtctc tctgccgagt                                                     20

SEQ ID NO: 197          moltype = DNA   length = 20
FEATURE                 Location/Qualifiers
source                  1..20
                        mol_type = other DNA
                        organism = Homo sapiens
SEQUENCE: 197
aggtcacccc tgcaccgact                                                     20

SEQ ID NO: 198          moltype = DNA   length = 20
FEATURE                 Location/Qualifiers
source                  1..20
                        mol_type = other DNA
                        organism = Homo sapiens
SEQUENCE: 198
cttactgtta gatttatatc                                                     20

SEQ ID NO: 199          moltype = DNA   length = 20
FEATURE                 Location/Qualifiers
source                  1..20
                        mol_type = other DNA
                        organism = Homo sapiens
SEQUENCE: 199
tatagcagag acacagacac                                                     20

SEQ ID NO: 200          moltype = DNA   length = 20
FEATURE                 Location/Qualifiers
source                  1..20
                        mol_type = other DNA
                        organism = Homo sapiens
SEQUENCE: 200
gtgacttggt gcaagctcaa                                                     20

SEQ ID NO: 201          moltype = DNA   length = 20
FEATURE                 Location/Qualifiers
source                  1..20
                        mol_type = other DNA
                        organism = Homo sapiens
SEQUENCE: 201
tctgcttgcc atttcgtcct                                                     20

SEQ ID NO: 202          moltype = DNA   length = 20
FEATURE                 Location/Qualifiers
source                  1..20
                        mol_type = other DNA
                        organism = Homo sapiens
SEQUENCE: 202
ctgttagcac agtatttcac                                                     20

SEQ ID NO: 203          moltype = DNA   length = 20
FEATURE                 Location/Qualifiers
source                  1..20
                        mol_type = other DNA
                        organism = Homo sapiens
SEQUENCE: 203
ccaaaggaag taaacgatac                                                     20

SEQ ID NO: 204          moltype = DNA   length = 20
FEATURE                 Location/Qualifiers
source                  1..20
                        mol_type = other DNA
                        organism = Homo sapiens
SEQUENCE: 204
atgttccaga tgtccagata                                                     20

SEQ ID NO: 205          moltype = DNA   length = 20
FEATURE                 Location/Qualifiers
source                  1..20
                        mol_type = other DNA
                        organism = Homo sapiens
SEQUENCE: 205
cttcttctta atcccatatc                                                     20
```

```
SEQ ID NO: 206          moltype = DNA  length = 20
FEATURE                 Location/Qualifiers
source                  1..20
                        mol_type = other DNA
                        organism = Homo sapiens
SEQUENCE: 206
agtttagtcg cgttccttcc                                                    20

SEQ ID NO: 207          moltype = DNA  length = 20
FEATURE                 Location/Qualifiers
source                  1..20
                        mol_type = other DNA
                        organism = Homo sapiens
SEQUENCE: 207
cactgtgcaa cggtgtgact                                                    20

SEQ ID NO: 208          moltype = DNA  length = 20
FEATURE                 Location/Qualifiers
source                  1..20
                        mol_type = other DNA
                        organism = Homo sapiens
SEQUENCE: 208
ggatgtccac aattgccagc                                                    20

SEQ ID NO: 209          moltype = DNA  length = 20
FEATURE                 Location/Qualifiers
source                  1..20
                        mol_type = other DNA
                        organism = Homo sapiens
SEQUENCE: 209
aactgagagt gccttcatta                                                    20

SEQ ID NO: 210          moltype = DNA  length = 20
FEATURE                 Location/Qualifiers
source                  1..20
                        mol_type = other DNA
                        organism = Homo sapiens
SEQUENCE: 210
gacagggaac tacacagtga                                                    20

SEQ ID NO: 211          moltype = AA  length = 965
FEATURE                 Location/Qualifiers
REGION                  1..965
                        note = Synthetic
source                  1..965
                        mol_type = protein
                        organism = synthetic construct
SEQUENCE: 211
MGTSLLCWMA LCLLGADHAD ACPYSNPSLC SGGGGSELPT QGTFSNVSTN VSPAKPTTTA   60
CPYSNPSLCS GGGGSPAPRP PTPAPTIASQ PLSLRPEACR PAAGGAVHTR GLDFACDIYI  120
WAPLAGTCGV LLLSLVITLY CNHRNRRRVC KCPRPVVRSG SGQCTNYALL KLAGDVESNP  180
GPPTGMVCLK LPGGSCMTAL TVTLMVLSSP LALASDENPV VHFFKNIVTP RTPPGGGGSG  240
GGGSGGSGDT RPRFLWQPKR ECHFFNGTER VRFLDRYFYN QEESVRFDSD VGEFRAVTEL  300
GRPDAEYWNS QKDILEQARA AVDTYCRHNY GVVESFTVQR RVQPKVTVYP SKTQPLQHHN  360
LLVCSVSGFY PGSIEVRWFL NGQEEKAGMV STGLIQNGDW TFQTLVMLET VPRSGEVYTC  420
QVEHPSVTSP LTVEWRARSE SAQSKMLSGV GGFVLGLLFL GAGLFIYFRN QTSRVKFSRS  480
ADAPAYQQGQ NQLYNELNLG RREEYDVLDK RRGRDPEMGG KPRRKNPQEG LYNELQKDKM  540
AEAYSEIGMK GERRRGKGHD GLYQGLSTAT KDTYDALHMQ ALPPRGSSGS GEGRGSLLTC  600
GDVEENPGPM AISGVPVLGF FIIAVLMSAQ ESWAIKEEHV IIQAEFYLNP DQSGEFMFDF  660
DGDEIFHVDM AKKETVWRLE EFGRFASFEA QGALANIAVD KANLEIMTKR SNYTPITNVP  720
PEVTVLTNSP VELREPNVLI CFIDKFTPPV VNVTWLRNGK PVTTGVSETV FLPREDHLFR  780
KFHYLPFLPS TEDVYDCRVE HWGLDEPLLK HWEFDAPSPL PETTENVVCA LGLTVGLVGI  840
IIGTIFIIKG LTSRVKFSRS ADAPAYQQGQ NQLYNELNLG RREEYDVLDK RRGRDPEMGG  900
KPRRKNPQEG LYNELQKDKM AEAYSEIGMK GERRRGKGHD GLYQGLSTAT KDTYDALHMQ  960
ALPPR                                                              965

SEQ ID NO: 212          moltype = DNA  length = 20
FEATURE                 Location/Qualifiers
source                  1..20
                        mol_type = other DNA
                        organism = Homo sapiens
SEQUENCE: 212
attgtggaca tccagtctgg                                                    20

SEQ ID NO: 213          moltype = DNA  length = 20
FEATURE                 Location/Qualifiers
source                  1..20
                        mol_type = other DNA
```

-continued

```
                            organism = Homo sapiens
SEQUENCE: 213
tcgctgaccg tgaacgatac                                                    20

SEQ ID NO: 214              moltype = DNA  length = 20
FEATURE                     Location/Qualifiers
source                      1..20
                            mol_type = other DNA
                            organism = Homo sapiens
SEQUENCE: 214
tggggccact cgatccttga                                                    20

SEQ ID NO: 215              moltype = DNA  length = 20
FEATURE                     Location/Qualifiers
source                      1..20
                            mol_type = other DNA
                            organism = Homo sapiens
SEQUENCE: 215
gcagatgacc accagcgtcg                                                    20

SEQ ID NO: 216              moltype = DNA  length = 20
FEATURE                     Location/Qualifiers
source                      1..20
                            mol_type = other DNA
                            organism = Homo sapiens
SEQUENCE: 216
tcaggcctta cctgaggcga                                                    20

SEQ ID NO: 217              moltype = DNA  length = 20
FEATURE                     Location/Qualifiers
source                      1..20
                            mol_type = other DNA
                            organism = Homo sapiens
SEQUENCE: 217
catctgcaca gcagtcatcg                                                    20

SEQ ID NO: 218              moltype = DNA  length = 20
FEATURE                     Location/Qualifiers
source                      1..20
                            mol_type = other DNA
                            organism = Homo sapiens
SEQUENCE: 218
attgaagtag tcatgcagct                                                    20

SEQ ID NO: 219              moltype = DNA  length = 20
FEATURE                     Location/Qualifiers
source                      1..20
                            mol_type = other DNA
                            organism = Homo sapiens
SEQUENCE: 219
aggcacagta gaagccgtat                                                    20

SEQ ID NO: 220              moltype = DNA  length = 20
FEATURE                     Location/Qualifiers
source                      1..20
                            mol_type = other DNA
                            organism = Homo sapiens
SEQUENCE: 220
gctgtctatc atccccaata                                                    20

SEQ ID NO: 221              moltype = DNA  length = 20
FEATURE                     Location/Qualifiers
source                      1..20
                            mol_type = other DNA
                            organism = Homo sapiens
SEQUENCE: 221
acttaccacc gaccatgcat                                                    20

SEQ ID NO: 222              moltype = DNA  length = 20
FEATURE                     Location/Qualifiers
source                      1..20
                            mol_type = other DNA
                            organism = Homo sapiens
SEQUENCE: 222
cacactttag agtgagcgtc                                                    20

SEQ ID NO: 223              moltype = DNA  length = 20
FEATURE                     Location/Qualifiers
source                      1..20
```

```
                            mol_type = other DNA
                            organism = Homo sapiens
SEQUENCE: 223
ctccagtggc tgaccccctc                                               20

SEQ ID NO: 224              moltype = DNA  length = 20
FEATURE                     Location/Qualifiers
source                      1..20
                            mol_type = other DNA
                            organism = Homo sapiens
SEQUENCE: 224
ccacagcagc ccaccagtac                                               20

SEQ ID NO: 225              moltype = DNA  length = 20
FEATURE                     Location/Qualifiers
source                      1..20
                            mol_type = other DNA
                            organism = Homo sapiens
SEQUENCE: 225
ttataataga tgcagcgata                                               20

SEQ ID NO: 226              moltype = DNA  length = 20
FEATURE                     Location/Qualifiers
source                      1..20
                            mol_type = other DNA
                            organism = Homo sapiens
SEQUENCE: 226
tcattgtgac tgttgtccga                                               20

SEQ ID NO: 227              moltype = DNA  length = 20
FEATURE                     Location/Qualifiers
source                      1..20
                            mol_type = other DNA
                            organism = Homo sapiens
SEQUENCE: 227
gccaggcacc gtgatccccc                                               20

SEQ ID NO: 228              moltype = DNA  length = 20
FEATURE                     Location/Qualifiers
source                      1..20
                            mol_type = other DNA
                            organism = Homo sapiens
SEQUENCE: 228
catccttatc cccggtaccc                                               20

SEQ ID NO: 229              moltype = DNA  length = 20
FEATURE                     Location/Qualifiers
source                      1..20
                            mol_type = other DNA
                            organism = Homo sapiens
SEQUENCE: 229
cagagagttc tgagctcgac                                               20

SEQ ID NO: 230              moltype = DNA  length = 20
FEATURE                     Location/Qualifiers
source                      1..20
                            mol_type = other DNA
                            organism = Homo sapiens
SEQUENCE: 230
agtgttgctg ggggcggtcg                                               20

SEQ ID NO: 231              moltype = DNA  length = 20
FEATURE                     Location/Qualifiers
source                      1..20
                            mol_type = other DNA
                            organism = Homo sapiens
SEQUENCE: 231
gacgatgcag agttccgtga                                               20

SEQ ID NO: 232              moltype = DNA  length = 20
FEATURE                     Location/Qualifiers
source                      1..20
                            mol_type = other DNA
                            organism = Homo sapiens
SEQUENCE: 232
actcacagga cacgttgaga                                               20

SEQ ID NO: 233              moltype = DNA  length = 20
FEATURE                     Location/Qualifiers
```

-continued

```
source                  1..20
                        mol_type = other DNA
                        organism = Homo sapiens
SEQUENCE: 233
taccctggcc cagtagttca                                                     20

SEQ ID NO: 234          moltype = DNA   length = 20
FEATURE                 Location/Qualifiers
source                  1..20
                        mol_type = other DNA
                        organism = Homo sapiens
SEQUENCE: 234
accttcgtct gtatgctgtt                                                     20

SEQ ID NO: 235          moltype = DNA   length = 20
FEATURE                 Location/Qualifiers
source                  1..20
                        mol_type = other DNA
                        organism = Homo sapiens
SEQUENCE: 235
accaaacagc atacagacga                                                     20

SEQ ID NO: 236          moltype = DNA   length = 20
FEATURE                 Location/Qualifiers
source                  1..20
                        mol_type = other DNA
                        organism = Homo sapiens
SEQUENCE: 236
ctactctatg atccagtccc                                                     20

SEQ ID NO: 237          moltype = DNA   length = 20
FEATURE                 Location/Qualifiers
source                  1..20
                        mol_type = other DNA
                        organism = Homo sapiens
SEQUENCE: 237
actccgtcag ctcgttagaa                                                     20

SEQ ID NO: 238          moltype = DNA   length = 20
FEATURE                 Location/Qualifiers
source                  1..20
                        mol_type = other DNA
                        organism = Homo sapiens
SEQUENCE: 238
gttcatactc tcttcgtcat                                                     20

SEQ ID NO: 239          moltype = DNA   length = 20
FEATURE                 Location/Qualifiers
source                  1..20
                        mol_type = other DNA
                        organism = Homo sapiens
SEQUENCE: 239
agagtagcag ctcacataac                                                     20

SEQ ID NO: 240          moltype = DNA   length = 20
FEATURE                 Location/Qualifiers
source                  1..20
                        mol_type = other DNA
                        organism = Homo sapiens
SEQUENCE: 240
ttccagagct cacaacgacc                                                     20

SEQ ID NO: 241          moltype = DNA   length = 20
FEATURE                 Location/Qualifiers
source                  1..20
                        mol_type = other DNA
                        organism = Homo sapiens
SEQUENCE: 241
atagtcctgt ccatatttgc                                                     20

SEQ ID NO: 242          moltype = DNA   length = 20
FEATURE                 Location/Qualifiers
source                  1..20
                        mol_type = other DNA
                        organism = Homo sapiens
SEQUENCE: 242
agatactcac gatctcattg                                                     20

SEQ ID NO: 243          moltype = DNA   length = 20
```

```
FEATURE           Location/Qualifiers
source            1..20
                  mol_type = other DNA
                  organism = Homo sapiens
SEQUENCE: 243
aggtcaagga ttgtacgccc                                           20

SEQ ID NO: 244    moltype = DNA   length = 20
FEATURE           Location/Qualifiers
source            1..20
                  mol_type = other DNA
                  organism = Homo sapiens
SEQUENCE: 244
gaagtccctg caccacgacc                                           20

SEQ ID NO: 245    moltype = DNA   length = 20
FEATURE           Location/Qualifiers
source            1..20
                  mol_type = other DNA
                  organism = Homo sapiens
SEQUENCE: 245
tttggttgtt ccgttgctgt                                           20

SEQ ID NO: 246    moltype = DNA   length = 20
FEATURE           Location/Qualifiers
source            1..20
                  mol_type = other DNA
                  organism = Homo sapiens
SEQUENCE: 246
tgatcgaccc tccgccagaa                                           20

SEQ ID NO: 247    moltype = DNA   length = 20
FEATURE           Location/Qualifiers
source            1..20
                  mol_type = other DNA
                  organism = Homo sapiens
SEQUENCE: 247
gggtcgatca tctattaata                                           20

SEQ ID NO: 248    moltype = DNA   length = 20
FEATURE           Location/Qualifiers
source            1..20
                  mol_type = other DNA
                  organism = Homo sapiens
SEQUENCE: 248
tcctttgcgg aatgtagtcc                                           20

SEQ ID NO: 249    moltype = DNA   length = 20
FEATURE           Location/Qualifiers
source            1..20
                  mol_type = other DNA
                  organism = Homo sapiens
SEQUENCE: 249
ctatgtatcc tttcggcatg                                           20

SEQ ID NO: 250    moltype = DNA   length = 20
FEATURE           Location/Qualifiers
source            1..20
                  mol_type = other DNA
                  organism = Homo sapiens
SEQUENCE: 250
tcttctgccg tatgatatag                                           20

SEQ ID NO: 251    moltype = DNA   length = 20
FEATURE           Location/Qualifiers
source            1..20
                  mol_type = other DNA
                  organism = Homo sapiens
SEQUENCE: 251
gtgagacatg atctcccgaa                                           20

SEQ ID NO: 252    moltype = DNA   length = 20
FEATURE           Location/Qualifiers
source            1..20
                  mol_type = other DNA
                  organism = Homo sapiens
SEQUENCE: 252
atgtcgatgc agcaaacctc                                           20
```

| | | |
|---|---|---|
| SEQ ID NO: 253<br>FEATURE<br>source<br><br>SEQUENCE: 253<br>attatacata aacccatctc | moltype = DNA   length = 20<br>Location/Qualifiers<br>1..20<br>mol_type = other DNA<br>organism = Homo sapiens | <br><br><br><br><br>20 |
| SEQ ID NO: 254<br>FEATURE<br>source<br><br>SEQUENCE: 254<br>aatggactct ggaatatccc | moltype = DNA   length = 20<br>Location/Qualifiers<br>1..20<br>mol_type = other DNA<br>organism = Homo sapiens | <br><br><br><br><br>20 |
| SEQ ID NO: 255<br>FEATURE<br>source<br><br>SEQUENCE: 255<br>atagagacaa tcttacccgc | moltype = DNA   length = 20<br>Location/Qualifiers<br>1..20<br>mol_type = other DNA<br>organism = Homo sapiens | <br><br><br><br><br>20 |
| SEQ ID NO: 256<br>FEATURE<br>source<br><br>SEQUENCE: 256<br>aagattgtct ctatctgcgc | moltype = DNA   length = 20<br>Location/Qualifiers<br>1..20<br>mol_type = other DNA<br>organism = Homo sapiens | <br><br><br><br><br>20 |
| SEQ ID NO: 257<br>FEATURE<br>source<br><br>SEQUENCE: 257<br>aaatgtgatt gccttcgcca | moltype = DNA   length = 20<br>Location/Qualifiers<br>1..20<br>mol_type = other DNA<br>organism = Homo sapiens | <br><br><br><br><br>20 |
| SEQ ID NO: 258<br>FEATURE<br>source<br><br>SEQUENCE: 258<br>cgtttgtacc gtccctcttc | moltype = DNA   length = 20<br>Location/Qualifiers<br>1..20<br>mol_type = other DNA<br>organism = Homo sapiens | <br><br><br><br><br>20 |
| SEQ ID NO: 259<br>FEATURE<br>source<br><br>SEQUENCE: 259<br>tgcgatccat caagaccacc | moltype = DNA   length = 20<br>Location/Qualifiers<br>1..20<br>mol_type = other DNA<br>organism = Homo sapiens | <br><br><br><br><br>20 |
| SEQ ID NO: 260<br>FEATURE<br>source<br><br>SEQUENCE: 260<br>ttgatattta ggcttgccga | moltype = DNA   length = 20<br>Location/Qualifiers<br>1..20<br>mol_type = other DNA<br>organism = Homo sapiens | <br><br><br><br><br>20 |
| SEQ ID NO: 261<br>FEATURE<br>source<br><br>SEQUENCE: 261<br>agtcgtcgac gcgccgcagc | moltype = DNA   length = 20<br>Location/Qualifiers<br>1..20<br>mol_type = other DNA<br>organism = Homo sapiens | <br><br><br><br><br>20 |
| SEQ ID NO: 262<br>FEATURE<br>source<br><br>SEQUENCE: 262<br>agcggcccat caggacgctt | moltype = DNA   length = 20<br>Location/Qualifiers<br>1..20<br>mol_type = other DNA<br>organism = Homo sapiens | <br><br><br><br><br>20 |

```
SEQ ID NO: 263           moltype = DNA  length = 20
FEATURE                  Location/Qualifiers
source                   1..20
                         mol_type = other DNA
                         organism = Homo sapiens
SEQUENCE: 263
gcggcgcgtc gacgacttcg                                               20

SEQ ID NO: 264           moltype = DNA  length = 20
FEATURE                  Location/Qualifiers
source                   1..20
                         mol_type = other DNA
                         organism = Homo sapiens
SEQUENCE: 264
gtgtaacata cctggaggac                                               20

SEQ ID NO: 265           moltype = DNA  length = 20
FEATURE                  Location/Qualifiers
source                   1..20
                         mol_type = other DNA
                         organism = Homo sapiens
SEQUENCE: 265
tacatctgca cttggtattc                                               20

SEQ ID NO: 266           moltype = DNA  length = 20
FEATURE                  Location/Qualifiers
source                   1..20
                         mol_type = other DNA
                         organism = Homo sapiens
SEQUENCE: 266
ctaaaactta cttggtgcaa                                               20

SEQ ID NO: 267           moltype = DNA  length = 20
FEATURE                  Location/Qualifiers
source                   1..20
                         mol_type = other DNA
                         organism = Homo sapiens
SEQUENCE: 267
tctcaactct ttctcgaagc                                               20

SEQ ID NO: 268           moltype = DNA  length = 20
FEATURE                  Location/Qualifiers
source                   1..20
                         mol_type = other DNA
                         organism = Homo sapiens
SEQUENCE: 268
ctgcctgatc tcatagagtc                                               20

SEQ ID NO: 269           moltype = DNA  length = 20
FEATURE                  Location/Qualifiers
source                   1..20
                         mol_type = other DNA
                         organism = Homo sapiens
SEQUENCE: 269
cagatactta ctcataagtc                                               20

SEQ ID NO: 270           moltype = DNA  length = 20
FEATURE                  Location/Qualifiers
source                   1..20
                         mol_type = other DNA
                         organism = Homo sapiens
SEQUENCE: 270
cgctgagaaa tgactgcacg                                               20

SEQ ID NO: 271           moltype = DNA  length = 20
FEATURE                  Location/Qualifiers
source                   1..20
                         mol_type = other DNA
                         organism = Homo sapiens
SEQUENCE: 271
catatacttc ttcaccagtt                                               20

SEQ ID NO: 272           moltype = DNA  length = 20
FEATURE                  Location/Qualifiers
source                   1..20
                         mol_type = other DNA
                         organism = Homo sapiens
SEQUENCE: 272
```
atgtactcac acatctggat                                                    20

SEQ ID NO: 273         moltype = DNA   length = 20
FEATURE                Location/Qualifiers
source                 1..20
                       mol_type = other DNA
                       organism = Homo sapiens SEQUENCE: 273
accgaatgtc ccgcgtgcaa                                                    20

SEQ ID NO: 274         moltype = DNA   length = 20
FEATURE                Location/Qualifiers
source                 1..20
                       mol_type = other DNA
                       organism = Homo sapiens SEQUENCE: 274
gcctttgcac gcgggacatt                                                    20

SEQ ID NO: 275         moltype = DNA   length = 20
FEATURE                Location/Qualifiers
source                 1..20
                       mol_type = other DNA
                       organism = Homo sapiens SEQUENCE: 275
ggggaccctg aaagaatacg                                                    20

SEQ ID NO: 276         moltype = DNA   length = 20
FEATURE                Location/Qualifiers
source                 1..20
                       mol_type = other DNA
                       organism = Homo sapiens SEQUENCE: 276
cctgcgctgg agaaactatt                                                    20

SEQ ID NO: 277         moltype = DNA   length = 20
FEATURE                Location/Qualifiers
source                 1..20
                       mol_type = other DNA
                       organism = Homo sapiens SEQUENCE: 277
ccttgtagta actgcccagc                                                    20

SEQ ID NO: 278         moltype = DNA   length = 20
FEATURE                Location/Qualifiers
source                 1..20
                       mol_type = other DNA
                       organism = Homo sapiens SEQUENCE: 278
catagtagcc actctgttgc                                                    20

SEQ ID NO: 279         moltype = DNA   length = 20
FEATURE                Location/Qualifiers
source                 1..20
                       mol_type = other DNA
                       organism = Homo sapiens SEQUENCE: 279
caatatcaac gtaatagttc                                                    20

SEQ ID NO: 280         moltype = DNA   length = 20
FEATURE                Location/Qualifiers
source                 1..20
                       mol_type = other DNA
                       organism = Homo sapiens SEQUENCE: 280
gacttagtgc aatgcaagac                                                    20

SEQ ID NO: 281         moltype = DNA   length = 20
FEATURE                Location/Qualifiers
source                 1..20
                       mol_type = other DNA
                       organism = Homo sapiens SEQUENCE: 281
gatattgctg attaagtccc                                                    20

SEQ ID NO: 282         moltype = DNA   length = 20
FEATURE                Location/Qualifiers
source                 1..20
                       mol_type = other DNA
                       organism = Homo sapiens

```
                                              -continued

SEQUENCE: 282
gcgggccgac cgcatttggg                                                    20

SEQ ID NO: 283         moltype = DNA   length = 20
FEATURE                Location/Qualifiers
source                 1..20
                       mol_type = other DNA
                       organism = Homo sapiens
SEQUENCE: 283
catattacat cggatatctg                                                    20

SEQ ID NO: 284         moltype = DNA   length = 20
FEATURE                Location/Qualifiers
source                 1..20
                       mol_type = other DNA
                       organism = Homo sapiens
SEQUENCE: 284
actcttctgc cggacacttg                                                    20

SEQ ID NO: 285         moltype = DNA   length = 20
FEATURE                Location/Qualifiers
source                 1..20
                       mol_type = other DNA
                       organism = Homo sapiens
SEQUENCE: 285
ttatagagga accctactaa                                                    20

SEQ ID NO: 286         moltype = DNA   length = 20
FEATURE                Location/Qualifiers
source                 1..20
                       mol_type = other DNA
                       organism = Homo sapiens
SEQUENCE: 286
ttgtgggcac cttactgagt                                                    20

SEQ ID NO: 287         moltype = DNA   length = 20
FEATURE                Location/Qualifiers
source                 1..20
                       mol_type = other DNA
                       organism = Homo sapiens
SEQUENCE: 287
cgaacacatc gctgacaact                                                    20

SEQ ID NO: 288         moltype = DNA   length = 20
FEATURE                Location/Qualifiers
source                 1..20
                       mol_type = other DNA
                       organism = Homo sapiens
SEQUENCE: 288
gttaacgttt ccactttacc                                                    20

SEQ ID NO: 289         moltype = DNA   length = 20
FEATURE                Location/Qualifiers
source                 1..20
                       mol_type = other DNA
                       organism = Homo sapiens
SEQUENCE: 289
ttcccgctga gcctcgtcca                                                    20

SEQ ID NO: 290         moltype = DNA   length = 20
FEATURE                Location/Qualifiers
source                 1..20
                       mol_type = other DNA
                       organism = Homo sapiens
SEQUENCE: 290
tatctaattt atcgtcttcc                                                    20

SEQ ID NO: 291         moltype = DNA   length = 20
FEATURE                Location/Qualifiers
source                 1..20
                       mol_type = other DNA
                       organism = Homo sapiens
SEQUENCE: 291
ttcggagcat cagtcgttga                                                    20

SEQ ID NO: 292         moltype = DNA   length = 20
FEATURE                Location/Qualifiers
source                 1..20
                       mol_type = other DNA
```

```
                            organism = Homo sapiens
SEQUENCE: 292
ttcaacgact gatgctccga                                                    20

SEQ ID NO: 293              moltype = DNA   length = 20
FEATURE                     Location/Qualifiers
source                      1..20
                            mol_type = other DNA
                            organism = Homo sapiens
SEQUENCE: 293
catgcactct gtttgcgaag                                                    20

SEQ ID NO: 294              moltype = DNA   length = 19
FEATURE                     Location/Qualifiers
source                      1..19
                            mol_type = other DNA
                            organism = Homo sapiens
SEQUENCE: 294
ttctcccaga accaaacga                                                     19

SEQ ID NO: 295              moltype = DNA   length = 20
FEATURE                     Location/Qualifiers
source                      1..20
                            mol_type = other DNA
                            organism = Homo sapiens
SEQUENCE: 295
gatgatgtct gcctcgcgcc                                                    20

SEQ ID NO: 296              moltype = DNA   length = 20
FEATURE                     Location/Qualifiers
source                      1..20
                            mol_type = other DNA
                            organism = Homo sapiens
SEQUENCE: 296
atgccccatc ttcaattgtc                                                    20

SEQ ID NO: 297              moltype = DNA   length = 20
FEATURE                     Location/Qualifiers
source                      1..20
                            mol_type = other DNA
                            organism = Homo sapiens
SEQUENCE: 297
tattcggcca tcaaaggagc                                                    20

SEQ ID NO: 298              moltype = DNA   length = 20
FEATURE                     Location/Qualifiers
source                      1..20
                            mol_type = other DNA
                            organism = Homo sapiens
SEQUENCE: 298
gactaagcct caactccaac                                                    20

SEQ ID NO: 299              moltype = DNA   length = 20
FEATURE                     Location/Qualifiers
source                      1..20
                            mol_type = other DNA
                            organism = Homo sapiens
SEQUENCE: 299
tatacaagct attagctgcg                                                    20

SEQ ID NO: 300              moltype = DNA   length = 20
FEATURE                     Location/Qualifiers
source                      1..20
                            mol_type = other DNA
                            organism = Homo sapiens
SEQUENCE: 300
gaactacatc gctgagcttc                                                    20

SEQ ID NO: 301              moltype = DNA   length = 20
FEATURE                     Location/Qualifiers
source                      1..20
                            mol_type = other DNA
                            organism = Homo sapiens
SEQUENCE: 301
gccatcctat tgtgagtttc                                                    20

SEQ ID NO: 302              moltype = DNA   length = 20
FEATURE                     Location/Qualifiers
source                      1..20
```

```
                              mol_type = other DNA
                              organism = Homo sapiens
SEQUENCE: 302
tgtctccaat ttaactaacg                                               20

SEQ ID NO: 303                moltype = DNA   length = 20
FEATURE                       Location/Qualifiers
source                        1..20
                              mol_type = other DNA
                              organism = Homo sapiens
SEQUENCE: 303
aaggaatagt cacctccgta                                               20

SEQ ID NO: 304                moltype = DNA   length = 20
FEATURE                       Location/Qualifiers
source                        1..20
                              mol_type = other DNA
                              organism = Homo sapiens
SEQUENCE: 304
aatgggcat tataacaacg                                                20

SEQ ID NO: 305                moltype = DNA   length = 20
FEATURE                       Location/Qualifiers
source                        1..20
                              mol_type = other DNA
                              organism = Homo sapiens
SEQUENCE: 305
ggtgaggttc gtggtgttcg                                               20

SEQ ID NO: 306                moltype = DNA   length = 20
FEATURE                       Location/Qualifiers
source                        1..20
                              mol_type = other DNA
                              organism = Homo sapiens
SEQUENCE: 306
gtgcagcaat cgtcgactac                                               20

SEQ ID NO: 307                moltype = DNA   length = 20
FEATURE                       Location/Qualifiers
source                        1..20
                              mol_type = other DNA
                              organism = Homo sapiens
SEQUENCE: 307
aatcccggta tacaatcaaa                                               20

SEQ ID NO: 308                moltype = DNA   length = 20
FEATURE                       Location/Qualifiers
source                        1..20
                              mol_type = other DNA
                              organism = Homo sapiens
SEQUENCE: 308
ctcgagttgc ttgacttacg                                               20

SEQ ID NO: 309                moltype = DNA   length = 20
FEATURE                       Location/Qualifiers
source                        1..20
                              mol_type = other DNA
                              organism = Homo sapiens
SEQUENCE: 309
ggctcacggc tattcggccg                                               20

SEQ ID NO: 310                moltype = DNA   length = 20
FEATURE                       Location/Qualifiers
source                        1..20
                              mol_type = other DNA
                              organism = Homo sapiens
SEQUENCE: 310
gcgtctccgt gacaattacc                                               20

SEQ ID NO: 311                moltype = DNA   length = 20
FEATURE                       Location/Qualifiers
source                        1..20
                              mol_type = other DNA
                              organism = Homo sapiens
SEQUENCE: 311
ccgacaggtc cacgtagcgc                                               20

SEQ ID NO: 312                moltype = DNA   length = 20
FEATURE                       Location/Qualifiers
```

```
source                   1..20
                         mol_type = other DNA
                         organism = Homo sapiens
SEQUENCE: 312
cccacattta cgcctatcct                                                    20

SEQ ID NO: 313           moltype = DNA   length = 20
FEATURE                  Location/Qualifiers
source                   1..20
                         mol_type = other DNA
                         organism = Homo sapiens
SEQUENCE: 313
taacattaat agcagctcga                                                    20

SEQ ID NO: 314           moltype = DNA   length = 20
FEATURE                  Location/Qualifiers
source                   1..20
                         mol_type = other DNA
                         organism = Homo sapiens
SEQUENCE: 314
gaccccagcc acaacgacac                                                    20

SEQ ID NO: 315           moltype = DNA   length = 20
FEATURE                  Location/Qualifiers
source                   1..20
                         mol_type = other DNA
                         organism = Homo sapiens
SEQUENCE: 315
ccccaccaaa tttgtccaat                                                    20

SEQ ID NO: 316           moltype = DNA   length = 20
FEATURE                  Location/Qualifiers
source                   1..20
                         mol_type = other DNA
                         organism = Homo sapiens
SEQUENCE: 316
gaggccctat tggacaaatt                                                    20

SEQ ID NO: 317           moltype = DNA   length = 20
FEATURE                  Location/Qualifiers
source                   1..20
                         mol_type = other DNA
                         organism = Homo sapiens
SEQUENCE: 317
gttgctccgt gccacatctg                                                    20

SEQ ID NO: 318           moltype = DNA   length = 20
FEATURE                  Location/Qualifiers
source                   1..20
                         mol_type = other DNA
                         organism = Homo sapiens
SEQUENCE: 318
ccatacttac tccgcagagc                                                    20

SEQ ID NO: 319           moltype = DNA   length = 20
FEATURE                  Location/Qualifiers
source                   1..20
                         mol_type = other DNA
                         organism = Homo sapiens
SEQUENCE: 319
tatggtgcgt tctacagcga                                                    20

SEQ ID NO: 320           moltype = DNA   length = 20
FEATURE                  Location/Qualifiers
source                   1..20
                         mol_type = other DNA
                         organism = Homo sapiens
SEQUENCE: 320
cccgacggct ctgcagttaa                                                    20

SEQ ID NO: 321           moltype = DNA   length = 20
FEATURE                  Location/Qualifiers
source                   1..20
                         mol_type = other DNA
                         organism = Homo sapiens
SEQUENCE: 321
tcggtgcagc tccacgactc                                                    20

SEQ ID NO: 322           moltype = DNA   length = 20
```

| | | |
|---|---|---|
| FEATURE | Location/Qualifiers | |
| source | 1..20 | |
| | mol_type = other DNA | |
| | organism = Homo sapiens | |
| SEQUENCE: 322 | | |
| aactattcat gctaccgggc | | 20 |
| SEQ ID NO: 323 | moltype = DNA length = 20 | |
| FEATURE | Location/Qualifiers | |
| source | 1..20 | |
| | mol_type = other DNA | |
| | organism = Homo sapiens | |
| SEQUENCE: 323 | | |
| cgtggtgcag cttcgtgccc | | 20 |
| SEQ ID NO: 324 | moltype = DNA length = 20 | |
| FEATURE | Location/Qualifiers | |
| source | 1..20 | |
| | mol_type = other DNA | |
| | organism = Homo sapiens | |
| SEQUENCE: 324 | | |
| agatgcctca acttggagcc | | 20 |
| SEQ ID NO: 325 | moltype = DNA length = 20 | |
| FEATURE | Location/Qualifiers | |
| source | 1..20 | |
| | mol_type = other DNA | |
| | organism = Homo sapiens | |
| SEQUENCE: 325 | | |
| tttgagttgc attgtgaacg | | 20 |
| SEQ ID NO: 326 | moltype = DNA length = 20 | |
| FEATURE | Location/Qualifiers | |
| source | 1..20 | |
| | mol_type = other DNA | |
| | organism = Homo sapiens | |
| SEQUENCE: 326 | | |
| attcgctgta tgaaggaaga | | 20 |
| SEQ ID NO: 327 | moltype = DNA length = 20 | |
| FEATURE | Location/Qualifiers | |
| source | 1..20 | |
| | mol_type = other DNA | |
| | organism = Homo sapiens | |
| SEQUENCE: 327 | | |
| ttcctacaca atgcgttgcc | | 20 |
| SEQ ID NO: 328 | moltype = DNA length = 20 | |
| FEATURE | Location/Qualifiers | |
| source | 1..20 | |
| | mol_type = other DNA | |
| | organism = Homo sapiens | |
| SEQUENCE: 328 | | |
| gatattggca taagcctccc | | 20 |
| SEQ ID NO: 329 | moltype = DNA length = 20 | |
| FEATURE | Location/Qualifiers | |
| source | 1..20 | |
| | mol_type = other DNA | |
| | organism = Homo sapiens | |
| SEQUENCE: 329 | | |
| tcaactgcga ccagttcagc | | 20 |
| SEQ ID NO: 330 | moltype = DNA length = 20 | |
| FEATURE | Location/Qualifiers | |
| source | 1..20 | |
| | mol_type = other DNA | |
| | organism = Homo sapiens | |
| SEQUENCE: 330 | | |
| tcgtatgtgc cctcgtcaga | | 20 |
| SEQ ID NO: 331 | moltype = DNA length = 20 | |
| FEATURE | Location/Qualifiers | |
| source | 1..20 | |
| | mol_type = other DNA | |
| | organism = Homo sapiens | |
| SEQUENCE: 331 | | |
| gagtgaatca gaccttcaac | | 20 |

-continued

| | | |
|---|---|---|
| SEQ ID NO: 332<br>FEATURE<br>source | moltype = DNA   length = 20<br>Location/Qualifiers<br>1..20<br>mol_type = other DNA<br>organism = Homo sapiens | |
| SEQUENCE: 332<br>tatggcccga gtacaagaac | | 20 |
| SEQ ID NO: 333<br>FEATURE<br>source | moltype = DNA   length = 20<br>Location/Qualifiers<br>1..20<br>mol_type = other DNA<br>organism = Homo sapiens | |
| SEQUENCE: 333<br>gtaaccgtgt atagatgagc | | 20 |
| SEQ ID NO: 334<br>FEATURE<br>source | moltype = DNA   length = 20<br>Location/Qualifiers<br>1..20<br>mol_type = other DNA<br>organism = Homo sapiens | |
| SEQUENCE: 334<br>atactcgata gttgaattct | | 20 |
| SEQ ID NO: 335<br>FEATURE<br>source | moltype = DNA   length = 20<br>Location/Qualifiers<br>1..20<br>mol_type = other DNA<br>organism = Homo sapiens | |
| SEQUENCE: 335<br>catcagatct ttcaggtata | | 20 |
| SEQ ID NO: 336<br>FEATURE<br>source | moltype = DNA   length = 20<br>Location/Qualifiers<br>1..20<br>mol_type = other DNA<br>organism = Homo sapiens | |
| SEQUENCE: 336<br>actcacgctg gatagcctcc | | 20 |
| SEQ ID NO: 337<br>FEATURE<br>source | moltype = DNA   length = 20<br>Location/Qualifiers<br>1..20<br>mol_type = other DNA<br>organism = Homo sapiens | |
| SEQUENCE: 337<br>gagtagcgcg agcacagcta | | 20 |
| SEQ ID NO: 338<br>FEATURE<br>source | moltype = DNA   length = 20<br>Location/Qualifiers<br>1..20<br>mol_type = other DNA<br>organism = Homo sapiens | |
| SEQUENCE: 338<br>cagtaagtca acttcaatgt | | 20 |
| SEQ ID NO: 339<br>FEATURE<br>source | moltype = DNA   length = 20<br>Location/Qualifiers<br>1..20<br>mol_type = other DNA<br>organism = Homo sapiens | |
| SEQUENCE: 339<br>ggttgttgca agattgaccc | | 20 |
| SEQ ID NO: 340<br>FEATURE<br>source | moltype = DNA   length = 20<br>Location/Qualifiers<br>1..20<br>mol_type = other DNA<br>organism = Homo sapiens | |
| SEQUENCE: 340<br>gaggaactct aagtatcccc | | 20 |
| SEQ ID NO: 341<br>FEATURE<br>source | moltype = DNA   length = 20<br>Location/Qualifiers<br>1..20<br>mol_type = other DNA<br>organism = Homo sapiens | |
| SEQUENCE: 341<br>tctggttgcc ttggtaggat | | 20 |

```
SEQ ID NO: 342          moltype = DNA   length = 20
FEATURE                 Location/Qualifiers
source                  1..20
                        mol_type = other DNA
                        organism = Homo sapiens
SEQUENCE: 342
cgcagccaca agttcgtgcc                                                  20

SEQ ID NO: 343          moltype = DNA   length = 20
FEATURE                 Location/Qualifiers
source                  1..20
                        mol_type = other DNA
                        organism = Homo sapiens
SEQUENCE: 343
ggagctgggt ggccgcatat                                                  20

SEQ ID NO: 344          moltype = DNA   length = 20
FEATURE                 Location/Qualifiers
source                  1..20
                        mol_type = other DNA
                        organism = Homo sapiens
SEQUENCE: 344
cccgaacagc aggtcgttaa                                                  20

SEQ ID NO: 345          moltype = DNA   length = 20
FEATURE                 Location/Qualifiers
source                  1..20
                        mol_type = other DNA
                        organism = Homo sapiens
SEQUENCE: 345
ctcttacctg taccataacc                                                  20

SEQ ID NO: 346          moltype = DNA   length = 20
FEATURE                 Location/Qualifiers
source                  1..20
                        mol_type = other DNA
                        organism = Homo sapiens
SEQUENCE: 346
aatgcctccg cttatgttgc                                                  20

SEQ ID NO: 347          moltype = DNA   length = 20
FEATURE                 Location/Qualifiers
source                  1..20
                        mol_type = other DNA
                        organism = Homo sapiens
SEQUENCE: 347
tggcattggc cacgaagaaa                                                  20

SEQ ID NO: 348          moltype = DNA   length = 20
FEATURE                 Location/Qualifiers
source                  1..20
                        mol_type = other DNA
                        organism = Homo sapiens
SEQUENCE: 348
cgactacttc ggtagtatgc                                                  20

SEQ ID NO: 349          moltype = DNA   length = 20
FEATURE                 Location/Qualifiers
source                  1..20
                        mol_type = other DNA
                        organism = Homo sapiens
SEQUENCE: 349
cagcatacta ccgaagtagt                                                  20

SEQ ID NO: 350          moltype = DNA   length = 20
FEATURE                 Location/Qualifiers
source                  1..20
                        mol_type = other DNA
                        organism = Homo sapiens
SEQUENCE: 350
gtgtttgtgt acatcaactc                                                  20

SEQ ID NO: 351          moltype = DNA   length = 43
FEATURE                 Location/Qualifiers
source                  1..43
                        mol_type = other DNA
                        organism = Homo sapiens
SEQUENCE: 351
```

```
tgacttccag agagcaatat ggctggttcc ccaacatgcc tca                      43

SEQ ID NO: 352          moltype = DNA  length = 17
FEATURE                 Location/Qualifiers
source                  1..17
                        mol_type = other DNA
                        organism = Homo sapiens
SEQUENCE: 352
tgacttccag agagcaa                                                   17

SEQ ID NO: 353          moltype = AA  length = 969
FEATURE                 Location/Qualifiers
source                  1..969
                        mol_type = protein
                        organism = Homo sapiens
SEQUENCE: 353
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASNNG GKQALETVQR LLPVLCQAHG LTPEQVVAIA SNIGGKQALE TVQRLLPVLC   240
QAHGLTPEQV VAIASHDGGK QALETVQRLL PVLCQAHGLT PEQVVAIASN GGKQALETV    300
QRLLPVLCQA HGLTPEQVVA IASNGGGKQA LETVQRLLPV LCQAHGLTPE QVVAIASHDG   360
GKQALETVQR LLPVLCQAHG LTPEQVVAIA SHDGGKQALE TVQRLLPVLC QAHGLTPEQV   420
VAIASNIGGK QALETVQRLL PVLCQAHGLT PEQVVAIASN NGGKQALETV QRLLPVLCQA   480
HGLTPEQVVA IASNIGGKQA LETVQRLLPV LCQAHGLTPE QVVAIASNNG GKQALETVQR   540
LLPVLCQAHG LTPEQVVAIA SNIGGKQALE TVQRLLPVLC QAHGLTPEQV VAIASNNGGK   600
QALETVQRLL PVLCQAHGLT PEQVVAIASH DGGKQALETV QRLLPVLCQA HGLTPEQVVA   660
IASNIGGKQA LETVQRLLPV LCQAHGLTPE QVVAIASNIG GRPALESIVA QLSRPDPALA   720
ALTNDHLVAL ACLGGRPALD AVKKGLPHAP ALIKRTNRRI PERTSHRVAG SQLVKSELEE   780
KKSELRHKLK YVPHEYIELI EIARNSTQDR ILEMKVMEFF MKVYGYRGKH LGGSRKPDGA   840
IYTVGSPIDY GVIVDTKAYS GGYNLPIGQA DEMQRYVEEN QTRNKHINPN EWWKVYPSSV   900
TEFKFLFVSG HFKGNYKAQL TRLNHITNCN GAVLSVEELL IGGEMIKAGT LTLEEVRRKF   960
NNGEINFRS                                                          969

SEQ ID NO: 354          moltype = DNA  length = 17
FEATURE                 Location/Qualifiers
source                  1..17
                        mol_type = other DNA
                        organism = Homo sapiens
SEQUENCE: 354
aacatgcctc accctca                                                   17

SEQ ID NO: 355          moltype = AA  length = 969
FEATURE                 Location/Qualifiers
source                  1..969
                        mol_type = protein
                        organism = Homo sapiens
SEQUENCE: 355
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASNNG GKQALETVQR LLPVLCQAHG LTPEQVVAIA SNIGGKQALE TVQRLLPVLC   240
QAHGLTPEQV VAIASNNGGK QALETVQRLL PVLCQAHGLT PEQVVAIASN NGGKQALETV   300
QRLLPVLCQA HGLTPEQVVA IASNNGGKQA LETVQRLLPV LCQAHGLTPE QVVAIASNGG   360
GKQALETVQR LLPVLCQAHG LTPEQVVAIA SNNGGKQALE TVQRLLPVLC QAHGLTPEQV   420
VAIASNIGGK QALETVQRLL PVLCQAHGLT PEQVVAIASN NGGKQALETV QRLLPVLCQA   480
HGLTPEQVVA IASNNGGKQA LETVQRLLPV LCQAHGLTPE QVVAIASHDG GKQALETVQR   540
LLPVLCQAHG LTPEQVVAIA SNIGGKQALE TVQRLLPVLC QAHGLTPEQV VAIASNGGGK   600
QALETVQRLL PVLCQAHGLT PEQVVAIASN NGGKQALETV QRLLPVLCQA HGLTPEQVVA   660
IASNGGGKQA LETVQRLLPV LCQAHGLTPE QVVAIASNGG GRPALESIVA QLSRPDPALA   720
ALTNDHLVAL ACLGGRPALD AVKKGLPHAP ALIKRTNRRI PERTSHRVAG SQLVKSELEE   780
KKSELRHKLK YVPHEYIELI EIARNSTQDR ILEMKVMEFF MKVYGYRGKH LGGSRKPDGA   840
IYTVGSPIDY GVIVDTKAYS GGYNLPIGQA DEMQRYVEEN QTRNKHINPN EWWKVYPSSV   900
TEFKFLFVSG HFKGNYKAQL TRLNHITNCN GAVLSVEELL IGGEMIKAGT LTLEEVRRKF   960
NNGEINFRS                                                          969

SEQ ID NO: 356          moltype = DNA  length = 49
FEATURE                 Location/Qualifiers
source                  1..49
                        mol_type = other DNA
                        organism = Homo sapiens
SEQUENCE: 356
ttccagagag caatatggct ggttccccaa catgcctcac cctcatcta                49

SEQ ID NO: 357          moltype = DNA  length = 17
FEATURE                 Location/Qualifiers
source                  1..17
                        mol_type = other DNA
                        organism = Homo sapiens
```

```
SEQUENCE: 357
ttccagagag caatatg                                                         17

SEQ ID NO: 358          moltype = AA   length = 969
FEATURE                 Location/Qualifiers
source                  1..969
                        mol_type = protein
                        organism = Homo sapiens
SEQUENCE: 358
MDYKDHDGDY KDHDIDYKDD DDKMAPKKKR KVGIHGVPAA VDLRTLGYSQ QQQEKIKPKV   60
RSTVAQHHEA LVGHGFTHAH IVALSQHPAA LGTVAVKYQD MIAALPEATH EAIVGVGKQW  120
SGARALEALL TVAGELRGPP LQLDTGQLLK IAKRGGVTAV EAVHAWRNAL TGAPLNLTPE  180
QVVAIASNGG GKQALETVQR LLPVLCQAHG LTPEQVVAIA SHDGGKQALE TVQRLLPVLC  240
QAHGLTPEQV VAIASHDGGK QALETVQRLL PVLCQAHGLT PEQVVAIASN IGGKQALETV  300
QRLLPVLCQA HGLTPEQVVA IASNNGGKQA LETVQRLLPV LCQAHGLTPE QVVAIASNIG  360
GKQALETVQR LLPVLCQAHG LTPEQVVAIA SNNGGKQALE TVQRLLPVLC QAHGLTPEQV  420
VAIASNIGGK QALETVQRLL PVLCQAHGLT PEQVVAIASN NGGKQALETV QRLLPVLCQA  480
HGLTPEQVVA IASNDGGKQA LETVQRLLPV LCQAHGLTPE QVVAIASNIG GKQALETVQR  540
LLPVLCQAHG LTPEQVVAIA SNIGGKQALE TVQRLLPVLC QAHGLTPEQV VAIASNGGGK  600
QALETVQRLL PVLCQAHGLT PEQVVAIASN IGGKQALETV QRLLPVLCQA HGLTPEQVVA  660
IASNGGGKQA LETVQRLLPV LCQAHGLTPE QVVAIASNNG GRPALESIVA QLSRPDPALA  720
ALTNDHLVAL ACLGGRPALD AVKKGLPHAP ALIKRTNRRI PERTSHRVAG SQLVKSELEE  780
KKSELRHKLK YVPHEYIELI EIARNSTQDR ILEMKVMEFF MKVYGYRGKH LGGSRKPDGA  840
IYTVGSPIDY GVIVDTKAYS GGYNLPIGQA DEMQRYVEEN QTRNKHINPN EWWKVYPSSV  900
TEFKFLFVSG HFKGNYKAQL TRLNHITNCN GAVLSVEELL IGGEMIKAGT LTLEEVRRKF  960
NNGEINFRS                                                          969

SEQ ID NO: 359          moltype = DNA  length = 17
FEATURE                 Location/Qualifiers
source                  1..17
                        mol_type = other DNA
                        organism = Homo sapiens
SEQUENCE: 359
tgcctcaccc tcatcta                                                         17

SEQ ID NO: 360          moltype = AA   length = 969
FEATURE                 Location/Qualifiers
source                  1..969
                        mol_type = protein
                        organism = Homo sapiens
SEQUENCE: 360
MDYKDHDGDY KDHDIDYKDD DDKMAPKKKR KVGIHGVPAA VDLRTLGYSQ QQQEKIKPKV   60
RSTVAQHHEA LVGHGFTHAH IVALSQHPAA LGTVAVKYQD MIAALPEATH EAIVGVGKQW  120
SGARALEALL TVAGELRGPP LQLDTGQLLK IAKRGGVTAV EAVHAWRNAL TGAPLNLTPE  180
QVVAIASNIG GKQALETVQR LLPVLCQAHG LTPEQVVAIA SNNGGKQALE TVQRLLPVLC  240
QAHGLTPEQV VAIASNIGGK QALETVQRLL PVLCQAHGLT PEQVVAIASN GGGKQALETV  300
QRLLPVLCQA HGLTPEQVVA IASNNGGKQA LETVQRLLPV LCQAHGLTPE QVVAIASNIG  360
GKQALETVQR LLPVLCQAHG LTPEQVVAIA SNNGGKQALE TVQRLLPVLC QAHGLTPEQV  420
VAIASNNGGK QALETVQRLL PVLCQAHGLT PEQVVAIASN NGGKQALETV QRLLPVLCQA  480
HGLTPEQVVA IASNGGGKQA LETVQRLLPV LCQAHGLTPE QVVAIASNNG GKQALETVQR  540
LLPVLCQAHG LTPEQVVAIA SNIGGKQALE TVQRLLPVLC QAHGLTPEQV VAIASNNGGK  600
QALETVQRLL PVLCQAHGLT PEQVVAIASN NGGKQALETV QRLLPVLCQA HGLTPEQVVA  660
IASHDGGKQA LETVQRLLPV LCQAHGLTPE QVVAIASNIG GRPALESIVA QLSRPDPALA  720
ALTNDHLVAL ACLGGRPALD AVKKGLPHAP ALIKRTNRRI PERTSHRVAG SQLVKSELEE  780
KKSELRHKLK YVPHEYIELI EIARNSTQDR ILEMKVMEFF MKVYGYRGKH LGGSRKPDGA  840
IYTVGSPIDY GVIVDTKAYS GGYNLPIGQA DEMQRYVEEN QTRNKHINPN EWWKVYPSSV  900
TEFKFLFVSG HFKGNYKAQL TRLNHITNCN GAVLSVEELL IGGEMIKAGT LTLEEVRRKF  960
NNGEINFRS                                                          969

SEQ ID NO: 361          moltype = DNA  length = 49
FEATURE                 Location/Qualifiers
source                  1..49
                        mol_type = other DNA
                        organism = Homo sapiens
SEQUENCE: 361
ttgactctat tgtctggacc ttcaacacaa ccctcttgt caccataca                       49

SEQ ID NO: 362          moltype = DNA  length = 17
FEATURE                 Location/Qualifiers
source                  1..17
                        mol_type = other DNA
                        organism = Homo sapiens
SEQUENCE: 362
ttgactctat tgtctgg                                                         17

SEQ ID NO: 363          moltype = AA   length = 969
FEATURE                 Location/Qualifiers
source                  1..969
                        mol_type = protein
```

-continued

```
                         organism = Homo sapiens
SEQUENCE: 363
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASNGG GKQALETVQR LLPVLCQAHG LTPEQVVAIA SNGGKQALE  TVQRLLPVLC   240
QAHGLTPEQV VAIASNIGGK QALETVQRLL PVLCQAHGLT PEQVVAIASH DGGKQALETV   300
QRLLPVLCQA HGLTPEQVVA IASNGGGKQA LETVQRLLPV LCQAHGLTPE QVVAIASHDG   360
GKQALETVQR LLPVLCQAHG LTPEQVVAIA SNGGKQALE  TVQRLLPVLC QAHGLTPEQV   420
VAIASNIGGK QALETVQRLL PVLCQAHGLT PEQVVAIASN GGKQALETV  QRLLPVLCQA   480
HGLTPEQVVA IASNGGGKQA LETVQRLLPV LCQAHGLTPE QVVAIASNNG GKQALETVQR   540
LLPVLCQAHG LTPEQVVAIA SNGGGKQALE TVQRLLPVLC QAHGLTPEQV VAIASHDGGK   600
QALETVQRLL PVLCQAHGLT PEQVVAIASN GGGKQALETV QRLLPVLCQA HGLTPEQVVA   660
IASNNGGKQA LETVQRLLPV LCQAHGLTPE QVVAIASNNG GRPALESIVA QLSRPDPALA   720
ALTNDHLVAL ACLGGRPALD AVKKGLPHAP ALIKRTNRRI PERTSHRVAG SQLVKSELEE   780
KKSELRHKLK YVPHEYIELI EIARNSTQDR ILEMKVMEFF MKVYGYRGKH LGGSRKPDGA   840
IYTVGSPIDY GVIVDTKAYS GGYNLPIGQA DEMQRYVEEN QTRNKHINPN EWWKVYPSSV   900
TEFKFLFVSG HFKGNYKAQL TRLNHITNCN GAVLSVEELL IGGEMIKAGT LTLEEVRRKF   960
NNGEINFRS                                                          969

SEQ ID NO: 364        moltype = DNA  length = 17
FEATURE               Location/Qualifiers
source                1..17
                      mol_type = other DNA
                      organism = Homo sapiens
SEQUENCE: 364
cctcttgtca ccataca                                                  17

SEQ ID NO: 365        moltype = AA  length = 969
FEATURE               Location/Qualifiers
source                1..969
                      mol_type = protein
                      organism = Homo sapiens
SEQUENCE: 365
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASNNG GKQALETVQR LLPVLCQAHG LTPEQVVAIA SNGGGKQALE TVQRLLPVLC   240
QAHGLTPEQV VAIASNIGGK QALETVQRLL PVLCQAHGLT PEQVVAIASN GGGKQALETV   300
QRLLPVLCQA HGLTPEQVVA IASNNGGKQA LETVQRLLPV LCQAHGLTPE QVVAIASNNG   360
GKQALETVQR LLPVLCQAHG LTPEQVVAIA SNGGGKQALE TVQRLLPVLC QAHGLTPEQV   420
VAIASNNGGK QALETVQRLL PVLCQAHGLT PEQVVAIASN IGGKQALETV QRLLPVLCQA   480
HGLTPEQVVA IASHDGGKQA LETVQRLLPV LCQAHGLTPE QVVAIASNIG GKQALETVQR   540
LLPVLCQAHG LTPEQVVAIA SNIGGKQALE TVQRLLPVLC QAHGLTPEQV VAIASNNGGK   600
QALETVQRLL PVLCQAHGLT PEQVVAIASN IGGKQALETV QRLLPVLCQA HGLTPEQVVA   660
IASNNGGKQA LETVQRLLPV LCQAHGLTPE QVVAIASNNG GRPALESIVA QLSRPDPALA   720
ALTNDHLVAL ACLGGRPALD AVKKGLPHAP ALIKRTNRRI PERTSHRVAG SQLVKSELEE   780
KKSELRHKLK YVPHEYIELI EIARNSTQDR ILEMKVMEFF MKVYGYRGKH LGGSRKPDGA   840
IYTVGSPIDY GVIVDTKAYS GGYNLPIGQA DEMQRYVEEN QTRNKHINPN EWWKVYPSSV   900
TEFKFLFVSG HFKGNYKAQL TRLNHITNCN GAVLSVEELL IGGEMIKAGT LTLEEVRRKF   960
NNGEINFRS                                                          969

SEQ ID NO: 366        moltype = DNA  length = 49
FEATURE               Location/Qualifiers
source                1..49
                      mol_type = other DNA
                      organism = Homo sapiens
SEQUENCE: 366
ttccctccca ggcagctcac agtgtgccac catggagttg ggcccccta               49

SEQ ID NO: 367        moltype = DNA  length = 18
FEATURE               Location/Qualifiers
source                1..18
                      mol_type = other DNA
                      organism = Homo sapiens
SEQUENCE: 367
ttccctccca ggcagctc                                                 18

SEQ ID NO: 368        moltype = AA  length = 1003
FEATURE               Location/Qualifiers
source                1..1003
                      mol_type = protein
                      organism = Homo sapiens
SEQUENCE: 368
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASNGG GKQALETVQR LLPVLCQAHG LTPEQVVAIA SHDGGKQALE TVQRLLPVLC   240
QAHGLTPEQV VAIASHDGGK QALETVQRLL PVLCQAHGLT PEQVVAIASH DGGKQALETV   300
```

```
QRLLPVLCQA HGLTPEQVVA IASNGGGKQA LETVQRLLPV LCQAHGLTPE QVVAIASHDG    360
GKQALETVQR LLPVLCQAHG LTPEQVVAIA SHDGGKQALE TVQRLLPVLC QAHGLTPEQV    420
VAIASHDGGK QALETVQRLL PVLCQAHGLT PEQVVAIASN IGGKQALETV QRLLPVLCQA    480
HGLTPEQVVA IASNNGGKQA LETVQRLLPV LCQAHGLTPE QVVAIASNNG GKQALETVQR    540
LLPVLCQAHG LTPEQVVAIA SHDGGKQALE TVQRLLPVLC QAHGLTPEQV VAIASNIGGK    600
QALETVQRLL PVLCQAHGLT PEQVVAIASN NGGKQALETV QRLLPVLCQA HGLTPEQVVA    660
IASHDGGKQA LETVQRLLPV LCQAHGLTPE QVVAIASNGG KQALETVQR LLPVLCQAHG     720
LTPEQVVAIA SHDGGRPALE SIVAQLSRPD PALAALTNDH LVALACLGGR PALDAVKKGL    780
PHAPALIKRT NRRIPERTSH RVAGSQLVKS ELEEKKSELR HKLKYVPHEY IELIEIARNS    840
TQDRILEMKV MEFFMKVYGY RGKHLGSRK PDGAIYTVGS PIDYGVIVDT KAYSGGYNLP     900
IGQADEMQRY VEENQTRNKH INPNEWWKVY PSSVTEFKFL FVSGHFKGNY KAQLTRLNHI    960
TNCNGAVLSV EELLIGGEMI KAGTLTLEEV RRKFNNGEIN FRS                     1003

SEQ ID NO: 369          moltype = DNA  length = 17
FEATURE                 Location/Qualifiers
source                  1..17
                        mol_type = other DNA
                        organism = Homo sapiens
SEQUENCE: 369
tggagttggg gcccta                                                    17

SEQ ID NO: 370          moltype = AA  length = 969
FEATURE                 Location/Qualifiers
source                  1..969
                        mol_type = protein
                        organism = Homo sapiens
SEQUENCE: 370
MDYKDHDGDY KDHDIDYKDD DDKMAPKKKR KVGIHGVPAA VDLRTLGYSQ QQQEKIKPKV     60
RSTVAQHHEA LVGHGFTHAH IVALSQHPAA LGTVAVKYQD MIAALPEATH EAIVGVGKQW    120
SGARALEALL TVAGELRGPP LQLDTGQLLK IAKRGGVTAV EAVHAWRNAL TGAPLNLTPE    180
QVVAIASNIG GKQALETVQR LLPVLCQAHG LTPEQVVAIA SNNGGKQALE TVQRLLPVLC    240
QAHGLTPEQV VAIASNNGGK QALETVQRLL PVLCQAHGLT PEQVVAIASN NGGKQALETV    300
QRLLPVLCQA HGLTPEQVVA IASNNGGKQA LETVQRLLPV LCQAHGLTPE QVVAIASHDG    360
GKQALETVQR LLPVLCQAHG LTPEQVVAIA SHDGGKQALE TVQRLLPVLC QAHGLTPEQV    420
VAIASHDGGK QALETVQRLL PVLCQAHGLT PEQVVAIASH DGGKQALETV QRLLPVLCQA    480
HGLTPEQVVA IASNIGGKQA LETVQRLLPV LCQAHGLTPE QVVAIASNIG GKQALETVQR    540
LLPVLCQAHG LTPEQVVAIA SHDGGKQALE TVQRLLPVLC QAHGLTPEQV VAIASNGGGK    600
QALETVQRLL PVLCQAHGLT PEQVVAIASH DGGKQALETV QRLLPVLCQA HGLTPEQVVA    660
IASHDGGKQA LETVQRLLPV LCQAHGLTPE QVVAIASNIG GRPALESIVA QLSRPDPALA    720
ALTNDHLVAL ACLGGRPALD AVKKGLPHAP ALIKRTNRRI PERTSHRVAG SQLVKSELEE    780
KKSELRHKLK YVPHEYIELI EIARNSTQDR ILEMKVMEFF MKVYGYRGKH LGGSRKPDGA    840
IYTVGSPIDY GVIVDTKAYS GGYNLPIGQA DEMQRYVEEN QTRNKHINPN EWWKVYPSSV    900
TEFKFLFVSG HFKGNYKAQL TRLNHITNCN GAVLSVEELL IGGEMIKAGT LTLEEVRRKF    960
NNGEINFRS                                                           969

SEQ ID NO: 371          moltype = DNA  length = 49
FEATURE                 Location/Qualifiers
source                  1..49
                        mol_type = other DNA
                        organism = Homo sapiens
SEQUENCE: 371
ttcctcctac tcaccatcag cctcctggtt atggtacagg taagagcaa                49

SEQ ID NO: 372          moltype = DNA  length = 17
FEATURE                 Location/Qualifiers
source                  1..17
                        mol_type = other DNA
                        organism = Homo sapiens
SEQUENCE: 372
ttcctcctac tcaccat                                                   17

SEQ ID NO: 373          moltype = AA  length = 969
FEATURE                 Location/Qualifiers
source                  1..969
                        mol_type = protein
                        organism = Homo sapiens
SEQUENCE: 373
MDYKDHDGDY KDHDIDYKDD DDKMAPKKKR KVGIHGVPAA VDLRTLGYSQ QQQEKIKPKV     60
RSTVAQHHEA LVGHGFTHAH IVALSQHPAA LGTVAVKYQD MIAALPEATH EAIVGVGKQW    120
SGARALEALL TVAGELRGPP LQLDTGQLLK IAKRGGVTAV EAVHAWRNAL TGAPLNLTPE    180
QVVAIASNGG KQALETVQR LLPVLCQAHG LTPEQVVAIA SHDGGKQALE TVQRLLPVLC     240
QAHGLTPEQV VAIASHDGGK QALETVQRLL PVLCQAHGLT PEQVVAIASN GGKQALETV     300
QRLLPVLCQA HGLTPEQVVA IASHDGGKQA LETVQRLLPV LCQAHGLTPE QVVAIASNGG    360
GKQALETVQR LLPVLCQAHG LTPEQVVAIA SNGGKQALE TVQRLLPVLC QAHGLTPEQV     420
VAIASNIGGK QALETVQRLL PVLCQAHGLT PEQVVAIASH DGGKQALETV QRLLPVLCQA    480
HGLTPEQVVA IASNGGGKQA LETVQRLLPV LCQAHGLTPE QVVAIASHDG GKQALETVQR    540
LLPVLCQAHG LTPEQVVAIA SNIGGKQALE TVQRLLPVLC QAHGLTPEQV VAIASHDGGK    600
QALETVQRLL PVLCQAHGLT PEQVVAIASH DGGKQALETV QRLLPVLCQA HGLTPEQVVA    660
IASNIGGKQA LETVQRLLPV LCQAHGLTPE QVVAIASNGG GRPALESIVA QLSRPDPALA    720
```

```
ALTNDHLVAL ACLGGRPALD AVKKGLPHAP ALIKRTNRRI PERTSHRVAG SQLVKSELEE    780
KKSELRHKLK YVPHEYIELI EIARNSTQDR ILEMKVMEFF MKVYGYRGKH LGGSRKPDGA    840
IYTVGSPIDY GVIVDTKAYS GGYNLPIGQA DEMQRYVEEN QTRNKHINPN EWWKVYPSSV    900
TEFKFLFVSG HFKGNYKAQL TRLNHITNCN GAVLSVEELL IGGEMIKAGT LTLEEVRRKF    960
NNGEINFRS                                                           969

SEQ ID NO: 374            moltype = DNA   length = 17
FEATURE                   Location/Qualifiers
source                    1..17
                          mol_type = other DNA
                          organism = Homo sapiens
SEQUENCE: 374
ggtacaggta agagcaa                                                  17

SEQ ID NO: 375            moltype = AA   length = 969
FEATURE                   Location/Qualifiers
source                    1..969
                          mol_type = protein
                          organism = Homo sapiens
SEQUENCE: 375
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW    120
SGARALEALL TVAGELRGPP LQLDTGQLLK IAKRGGVTAV EAVHAWRNAL TGAPLNLTPE    180
QVVAIASNGG GKQALETVQR LLPVLCQAHG LTPEQVVAIA SNNGGKQALE TVQRLLPVLC    240
QAHGLTPEQV VAIASHDGGK QALETVQRLL PVLCQAHGLT PEQVVAIASN GGGKQALETV    300
QRLLPVLCQA HGLTPEQVVA IASHDGGKQA LETVQRLLPV LCQAHGLTPE QVVAIASNGG    360
GKQALETVQR LLPVLCQAHG LTPEQVVAIA SNGGGKQALE TVQRLLPVLC QAHGLTPEQV    420
VAIASNIGGK QALETVQRLL PVLCQAHGLT PEQVVAIASH DGGKQALETV QRLLPVLCQA    480
HGLTPEQVVA IASHDGGKQA LETVQRLLPV LCQAHGLTPE QVVAIASNGG GKQALETVQR    540
LLPVLCQAHG LTPEQVVAIA SNNGGKQALE TVQRLLPVLC QAHGLTPEQV VAIASNGGGK    600
QALETVQRLL PVLCQAHGLT PEQVVAIASN IGGKQALETV QRLLPVLCQA HGLTPEQVVA    660
IASHDGGKQA LETVQRLLPV LCQAHGLTPE QVVAIASHDG GRPALESIVA QLSRPDPALA    720
ALTNDHLVAL ACLGGRPALD AVKKGLPHAP ALIKRTNRRI PERTSHRVAG SQLVKSELEE    780
KKSELRHKLK YVPHEYIELI EIARNSTQDR ILEMKVMEFF MKVYGYRGKH LGGSRKPDGA    840
IYTVGSPIDY GVIVDTKAYS GGYNLPIGQA DEMQRYVEEN QTRNKHINPN EWWKVYPSSV    900
TEFKFLFVSG HFKGNYKAQL TRLNHITNCN GAVLSVEELL IGGEMIKAGT LTLEEVRRKF    960
NNGEINFRS                                                           969

SEQ ID NO: 376            moltype = DNA   length = 49
FEATURE                   Location/Qualifiers
source                    1..49
                          mol_type = other DNA
                          organism = Homo sapiens
SEQUENCE: 376
ttgtcccaca gatatccaga accctgaccc tgccgtgtac cagctgaga               49

SEQ ID NO: 377            moltype = DNA   length = 17
FEATURE                   Location/Qualifiers
source                    1..17
                          mol_type = other DNA
                          organism = Homo sapiens
SEQUENCE: 377
ttgtcccaca gatatcc                                                  17

SEQ ID NO: 378            moltype = AA   length = 969
FEATURE                   Location/Qualifiers
source                    1..969
                          mol_type = protein
                          organism = Homo sapiens
SEQUENCE: 378
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW    120
SGARALEALL TVAGELRGPP LQLDTGQLLK IAKRGGVTAV EAVHAWRNAL TGAPLNLTPE    180
QVVAIASNGG GKQALETVQR LLPVLCQAHG LTPEQVVAIA SNNGGKQALE TVQRLLPVLC    240
QAHGLTPEQV VAIASNGGGK QALETVQRLL PVLCQAHGLT PEQVVAIASH DGKQALETV     300
QRLLPVLCQA HGLTPEQVVA IASHDGGKQA LETVQRLLPV LCQAHGLTPE QVVAIASHDG    360
GKQALETVQR LLPVLCQAHG LTPEQVVAIA SNIGGKQALE TVQRLLPVLC QAHGLTPEQV    420
VAIASHDGGK QALETVQRLL PVLCQAHGLT PEQVVAIASN GGKQALETV QRLLPVLCQA     480
HGLTPEQVVA IASNNGGKQA LETVQRLLPV LCQAHGLTPE QVVAIASNIG KQALETVQR     540
LLPVLCQAHG LTPEQVVAIA SNGGGKQALE TVQRLLPVLC QAHGLTPEQV VAIASNIGGK    600
QALETVQRLL PVLCQAHGLT PEQVVAIASN GGGKQALETV QRLLPVLCQA HGLTPEQVVA    660
IASHDGGKQA LETVQRLLPV LCQAHGLTPE QVVAIASHDG GRPALESIVA QLSRPDPALA    720
ALTNDHLVAL ACLGGRPALD AVKKGLPHAP ALIKRTNRRI PERTSHRVAG SQLVKSELEE    780
KKSELRHKLK YVPHEYIELI EIARNSTQDR ILEMKVMEFF MKVYGYRGKH LGGSRKPDGA    840
IYTVGSPIDY GVIVDTKAYS GGYNLPIGQA DEMQRYVEEN QTRNKHINPN EWWKVYPSSV    900
TEFKFLFVSG HFKGNYKAQL TRLNHITNCN GAVLSVEELL IGGEMIKAGT LTLEEVRRKF    960
NNGEINFRS                                                           969

SEQ ID NO: 379            moltype = DNA   length = 17
```

```
FEATURE              Location/Qualifiers
source               1..17
                     mol_type = other DNA
                     organism = Homo sapiens
SEQUENCE: 379
ccgtgtacca gctgaga                                                      17

SEQ ID NO: 380       moltype = AA   length = 969
FEATURE              Location/Qualifiers
source               1..969
                     mol_type = protein
                     organism = Homo sapiens
SEQUENCE: 380
MDYKDHDGDY KDHDIDYKDD DDKMAPKKKR KVGIHGVPAA VDLRTLGYSQ QQQEKIKPKV    60
RSTVAQHHEA LVGHGFTHAH IVALSQHPAA LGTVAVKYQD MIAALPEATH EAIVGVGKQW   120
SGARALEALL TVAGELRGPP LQLDTGQLLK IAKRGGVTAV EAVHAWRNAL TGAPLNLTPE   180
QVVAIASHDG GKQALETVQR LLPVLCQAHG LTPEQVVAIA SNGGGKQALE TVQRLLPVLC   240
QAHGLTPEQV VAIASHDGGK QALETVQRLL PVLCQAHGLT PEQVVAIASN IGGKQALETV   300
QRLLPVLCQA HGLTPEQVVA IASNNGGKQA LETVQRLLPV LCQAHGLTPE QVVAIASHDG   360
GKQALETVQR LLPVLCQAHG LTPEQVVAIA SNGGGKQALE TVQRLLPVLC QAHGLTPEQV   420
VAIASNNGGK QALETVQRLL PVLCQAHGLT PEQVVAIASN NGGKQALETV QRLLPVLCQA   480
HGLTPEQVVA IASNGGGKQA LETVQRLLPV LCQAHGLTPE QVVAIASNIG GKQALETVQR   540
LLPVLCQAHG LTPEQVVAIA SHDGGKQALE TVQRLLPVLC QAHGLTPEQV VAIASNIGGK   600
QALETVQRLL PVLCQAHGLT PEQVVAIASH DGGKQALETV QRLLPVLCQA HGLTPEQVVA   660
IASNNGGKQA LETVQRLLPV LCQAHGLTPE QVVAIASNNG GRPALESIVA QLSRPDPALA   720
ALTNDHLVAL ACLGGRPALD AVKKGLPHAP ALIKRTNRRI PERTSHRVAG SQLVKSELEE   780
KKSELRHKLK YVPHEYIELI EIARNSTQDR ILEMKVMEFF MKVYGYRGKH LGGSRKPDGA   840
IYTVGSPIDY GVIVDTKAYS GGYNLPIGQA DEMQRYVEEN QTRNKHINPN EWWKVYPSSV   900
TEFKFLFVSG HFKGNYKAQL TRLNHITNCN GAVLSVEELL IGGEMIKAGT LTLEEVRRKF   960
NNGEINFRS                                                           969

SEQ ID NO: 381       moltype = DNA  length = 49
FEATURE              Location/Qualifiers
source               1..49
                     mol_type = other DNA
                     organism = Homo sapiens
SEQUENCE: 381
ttctccccag ccctgctcgt ggtgaccgaa ggggacaacg ccaccttca                   49

SEQ ID NO: 382       moltype = AA   length = 936
FEATURE              Location/Qualifiers
source               1..936
                     mol_type = protein
                     organism = Homo sapiens
SEQUENCE: 382
MGDPKKKRKV IDYPYDVPDY AIDIADLRTL GYSQQQQEKI KPKVRSTVAQ HHEALVGHGF    60
THAHIVALSQ HPAALGTVAV KYQDMIAALP EATHEAIVGV GKQWSGARAL EALLTVAGEL   120
RGPPLQLDTG QLLKIAKRGG VTAVEAVHAW RNALTGAPLN LTPQQVVAIA SNGGGKQALE   180
TVQRLLPVLC QAHGLTPEQV VAIASHDGGK QALETVQRLL PVLCQAHGLT PQQVVAIASN   240
GGGKQALETV QRLLPVLCQA HGLTPEQVVA IASHDGGKQA LETVQRLLPV LCQAHGLTPE   300
QVVAIASHDG GKQALETVQR LLPVLCQAHG LTPEQVVAIA SHDGGKQALE TVQRLLPVLC   360
QAHGLTPEQV VAIASHDGGK QALETVQRLL PVLCQAHGLT PEQVVAIASN IGGKQALETV   420
QALLPVLCQA HGLTPQQVVA IASNNGGKQA LETVQRLLPV LCQAHGLTPE QVVAIASHDG   480
GKQALETVQR LLPVLCQAHG LTPEQVVAIA SHDGGKQALE TVQRLLPVLC QAHGLTPEQV   540
VAIASHDGGK QALETVQRLL PVLCQAHGLT PQQVVAIASN GGGKQALETV QRLLPVLCQA   600
HGLTPQQVVA IASNNGGKQA LETVQRLLPV LCQAHGLTPE QVVAIASHDG GKQALETVQR   660
LLPVLCQAHG LTPQQVVAIA SNGGGRPALE SIVAQLSRPD PALAALTNDH LVALACLGGR   720
PALDAVKKGL GDPISRSQLV KSELEEKKSE LRHKLKYVPH EYIELIEIAR NSTQDRILEM   780
KVMEFFMKVY GYRGKHLGGS RKPDGAIYTV GSPIDYGVIV DTKAYSGGYN LPIGQADEMQ   840
RYVEENQTRN KHINPNEWWK VYPSSVTEFK FLFVSGHFKG NYKAQLTRLN HITNCNGAVL   900
SVEELLIGGE MIKAGTLTLE EVRRKFNNGE INFAAD                             936

SEQ ID NO: 383       moltype = AA   length = 941
FEATURE              Location/Qualifiers
source               1..941
                     mol_type = protein
                     organism = Homo sapiens
SEQUENCE: 383
MGDPKKKRKV IDKETAAAKF ERQHMDSIDI ADLRTLGYSQ QQQEKIKPKV RSTVAQHHEA    60
LVGHGFTHAH IVALSQHPAA LGTVAVKYQD MIAALPEATH EAIVGVGKQW SGARALEALL   120
TVAGELRGPP LQLDTGQLLK IAKRGGVTAV EAVHAWRNAL TGAPLNLTPE QVVAIASHDG   180
GKQALETVQR LLPVLCQAHG LTPQQVVAIA SNGGGKQALE TVQRLLPVLC QAHGLTPEQV   240
VAIASHDGGK QALETVQRLL PVLCQAHGLT PQQVVAIASN GGGKQALETV QRLLPVLCQA   300
HGLTPQQVVA IASNGGGKQA LETVQRLLPV LCQAHGLTPQ QVVAIASNGG GKQALETVQR   360
LLPVLCQAHG LTPQQVVAIA SNGGGKQALE TVQRLLPVLC QAHGLTPEQV VAIASNIGGK   420
QALETVQALL PVLCQAHGLT PQQVVAIASN GGGKQALETV QRLLPVLCQA HGLTPEQVVA   480
IASHDGKQA LETVQRLLPV LCQAHGLTPQ QVVAIASNGG GKQALETVQR LLPVLCQAHG   540
LTPQQVVAIA SNGGGKQALE TVQRLLPVLC QAHGLTPEQV VAIASNGGKQ ALETVQRLLP   600
VLCQAHGLTP QQVVAIASNN GGKQALETVQ RLLPVLCQAH GLTPEQVVAI ASHDGGKQAL   660
```

| | | |
|---|---|---|
| ETVQRLLPVL | CQAHGLTPQQ VVAIASNGGG RPALESIVAQ LSRPDPALAA LTNDHLVALA | 720 |
| CLGGRPALDA | VKKGLGDPIS RSQLVKSELE EKKSELRHKL KYVPHEYIEL IEIARNSTQD | 780 |
| RILEMKVMEF | FMKVYGYRGK HLGGSRKPDG AIYTVGSPID YGVIVDTKAY SGGYNLPIGQ | 840 |
| ADEMQRYVEE | NQTRNKHINP NEWWKVYPSS VTEFKFLFVS GHFKGNYKAQ LTRLNHITNC | 900 |
| NGAVLSVEEL | LIGGEMIKAG TLTLEEVRRK FNNGEINFAA D | 941 |

```
SEQ ID NO: 384          moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 384
gagaatcaaa atcggtgaat gttttagagc tagaaatagc aagttaaaat aaggctagtc   60
cgttatcaac ttgaaaaagt ggcaccgagt cggtgctttt                        100

SEQ ID NO: 385          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 385
agcgctctcg tacagagttg g                                             21

SEQ ID NO: 386          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 386
aaaaaaagca ccgactcggt gcc                                           23

SEQ ID NO: 387          moltype = RNA   length = 100
FEATURE                 Location/Qualifiers
misc_feature            1..100
                        note = Synthetic
misc_feature            1
                        note = 2'OMe
misc_feature            1..2
                        note = phosphorothioate
misc_feature            2..3
                        note = phosphorothioate
misc_feature            3..4
                        note = phosphorothioate
misc_feature            96
                        note = 2'OMe
misc_feature            97..98
                        note = phosphorothioate
misc_feature            98..99
                        note = phosphorothioate
misc_feature            99..100
                        note = phosphorothioate
source                  1..100
                        mol_type = other RNA
                        organism = synthetic construct
SEQUENCE: 387
gagaatcaaa atcggtgaat gttttagagc tagaaatagc aagttaaaat aaggctagtc   60
cgttatcaac ttgaaaaagt ggcaccgagt cggtgctttt                        100

SEQ ID NO: 388          moltype = AA    length = 20
FEATURE                 Location/Qualifiers
REGION                  1..20
                        note = Synthetic
source                  1..20
                        mol_type = protein
                        organism = synthetic construct
SEQUENCE: 388
MDPKGLLSLT FVLFLSLAFG                                               20

SEQ ID NO: 389          moltype = AA    length = 495
FEATURE                 Location/Qualifiers
REGION                  1..495
                        note = Synthetic
source                  1..495
```

```
                        mol_type = protein
                        organism = synthetic construct
SEQUENCE: 389
METDTLLLWV LLLWVPGSTG EVQLQQSGPE LIKPGASVKM SCKASGYTFT SYVMHWVKQK    60
PGQGLEWIGY INPYNDGTKY NEKFKGKATL TSDKSSSTAY MELSSLTSED SAVYYCARGT   120
YYYGSRVFDY WGQGTTLTVS SGGGGSGGGG SGGGGSDIVM TQAAPSIPVT PGESVSISCR   180
SSKSLLNSNG NTYLYWFLQR PGQSPQLLIY RMSNLASGVP DRFSGSGSGT AFTLRISRVE   240
AEDVGVYYCM QHLEYPFTFG AGTKLELKRS DPTTTPAPRP PTPAPTIASQ PLSLRPEACR   300
PAAGGAVHTR GLDFACDIYI WAPLAGTCGV LLLSLVITLY CKRGRKKLLY IFKQPFMRPV   360
QTTQEEDGCS CRFPEEEEGG CELRVKFSRS ADAPAYQQGQ NQLYNELNLG RREEYDVLDK   420
RRGRDPEMGG KPRRKNPQEG LYNELQKDKM AEAYSEIGMK GERRRGKGHD GLYQGLSTAT   480
KDTYDALHMQ ALPPR                                                   495

SEQ ID NO: 390          moltype = DNA  length = 1485
FEATURE                 Location/Qualifiers
misc_feature            1..1485
                        note = Synthetic
source                  1..1485
                        mol_type = other DNA
                        organism = synthetic construct
SEQUENCE: 390
atggagacag acactcttct cctttgggtc ttgctgctgt gggttcccgg aagcacagga    60
gaagtacagt tgcaacagtc tgggccagaa ctcatcaaac ccggagcttc tgtaaaaatg   120
tcatgcaaag ctagtggata cattttact tcttacgtga tgcactgggt aaaacagaaa    180
cctggtcagg ggcttgagtg gatcgggtac attaacccat ataatgacgg caccaaatat   240
aacgagaaat tcaagggaaa ggctacgctt acatcagata gtccagtga caccgcttat   300
atggaactta gcagccttac ttccgaagat tccgcggtgt attactgcgc gagagggact   360
tactactacg ggagtcgagt attcgattat tggggtcaag gcacgacgct cacggtgagc   420
tcaggtggtg gagggtctgg gggtggcggc agtggtgggg gggctcaga catcgtgatg   480
acccagcag caccttctat cccggtaacc ccaggcgagt ctgtatctat cagttgtcgg   540
tccagcaagt ctcttctcaa cagtaatggc aatacatatc tttactggtt cctccaaagg   600
cctgggcaaa gtcctcaact tctttatatt cggatgtcca atcttgcgag tggcgtaccc   660
gacaggtttt cagggtctgg gagcggaaca gcttttacgt tgagaatatc cagggtagaa   720
gctgaggacg tcggtgtata ttattgcatg caacatctcg aatacccctt taccttcggc   780
gctggtacaa agtctcgaatt gaaacgcagc gatccaacca cgacgccagc gccacgacca   840
cctacgcccg ctccaactat tgcctcccag cccctgagtc ttcggccaga agcgtgtaga   900
cctgctgccg gcggggccgt tcatacgcgg ggccttgact ttgcatgtga tatctatata   960
tgggctcctt tggcgggaac ttgcggagtg cttctttgt cactcgtgat aacgttgtat  1020
tgtaaaaggg gtcgaaagaa actcctctat atatttaagc agccctttat gaggcccgtg  1080
caaacaacac aagaagagga cggatgctct tgtcgattcc cggaagagga ggagggggg  1140
tgtgagctta gggtcaagtt ttctcgctct gccgacgcgc cagcctatca acagggccaa  1200
aaccagctgt ataacgaact caacctcggg cgccggaag agtatgacgt ccttgacaaa  1260
cggcgggtc gcgaccctga aatgggtgga aaaccgaggc gaaagaaccc ccaggaggga  1320
ctttacaacg aattgcaaaa agacaagatg gccgaagcct attccgaaat tggaatgaaa  1380
ggcgagcgga gacgaggtaa ggggcatgac ggcctgtatc aagggctctc tacggccacg  1440
aaggatactt acgacgccct tcatatgcaa gctcttccac cacgg                 1485

SEQ ID NO: 391          moltype = AA  length = 374
FEATURE                 Location/Qualifiers
source                  1..374
                        mol_type = protein
                        organism = Homo sapiens
SEQUENCE: 391
MSGESMNFSD VFDSSEDYFV SVNTSYYSVD SEMLLCSLQE VRQFSRLFVP IAYSLICVFG    60
LLGNILVVIT FAFYKKARSM TDVYLLNMAI ADILFVLTLP FWAVSHATGA WVFSNATCKL   120
LKGIYAINFN CGMLLLTCIS MDRYIAIVQA TKSFRLRSRT LPRSKIICLV VWGLSVIISS   180
STFVFNQKYN TQGSDVCEPK YQTVSEPIRW KLLMLGLELL FGFFIPLMFM IPCYTFIVKT   240
LVQAQNSKRH KAIRVIIAVV LVFLACQIPH NMVLLVTAAN LGKMNRSCQS EKLIGYTKTV   300
TEVLAFLHCC LNPVLYAFIG QKFRNYFLKI LKDLWCVRRK YKSSGFSCAG RYSENISRQT   360
SETADNDNAS SFTM                                                    374

SEQ ID NO: 392          moltype = DNA  length = 1122
FEATURE                 Location/Qualifiers
misc_feature            1..1122
                        note = Synthetic
source                  1..1122
                        mol_type = other DNA
                        organism = synthetic construct
SEQUENCE: 392
atgagtgggg aaagtatgaa cttcagcgat gtatttgact cctccgaaga ttactttgta    60
tctgtgaata cgagctatta ctccgtcgat agtgaaatgc tgctctctag tctccaagaa   120
gtccgccaat tcagtcgcct cttcgttccc atcgcgtact cccttatttg tgtttttggc   180
cttctgggta acatcctggt tgtaatcaca ttcgcttttt ataaaaaagc tcggagtatg   240
actgatgttt accttcttaa catggctata gcggacattc tttttgtgct tactctccca   300
ttctgggctg tgagccatgc aacaggggcg tgggtttttt caaatgccac atgtaagctg   360
cttaaaggga tctatgcaat aaacttcaat tgcgggatgc tcctgctgac atgcatcagt   420
atggatcgat acatagctat agtacaggcg actaagtcct tccgcctgcg atcccgcaca   480
ctgcctagga gcaaaattat ttgcctcgtc gtatggggc tctcagtgat catctcctcc   540
agtacgtttg tctttaacca gaaatataac acacagggt ctgatgtatg tgaaccaaag   600
```

```
tatcagacag tgagtgaacc aatacggtgg aagttgctta tgttgggctt ggagctgctt    660
tttgggtttt tcatcccact gatgttcatg attttctgtt atacatttat tgttaagacc    720
ttggttcagg cgcaaaatag caagagacat aaggcaattc gagtcatcat tgccgtggtg    780
ttggtcttct tggcctgtca gatccccat aatatggttc tgctcgtcac cgccgctaac     840
ttgggtaaga tgaatcgatc ttgtcagtcc gagaagttga tggatacac caaaactgtg    900
acagaagtgc tggccttcct tcactgttgt ctgaacccag ttttgtatgc ttttatagga    960
cagaagtttc gaaattactt cttgaaaatc tcaaggacc tctggtgtgt tcgaaggaag    1020
tacaagagct ctggctttag ttgcgctggg cgctacagtg agaatatatc ccggcagacc    1080
tccgagactg ctgataatga caacgcaagt tccttcacta tg                       1122

SEQ ID NO: 393          moltype = DNA  length = 1122
FEATURE                 Location/Qualifiers
source                  1..1122
                        mol_type = other DNA
                        organism = Homo sapiens
SEQUENCE: 393
atgagcgggg aatcaatgaa tttcagcgat gttttcgact ccagtgaaga ttattttgtg    60
tcagtcaata cttcatatta ctcagttgat tctgagatgt tactatgtgc cttgcaggag    120
gtcaggcagt tctccaggct atttgtaccg attgcctact ccttgatctg tgtctttggc    180
ctcctgggga atattctggt ggtgatcacc tttgctttt ataagaaggc caggtctatg     240
acagacgtct atctcttgaa catggccatt gcagacatcc tctttgttct tactctccca    300
ttctgggcag tgagtcatgc cactggtgcg tgggttttca gcgatgccac gtgcaagttg    360
ctaaaaggca tctatgccat caactttaac tgcgggatgc tgctcctgac ttgcattagc    420
atggaccggt acatcgccat tgtacaggcg actaagtcat tccggctccg atccagaaca    480
ctaccgcgca cgaaaatcat ctgccttgtt gtgtgggggc tgtcagtcat catctccagc    540
tcaactttg tcttcaacca aaaatacaac acccaaggca gcgatgtctg taaacccaag    600
taccagactg tctcggagcc catcaggtgg aagctgctga tgttggggct tgagctactc    660
tttggtttct ttatccctt gatgttcatg atattttgtt acacgttcat tgtcaaaacc    720
ttggtgcaag ctcagaattc taaaaaggcac aaagccatcc gtgtaatcat agctgtggtg    780
cttgtgtttc tggcttgtca gattcctcat aacatggttc tcttgtgac ggctgcaaat     840
ttgggtaaaa tgaaccgatc ctgccagagc gaaaagctaa ttggctatac gaaaactgtc    900
acagaagtcc tggcttttcct gcactgctgc ctgaacctg tgctctacgc ttttattggg    960
cagaagttca gaaactactt tctgaagatc ttgaaggacc tgtggtgtgt gagaaggaag   1020
tacaagtcct caggcttctc ctgtgccggg aggtactcag aaaacatttc tcggcagacc   1080
agtgagaccg cagataacga caatgcgtcg tccttcacta tg                       1122

SEQ ID NO: 394          moltype = AA  length = 157
FEATURE                 Location/Qualifiers
REGION                  1..157
                        note = Synthetic
source                  1..157
                        mol_type = protein
                        organism = synthetic construct
SEQUENCE: 394
MGTSLLCWMA LCLLGADHAD ACPYSNPSLC SGGGGSELPT QGTFSNVSTN VSPAKPTTTA    60
CPYSNPSLCS GGGGSPAPRP PTPAPTIASQ PLSLRPEACR PAAGGAVHTR GLDFACDIYI   120
WAPLAGTCGV LLLSLVITLY CNHRNRRRVC KCPRPVV                             157

SEQ ID NO: 395          moltype = DNA  length = 471
FEATURE                 Location/Qualifiers
misc_feature            1..471
                        note = Synthetic
source                  1..471
                        mol_type = other DNA
                        organism = synthetic construct
SEQUENCE: 395
atgggtactt cactgttgtg ctggatggca ctttgtcttt tgggtgccga tcatgctgat    60
gcatgtccgt actccaatcc tagcctgtgc tccgggggg gagggagtga actccctaca    120
cagggaacct tctctaatgt ctccaccaac gtctcccctg caaaaccgac cacaacagct    180
tgcccctata gtaacccttc cctctgtagt ggagggggg gttcacctgc tccacgccct    240
cctaccccg cgccaacgat cgcgtcacaa ccgctcagtc ttaggccgga agcctgtagg    300
ccagcggctg gcggtgcggt tcatacgcgg ggattggatt tgcctgcga catttacatt    360
tgggctccg tggccggtac ttgtggggta ttgctgttgt ctcttgttat tacgctttat    420
tgcaatcaca ggaacaggcg acgagtatgc aaatgcccgc ggcccgtcgt g             471

SEQ ID NO: 396          moltype = AA  length = 28
FEATURE                 Location/Qualifiers
REGION                  1..28
                        note = Synthetic
source                  1..28
                        mol_type = protein
                        organism = synthetic construct
SEQUENCE: 396
MVCLKLPGGS CMTALTVTLM VLSSPLAL                                       28

SEQ ID NO: 397          moltype = DNA  length = 84
FEATURE                 Location/Qualifiers
misc_feature            1..84
                        note = Synthetic
```

```
source                    1..84
                          mol_type = other DNA
                          organism = synthetic construct
SEQUENCE: 397
atggtatgct tgaagctccc gggcgggtcc tgcatgaccg ctctcactgt tactcttatg    60
gtccttagtt caccgcttgc cctg                                           84

SEQ ID NO: 398            moltype =    length =
SEQUENCE: 398
000

SEQ ID NO: 399            moltype =    length =
SEQUENCE: 399
000

SEQ ID NO: 400            moltype = AA   length = 13
FEATURE                   Location/Qualifiers
REGION                    1..13
                          note = Synthetic
source                    1..13
                          mol_type = protein
                          organism = synthetic construct
SEQUENCE: 400
GGGGSGGGGS GGS                                                       13

SEQ ID NO: 401            moltype = DNA  length = 39
FEATURE                   Location/Qualifiers
misc_feature              1..39
                          note = Synthetic
source                    1..39
                          mol_type = other DNA
                          organism = synthetic construct
SEQUENCE: 401
ggggaggcg gatctggcgg aggcgggagt ggaggctca                            39

SEQ ID NO: 402            moltype = DNA  length = 555
FEATURE                   Location/Qualifiers
misc_feature              1..555
                          note = Synthetic
source                    1..555
                          mol_type = other DNA
                          organism = synthetic construct
SEQUENCE: 402
ggagacacaa gaccccgatt cttgtggcag cccaaaaggg agtgccattt ttcaatggg     60
acggaacgag ttcgcttcct tgatcggtac ttttacaacc aagaagagag tgtacggttc   120
gactcagatg tcggcgagtt ccgagcggtt acggaattgg ggcgacctga cgcggagtac   180
tggaactccc aaaaggatat tttggaacag gcacgagcac ctgtcgtgac ctattgtcga   240
cataattatg gtgtggtgga atcctttaca gttcagcggc gggtgcaacc taaagtgacc   300
gtgtatccat ctaaaacgca accctccaa caccataacc tcctggtgtg ttccgtaagc   360
ggcttctatc ccgggtcaat tgaggtcagg tggttcctca acgtcagga ggagaaggcc    420
ggaatggtaa gtactggtct tatccagaac ggagactgga ccttccaaac tttggtaatg   480
ttggaaacgg tgccgcgatc cggggaggtg tatacatgcc aagttgaaca cccgagtgtt   540
acgagccccc tgacg                                                     555

SEQ ID NO: 403            moltype = DNA  length = 2895
FEATURE                   Location/Qualifiers
misc_feature              1..2895
                          note = Synthetic
source                    1..2895
                          mol_type = other DNA
                          organism = synthetic construct
SEQUENCE: 403
atgggtactt cactgttgtg ctggatggca ctttgtcttt tgggtgccga tcatgctgat    60
gcatgtccgt actccaatcc tagcctgtgc tccggggagg gagggagtga actccctaca   120
cagggaacct tctctaatgt ctccaccaac gtctccctg caaaaccgac cacaacagct    180
tgccccctata gtaacccttc cctctgtagt ggagggggg gttcacctgc tccacgccct   240
cctaccccg cgccaacgat cgcgtcacaa ccgctcagtc ttaggccgga agcctgtagg   300
ccagcggctg gcggtcggt tcatacgcgg ggattggatt ttgcctgcga catttacatt    360
tgggctccge tggccggtac ttgtggggta ttgctgttgt ctcttgttat tacgctttat   420
tgcaatcaca ggaacaggcg acgagtatgc aaatgcccgc ggcccgtcgt gagatctggg   480
tccggccaat gtactaacta cgctttgttg aaactgctg gcgatgttga agtaacccc    540
ggtcctccaa caggtatggt atgcttgaag ctccgggcg gtcctgcat gaccgctctc    600
actgttactc ttatggtcct tagttcaccg cttgccctgg catctgatga gaatcccgtg   660
gttcatttt ttaagaacat cgtcacaccg cacacccac ctggggagg cggatctggc    720
ggaggcggga gtggaggctc aggagacaca agaccccgat tcttgtggca gcccaaaagg   780
gagtgccatt ttcaatgg gacgaacga gttcgcttcc ttgatcggta cttttacaac    840
caagaagaga gtgtacggtt cgactcagat gtcggcgagt ccgagcggt tacggaattg   900
gggcgaccta acgcggagta ctggaactcc caaaaggata ttttggagca ggcacgagca   960
gctgtggaca cctattgtcg acataattat ggtgtggtgg aatcctttac agttcagcgg  1020
```

```
cgggtgcaac ctaaagtgac cgtgtatcca tctaaaacgc aaccctcca acaccataac   1080
ctcctggtgt gttccgtaag cggcttctat cccgggtcaa ttgaggtcag gtggttcctc   1140
aacggtcagg aggagaaggc cggaatggta agtactggtc ttatccagaa cggagactgg   1200
accttccaaa ctttggtaat gttggaaacg gtgccgcgat ccggggaggt gtatacatgc   1260
caagttgaac acccgagtgt tacgagcccc ctgacggttg agtggagggc gcggtcagag   1320
agcgcacaat ctaaaatgct gtcaggagta ggcggatttg tactcggact cctcttttg    1380
ggcgctgggt tgtttatcta ctttagaaac caaacaagta gagtaaagtt ttcccgaagt    1440
gcggacgctc ccgcgtatca gcaaggtcaa aaccagcttt acaacgaact gaacttggga    1500
cgacgcgaag agtacgatgt tcttgataag cggagagggc gcgatcccga aatgggggga    1560
aagcctcgga ggaagaaccc acaagaaggc ctttataatg aactgcagaa ggacaagatg    1620
gcggaggcgt attccgaaat aggcatgaag ggtgaacgga ggagaggaaa gggacatgac    1680
ggactttatc aaggattgtc taccgcaact aaagacacct atgacgcgtt gcacatgcag    1740
gctctcccte cgagaggttc gagcggcagt ggagagggca gaggaagtct gctaacatgc    1800
ggtgacgtcg aggagaatcc tggcccaatg gcaatatctg gtgttcctgt cctcgggttt    1860
tttatcatag ccgtactgat gtcagcacag aatcatgggc cgataaaaga agagcacgtg    1920
ataatacagg cggagtttta tttgaacccg gaccagagcg tgagttcat gttcgatttt    1980
gatggcgacg agatatttca cgttgacatg gcaaaaagg aaacggtgtg gagacttgag    2040
gagtttggac gattcgcatc atttgaggca caaggagcac tcgccaatat ccgcggtgac    2100
aaggccaacc tggagatcat gacaaaacgc tccaattata cgcctatcac taatgtgccc    2160
cctgaggtta ctgtgctcac aaattctccc gtagaactta gggaacctaa cgtcctcata    2220
tgtttcatcg acaagttcac tcctccggtg gtcaatgtaa cgtggcttcg gaatggtaag    2280
ccggtcacca cgggtgtctc agagaccgta tttctgccca gagaagacca cctcttccgc    2340
aaatttcatt accttccctt tcttccttca acggaagacg tttacgactg cagggtcgaa    2400
cattgggggc ttgacgagcc acttctcaag cattgggagt cgacgcccc atcaccgctt    2460
ccagaaacga ctgaaaacgt tgtctgcgct cttggcctga cagtgggcct ggtaggcatt    2520
attatcggga ccatctttat catcaaaggt ttgacttccc gggtcaaatt tagcagatcc    2580
gctgacgcac cggcctacca gcagggccag aaccaactct acaacgagct gaatctcggc    2640
cgacgggaag agtatgacgt actcgacaag cggagaggtc gagaccctga tgggcggt    2700
aaaccgagac ggaaaaatcc ccaagagggt ctttataatg aactcagaa ggataagatg    2760
gctgaagcct attctgagat agggatgaaa ggcgagcggc ggaggggtaa gggccatgat    2820
ggcctttacc agggactctc cacggcaacc aaagatactt acgacgccct tcacatgcaa    2880
gccctcccgc cacgc                                                    2895

SEQ ID NO: 404           moltype = DNA  length = 39
FEATURE                  Location/Qualifiers
misc_feature             1..39
                         note = Synthetic
source                   1..39
                         mol_type = other DNA
                         organism = synthetic construct
SEQUENCE: 404
gttgagtgga gggcgcggtc agagagcgca caatctaaa                              39

SEQ ID NO: 405           moltype = AA  length = 1225
FEATURE                  Location/Qualifiers
REGION                   1..1225
                         note = Synthetic
source                   1..1225
                         mol_type = protein
                         organism = synthetic construct
SEQUENCE: 405
MGTSLLCWMA LCLLGADHAD ACPYSNPSLC SGGGGSELPT QGTFSNVSTN VSPAKPTTTA      60
CPYSNPSLCS GGGGSPAPRP PTPAPTIASQ PLSLRPEACR PAAGGAVHTR GLDFACDIYI     120
WAPLAGTCGV LLLSLVITLY CNHRNRRRVC KCPRPVVRSG SGQCTNYALL KLAGDVESNP     180
GPPTGMVCLK LPGGSCMTAL TVTLMVLSSP LALASDENPV VHFFKNIVTP RTPPGGGSGG     240
GGGSGGSGDT RPRFLWQPKR ECHFFNGTER VRFLDRYFYN QEESVRFDSD VGEFRAVTEL     300
GRPDAEYWNS QKDILEQARA AVDTYCRHNY GVVESFTVQR RVQPKVTVYP SKTQPLQHHN     360
LLVCSVSGFY PGSIEVRWFL NGQEEKAGMV STGLIQNGDW TFQTLVMLET VPRSGEVYTC     420
QVEHPSVTSP LTVEWRARSE SAQSKMLSGV GGFVLGLLFL GAGLFIYFRN QTSRVKFSRS     480
ADAPAYQQGQ NQLYNELNLG RREEYDVLDK RRGRDPEMGG KPRRKNPQEG LYNELQKDKM     540
AEAYSEIGMK GERRRGKGHD GLYQGLSTAT KDTYDALHMQ ALPPRGSSGS GEGRGSLLTC     600
GDVEENPGPM AISGVPVLGF FIIAVLMSAQ ESWAIKEEHV IIQAEFYLNP DQSGEFMFDF     660
DGDEIFHVDM AKKETVWRLE EFGRFASFEA QGALANIAVD KANLEIMTKR SNYTPITNVP     720
PEVTVLTNSP VELREPNVLI CFIDKFTPPV VNVTWLRNGK PVTTGVSETV FLPREDHLFR     780
KFHYLPFLPS TEDVYDCRVE HWGLDEPLLK HWEFDAPSPL PETTENVVCA LGLTVGLVGI     840
IIGTIFIIKG LTSRVKFSRS ADAPAYQQGQ NQLYNELNLG RREEYDVLDK RRGRDPEMGG     900
KPRRKNPQEG LYNELQKDKM AEAYSEIGMK GERRRGKGHD GLYQGLSTAT KDTYDALHMQ     960
ALPPRGSGAT NFSLLKQAGD VEENPGPVSK GEELFTGVVP ILVELDGDVN GHKFSVSGEG    1020
EGDATYGKLT LKFICTTGKL PVPWPTLVTT LTYGVQCFSR YPDHMKQHDF FKSAMPEGYV    1080
QERTIFFKDD GNYKTRAEVK FEGDTLVNRI ELKGIDFKED GNILGHKLEY NYNSHNVYIM    1140
ADKQKNGIKA NFKIRHNIED GSVQLADHYQ QNTPIGDGPV LLPDNHYLST QSALSKDPNE    1200
KRDHMVLLEF VTAAGITLGM DELYK                                         1225

SEQ ID NO: 406           moltype = DNA  length = 78
FEATURE                  Location/Qualifiers
misc_feature             1..78
                         note = Synthetic
source                   1..78
                         mol_type = other DNA
```

```
                    organism = synthetic construct
SEQUENCE: 406
atgctgtcag gagtaggcgg atttgtactc ggactcctct tttggggcgc tgggttgttt    60
atctacttta gaaaccaa                                                  78

SEQ ID NO: 407          moltype =   length =
SEQUENCE: 407
000

SEQ ID NO: 408          moltype =   length =
SEQUENCE: 408
000

SEQ ID NO: 409          moltype = DNA  length = 3678
FEATURE                 Location/Qualifiers
misc_feature            1..3678
                        note = Synthetic
source                  1..3678
                        mol_type = other DNA
                        organism = synthetic construct
SEQUENCE: 409
atgggtactt cactgttgtg ctggatggca ctttgtcttt tgggtgccga tcatgctgat    60
gcatgtccgt actccaatcc tagcctgtgc tccgggggg gagggagtga actccctaca   120
cagggaacct tctctaatgt ctccaccaac gtctccctg caaaaccgac acaacagct    180
tgccccctata gtaacccttc cctctgtagt ggaggggggg gttcacctgc tccacgccct   240
cctacccccg cgccaacgat cgcgtcacaa ccgtcagtc ttaggccgga agcctgtagg    300
ccagcggctg gcggtgcggt tcatacgcgg ggattggatt ttgcctgcga catttacatt   360
tgggctccgc tggccggtac ttgtggggta ttgctgttgt ctcttgttat tacgctttat   420
tgcaatcaca ggaacaggcg acgagtatgc aaatgcccgc ggcccgtcgt gagatctggg   480
tccggccaat gtactaacta cgcttttgtt aaactgctg gcgatgttga aagtaacccc   540
ggtcctccaa caggtatggt atgcttgaag ctcccgggcg gtcctgcat gaccgctctc    600
actgttactc ttatggtcct tagttcaccg cttgccctgg catctgatga aatcccgtg    660
gttcattttt ttaagaacat cgtcacaccg cgcaccccac ctgggggagg cggatctggc   720
ggaggcggga gtggaggctc aggagacaca agacccgat tcttgtggca gcccaaaagg   780
gagtgccatt ttttcaatgg gacggaacga gttcgcttcc ttgatcggta cttttacaac   840
caagaagaga gtgtacggtt cgactcagat gtcggcgagt tccgagcggt tacggaattg   900
gggcgacctg acgcggagta ctggaactcc caaaaggata ttttggagca ggcacgagca   960
gctgtggaca cctattgtcg acataattat ggtgtggtgg aatcctttac agttcagcgg  1020
cgggtgcaac ctaaagtgac cgtgtatcca tctaaaacgc aacccctcca acaccataac  1080
ctcctggtgt gttccgtaag cggcttctat cccgggtcaa ttgaggtcag gtggttcctc  1140
aacggtcagg aggagaaggc cggaatggta agtactggtc ttatccagaa cggagactgg  1200
accttccaaa ctttggtaat gttggaaacg gtgccgcgat ccggggaggt gtatacatgc  1260
caagttgaac accgagtgt tacgagcccc ctgacggtca agtggaggg gcggtcagag  1320
agcgcacaat ctaaaatgct gtcaggagta ggcggatttg tactcggact cctcttttg   1380
ggcgctgggt tgtttatcta cttttagaaac caaacaagta gagtaaagtt ttcccgaagt   1440
gcggacgctc ccgcgtatca gcaaggtcaa accagcttt acaacgaact gaacttggga   1500
cgacgcgaag agtacgatgt tcttgataag cggagagggc gcgatcccga aatggggga   1560
aagcctcgga ggaagaaccc acaagaaggc ctttataatg aactgcagaa ggacaagatg   1620
gcggaggcgt attccgaaat aggcatgaag ggtgaacgga ggagaggaa gggacatgac   1680
ggactttatc aaggattgtc taccgcaact aaagacacct atgacgcgtt gcacatgcag   1740
gctctccctc cgagaggttc gagcggcagt ggagagggca gaggaagtct gctaacctag   1800
ggtgacgtcg aggagaatcc tggcccaatg gcaatatctg tgttcctgt cctcgggttt    1860
tttatcatag ccgtactgat gtcagcacag gaatcatggg cgataaaaga gagcacgtg    1920
ataatacagg cggagttta tttgaacccg accagagcg tgagttcat gttcgatttt    1980
gatgcgacg agatatttca cgttgacatg gcaaaaaagg aaacggtgtg gagacttgag   2040
gagtttggac gattcgcatc atttgaggca caaggagcac tcgccaatat cgcggtggac   2100
aaggccaacc tggagatcat gacaaaacgc tccaattata cgcctatcac taatgtgccc   2160
cctgaggtta ctgtgctcac aaattctccc gtagaactta gggaacctaa cgtcctcata   2220
tgtttcatcg acaagttcac tcctccggtg gtcaatgtaa cgtggcttcg gaatggtaag   2280
ccggtcacca cgggtgtctc agagacttga tttctgccca gagaagacca cctcttccgc   2340
aaatttcatt accttccctt tcttccttca acggaagacg tttacgactg cagggtcgaa   2400
cattgggggc ttgacgagcc acttctcaag cattgggagt cgacgcccc atcaccgctt    2460
ccagaaacga ctgaaaacgt tgtctgcgct cttggcctga cagtgggcct ggtaggcatt    2520
attatcggga ccatctttat catcaaaggt ttgacttccc gggtcaaatt tagcagatcc   2580
gctgacgcac cggcctacca gcagggccag aaccaactct acaacgagct gaatctcggc   2640
cgacgggaag agtatgacgt actcgacaag cggagaggtc gagaccctga tgggcggt   2700
aaaccgagac ggaaaaatcc caagagggt ctttataatg aactccagaa ggataagatg   2760
gctgaagcct attctgagat agggatgaaa ggcgagcggc ggagggtaa gggccatgat   2820
ggcctttacc agggactctc cacggcaacc aaagatactt acgacgccct tcacatgcaa   2880
gccctcccgc cacgcggatc cggcgcaaca aacttctctc tgctgaaaca agccggagat   2940
gtcgaagaga atcctggacc ggtgagcaag ggcgaggagc tgttcaccgg ggtggtgccc   3000
atcctggtcg agctggacgg cgacgtaaac ggccacaagt tcagcgtgtc tggcgagggc   3060
gagggcgatg ccacctacgg caagctgacc ctgaagttca tctgcaccac cggcaagctg   3120
cccgtgccct ggccccacct cgtgaccacc ctgacctacg gcgtgcagtg cttcagccgc   3180
taccccgacc acatgaagca gcacgacttc ttcaagtccg ccatgcccga aggctacgtc   3240
caggagcgca ccatcttctt caaggacgac ggcaactaca agacccgcgc cgaggtgaag   3300
ttcgagggcg acaccctggt gaaccgcatc gagctgaagg gcatcgactt caaggaggac   3360
ggcaacatcc tggggcacaa gctggagtac aactacaaca gccacaacgt ctatatcatg   3420
gccgacaagc agaagaacgg catcaaggcg aacttcaaga tccgccacaa catcgaggac   3480
```

```
ggcagcgtgc agctcgccga ccactaccag cagaacaccc ccatcggcga cggcccgtg    3540
ctgctgcccg acaaccacta cctgagcacc cagtccgccc tgagcaaaga ccccaacgag   3600
aagcgcgatc acatggtcct gctggagttc gtgaccgccg ccgggatcac tctcggcatg   3660
gacgagctgt acaagtaa                                                 3678
```

```
SEQ ID NO: 410          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 410
agagtaaagt tttcccgaag tgcggacgct cccgcgtatc agcaaggtca aaaccagctt    60
tacaacgaac tgaacttggg acgacgcgaa gagtacgatg ttcttgataa gcggagaggg   120
cgcgatcccg aaatggggg aaagcctcgg aggaagaacc cacaagaagg ccttatataat  180
gaactgcaga aggacaagat ggcggaggcg tattccgaaa taggcatgaa gggtgaacgg   240
aggagaggaa agggacatga cggactttat caaggattgt ctaccgcaac taagacacc    300
tatgacgcgt tgcacatgca ggctctccct ccgaga                            336

SEQ ID NO: 411          moltype = DNA  length = 58
FEATURE                 Location/Qualifiers
misc_feature            1..58
                        note = Synthetic
source                  1..58
                        mol_type = other DNA
                        organism = synthetic construct
SEQUENCE: 411
gatgagaatc ccgtggttca ttttttaag aacatcgtca caccgcgcac cccacctg      58

SEQ ID NO: 412          moltype = AA  length = 400
FEATURE                 Location/Qualifiers
REGION                  1..400
                        note = Synthetic
source                  1..400
                        mol_type = protein
                        organism = synthetic construct
SEQUENCE: 412
MVCLKLPGGS CMTALTVTLM VLSSPLALAS DENPVVHFFK NIVTPRTPPG GGGSGGGGSG    60
GSGDTRPRFL WQPKRECHFF NGTERVRFLD RYFYNQEESV RFDSDVGEFR AVTELGRPDA   120
EYWNSQKDIL EQARAAVDTY CRHNYGVVES FTVQRRVQPK VTVYPSKTQP LQHHNLLVCS   180
VSGFYPGSIE VRWFLNGQEE KAGMVSTGLI QNGDWTFQTL VMLETVPRSG EVYTCQVEHP   240
SVTSPLTVEW RARSESAQSK MLSGVGGFVL GLLFLGAGLF IYFRNQTSRV KFSRSADAPA   300
YQQGQNQLYN ELNLGRREEY DVLDKRRGRD PEMGGKPRRK NPQEGLYNEL QKDKMAEAYS   360
EIGMKGERRR GKGHDGLYQG LSTATKDTYD ALHMQALPPR                        400

SEQ ID NO: 413          moltype = DNA  length = 1200
FEATURE                 Location/Qualifiers
misc_feature            1..1200
                        note = Synthetic
source                  1..1200
                        mol_type = other DNA
                        organism = synthetic construct
SEQUENCE: 413
atggtatgct tgaagctccc gggcgggtcc tgcatgaccg ctctcactgt tactcttatg    60
gtccttagtt caccgcttgc cctggcatct gatgagaatc ccgtggttca ttttttaag   120
aacatcgtca caccgcgcac cccacctggg gaggcggat ctggcggagg cgggagtgga   180
ggctcaggag acacaagacc ccgattcttg tggcagccca aagggagtg ccatttttc    240
aatgggacgg aacgagttcg cttccttgat cggtactttt acaaccaaga agagagtgta   300
cggttcgact cagatgtcgg cgagttccga gcggttacgg aattgggcg acctgacgcg   360
gagtactgga actcccaaaa ggatatttg gagcaggcac gagcagctgt ggacacctat   420
tgtcgacata attatggtgt ggtggaatcc tttacagttc agcggcgggt gcaacctaaa   480
gtgaccgtgt atccatctaa aacgcaaccc ctccaacacc ataacctcct ggtgtgttcc   540
gtaagcggct tctatcccgg gtcaattgag gtcaggtggt tcctcaacgg tcaggaggag   600
aaggccggaa tggtaagtac tggtcttatc cagaacgag actggacctt ccaaactttg   660
gtaatgttgg aaacggtgcc cgcgatccgg gaggtgtata catgccaagt gaacacccg   720
agtgttacga gcccccctgac ggttgagtgg agggcgcgt cagagagcgc acaatctaaa   780
atgctgtcag gagtaggcgg atttgtactc ggactcctct ttttgggcgc tgggttgttt   840
atctacttta gaaaccaaac aagtagagta aagttttccc gaagtgcgga cgctcccgcg   900
tatcagcaag gtcaaaacca gctttacaac gaactgaact tgggacgacg aagagtac    960
gatgttcttg ataagcggag agggcgcgat cccgaaatgg ggaaagcc tcggaggaag   1020
aacccacaag aaggccttta taatgaactg cagaaggaca agatggcgga ggcgtattcc   1080
gaaataggca tgaaggtga acggaggaga ggaaagggac atgacggact ttatcaagga   1140
ttgtctaccg caactaaaga cacctatgac gcgttgcaca tgcaggctct ccctccgaga  1200

SEQ ID NO: 414          moltype = DNA  length = 75
FEATURE                 Location/Qualifiers
misc_feature            1..75
                        note = Synthetic
```

```
source                  1..75
                        mol_type = other DNA
                        organism = synthetic construct
SEQUENCE: 414
atggcaatat ctggtgttcc tgtcctcggg ttttttatca tagccgtact gatgtcagca    60
caggaatcat gggcg                                                    75

SEQ ID NO: 415          moltype = DNA  length = 534
FEATURE                 Location/Qualifiers
misc_feature            1..534
                        note = Synthetic
source                  1..534
                        mol_type = other DNA
                        organism = synthetic construct
SEQUENCE: 415
ataaagaag agcacgtgat aatacaggcg gagttttatt tgaacccgga ccagagcggt     60
gagttcatgt tcgattttga tggcgacgag atatttcacg ttgacatggc aaaaaaggaa   120
acggtgtgga gacttgagga gtttggacga ttcgcatcat ttgaggcaca aggagcactc   180
gccaatatcg cggtggacaa ggccaacctg gagatcatga caaaacgctc caattatacg   240
cctatcacta atgtgccccc tgaggttact gtgctcacaa attctcccgt agaacttagg   300
gaacctaacg tcctcatatg tttcatcgac aagttcactc ctccggtggt caatgtaacg   360
tggcttcgga atggtaagcc ggtcaccacg ggtgtctcaa agaccgtatt tctgcccaga   420
gaagaccacc tcttccgcaa atttcattac cttcccttc ttccttcaac ggaagacgtt    480
tacgactgca gggtcgaaca ttgggggctt gacgagccac ttctcaagca ttgg         534

SEQ ID NO: 416          moltype = AA  length = 23
FEATURE                 Location/Qualifiers
REGION                  1..23
                        note = Synthetic
source                  1..23
                        mol_type = protein
                        organism = synthetic construct
SEQUENCE: 416
NVVCALGLTV GLVGIIIGTI FII                                           23

SEQ ID NO: 417          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 417
gagttcgacg ccccatcacc gcttccagaa acgactgaa                          39

SEQ ID NO: 418          moltype = AA  length = 26
FEATURE                 Location/Qualifiers
REGION                  1..26
                        note = Synthetic
source                  1..26
                        mol_type = protein
                        organism = synthetic construct
SEQUENCE: 418
NVVCALGLTV GLVGIIIGTI FIIKGL                                        26

SEQ ID NO: 419          moltype = DNA  length = 78
FEATURE                 Location/Qualifiers
misc_feature            1..78
                        note = Synthetic
source                  1..78
                        mol_type = other DNA
                        organism = synthetic construct
SEQUENCE: 419
aacgttgtct gcgctcttgg cctgacagtg ggcctggtag gcattattat cgggaccatc    60
tttatcatca aagtttg                                                  78

SEQ ID NO: 420          moltype =   length =
SEQUENCE: 420
000

SEQ ID NO: 421          moltype =   length =
SEQUENCE: 421
000

SEQ ID NO: 422          moltype = DNA  length = 336
FEATURE                 Location/Qualifiers
misc_feature            1..336
                        note = Synthetic
source                  1..336
```

```
                        mol_type = other DNA
                        organism = synthetic construct
SEQUENCE: 422
cgggtcaaat ttagcagatc cgctgacgca ccggcctacc agcagggcca gaaccaactc  60
tacaacgagc tgaatctcgg ccgacgggaa gagtatgacg tactcgacaa gcggagaggt  120
cgagaccctg agatgggcgg taaaccgaga cggaaaaatc cccaagaggg tcttttataat 180
gaactccaga aggataagat ggctgaagcc tattctgaga tagggatgaa aggcgagcgg  240
cggaggggta agggccatga tggcctttac cagggactct ccacggcaac caaagatact  300
tacgacgccc ttcacatgca agccctcccg ccacgc                             336

SEQ ID NO: 423         moltype = AA length = 356
FEATURE                Location/Qualifiers
REGION                 1..356
                       note = Synthetic
source                 1..356
                       mol_type = protein
                       organism = synthetic construct
SEQUENCE: 423
MAISGVPVLG FFIIAVLMSA QESWAIKEEH VIIQAEFYLN PDQSGEFMFD FDGDEIFHVD  60
MAKKETVWRL EEFGRFASFE AQGALANIAV DKANLEIMTK RSNYTPITNV PPEVTVLTNS  120
PVELREPNVL ICFIDKFTPP VVNVTWLRNG KPVTTGVSET VFLPREDHLF RKFHYLPFLP  180
STEDVYDCRV EHWGLDEPLL KHWEFDAPSP LPETTENVVC ALGLTVGLVG IIIGTIFIIK  240
GLTSRVKFSR SADAPAYQQG QNQLYNELNL GRREEYDVLD KRRGRDPEMG GKPRRKNPQE  300
GLYNELQKDK MAEAYSEIGM KGERRRGKGH DGLYQGLSTA TKDTYDALHM QALPPR       356

SEQ ID NO: 424         moltype = DNA length = 1068
FEATURE                Location/Qualifiers
misc_feature           1..1068
                       note = Synthetic
source                 1..1068
                       mol_type = other DNA
                       organism = synthetic construct
SEQUENCE: 424
atggcaatat ctggtgttcc tgtcctcggg ttttttatca tagccgtact gatgtcagca  60
caggaatcat gggcgataaa agaagagcac gtgataatac aggcggagtt ttatttgaac  120
ccggaccaga gcgtgagtt catgttcgat tttgatggcg acgagatatt tcacgttgac  180
atggcaaaaa aggaaacggt gtggagactt gaggagtttg gacgattcgc atcatttgag  240
gcacaaggag cactcgccaa tatcgcgtg gacaaggcca acctggagat catgacaaag  300
cgctccaatt atacgcctat cactaatgtg cccctgagg ttactgtgct cacaaattct  360
cccgtagaac ttagggaacc taacgtcctc atatgtttca tcgacaagtt cactcctccg  420
gtggtcaatg taacgtggct tcggaatggt aagccggtca ccacgggtgt ctcagagacc  480
gtatttctgc ccagagaaga ccactctctt cgcaaatttc attaccttcc ctttcttcct  540
tcaacggaag acgtttacga ctgcagggtc gaacattggg gcttgacga gccacttctt  600
aagcattggg agttcgacgc cccatcaccg cttccagaaa cgactgaaaa cgttgtctgc  660
gctcttggcc tgacagtggg cctggtaggc attattatcg ggaccatctt tatcatcaaa  720
ggtttgactt cccgggtcaa atttagcaga tccgctgacg caccggccta ccagcagggc  780
cagaaccaac tctacaacga gctgaatctc ggccgacgag gtactacgac  840
aagcggagag gtcgagaccc tgagatgggc ggtaaaccga gacggaaaaa tccccaagag  900
ggtctttata tgaactcca aggataag atggctgaag cctattctga gatagggatg  960
aaaggcgagc ggcggagggg taagggccat gatggccttt accagggact ctccacggca  1020
accaaagata cttacgacgc ccttcacatg caagccctcc cgccacgc              1068

SEQ ID NO: 425         moltype = AA length = 893
FEATURE                Location/Qualifiers
REGION                 1..893
                       note = Synthetic
source                 1..893
                       mol_type = protein
                       organism = synthetic construct
SEQUENCE: 425
METDTLLLWV LLLWVPGSTG EVQLQQSGPE LIKPGASVKM SCKASGYTFT SYVMHWVKQK  60
PGQGLEWIGY INPYNDGTKY NEKFKGKATL TSDKSSSTAY MELSSLTSED SAVYYCARGT  120
YYYSRVFDY WGQGTTLTVS SGGGGSGGGG SGGGGSDIVM TQAAPSIPVT PGESVSISCR  180
SSKSLLNSNG NTYLYWFLQR PGQSPQLLIY RMSNLASGVP DRFSGSGSGT AFTLRISRVE  240
AEDVGVYYCM QHLEYPFTFG AGTKLELKRS DPTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPRGSSGS GEGRGSLLTC GDVEENPGPM SGESMNFSDV FDSSEDYFVS  540
VNTSYYSVDS EMLLCSLQEV RQFSRLFVPI AYSLICVFGL LGNILVVITF AFYKKARSMT  600
DVYLLNMAIA DILFVLTLPF WAVSHATGAW VFSNATCKLL KGIYAINFNC GMLLLTCISM  660
DRYIAIVQAT KSFRLRSRTL PRSKIICLVV WGLSVIISSS TFVFNQKYNT QGSDVCEPKY  720
QTVSEPIRWK LLMLGLELLF GFFIPLMFMI FCYTFIVKTL VQAQNSKRHK AIRVIIAVVL  780
VFLACQIPHN MVLLVTAANL GKMNRSCQSE KLIGYTKTVT EVLAFLHCCL NPVLYAFIGQ  840
KFRNYFLKIL KDLWCVRRKY KSSGFSCAGR YSENISRQTS ETADNDNASS FTM         893

SEQ ID NO: 426         moltype = DNA length = 2679
FEATURE                Location/Qualifiers
misc_feature           1..2679
```

```
                        note = Synthetic
source                  1..2679
                        mol_type = other DNA
                        organism = synthetic construct
SEQUENCE: 426
atggagacag acactcttct cctttgggtc ttgctgctgt gggttccgg aagcacagga    60
gaagtacagt tgcaacagtc tgggccagaa ctcatcaaac ccggagcttc tgtaaaaatg   120
tcatgcaaag ctagtggata tacatttact tcttacgtga tgcactgggt aaaacagaaa   180
cctggtcagg ggcttgagtg gatcgggtac attaacccat ataatgacgg caccaaatat   240
aacgagaaat tcaagggaaa ggctacgctt acatcagata agtccagtga caccgcttat   300
atggaactta gcagccttac ttccgaagat tccgcggtgt attactgcgc gagagggact   360
tactactacg ggagtcgagt attcgattat tggggtcaag gcacgacgct cacggtgagc   420
tcaggtggtg gagggtctgg gggtggcggc agtggtgggg gggctcaga catcgtgatg   480
acccaggcag caccttctat cccggtaacc ccaggcgagt ctgtatctat cagttgtcgg   540
tccagcaagt ctcttctcaa cagtaatggc aatacatatc tttactggtt cctccaaagg   600
cctgggcaaa gtcctcaact tcttatatat cggatgtcca atcttgcgag tggcgtaccc   660
gacaggtttt cagggtctgg gagcggaaca gcttttacgt tgagaatatc cagggtagaa   720
gctgaggacg tcggtgtata ttattgcatg caacatctcg aatacccctt taccttcggc   780
gctggtacaa agctcgaatt gaaacgcagc gatccaacca cgacgccagc gccacgacca   840
cctacgcccg ctccaactat tgcctcccag cccctgagtc ttcggccaga agcgtgtaga   900
cctgctgccg gcggggccgt tcatacgcgg ggccttgact ttgcatgtga tatctatata   960
tgggctcctt tggcgggaac ttgcggagtg ctttctttgt cactcgtgat aacgttgtat  1020
tgtaaaaggg gtcgaaagaa actcctctat atatttaagc agcccttat gaggcccgtg  1080
caaacaacac aagaagagga cggatgctct tgtcgattcc cggaagagga ggagggggg   1140
tgtgagctta gggtcaagtt ttctcgctct gccgacgcgc cagcctatca acagggccaa  1200
aacgctgt ataacgaact caacctcggg cgccgggaac agtatgacgt ccttgacaaa    1260
cggcgcggtc gcgaccctga aatgggtgga aaaccgagcg gaaagaaccc ccaggaggga  1320
ctttacaacg aattgcaaaa agacaagatg gccgaagcct attccgaaat tggaatgaaa  1380
ggcgagcgga gacgaggtaa ggggcatgac ggcctgtatc aagggctctc tacggccacg  1440
aaggatactt acgacgccct tcatatgcaa gctcttccac cacggggttc gagcggcagt  1500
ggagagggca gaggaagtct gctaacatgc ggtgacgtcg aggagaatcc tggcccaatg  1560
agtgggaaa gtatgaactt cagcgatgta tttgactcct ccgaagatta ctttgtatct   1620
gtgaatacga gctattactc cgtcgatagt gaaatgctgc tctgtagtct ccaagaagtc  1680
cgccaattca gtcgcctctt cgttcccatc gcgtactccc tctatttgtgt ttttggcctt  1740
ctgggtaaca tcctggttgt aatcacattc gctttctata aaaagctcg gagtatgact  1800
gatgtttacc ttcttaacat ggctatagcc gacattcttt ttgtgcttac tctcccattc  1860
tgggctgtga gccatgcaac aggggcgtgg gttttttcaa atgccacatg taagctgctt  1920
aaagggatct atgcaataaa cttcaattgc gggatgctcc tgctgacatg catcagtatg  1980
gatcgataca tagctatagt acaggcgact aagtcctccg gctgcgatc ccgcacactg    2040
cctaggagca aaattatttg cctcgtcgta tgggggctct cagtgatcat ctcctccagt  2100
acgtttgtct ttaaccagaa atataacaca cagggttctg atgtatgtga accaaagtat  2160
cagacagtga gtgaaccaat acggtggaag ttgcttatgt ttgggcttgga gctgctttt   2220
gggttttca tcccactgat gttcatgatt ttctgttata cattttattg taagaccttg    2280
gttcaggcgc aaaatagcaa gagacataag gcaattcgag tcatcattgc cgtggtgttg  2340
gtcttcttgg cctgtcagat cccccataat atggttctgc tcgtcaccgc cgctaacttg  2400
ggtaagatga atcgatcttg tcagtccgag aagttgatcg atacaccaa aactgtgaca    2460
gaagtgctgg ccttccttca ctgttgtctg aacccagttt tgtatgcttt tataggacag  2520
aagtttcgaa attacttctt gaaaatcctc aaggacctct ggtgtgttcg aaggaagtac  2580
aagagctctg gctttagttg cgctgggcgc tacagtgaga atatatcccg gcagacctcc  2640
gagactgctg ataatgacaa cgcaagttcc ttcactatg                          2679

SEQ ID NO: 427          moltype = AA  length = 238
FEATURE                 Location/Qualifiers
REGION                  1..238
                        note = Synthetic
source                  1..238
                        mol_type = protein
                        organism = synthetic construct
SEQUENCE: 427
VSKGEELFTG VVPILVELDG DVNGHKFSVS GEGEGDATYG KLTLKFICTT GKLPVPWPTL    60
VTTLTYGVQC FSRYPDHMKQ HDFFKSAMPE GYVQERTIFF KDDGNYKTRA EVKFEGDTLV   120
NRIELKGIDF KEDGNILGHK LEYNYNSHNV YIMADKQKNG IKANFKIRHN IEDGSVQLAD   180
HYQQNTPIGD GPVLLPDNHY LSTQSALSKD PNEKRDHMVL LEFVTAAGIT LGMDELYK     238

SEQ ID NO: 428          moltype = DNA  length = 717
FEATURE                 Location/Qualifiers
misc_feature            1..717
                        note = Synthetic
source                  1..717
                        mol_type = other DNA
                        organism = synthetic construct
SEQUENCE: 428
gtgagcaagg gcgaggagct gttcaccggg gtggtgccca tcctggtcga gctggacggc    60
gacgtaaacg gccacaagtt cagcgtgtct ggcgagggcg agggcgatgc cacctacggc   120
aagctgaccc tgaagttcat ctgcaccacc ggcaagctgc ccgtgccctg gcccaccctc   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
```

```
ctggagtaca actacaacag ccacaacgtc tatatcatgg ccgacaagca gaagaacggc    480
atcaaggcga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg     660
ctggagttcg tgaccgccgc cgggatcact ctcggcatgg acgagctgta caagtaa       717

SEQ ID NO: 429          moltype = AA   length = 1153
FEATURE                 Location/Qualifiers
REGION                  1..1153
                        note = Synthetic
source                  1..1153
                        mol_type = protein
                        organism = synthetic construct
SEQUENCE: 429
METDTLLLWV LLLWVPGSTG EVQLQQSGPE LIKPGASVKM SCKASGYTFT SYVMHWVKQK      60
PGQGLEWIGY INPYNDGTKY NEKFKGKATL TSDKSSSTAY MELSSLTSED SAVYYCARGT     120
YYYGSRVFDY WGQGTTLTVS SGGGGSGGGG SGGGGSDIVM TQAAPSIPVT PGESVSISCR     180
SSKSLLNSNG NTYLYWFLQR PGQSPQLLIY RMSNLASGVP DRFSGSGSGT AFTLRISRVE     240
AEDVGVYYCM QHLEYPFTFG AGTKLELKRS DPTTTPAPRP PTPAPTIASQ PLSLRPEACR     300
PAAGGAVHTR GLDFACDIYI WAPLAGTCGV LLLSLVITLY CKRGRKKLLY IFKQPFMRPV     360
QTTQEEDGCS CRFPEEEEGG CELRVKFSRS ADAPAYQQGQ NQLYNELNLG RREEYDVLDK     420
RRGRDPEMGG KPRRKNPQEG LYNELQKDKM AEAYSEIGMK GERRRGKGHD GLYQGLSTAT     480
KDTYDALHMQ ALPPRGSSGS GEGRGSLLTC GDVEENPGPM SGESMNFSDV FDSSEDYFVS     540
VNTSYYSVDS EMLLCSLQEV RQFSRLFVPI AYSLICVFGL LGNILVVITF AFYKKARSMT     600
DVYLLNMAIA DILFVLTLPF WAVSHATGAW VFSNATCKLL KGIYAINFNC GMLLLTCISM     660
DRYIAIVQAT KSFRLRSRTL PRSKIICLVV WGLSVIISSS TFVFNQKYNT QGSDVCEPKY     720
QTVSEPIRWK LLMLGLELLF GFFIPLMFMI FCYTFIVKTL VQAQNSKRHK AIRVIIAVVL     780
VPLACQIPHN MVLLVTAANL GKMNRSCQSE KLIGYTKTVT EVLAFLHCCL NPVLYAFIGQ     840
KFRNYFLKIL KDLWCVRRKY KSSGFSCAGR YSENISRQTS ETADNDNASS FTMGSGATNF     900
SLLKQAGDVE ENPGPVSKGE ELFTGVVPIL VELDGDVNGH KFSVSGEGEG DATYGKLTLK     960
FICTTGKLPV PWPTLVTTLT YGVQCFSRYP DHMKQHDFFK SAMPEGYVQE RTIFFKDDGN    1020
YKTRAEVKFE GDTLVNRIEL KGIDFKEDGN ILGHKLEYNY NSHNVYIMAD KQKNGIKANF    1080
KIRHNIEDGS VQLADHYQQN TPIGDGPVLL PDNHYLSTQS ALSKDPNEKR DHMVLLEFVT    1140
AAGITLGMDE LYK                                                      1153

SEQ ID NO: 430          moltype = DNA   length = 3462
FEATURE                 Location/Qualifiers
misc_feature            1..3462
                        note = Synthetic
source                  1..3462
                        mol_type = other DNA
                        organism = synthetic construct
SEQUENCE: 430
atggagacag acactcttct cctttgggtc ttgctgctgt gggttccgg aagcacagga      60
gaagtacagt tgcaacagtc tgggccagaa ctcatcaaac ccggagcttc tgtaaaaatg    120
tcatgcaaag ctagtggata cacttttact tcttacgtga tgcactgggt aaaacagaaa    180
cctcagg ggcttgagtg gatcgggtac attaaccgat ataatgacgg caccaaaatat     240
aacgagaaat tcaagggaaa ggctacgctt acatcagata agtccagtag cacccgctat    300
atggaactta gcagccttac ttccgaagat tccgcggtgt attactgcgc gagagggact    360
tactactacg ggagtcgagt attcgattat tggggtcaag gcacgacgct cacggtgagc    420
tcaggtgggg gagggtctgg gggtggcggc agtggtgggg ggggtctcaga catcgtgatg    480
acccaggcag caccttctat cccggtaacc ccaggcgagt ctgtatctat cagttgtcgg    540
tccagcaagt ctcttctcaa cagtaatggc aatacatatc tttactggtt cctccaaagg    600
cctgggcaaa gtcctcaact tcttatatat cggatgtcca atcttgcgag tggcgtaccc    660
gacaggtttt cagggtctgg gagcggaaca gcttttacgt tgaagaatatc cagggtagaa   720
gctgaggacg tcggtgtata ttattgcatg caacatctcg aataccccttt taccttcggc   780
gctggtacaa agctcgaatt gaaacgcagc gatccaacca cgacgccagc gccacgacca    840
cctacgcccc tccaactat tgcctccag cccctgagtc ttcggccaga agcgtgtaga     900
cctgctgccg gcgggggccgt tcatacgcgg ggctctgact ttgcatgtga tatctatata   960
tgggctcctt tggcgggaac ttgcgggagtg cttcttttgt cactcgttgat aacgttgat   1020
tgtaaaaggg gtcgaaagaa actcctctat atatttaagc agccctttat gaggcccgtg   1080
caaacaaacac aagaagagga cggatgctct tgtcgattcc cggaagagga ggaggggggg   1140
tgtgagctta gggtcaagtt ttctcgctct gccgacgcgc cagcctatca acaggcaa      1200
aaccagctgt ataacgaact caacctcggg cgccgggaag agtatgacgt ccttgacaaa    1260
cggcgcggtc gcgaccctga aatgggtgga aaaccgaggc gaaagaaccc ccaggaggga    1320
ctttacaacg aattgcaaaa agacaagatg gccgaagcct attccgaaat tggaatgaaa    1380
ggcgagcgga gacgaggtaa ggggcatgac ggcctgtatc aagggctctc tacggccacg    1440
aaggatactt acgacgccct tcatatgcaa gctcttccac cacgggggttc gagcggcagt   1500
ggagagggca gaggaagtct gctaacatgc ggtgacgtcg aggagaatcc tggcccaatg    1560
agtgggaaa gtatgaactt cagcgatgta tttgactcct ccgaagatta ctttgtatct     1620
gtgaatacga gctattactc cgtcgatagt gaaatgctgc tctgtagtct ccaagaagtc    1680
cgccaattca gtcgcctctt cgttcccatc gcgtactccc ttatttgtgt ttttggcctt    1740
ctgggtaaca tcctggttgt aatcacattc gcttttctata aaaaagctcg gagtatgact    1800
gatgtttacc ttcttaacat ggctatagcg gacattcttt ttgtcttac tctcccattc    1860
tgggctgtga gccatgcaac aggggcgtgg gttttttcaa atgccacatg taagctgctt   1920
aaagggatct atgcaataaa cttcaattgc gggatgctcc tgctgacatg catcagtatg    1980
gatcgataca tagctatagt acaggcgact aagtcctttcc gctgcgatcc cgcacactg    2040
cctaggagca aaattatttg cctcgtcgta tgggggctct cagtgatcat ctcctccagt    2100
acgtttgtct ttaaccagaa atataacaca cagggttctg atgtatgtga accaaagtat    2160
```

-continued

```
cagacagtga gtgaaccaat acggtggaag ttgcttatgt tgggcttgga gctgcttttt  2220
gggttttca tcccactgat gttcatgatt ttctgttata catttattgt taagaccttg   2280
gttcaggcgc aaaatagcaa gagacataag gcaattcgag tcatcattgc cgtggtgttg  2340
gtcttcttgg cctgtcagat cccccataat atggttctgc tcgtcaccgc cgctaacttg  2400
ggtaagatga atcgatcttg tcagtccgag aagttgatcg gatacaccaa aactgtgaca  2460
gaagtgctgg ccttccttca ctgttgtctg aacccagttt tgtatgcttt tataggacag  2520
aagtttcgaa attacttctt gaaaatcctc aaggacctct ggtgtgttcg aaggaagtac  2580
aagagctctg gctttagttg cgctgggcgc tacagtgaga atatatcccg gcagacctcc  2640
gagactgctg ataatgacaa cgcaagttcc ttcactatgg gatccggcgc aacaaacttc  2700
tctctgctga aacaagccgg agatgtcgaa gagaatcctg gaccggtgag caagggcgag  2760
gagctgttca ccggggtggt gcccatcctg gtcgagctgg acggcgacgt aaacggccac  2820
aagttcagcg tgtctggcga gggcgagggc gatgccacct acggcaagct gaccctgaag  2880
ttcatctgca ccaccggcaa gctgcccgtg ccctggccca ccctcgtgac caccctgacc  2940
tacggcgtgc agtgcttcag ccgctacccc gaccacatga agcagcacga cttcttcaag  3000
tccgccatgc ccgaaggcta cgtccaggag cgcaccatct tcttcaagga cgacggcaac  3060
tacaagaccc gcgccgaggt gaagttcgag ggcgacaccc tggtgaaccg catcgagctg  3120
aagggcatcg acttcaagga ggacggcaac atcctgggc acaagctgga gtacaactac  3180
aacagccaca acgtctatat catggccgac aagcagaaga acggcatcaa ggcgaacttc  3240
aagatccgcc acaacatcga ggacggcagc gtgcagctcg ccgaccacta ccagcagaac  3300
acccccatcg gcgacggccc cgtgctgctg cccgacaacc actacctgag cacccagtcc  3360
gccctgagca agacccccaa cgagaagcgc gatcacatgg tcctgctgga gttcgtgacc  3420
gccgccggga tcactctcgg catggacgag ctgtacaagt aa                    3462

SEQ ID NO: 431        moltype = AA   length = 780
FEATURE               Location/Qualifiers
REGION                1..780
                      note = Synthetic
source                1..780
                      mol_type = protein
                      organism = synthetic construct
SEQUENCE: 431
MVCLKLPGGS CMTALTVTLM VLSSPLALAS DENPVVHFFK NIVTPRTPPG GGGSGGGGSG   60
GSGDTRPRFL WQPKRECHFF NGTERVRFLD RYFYNQEESV RFDSDVGEFR AVTELGRPDA  120
EYWNSQKDIL EQARAAVDTY CRHNYGVVES FTVQRRVQPK VTVYPSKTQP LQHHNLLVCS  180
VSGFYPGSIE VRWFLNGQEE KAGMVSTGLI QNGDWTFQTL VMLETVPRSG EVYTCQVEHP  240
SVTSPLTVEW RARSESAQSK MLSGVGGFVL GLLFLGAGLF IYFRNQTSRV KFSRSADAPA  300
YQQGQNQLYN ELNLGRREEY DVLDKRRGRD PEMGGKPRRK NPQEGLYNEL QKDKMAEAYS  360
EIGMKGERRR GKGHDGLYQG LSTATKDTYD ALHMQALPPR GSSGSGEGRG SLLTCGDVEE  420
NPGPMAISGV PVLGFFIIAV LMSAQESWAI KEEHVIIQAE FYLNPDQSGE FMFDFDGDEI  480
FHVDMAKKET VWRLEEFGRF ASFEAQGALA NIAVDKANLE IMTKRSNYTP ITNVPPEVTV  540
LTNSPVELRE PNVLICFIDK FTPPVVNVTW LRNGKPVTTG VSETVFLPRE DHLFRKFHYL  600
PFLPSTEDVY DCRVEHWGLD EPLLKHWEFD APSPLPETTE NVVCALGLTV GLVGIIIGTI  660
FIIKGLTSRV KFSRSADAPA YQQGQNQLYN ELNLGRREEY DVLDKRRGRD PEMGGKPRRK  720
NPQEGLYNEL QKDKMAEAYS EIGMKGERRR GKGHDGLYQG LSTATKDTYD ALHMQALPPR  780
```

What is claimed is:

1. A major histocompatibility complex (MHC)-based chimeric receptor, comprising:
   (i) an extracellular domain of an MHC molecule conjugated to an antigenic peptide from an antigen involved in an autoimmune disease; and
   (ii) a cytoplasmic signaling domain, at least one co-stimulatory domain, or a combination thereof;
   wherein the MHC molecule is a class I MHC; and
   wherein the extracellular domain of the chimeric receptor comprises an extracellular domain of the alpha chain of the class I MHC, which is fused to the antigenic peptide.

2. A genetically modified immune cell, which expresses an MHC-based chimeric receptor; which comprises:
   (i) an extracellular domain of an MHC molecule conjugated to an antigenic peptide from an antigen involved in an autoimmune disease; and
   (ii) a cytoplasmic signaling domain, at least one co-stimulatory domain, or a combination thereof;
   wherein the MHC molecule is a class I MHC, and
   wherein the extracellular domain of the chimeric receptor comprises an extracellular domain of the alpha chain of the class I MHC, which is fused to the antigenic peptide.

3. The genetically modified immune cell of claim 2, which is a T cell.

4. The genetically modified immune cell of claim 3,
   wherein the activity of the endogenous T cell receptor (TCR) is suppressed;
   wherein expression of the endogenous CD52 is disrupted;
   wherein the genetically modified immune cell further expresses a suicide gene, a marker gene or both;
   wherein the immune cell is further modified for lymph node delivery and retention;
   wherein the expression of endogenous sphingosine-1-phosphate receptor 1 is disrupted in the immune cell;
   wherein the immune cell is further modified to express one or more surface molecules for tertiary lymph node or ectopic lymph node delivery and retention;
   wherein the immune cell is modified with IL6ST knockout, IL6R knockout, or both;
   wherein the immune cell is further modified to express or overly express a chemokine receptor;
   wherein the immune cell is further modified to express or overly express an adhesion receptor; and/or
   wherein the immune cell further comprises a genetic modification that results in blockade of PD-1 signaling.

5. The genetically modified immune cell of claim 2, which is a regulatory T cell, wherein the regulatory T cell is CD25+.

6. The genetically modified immune cell of claim 5, wherein the regulatory T cell comprises a transgene coding for CD25; wherein the regulatory T cell comprises a transgene coding for FoxP3; and/or wherein the regulatory T cell further expresses a chimeric receptor specific to CD19, a chimeric receptor specific to CS-1, or both.

7. The genetically modified immune cell of claim 5, wherein the regulatory T cell displays an antibody specific to an autoantigen.

8. The genetically modified immune cell of claim 2, which is a cytotoxic lymphocyte, wherein the cytotoxic T cell is CD8+.

9. The genetically modified immune cell of claim 2, wherein the MHC-based chimeric receptor comprises the at least one co-stimulatory domain.

10. The genetically modified immune cell of claim 9, wherein the at least one co-stimulatory domain is a co-stimulatory domain from 4-1BB (CD137), a co-stimulatory domain from CD28, or a combination thereof.

11. The genetically modified immune cell of claim 9, wherein the MHC-based chimeric receptor is free of a cytoplasmic signaling domain.

12. The genetically modified immune cell of claim 2, wherein the MHC-based chimeric receptor further comprises a hinge domain located between (i) and (ii).

13. The genetically modified immune cell of claim 2, wherein the MHC-based chimeric receptor comprises a cytoplasmic signaling domain of CD3ζ.

14. The genetically modified immune cell of claim 2, wherein the antigenic peptide is from myelin basic protein (MBP), myelin oligodendrocyte glycoprotein (MOG), proteolipid protein (PLP), insulin, or glutamate decarboxylase.

15. The genetically modified immune cell of claim 2, wherein the class I MHC is a human class I MHC.

16. The genetically modified immune cell of claim 2, wherein the chimeric receptor is a fusion polypeptide comprising (i) the extracellular domain of the class I MHC molecule, and (ii) the cytoplasmic domain, the at least one co-stimulatory domain, or the combination thereof.

17. The genetically modified immune cell of claim 16, wherein the chimeric receptor is a fusion polypeptide, which comprises, from N-terminus to C-terminus, a signal peptide, a first peptide linker, the antigenic peptide, a second peptide linker, an extracellular domain of macroglobulin, a third peptide linker, the class I MHC molecule, a transmembrane domain, the at least one co-stimulatory domain, and CD3ζ.

* * * * *